(12) United States Patent
Erickson et al.

(10) Patent No.: US 9,593,154 B2
(45) Date of Patent: Mar. 14, 2017

(54) ENGINEERED POLYPEPTIDES HAVING ENHANCED DURATION OF ACTION

(71) Applicants: AMYLIN PHARMACEUTICALS, LLC, San Diego, CA (US); ASTRAZENECA PHARMACEUTICALS LP, Wilmington, DE (US)

(72) Inventors: Mary Erickson, San Diego, CA (US); David C. Litzinger, San Diego, CA (US); Soumitra S. Ghosh, San Diego, CA (US); Zijian Guo, San Diego, CA (US); Swetha Neravetla, San Diego, CA (US); Chengzao Sun, San Marcos, CA (US); Manoj P. Samant, Boston, MA (US); Odile E. Levy, San Diego, CA (US); Abhinandini Sharma, San Diego, CA (US); Lala Mamedova, San Diego, CA (US); Christopher J. Soares, La Jolla, CA (US)

(73) Assignees: AstraZeneca Pharmaceuticals LP, Wilmington, DE (US); Amylin Pharmaceuticals, LLC, San Diego, CA (US)

( * ) Notice: Subject to any disclaimer, the term of this patent is extended or adjusted under 35 U.S.C. 154(b) by 0 days.

(21) Appl. No.: 13/852,899

(22) Filed: Mar. 28, 2013

(65) Prior Publication Data

US 2014/0107019 A1    Apr. 17, 2014

Related U.S. Application Data

(63) Continuation of application No. PCT/US2011/053770, filed on Sep. 28, 2011.

(60) Provisional application No. 61/387,391, filed on Sep. 28, 2010, provisional application No. 61/422,085, filed on Dec. 10, 2010.

(51) Int. Cl.
    *C07K 14/605*   (2006.01)
    *A61K 47/48*    (2006.01)
    *C07K 14/575*   (2006.01)

(52) U.S. Cl.
    CPC ...... *C07K 14/605* (2013.01); *A61K 47/48284* (2013.01); *C07K 14/57563* (2013.01); *C07K 2319/00* (2013.01); *C07K 2319/21* (2013.01); *C07K 2319/70* (2013.01)

(58) Field of Classification Search
    None
    See application file for complete search history.

(56) References Cited

U.S. PATENT DOCUMENTS

| | | |
|---|---|---|
| 5,424,286 A | 6/1995 | Eng |
| 5,527,684 A | 6/1996 | Mabile et al. |
| 5,766,627 A | 6/1998 | Sankaram et al. |
| 6,296,842 B1 | 10/2001 | Jaworowicz et al. |
| 6,319,685 B1 | 11/2001 | Gilligian et al. |
| 6,326,468 B1 | 12/2001 | Canne et al. |
| 6,368,630 B1 | 4/2002 | Bernstein et al. |
| 6,379,703 B1 | 4/2002 | Lyons et al. |
| 6,379,704 B2 | 4/2002 | Wright et al. |
| 6,528,486 B1 | 3/2003 | Larsen et al. |
| 6,858,576 B1 | 2/2005 | Young et al. |
| 6,872,700 B1 | 3/2005 | Young et al. |
| 6,956,026 B2 | 10/2005 | Beeley et al. |
| 7,223,725 B1 | 5/2007 | Beeley et al. |
| 2007/0238669 A1 | 10/2007 | Haque et al. |
| 2008/0207512 A1 | 8/2008 | Roth et al. |
| 2008/0274952 A1 | 11/2008 | Soares et al. |
| 2009/0003869 A1 | 1/2009 | Takahashi |
| 2011/0097751 A1 | 4/2011 | Nicolaou et al. |
| 2014/0107019 A1* | 4/2014 | Erickson et al. ........... 514/4.8 |
| 2015/0133373 A1* | 5/2015 | Ren .............. A61K 38/2278 514/6.9 |

FOREIGN PATENT DOCUMENTS

| | | |
|---|---|---|
| CN | 101765608 | 6/2010 |
| CN | 103370083 | 10/2013 |
| EP | 2621538 | 8/2013 |
| HK | 1188710 | 5/2014 |
| JP | 2013545724 | 12/2013 |
| WO | 99/07404 A1 | 2/1999 |

(Continued)

OTHER PUBLICATIONS

Hongjian et al: "A Protease-Based Strategy for the Controlled Release of Therapeutic Peptides", Angewandte Chemie (International Ed. in English), vol. 122, No. 29, Jul. 5, 2010 (Jul. 5, 2010), pp. 5858-5853.*
Anderson et al. "The Versatile MHC Class I-related FcRn Protects IgG and Albumin from Degradation: Implications for Development of New Diagnostics and Therapeutics", Drug Metabolism and Pharmacokinetics, vol. 24, No. 4, Aug. 25, 2009 (Aug. 25, 2009), pp. 318-332.*
CN201180057092.1 , "Office Action", Jul. 17, 2014, 3 pages.
Hongjian Li et al., A Protease-Based Strategy for the Controlled Release of Therapeutic Peptides, *Angew. Chem. Int. Ed.*, 2010, 49(29): 4930-4933.
Eng et al., 1990, *J. Biol Chem.*, 265:20259-62.
Eng et al., 1992, *J. Biol Chem.*, 264:7402-7405.
Hargrove et al. Regulatory Peptides, 2007, 141:113-119.
Goke et al., 1993, *J. Biol Chem.*, 268:19650-55.
Eng et al., 1997, *J. Biol Chem.*, 272: 4108-15.
Johnson et al., *Protein Eng. Design & Selection*, 2008, 21:515-527.
Peters T. *Advances in Protein Chemistry*, 1985, 37:161.
McCurdy TR et al., *J. Lab. Clin. Med*, 2004, 143:115.
Dugaiczyk L et al., *roc Natl. Acad Sci. USA*, 1982, 79:71.
Peters, 1985, *ID.*; Nicholson JP et al., *Br J Anaesth*, 2000, 85:599.
He, XM and Carter, DC, *Nature*, 1992, 358:209.

(Continued)

*Primary Examiner* — Maury Audet
(74) *Attorney, Agent, or Firm* — Mintz Levin Cohn Ferris Glovsky and Popeo, P.C.

(57) ABSTRACT

Compounds are provided having inter alia good duration of action, high potency and/or convenient dosing regimens including oral administration. The compounds are engineered polypeptides which incorporate an albumin binding domain in combination with one or more biologically active polypeptides. Also provided are pharmaceutical compositions and methods of treatment for diseases and disorders including obesity and overweight, diabetes, dyslipidemia, hyperlipidemia, Alzheimer's disease, fatty liver disease, short bowel syndrome, Parkinson's disease, cardiovascular disease, and other and disorders of the central nervous system.

10 Claims, 26 Drawing Sheets

(56) References Cited

FOREIGN PATENT DOCUMENTS

| WO | 99/25727 | A2 | 5/1999 |
|---|---|---|---|
| WO | 99/25728 | A1 | 5/1999 |
| WO | 99/40788 | A1 | 8/1999 |
| WO | 00/41546 | A2 | 7/2000 |
| WO | 00/41548 | A2 | 7/2000 |
| WO | 2004/035623 | A2 | 4/2004 |
| WO | 2006/083254 | A1 | 8/2006 |
| WO | 2007/114838 | A1 | 10/2007 |
| WO | 2007/139941 | A2 | 12/2007 |
| WO | 2007/140284 | A2 | 12/2007 |
| WO | 2008/082274 | A1 | 7/2008 |
| WO | 2009/011544 | A2 | 1/2009 |
| WO | 2009/016043 | A2 | 2/2009 |
| WO | WO 2009/016043 | A2 | 2/2009 |
| WO | 2010/120476 | A2 | 10/2010 |
| WO | 2012/050923 | | 4/2012 |

OTHER PUBLICATIONS

Davies & Morries, *Pharm. Res.* (N.Y.), 1993, 10:1093-1095.
Cooper et al., *Biochem. Biophys. Acta*, 1989, 1014: 247-258.
Kopelman, *Nature*, 2000, 404: 635-43.
Rissanen et al., *Br. Med. J.*, 1990, 301: 835-7.
Perry et al., *Curr. Drug Targets*, 2004, 5(6): 565-571.
Holz et al., *J. Biol. Chem.*, 1995, 270(30): 17749-57.
Morley, Flood et al., *Am. J. Physiol.*, 1994, 267: R178-R184.
Levin, *Am. J. Physiol.*, 1994, 267: R527-R535.
Levin, *Am. J. Physiol.*, 1997, 273: R725-R730.
U.S. Appl. No. 60/034,905, filed Mar. 7, 2008. "Dynamic Mobile Service Control Development Architecture." Inventors James Hu, et al. 17 pages.
U.S. Appl. No. 60/055,404, filed Aug. 8, 1997. "Novel Exendins Agonist Compounds." Inventors Nigel Beeley, et al. 62 pages.
U.S. Appl. No. 60/065,442, filed Nov. 14, 1997. "Novel Exendin Agonist Compounds." Inventors Nigel Beeley, et al. 100 pages.
U.S. Appl. No. 60/066,029, filed Nov. 14, 1997. "Novel Exedin Agonist Compounds." Inventors Nigel Beeley et al. 122 pages.
U.S. Appl. No. 08/908,867, filed Aug. 8, 1997. "Methods for Regulating Gastrointestinal Motility." Inventor Andrew A. Young. 68 pages.
U.S. Appl. No. 08/694,954, filed Aug. 8, 1996. "Methods for Regulating Gastrointestinal Motility." Inventor Andrew A. Young. 42 pages.
Andersen, J.T. & Sandlie, I., "The Versatile MHC Class I-related FcRn Protects IgG and Albumin from Degradation: Implications for Development of New Diagnostics and Therapeutics", *Drug Metabolism and Pharmacokinetics*, 24(4):318-332 (2009).
Bertilsson et al., "Peptide Hormone Exendin-4 Stimulates Subventricular Zone Neurogenesis in the Adult Rodent Brain and Induces Recovery in an Animal Model of Parkinson's Disease", *Journal of Neuroscience Research*, 86:326-338 (2008).
Li et al., "A Protease-Based Strategy for the Controlled Release of Therapeutic Peptides**", *Angewandte Chemie*, 122:5050-5053 (2010).
International Preliminary Report on Patentability and Written Opinion dated Apr. 2, 2013 for International Application No. PCT/US2011/053770, 11 pages.
International Search Report and Written Opinion dated Apr. 26, 2012 for International Application No. PCT/US2011/053770, 20 pages.
Al-Sabah, S. et al. (Sep. 2003, e-published Aug. 26, 2003). "A model for receptor-peptide binding at the glucagon-like peptide-1 (GLP-1) receptor through the analysis of truncated ligands and receptors," *Br J Pharmacol* 140(2):339-346.
López De Maturana, R. et al. (Mar. 21, 2003, e-published Jan. 10, 2003). "The isolated N-terminal domain of the glucagon-like peptide-1 (GLP-1) receptor binds exendin peptides with much higher affinity than GLP-1," *J Biol Chem* 278(12):10195-10200.
Mann, R.J. et al. (Aug. 2010). "The major determinant of exendin-4/glucagon-like peptide 1 differential affinity at the rat glucagon-like peptide 1 receptor N-terminal domain is a hydrogen bond from SER-32 of exendin-4," *Br J Pharmacol* 160(8):1973-1984.
Underwood, C.R. et al. (Jan. 1, 2010, e-published Oct. 27, 2009). "Crystal structure of glucagon-like peptide-1 in complex with the extracellular domain of the glucagon-like peptide-1 receptor," *J Biol Chem* 285(1):723-730.

\* cited by examiner

*P< 0.05 vs Vehicle Control

*P< 0.05 vs Vehicle Control

*excludes glucometer readings of HI (>600)

ENGINEERED POLYPEPTIDES HAVING ENHANCED DURATION OF ACTION

CROSS-REFERENCE TO RELATED APPLICATIONS

This application is a continuation of International Patent Application No. PCT/US2011/053770, filed Sep. 28, 2011, which claims the benefit of U.S. Provisional Patent Applications 61/387,391, filed Sep. 28, 2010, and 61/422,085, filed Dec. 10, 2010, each of which is incorporated herein by reference in its entirety and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 92494-867804_ST25.TXT, created on Mar. 24, 2013, 114,846 bytes, machine format IBM-PC, MS-Windows operating system, is hereby incorporated by reference.

BACKGROUND OF THE INVENTION

The present application relates to compounds having good duration of action, high potency and/or convenient dosing regimens including oral administration, and method of use thereof. There are provided herein engineered polypeptides which incorporate an albumin binding domain in combination with a biologically active peptide. Without wishing to be bound by any theory, it is believed that because the engineered polypeptides described herein can bind albumin, the compounds can be sequestered (e.g., bound to albumin) while in the circulation leading to increased duration of action, due for example to decreased renal clearance and/or degradation. Diseases amendable to such treatment include obesity and overweight, diabetes, dyslipidemia, hyperlipidemia, short bowel syndrome, Alzheimer's disease, fatty liver disease, Parkinson's disease, cardiovascular disease, and other disorders of the central nervous system, or combinations thereof.

There remains a need to develop polypeptides useful in the above described metabolic diseases, conditions and disorders. Accordingly, it is an object of the present invention to provide engineered polypeptides with extended half-lives useful to treat the above conditions and methods for producing and using them.

Each patent, patent application, and publication cited herein is hereby incorporated herein by reference in its entirety and for all purposes.

BRIEF SUMMARY OF THE INVENTION

There are provided engineered polypeptide compounds having binding affinity for albumin and an additional therapeutic utility. The compounds are engineered polypeptides which include an albumin binding domain (ABD) polypeptide as defined herein capable of binding albumin and a hormone domain (HD) polypeptide, which HD polypeptides can be biologically active and can elicit a beneficial biological response, in covalent linkage with the ABD. Any of the ABD or HD polypeptides described herein can be optionally covalently bonded in the engineered polypeptide through a linker L, for example L1 as described herein. Without wishing to be bound by any theory, it is believed that because the engineered polypeptides described herein can bind albumin, the compounds can be sequestered in a subject leading to increased duration of action in the subject.

In a first aspect, there is provided an engineered polypeptide as described herein. The engineered polypeptide includes an albumin binding domain polypeptide (ABD) as described herein and a hormone domain (HD1). The hormone domain includes a polypeptide which is an exendin, a fragment of an exendin, or analog of an exendin.

In another aspect, there is provided a method for treating a disease or disorder in a subject in need of treatment. The method includes administering an engineered polypeptide as described herein to the subject.

In yet another aspect, there is provided a pharmaceutical composition which includes an engineered polypeptide compound described herein in combination with a pharmaceutically acceptable excipient.

In yet another aspect are polynucleotides encoding the engineered polypeptide and their intermediates, expression vectors bearing such polynucleotides, host cells expressing such polynucleotides, and means for their expression, synthesis, post-translational modification and isolation.

One advantage of the present invention is that the engineered polypeptides can be synthesized completely by recombinant methods, avoiding complex or additional synthetic or chemical steps and associated reactive reagents and catalysts. Consequently, the polypeptides of the present invention can be much less expensive to synthesize than chemically derivatized compounds of prolonged duration of action. In addition to a long duration of action (e.g., at least one week in a human subject, albeit once daily can also be achieved if desired), a further advantage is relatively small size, which can allow for oral delivery to improve patient compliance.

The compounds disclosed herein demonstrate surprising efficacy in an OGTT DOA (oral glucose tolerance test for duration of action) test of at least 24 hours and even longer to 2 days in mice, which translates to 7 days or longer in humans, a robust glycemic control and body weight loss in diabetic obese (ob/ob) mice, and provide a dose-dependent reduction of food intake over at least two days in mice. In normal rats, compound exposure lasts for several days (even as long as 4 days, which translates to at least once a week in humans) after subcutaneous and intravenous dosing. Compounds are stable in plasma and to plasma proteases, are active while bound to serum albumin, and surprisingly provide greater maximal in vivo efficacy than exendin-4 as shown herein. Even more surprisingly the compounds are suitable for oral delivery.

Figure 3A:
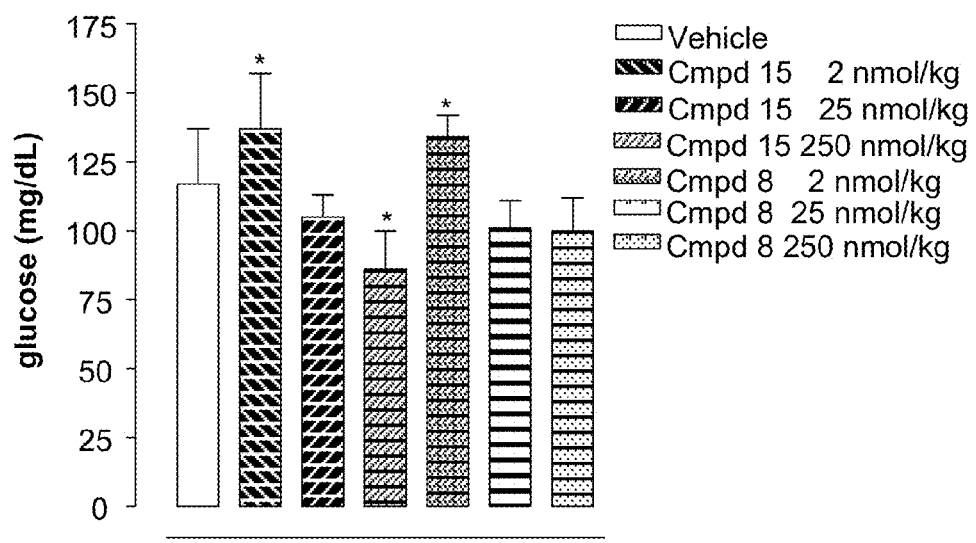
Figure 3B:
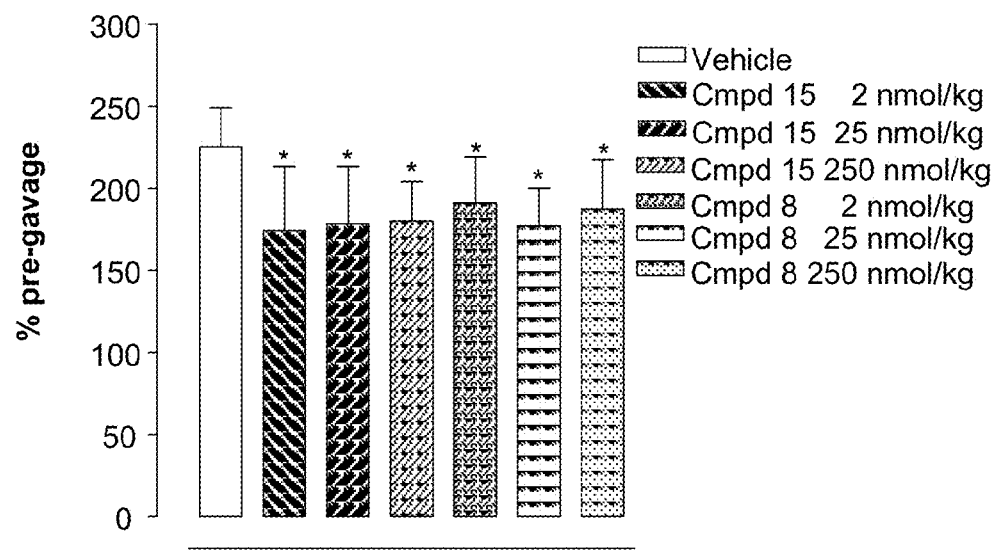

FIG. 3A: Blood glucose level (BGL) data histogram prior to gavage at 1-day post dosage of Cmpd 15 and Cmpd 8 in OGTT DOA test. Vehicle mean pre-gavage glucose: 117 mg/dL. Legend (left to right): vehicle (open); 2 nmol/kg Cmpd 15 (diagonal upper left to lower right); 25 nmol/kg Cmpd 15 (diagonal lower left to upper right); 250 nmol/kg Cmpd 15 (fine diagonal); 2 nmol/kg Cmpd 8 (tiled); 25 nmol/kg Cmpd 8 (horizontal lines); 250 nmol/kg Cmpd 8 (dotted). FIG. 3B: Change in blood glucose at 30 min. Vehicle mean pre-gavage glucose: 117 mg/dL. Legend: same as FIG. 1A. * p<0.5 vs. vehicle control; ANOVA, Dunnett's test.

Figure 4A:
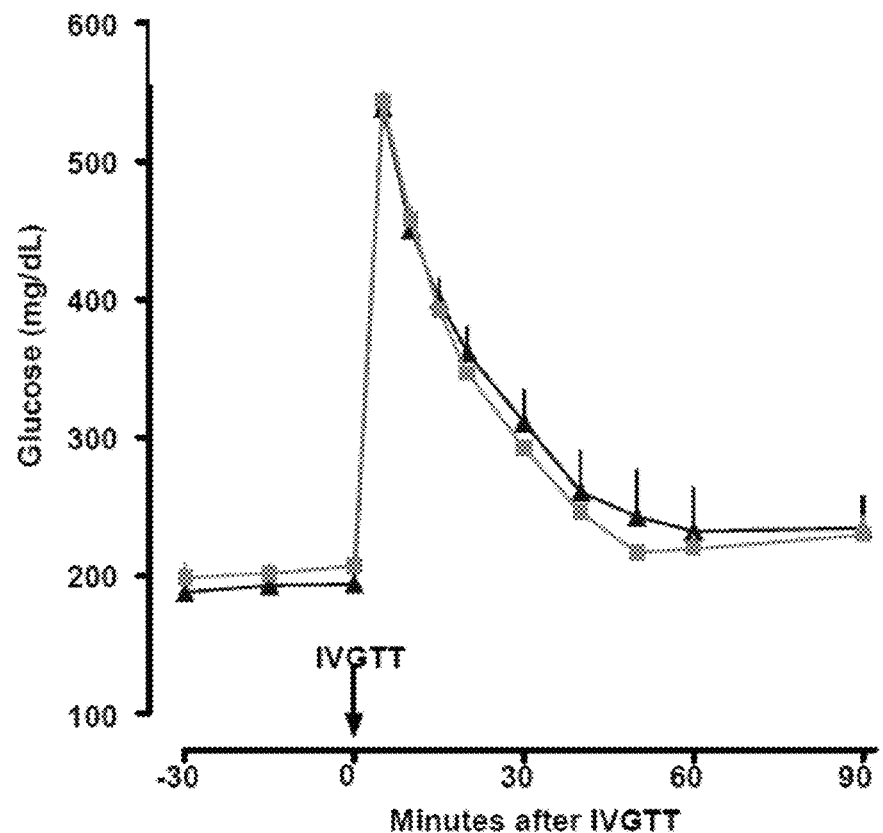
Figure 4B:
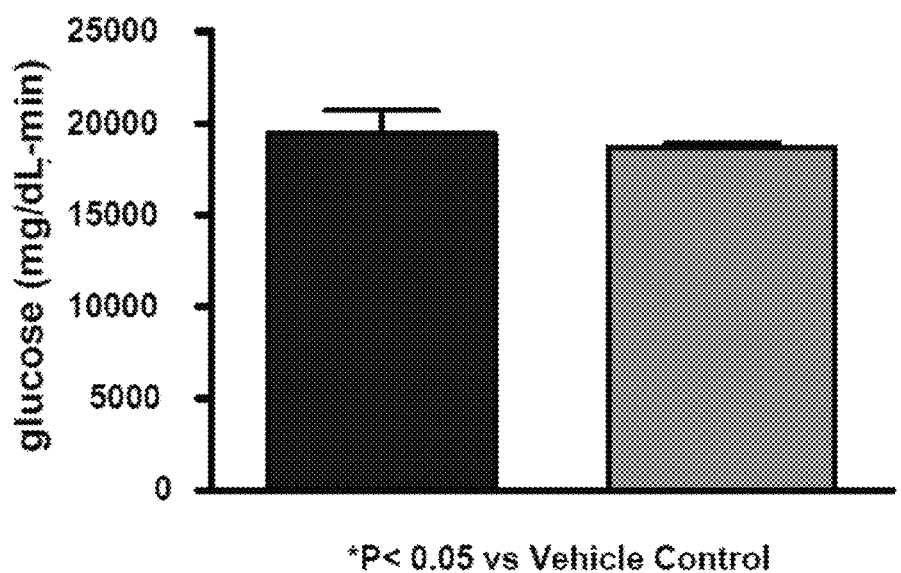
Figure 4C:
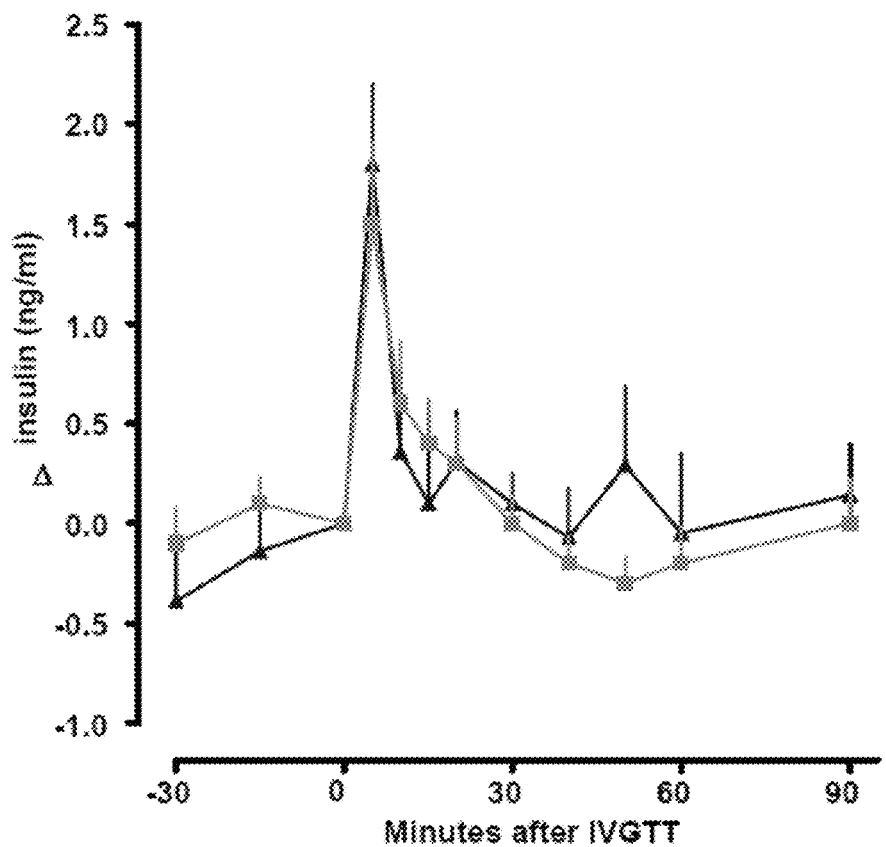
Figure 4D:
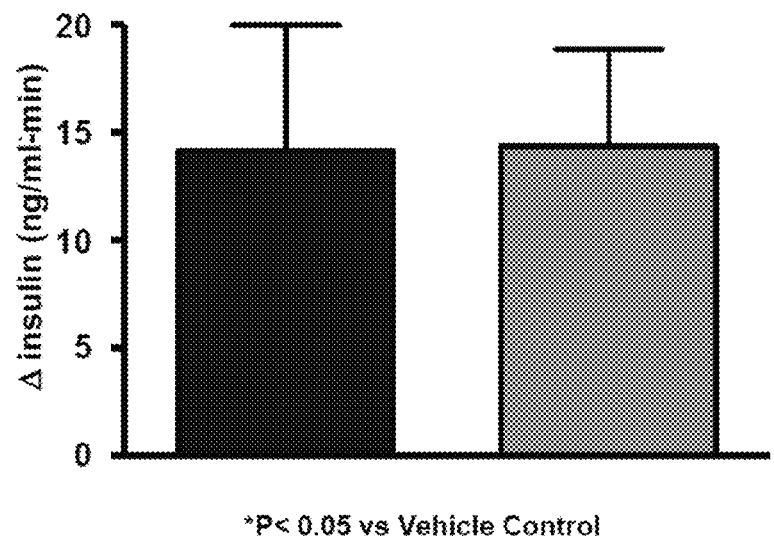
Figure 4E:
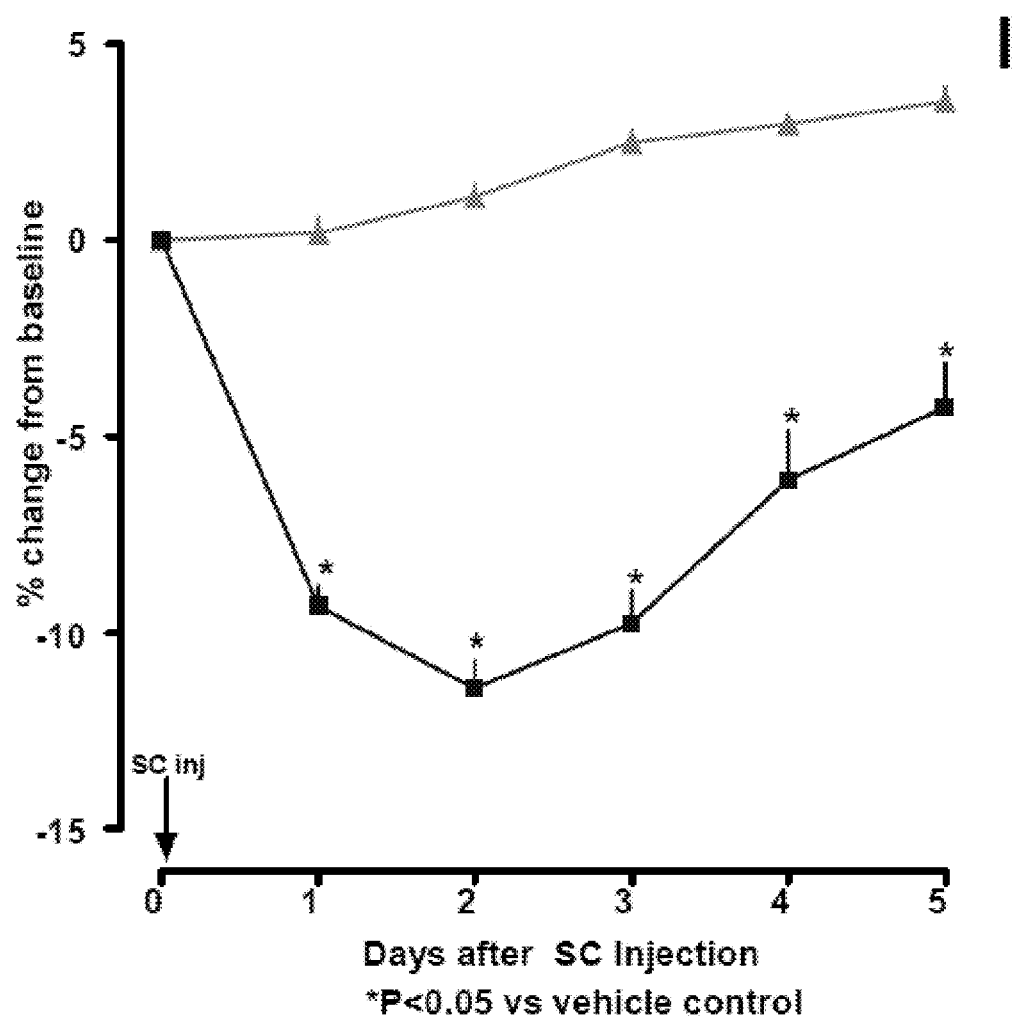
Figure 4F:
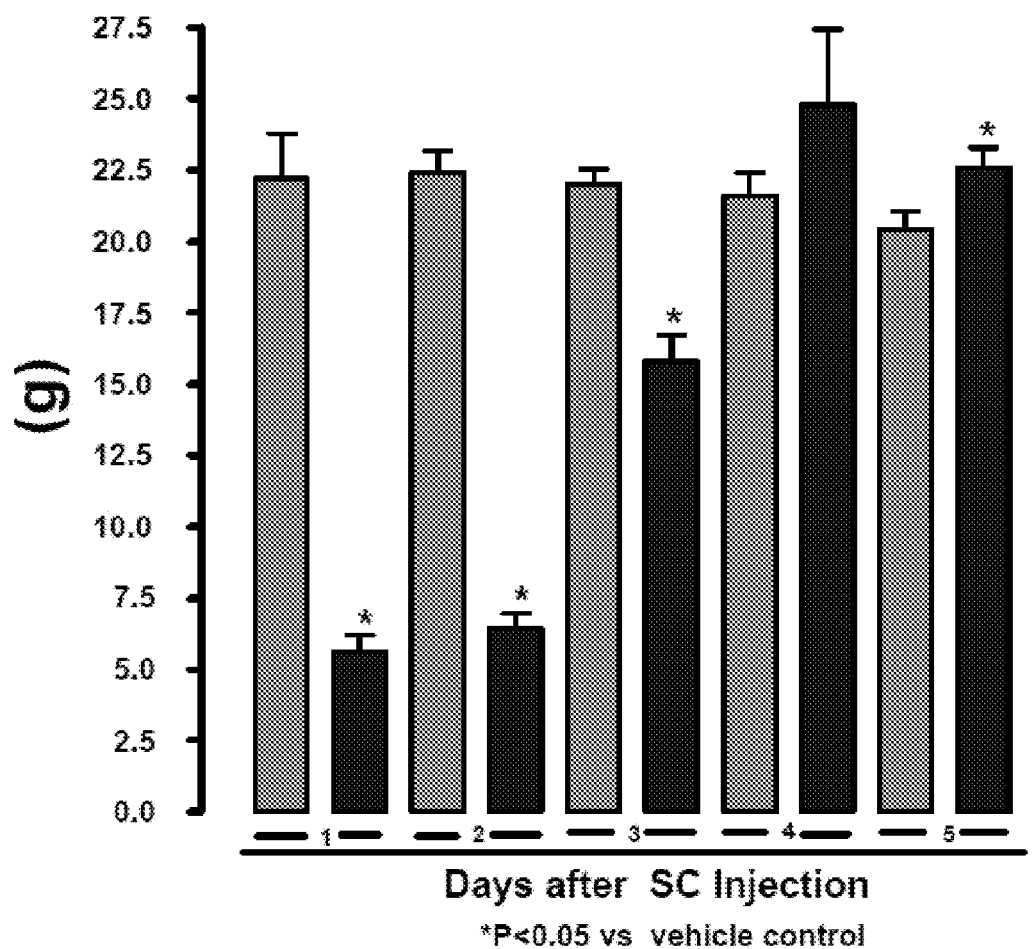

FIGS. 4A-4F: Effect of Cmpd 15 in HSD fed anesthetized rats. FIG. 4A: Glucose time course after intravenous glucose tolerance test (IVGTT). Legend: vehicle (Triangle tip up); Cmpd 15 at 240 nmol/kg (box). FIG. 4B: Histogram depicting glucose (AUC, 0-60 min) after IVGTT. Legend: vehicle (left); Cmpd 15 (right). FIG. 4C: Time course of insulin after IVGTT. Legend: As in FIG. 4A. FIG. 4D: Histogram depicting change in insulin (AUC, 0-30 min). Legend: As in FIG. 4B. FIG. 4E: Time course of change in body weight after sc injection of Cmpd 15. Legend: As in FIG. 4A. FIG. 4F: Histogram of daily food intake after sc injection of Cmpd 15. Legend: for each day, histogram depicts vehicle and Cmpd 15 (240 nmol/kg) in order left to right. *p<0.05 vs. vehicle control; Dunnett's test.

Figure 5A:
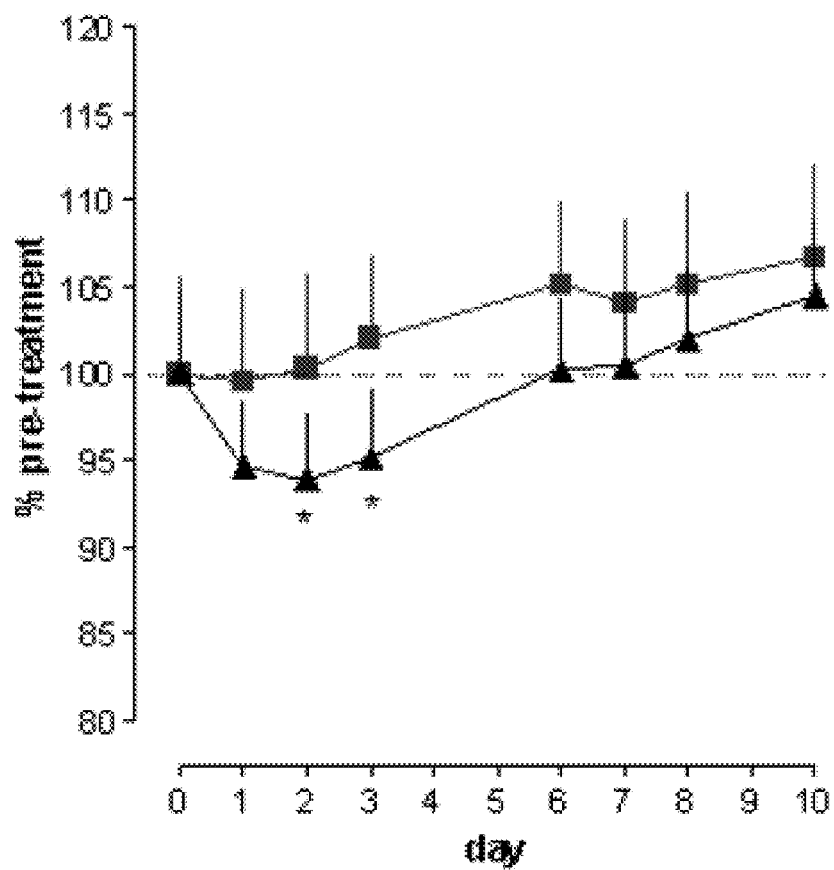
Figure 5B:
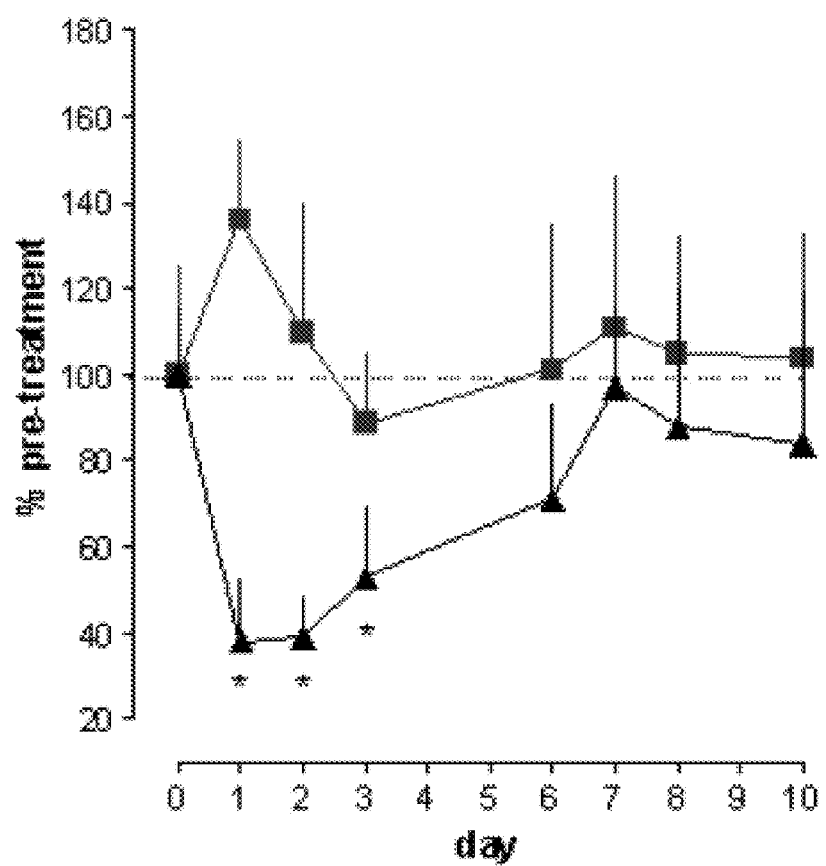
Figure 5C:
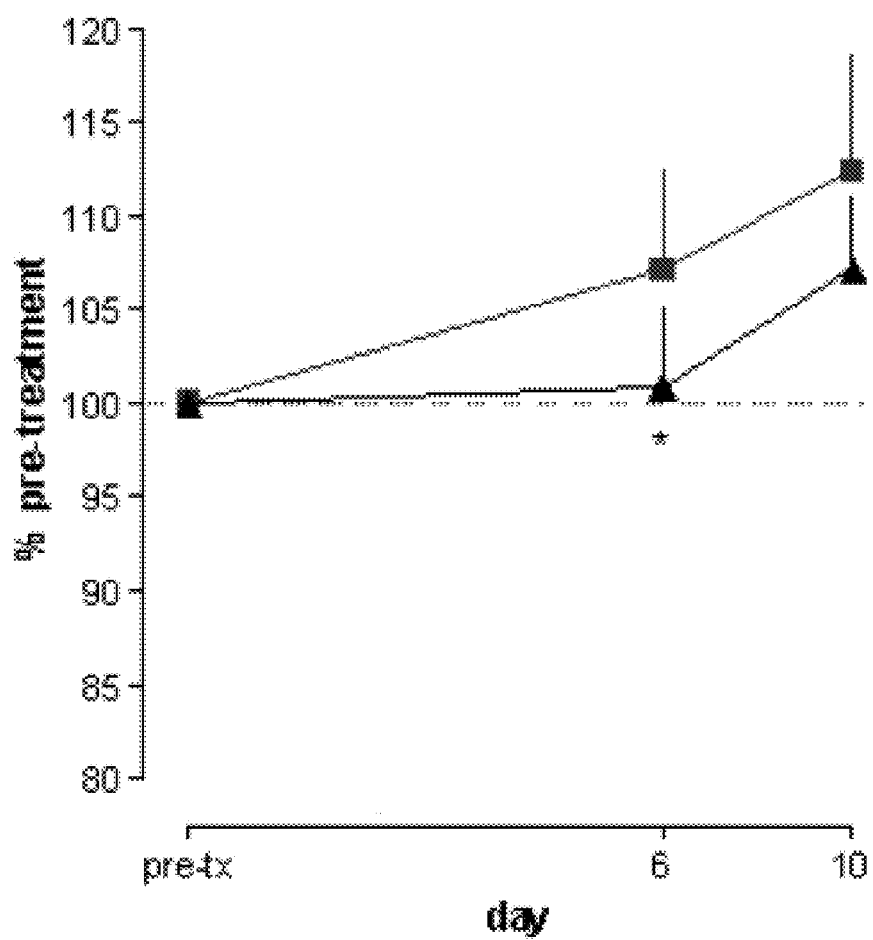

FIGS. 5A-5C: Effect of Cmpd 15 in ob/ob mice. FIG. 5A: Time course of change in body weight (0-10 days) after injection of Cmpd 15 at 250 nmol/kg. Legend: Vehicle (square); Cmpd 15 (triangle). FIG. 5B: Time course of change in blood glucose after dosage as described for FIG. 5A. Legend: As in FIG. 5A. FIG. 5C: Time course of change in $HbA_{1c}$ after dosage as described for FIG. 5A. Legend: As in FIG. 5A. * p<0.5 vs. vehicle control; ANOVA, Dunnett's test.

Figure 6A:
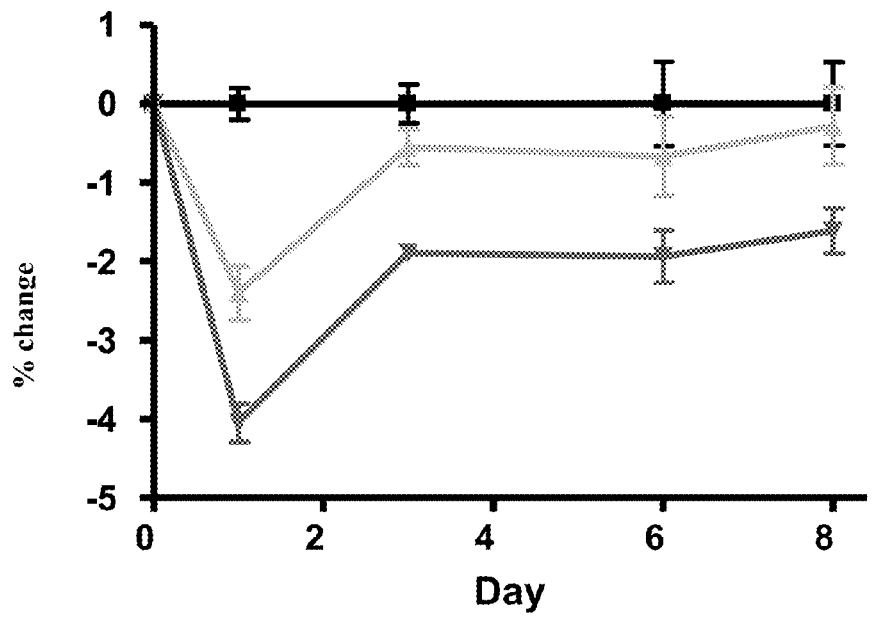
Figure 6B:
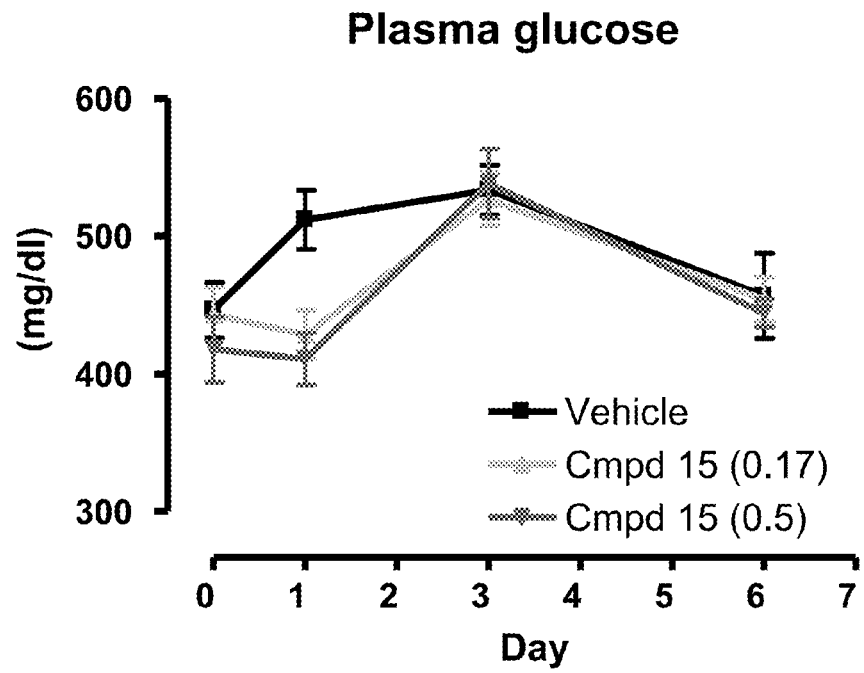

FIGS. 6A-6B: Effects of Cmpd 15 in Zucker Diabetic Fatty rats. FIG. 6A: Time course of change in body weight after treatment of Zucker Diabetic Fatty rats with Cmpd 15. FIG. 6B: Time course of plasma glucose (mg/dL) after treatment with Cmpd 15. Legend: Vehicle (solid box); Cmpd 15 (0.17 mg/kg) (triangle tip up); Cmpd 15 (0.5 mg/kg) (triangle tip down).

Figure 7:
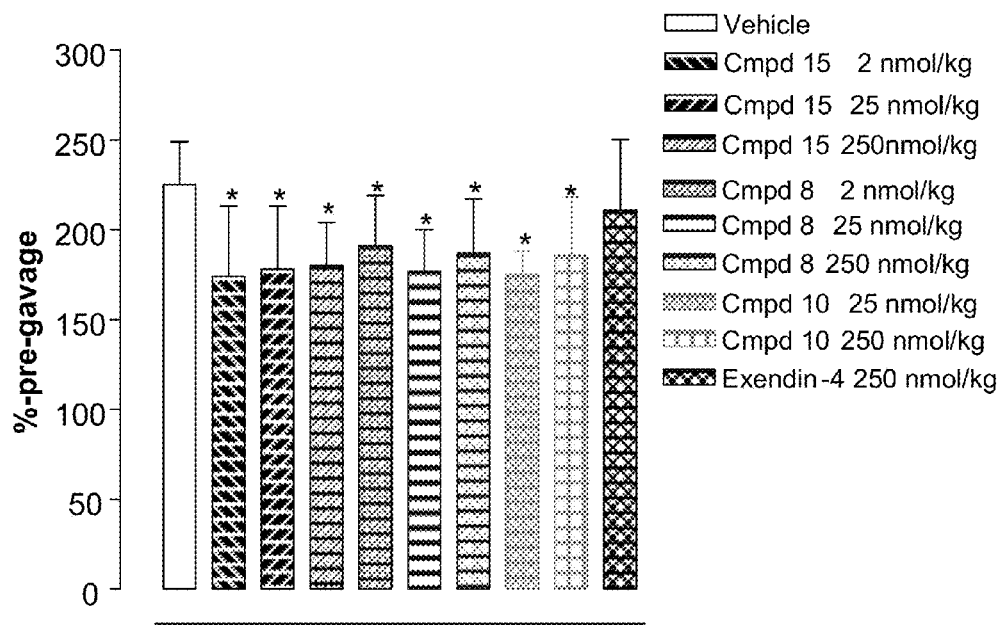

FIG. 7: Comparison in OGTT DOA. Effects of Cmpds 15, 8 and 10, compared with exendin-4, were evaluated as the change in blood glucose at 30 min (% pre-gavage). Legend: compounds in order left to right of histogram: vehicle; Cmpd 15 at 2 nmol/kg; Cmpd 15 at 25 nmol/kg; Cmpd 15 at 250 nmol/kg; Cmpd 8 at 2 nmol/kg; Cmpd 8 at 25 nmol/kg; Cmpd 8 at 250 nmol/kg; Cmpd 10 at 25 nmol/kg; Cmpd 10 at 250 nmol/kg; exendin-4 at 250 nmol/kg. * p<0.5 vs. vehicle control; ANOVA, Dunnett's test.

Figure 8:
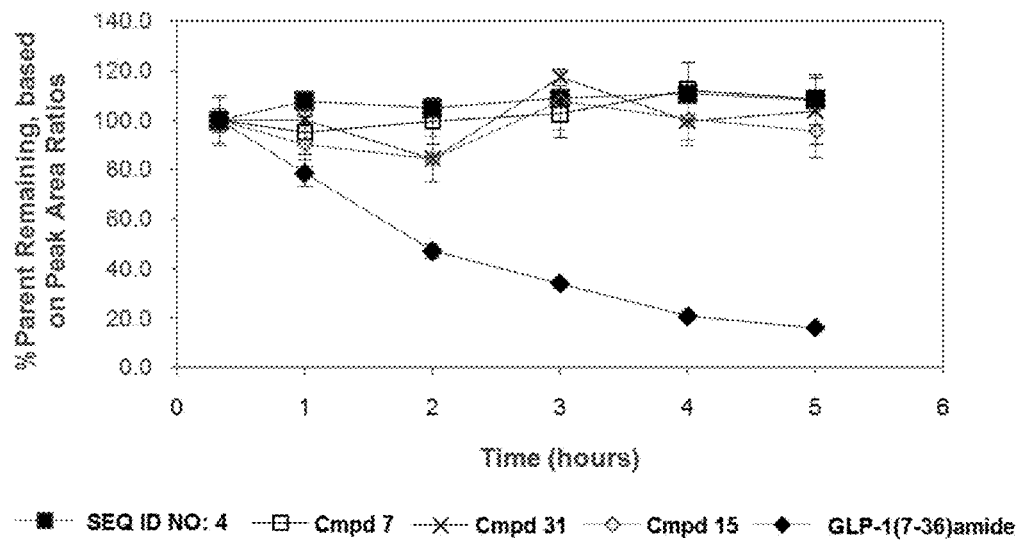

FIG. 8: Presents a time profile of percent of compound remaining in human plasma over a 5 hour time course. Legend: Peptide (SEQ ID NO:4) (closed box); Cmpd 7 (open box); Cmpd 31 (cross); Cmpd 15 (open diamond); GLP-1(7-36)amide (closed diamond).

Figure 9:
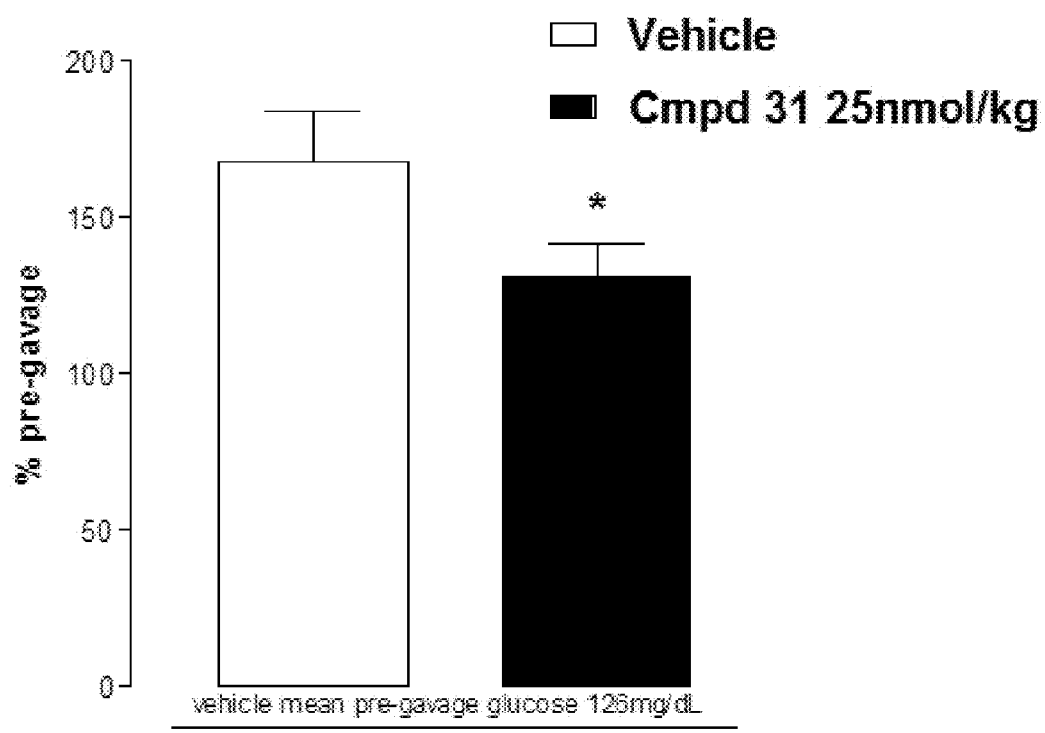

FIG. 9: Blood glucose level (BGL) data histogram prior to gavage at 1-day post dosage of Cmpd 31. Vehicle mean pre-gavage glucose: 126 mg/dL. Legend: vehicle (open), Cmpd 31 (25 nmol/kg; closed). Legend: same as FIG. 1A. * p<0.5 vs. vehicle control; ANOVA, Dunnett's test.

Figure 10A:
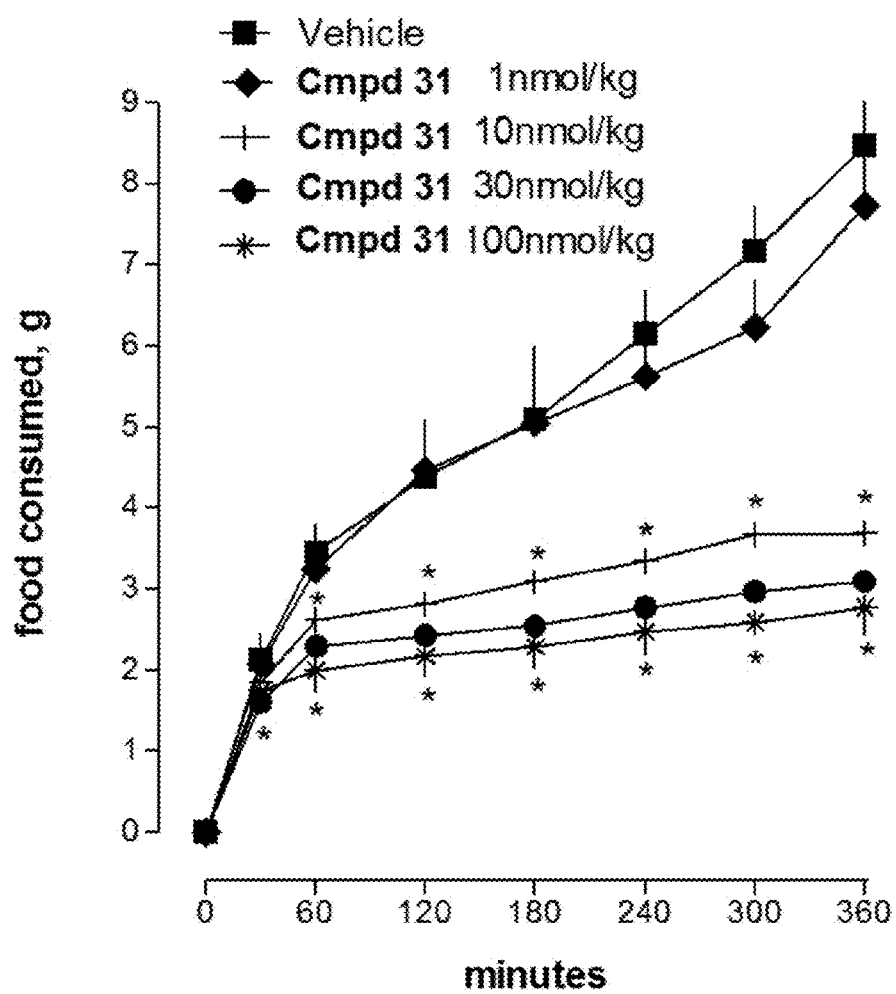
Figure 10B:
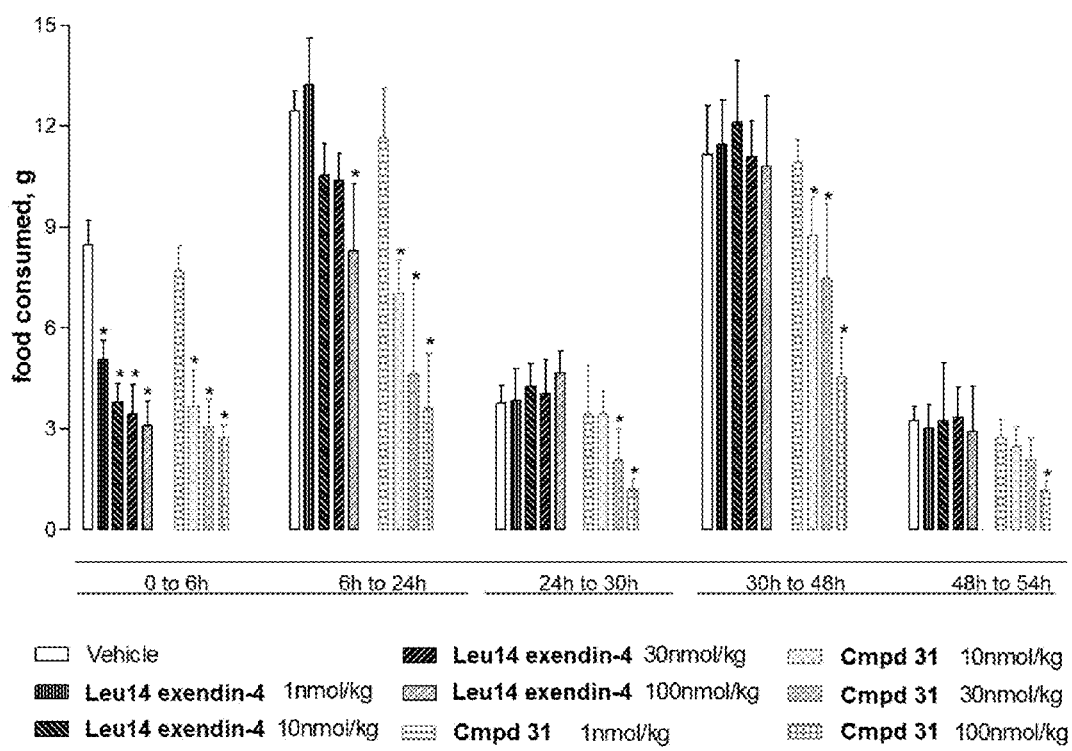

FIGS. 10A-10B:—FIG. 10A demonstrates time course of effect of Cmpd 31 on inhibiting food intake in normal mice over 6 hours. Legend: vehicle (box); Cmpd 31 at 1 nmol/kg (diamond); Cmpd 31 at 10 nmol/kg (cross); Cmpd 31 at 30 nmol/kg (circle); Cmpd 31 at 100 nmol/kg (star). FIG. 10B depicts histogram of results of effect of Cmpd 31 on inhibiting food intake in normal mice over 54 hours. Legend (left to right for each time period): vehicle (open); [$^{14}$Leu]exendin-4 at 1 nmol/kg (vertical lines); [$^{14}$Leu]exendin-4 at 10 nmol/kg (diagonal lines, upper left to lower right); [$^{14}$Leu]exendin-4 at 30 nmol/kg (diagonal lines, lower left to upper right); [$^{14}$Leu]exendin-4 at 100 nmol/kg (fine diagonal lines); Cmpd 31 at 1 nmol/kg (vertical lines); Cmpd 31 at 10 nmol/kg (light dots); Cmpd 31 at 30 nmol/kg (heavy dots); Cmpd 31 at 100 nmol/kg (checkered).

Figure 11A:
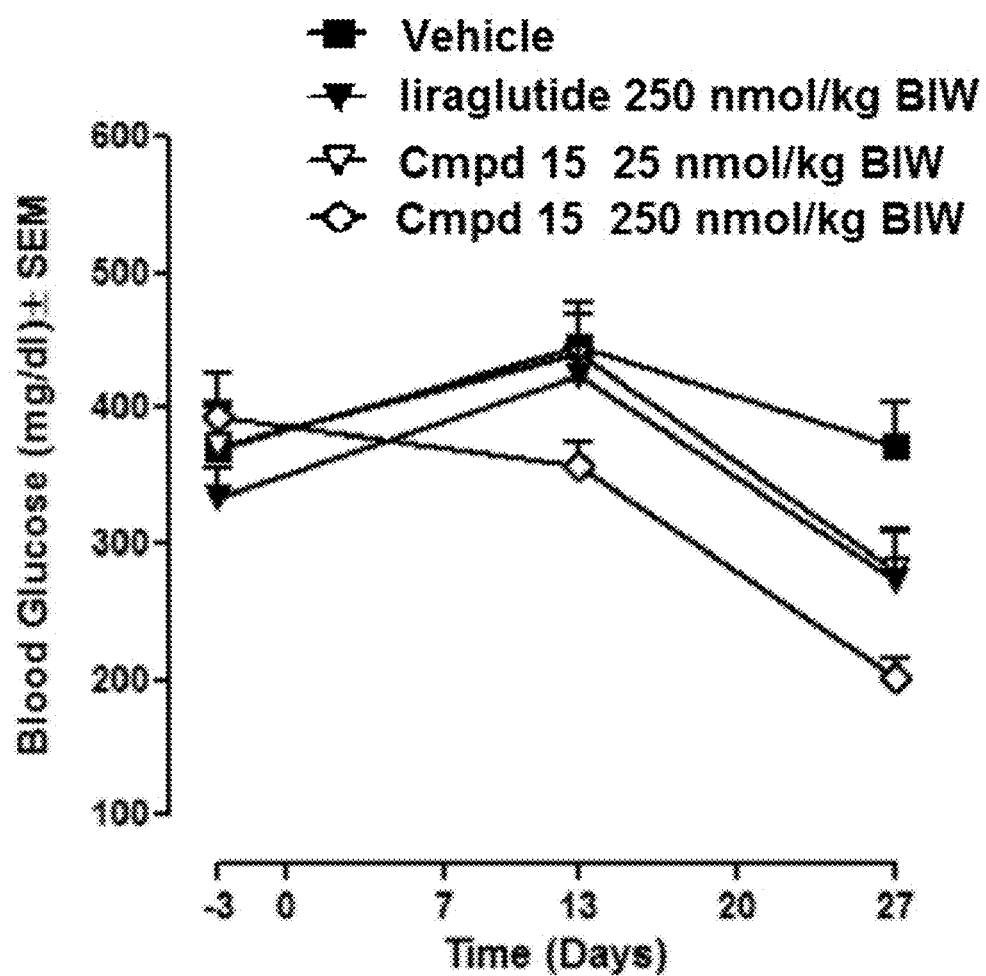
Figure 11B:
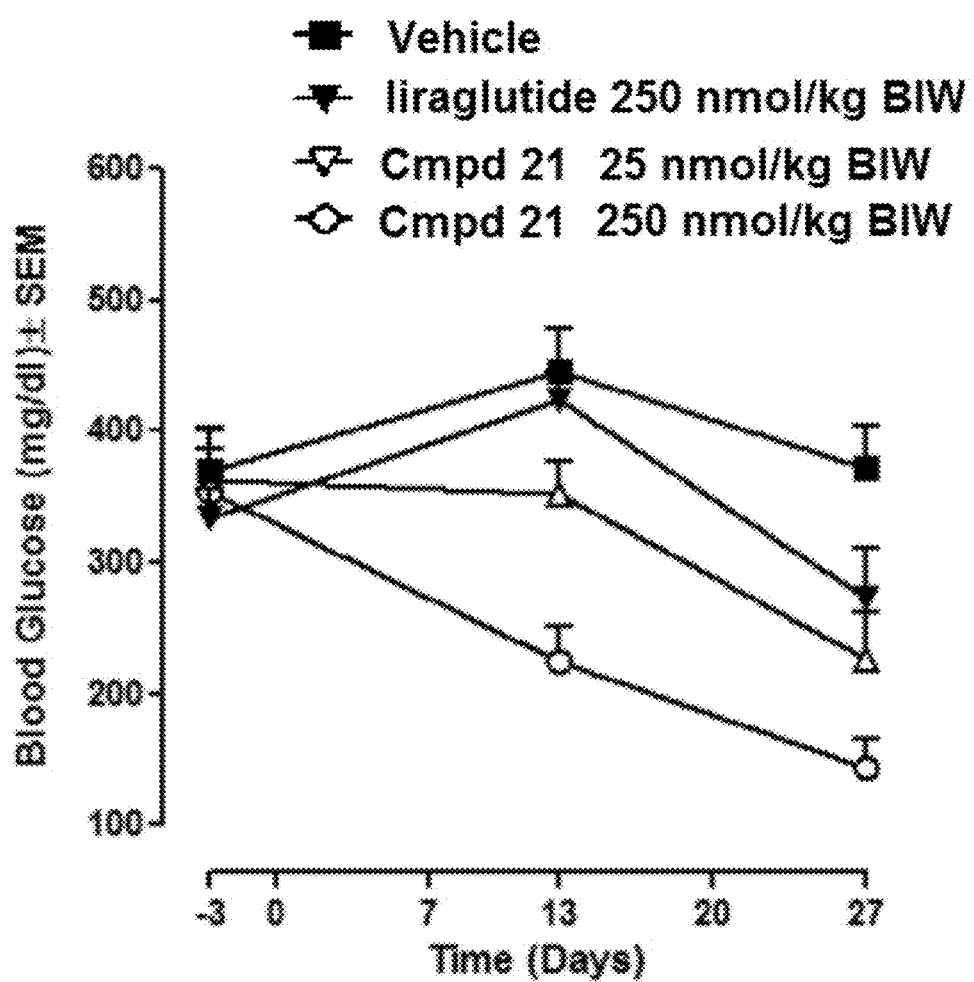
Figure 11C:
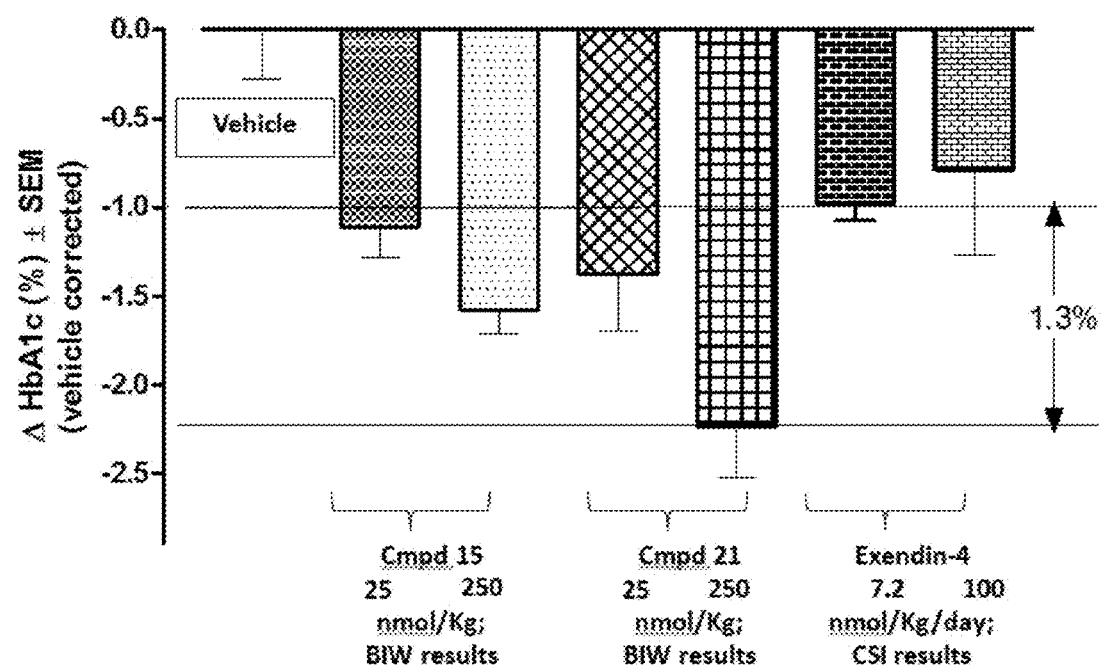
Figure 11D:
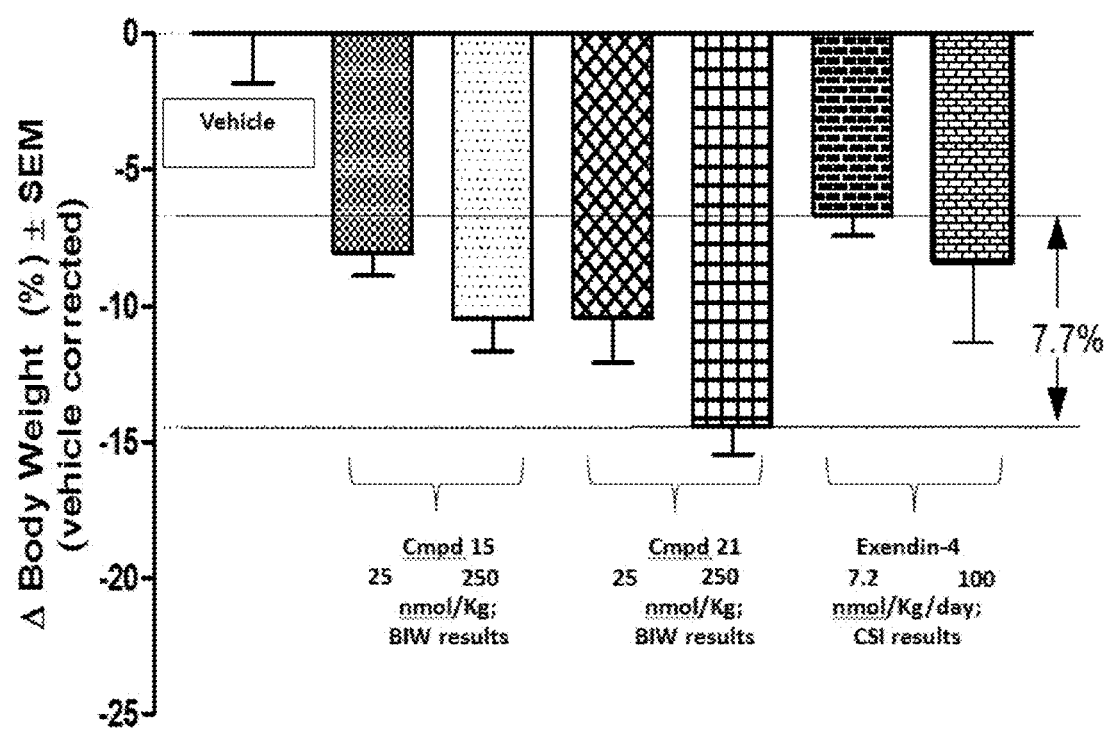

FIGS. 11A-11D: FIG. 11A (Cmpd 15) and FIG. 11B (Cmpd 21) depict time course of changes in blood glucose compared to liraglutide, all given twice weekly (BIW). Legend (FIGS. 11A-11B): vehicle (box); liraglutide at 250 nmol/kg BIW (closed triangle); test compound at 25 nmol/kg BIW (open triangle); test compound at 250 nmol/kg BIW (diamond). FIG. 11C depicts histogram showing lowering of HbA1c (% change from baseline) for Cmpd 15 and Cmpd 21 given twice weekly (BIW), compared to exendin-4 given by continuous subcutaneous infusion (CSI). Legend (left to right): vehicle (open); Cmpd 15 at 25 nmol/kg BIW (fine checkered); Cmpd 15 at 250 nmol/kg BIW (dotted); Cmpd 21 at 25 nmol/kg BIW (diagonal crosshatching); Cmpd 21 at 250 nmol/kg BIW (vertical-horizontal crosshatching); exendin-4 at 7.2 nmol/kg/day CSI (dark tiling); exendin-4 at 100 nmol/kg/day CSI (light tiling). FIG. 11D depicts reduction in body weight (% change from baseline) for Cmpd 15 and Cmpd 21 given twice weekly (BIW), compared to exendin-4 given by continuous subcutaneous infusion (CSI). Legend (left to right): as in FIG. 11C.

Figure 12A:
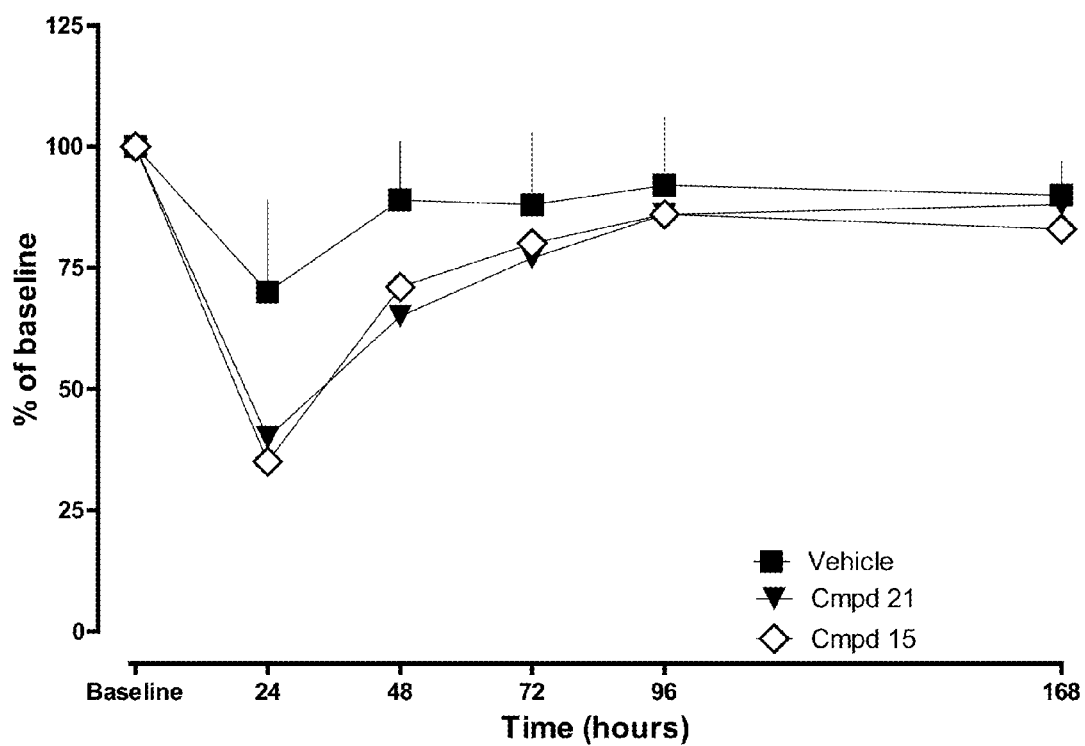
Figure 12B:
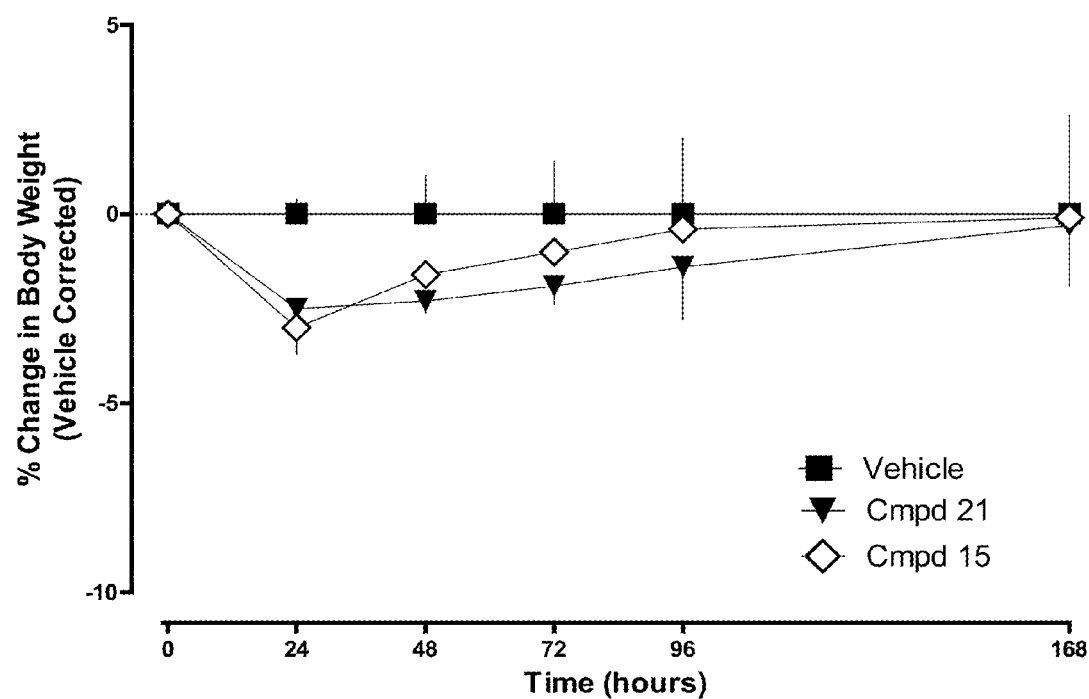
Figure 12C:
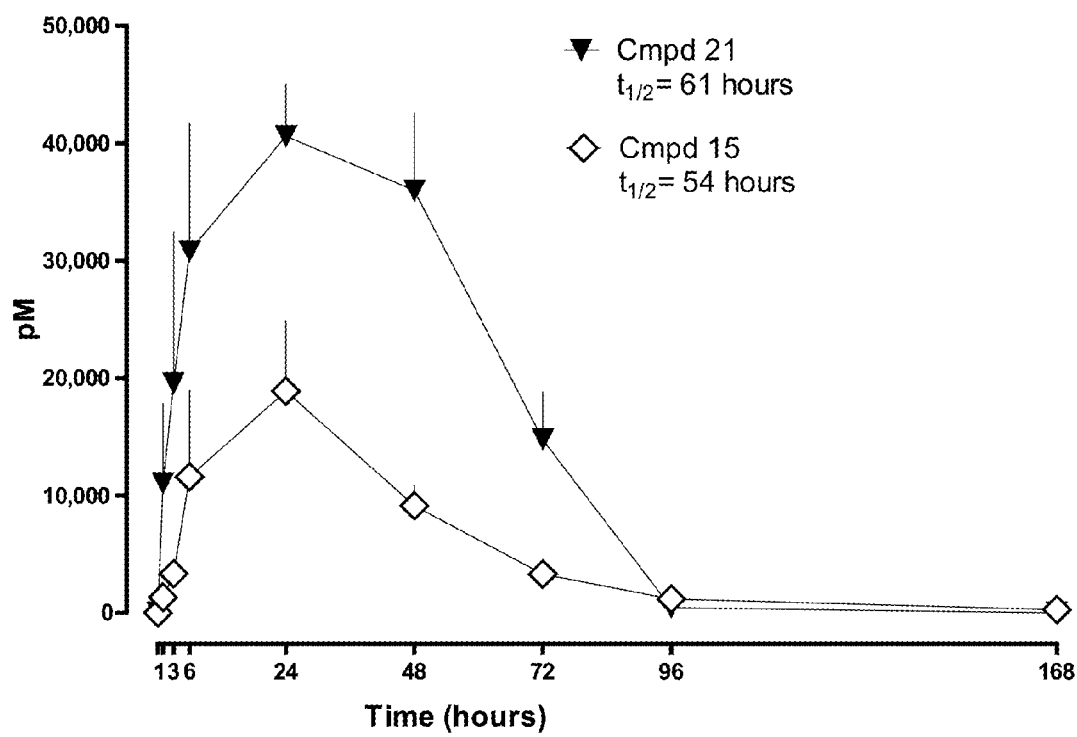

FIGS. 12A-12C: FIGS. 12A-12C depict pharmacokinetic (PK) profile and biological activity of exemplary engineered polypeptides Cmpd 15 and Cmpd 21 dosed subcutaneously in normal Harlan Sprague-Dawley (HSD) rats. FIG. 12A depicts effect of compounds to reduce food intake. FIG. 12B depicts effect of compounds to reduce body weight. FIG. 12C depicts a PK profile of the compounds after a single dose. Legend: vehicle (box); Cmpd 21 (triangle); Cmpd 15 (diamond).

Figure 13A:
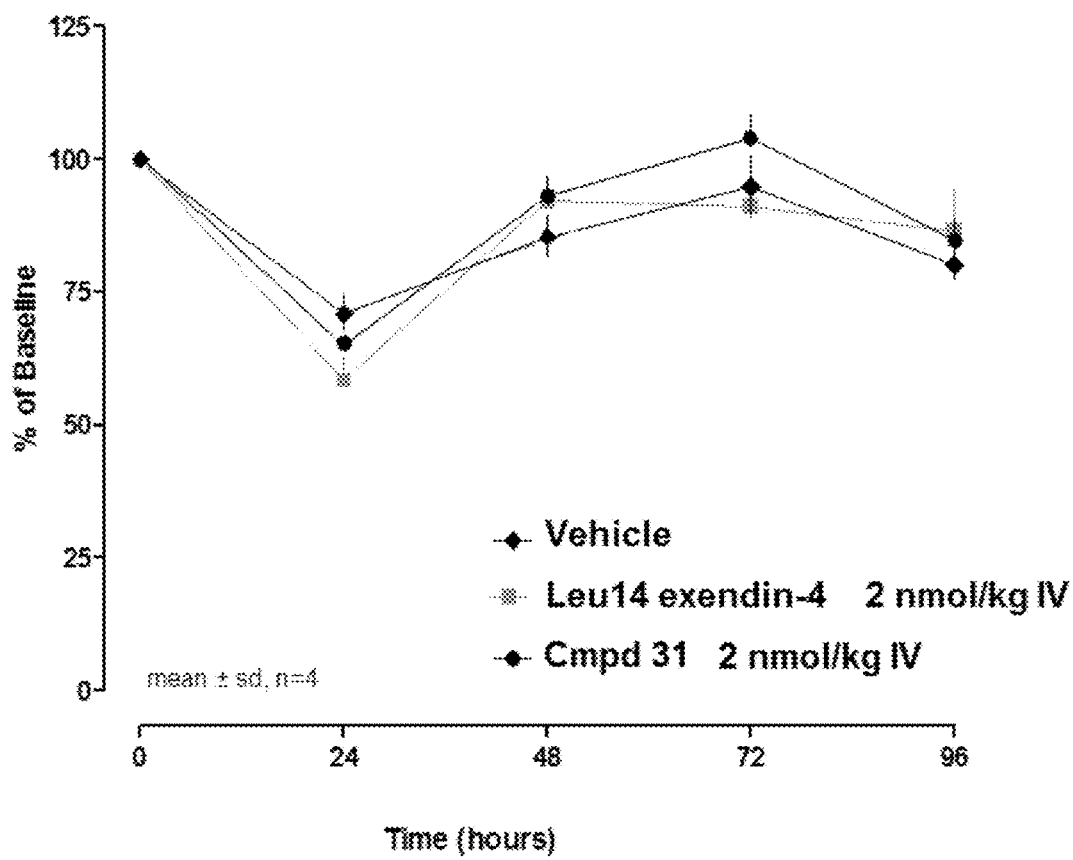
Figure 13B:
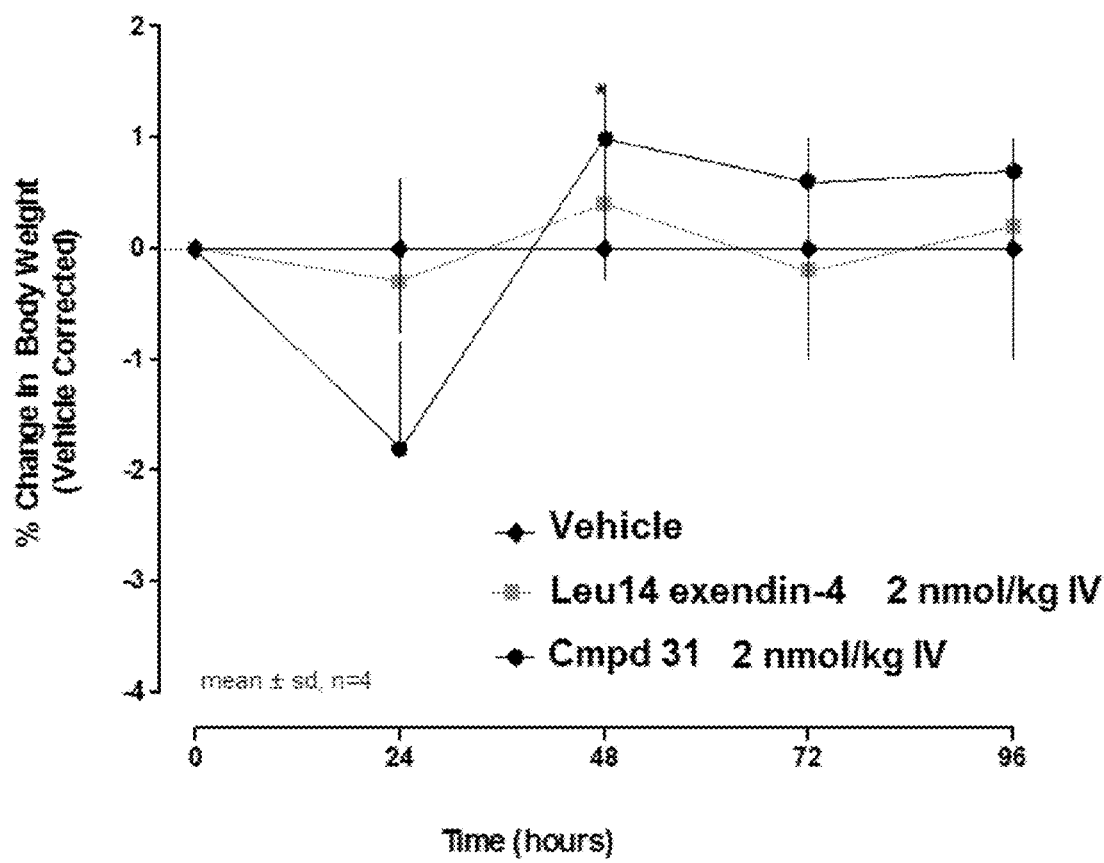
Figure 13C:
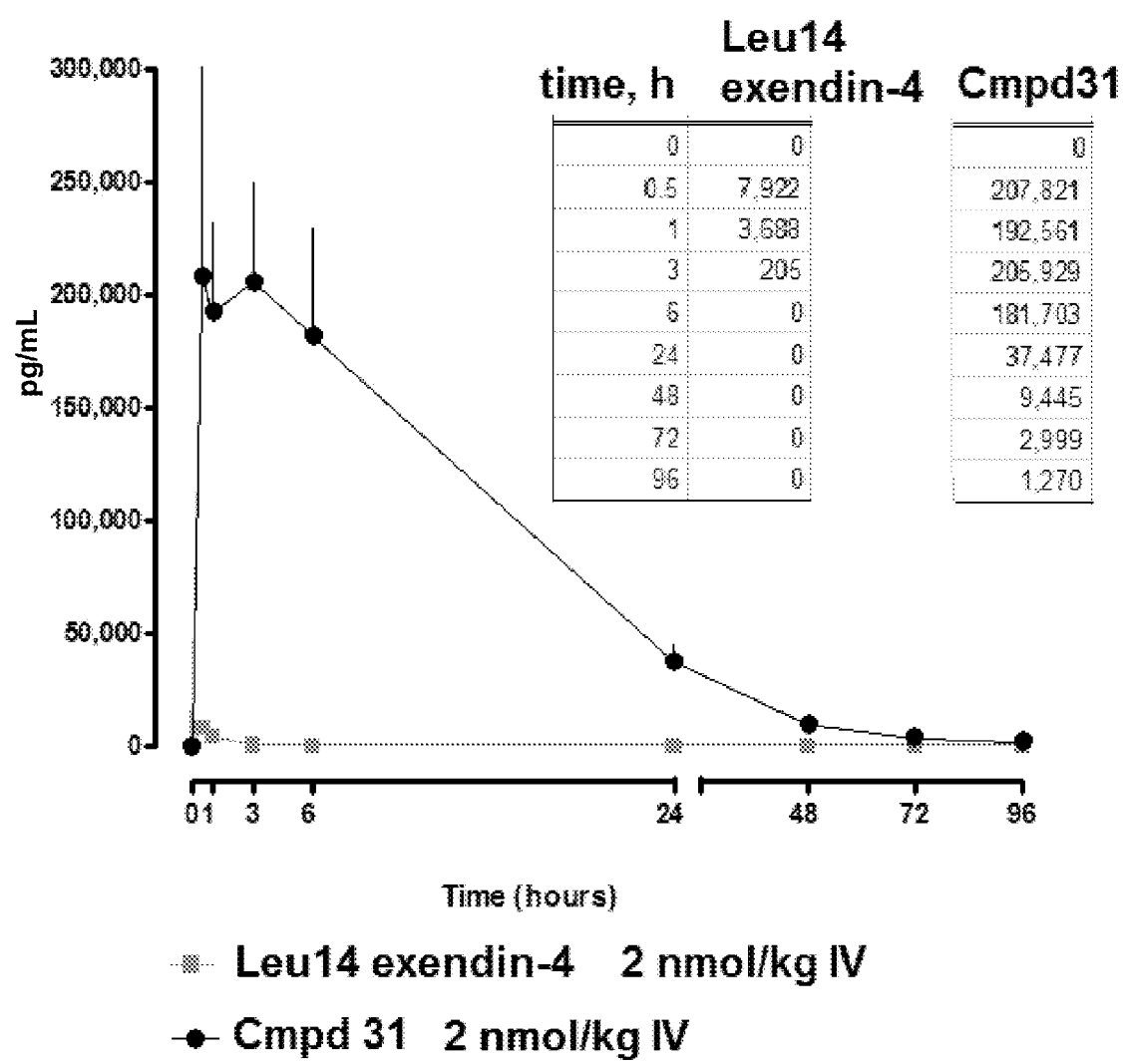

FIGS. 13A-13C: FIGS. 13A-13C depict pharmacokinetic (PK) profile and biological activity of an exemplary engineered polypeptide Cmpd 31 compared to unconjugated exendin analog dosed intravenously in normal Harlan Sprague-Dawley (HSD) rats. FIG. 13A depicts effect of compounds to reduce food intake. FIG. 13B depicts effect of compounds to reduce body weight. FIG. 13C depicts a PK profile of the compounds after a single dose. Inset: Tabulation of time versus PK results (pg/mL) for [$^{14}$Leu]exendin-4 at 2 nmol/kg IV and Cmpd 31 at 2 nmol/kg IV. Legend: vehicle (diamond); [$^{14}$Leu]exendin-4 at 2 nmol/kg IV (box); Cmpd 31 at 2 nmol/kg IV (circle).

Figure 14:
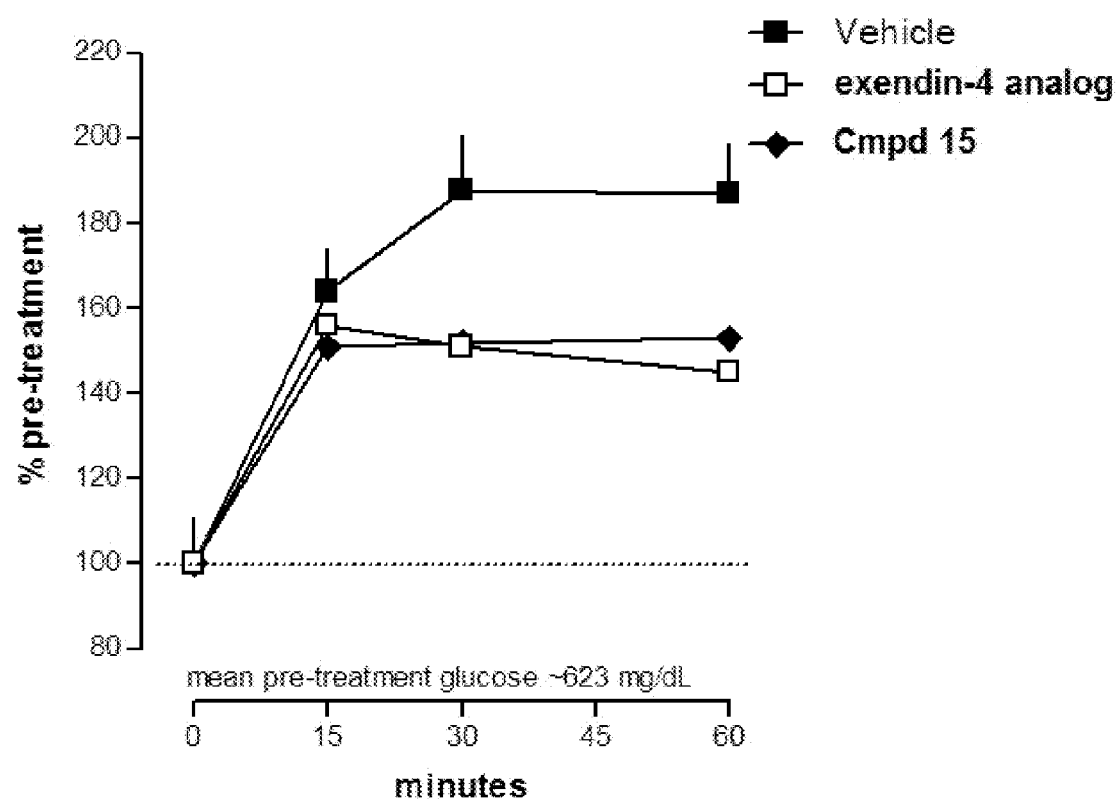

FIG. 14: This figure depicts a biological activity time course of an exemplary engineered polypeptide (Cmpd 15) compared to unconjugated exendin analog to lower blood glucose after oral delivery. See Example 18. Mean pre-treatment glucose: ~623 mg/dL. Legend: vehicle (closed box); exendin-4 analog (open box); Cmpd 15 (diamond).

DETAILED DESCRIPTION OF THE INVENTION

I. Definitions

"Obesity" and "overweight" refer to mammals having a weight greater than normally expected, and may be determined by, e.g., physical appearance, body mass index (BMI)

as known in the art, waist-to-hip circumference ratios, skinfold thickness, waist circumference, and the like. The Centers for Disease Control and Prevention (CDC) define overweight as an adult human having a BMI of 25 to 29.9; and define obese as an adult human having a BMI of 30 or higher. Additional metrics for the determination of obesity exist. For example, the CDC states that a person with a waist-to-hip ratio greater than 1.0 is overweight.

"Lean body mass" refers to the fat-free mass of the body, i.e., total body weight minus body fat weight is lean body mass. Lean body mass can be measured by methods such as hydrostatic weighing, computerized chambers, dual-energy X-ray absorptiometry, skin calipers, magnetic resonance imaging (MRI) and bioelectric impedance analysis (BIA) as known in the art.

"Mammal" refers to warm-blooded animals that generally have fur or hair, that give live birth to their progeny, and that feed their progeny with milk. Mammals include humans; companion animals (e.g., dogs, cats); farm animals (e.g., cows, horses, sheep, pigs, goats); wild animals; and the like. In one embodiment, the mammal is a female. In one embodiment, the mammal is a female human. In one embodiment, the mammal is a cat or dog. In one embodiment, the mammal is a diabetic mammal, e.g., a human having type 2 diabetes. In one embodiment, the mammal is an obese diabetic mammal, e.g., an obese mammal having type 2 diabetes. The term "subject" in the context of methods described herein refers to a mammal.

"Fragment" in the context of polypeptides refers herein in the customary chemical sense to a portion of a polypeptide. For example, a fragment can result from N-terminal deletion or C-terminal deletion of one or more residues of a parent polypeptide, and/or a fragment can result from internal deletion of one or more residues of a parent polypeptide. "Fragment" in the context of an antibody refers to a portion of an antibody which can be linked to a biologically active molecule to modulate solubility, distribution within a subject, and the like. For example, exendin-4(1-30) describes a biologically active fragment of exendin-4 where the exendin C-terminal "tail" of amino acids 31-39 is deleted. The term "parent" in the context of polypeptides refers, in the customary sense, to a polypeptide which serves as a reference structure prior to modification, e.g., insertion, deletion and/or substitution. The term "conjugate" in the context of engineered polypeptides described herein refers to covalent linkage between component polypeptides, e.g., ABD, HD1 and the like. The term "fusion" in the context of engineered polypeptides described herein refers to covalent linkage between component polypeptides, e.g., ABD, HD1 and the like, via either or both terminal amino or carboxy functional group of the peptide backbone. Engineered polypeptides can be synthetically or recombinantly made. Typically, fusions are made using recombinant biotechnology, however, can also be made by chemical synthesis and conjugation methods.

"Analog" as used herein in the context of polypeptides refers to a compound that has insertions, deletions and/or substitutions of amino acids relative to a parent compound. "Analog sequence" as used herein in the context of polypeptides refers to an amino acid sequence that has insertions, deletions and/or substitutions of amino acids relative to a parent amino acid sequence (e.g., wild-type sequence, native sequence). An analog may have superior stability, solubility, efficacy, half-life, and the like. In some embodiments, an analog is a compound having at least 50%, for example 50%, 55%, 60%, 65%, 70%, 75%, 80%, 85%, 90%, 95%, 98%, or even higher, sequence identity to the parent compound. In a preferred embodiment the analog has from 1 to 5 amino acid modifications selected independently from any one or combination of an insertion, deletion, addition and substitution. In any of the embodiments herein, the exendin analog can have from 1 to 5 amino acid modifications selected independently from any one or combination of an insertion, deletion, addition and substitution, and preferably retains at least 50%, for example 50%, 55%, 60%, 65%, 70%, 75%, 80%, 85%, 90%, 95%, 98%, or even higher, sequence identity to the parent compound, and even more preferably at least 80%, 85%, 90%, 95%, 98%, or even higher, sequence identity to the parent compound, and preferably the parent compound is exendin-4, exendin-4(1-38), exendin-4(1-37). exendin-4(1-36), exendin-4(1-35), exendin-4 (1-34). exendin-4(1-33), exendin-4(1-32), exendin-4(1-31), exendin-4(1-30), exendin-4(1-29) or exendin-4(1-28), and most preferably the parent compound has the sequence of exendin-4. In one embodiment at least amino acids corresponding to positions 1, 4, 6, 7 and 9 of exendin-4 are those as in native exendin-4, and further the one to five modifications are conservative amino acid substitutions at positions other than positions 1, 4, 6, 7 and 9 of exendin-4. For example, in yet a further embodiment of the embodiments herein, an exendin analog retains the amino acid at least as found in position 3, 4, 6, 5, 7, 8, 9, 10, 11, 13, 15, 18, 19, 22, 23, 25, 26, and/or 30 of exendin-4, and further preferably has no more than 1 to 5 of the remaining positions substituted with another amino acid, most preferably a chemically conservative amino acid. In all of the analogs herein, any substitution or modification at positions 1 and/or 2 will retain resistance to DPP-IV cleavage while retaining or improving insulinotropic activity as is known in the art for exendin-4 analogs, such as desamino-histidyl-exendin-4. As customary in the art, the term "conservative" in the context of amino acid substitutions refers to substitution which maintains properties of charge type (e.g., anionic, cationic, neutral, polar and the like), hydrophobicity or hydrophilicity, bulk (e.g., van der Waals contacts and the like), and/or functionality (e.g., hydroxy, amine, sulfhydryl and the like). The term "non-conservative" refers to an amino acid substitution which is not conservative.

"Identity," "sequence identity" and the like in the context of comparing two or more nucleic acids or polypeptide sequences, refer to two or more sequences or subsequences that are the same or have a specified percentage of amino acid residues or nucleotides that are the same (i.e., about 50% identity, preferably 50%, 55%, 60%, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a sequence comparison algorithms as known in the art, for example BLAST or BLAST 2.0. This definition includes sequences that have deletions and/or additions, as well as those that have substitutions, as well as naturally occurring, e.g., polymorphic or allelic variants, and man-made variants. In preferred algorithms, account is made for gaps and the like, as known in the art. For sequence comparison, typically one sequence acts as a reference sequence, to which test sequences are compared. When using a sequence comparison algorithm, test and reference sequences are entered into a computer, subsequence coordinates are designated if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters. Optimal alignment of sequences for comparison can be conducted, e.g., by the local homology algorithm of Smith & Waterman, 1981, *Adv. Appl. Math.* 2:482, by the homology alignment algorithm of Needleman & Wunsch, 1970, *J. Mol. Biol.* 48:443, by the search for similarity method of Pearson & Lipman, 1988, *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. See e.g., *Current Protocols in Molecular Biology* (Ausubel et al., eds. 1995 supplement)). Preferred examples of algorithms that are suitable for determining percent sequence identity and sequence similarity include the BLAST and BLAST 2.0 algorithms, which are described in Altschul et al., 1977, *Nucl. Acids Res.* 25:3389-3402 and Altschul et al., 1990, *J. Mol. Biol.* 215:403-410. BLAST and BLAST 2.0 are used, as known in the art, to determine percent sequence identity for the nucleic acids and proteins of the invention. Software for performing BLAST analyses is publicly available through the web site of the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., Id.). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, 1989, *Proc. Natl. Acad. Sci. USA* 89:10915) alignments (B) of 50, expectation (E) of 10, M=5, N=−4, and a comparison of both strands.

The term "about" in the context of a numeric value refers to +/−10% of the numeric value.

The terms "peptide" and "polypeptide" in the context of components of the engineered polypeptides described herein are synonymous.

II. Compounds

In a first aspect, engineered polypeptide compounds are provided with sequence which includes an albumin binding domain (ABD) polypeptide sequence and at least one polypeptide hormone domain (HD1) sequence. The terms "albumin binding domain," "ABD" and the like refer to polypeptides capable of binding albumin as described herein. The terms "hormone domain," "hormone domain polypeptide" and the like refer to a GP-1 receptor agonist polypeptide capable of eliciting a biological response in a subject. Exemplary hormone domains include, but are not limited to, an exendin, an exendin fragment, or an exendin analog.

It was surprisingly found that an exendin, exendin analog or active fragment can be fused to an very-high-affinity albumin binding domain (ABD) derived from the albumin-binding domains of bacterial protein G of *Streptococcus* strain G148, while retaining sufficient exendin-4 biological activity and having an extended duration of action, for example of at least 3 days and even 5 days in a rodent, which translates to at least a one week duration or longer in a human subject. "Duration of action" refers in the customary sense to allowing for more infrequent dosing in a therapeutic regimen. Thus, a prolonged duration of action will allowed for less frequent and/or more convenient dosing schedules. This was surprising in part because such ABD peptides have not been extensively demonstrated to be a robust platform as a therapeutic protein carrier, they are relatively hydrophobic which could interact adversely with an attached therapeutic peptide, and were not able to act as a carrier for at least one family of peptide hormones. Specifically, rat amylin when conjugated or fused to the ABDs described herein did not display any significant or long-acting in vivo activity in the same rodent models in which various exendin-ABD constructs were found to be active and with long duration of action.

Biologically Active Components.

Biologically active compound components contemplated for use in the compounds and methods described herein include the exendins. The terms "biologically active compound" and the like refer in the customary sense to compounds, e.g., polypeptides and the like, which can elicit a biological response.

Exendins.

The exendins are peptides that are found in the salivary secretions of the Gila monster and the Mexican Bearded Lizard, reptiles that are endogenous to Arizona and Northern Mexico. Exendin-3 is present in the salivary secretions of *Heloderma horridum* (Mexican Beaded Lizard), and exendin-4 is present in the salivary secretions of *Heloderma suspectum* (Gila monster). See Eng et al, 1990, *J. Biol. Chem.*, 265:20259-62; Eng et al, 1992, *J. Biol. Chem.*, 267:7402-7405. The sequences of exendin-3 and exendin-4, respectively, follow: HSDGTFTSDLSKQMEEEAVR-LFIEWLKNGGPSSGAPPPS-NH$_2$ (SEQ ID NO:1); HGEGTFTSDLSKQMEEEAVRLFIEWLKNGGPSSGAP-PPS-NH$_2$ (SEQ ID NO:2).

Hargrove et al. (*Regulatory Peptides*, 2007, 141:113-119) reported an exendin-4 peptide analog that is a full-length C-terminally amidated exendin-4 peptide analog with a single nucleotide difference at position 14 compared to native exendin-4. The sequence of [$^{14}$Leu]Exendin-4 is as follows: HGEGTFTSDLSKQLEEEAVRLFIEWLKNG-GPS SGAPPPS-NH$_2$ (SEQ ID NO:3). Another exendin-4 peptide analog is a chimera of the first 32 amino acids of exendin-4 having amino acid substitutions at positions 14 and 28 followed by a 5 amino acid sequence from the C-terminus of a non-mammalian (frog) GLP1: [Leu$^{14}$, Gln$^{28}$]Exendin-4(1-32)-fGLP-1(33-37). This compound has the following sequence: HGEGTFTSDLSKQLEEEAVR-LFIEWLKQGGPSKEIIS (SEQ ID NO:4). Also known in the art are C-terminally truncated, biologically active forms of exendin-4, such as exendin-4(1-28), exendin-4(1-29), exendin-4(1-30), exendin-4(1-31), exendin-4(1-32) and their amidated forms. All of these exendin analogs are suitable as components of the engineered polypeptides of the present invention. As is customary in the art, square brackets (i.e., "[ ]") in a peptidic compound name indicates substitution of the residue or chemical feature within the square brackets. For example, [$^{14}$Leu]Exendin-4, [$^{14}$Leu]Ex-4, and the like refer to exendin-4 having leucine at position 14. The numeric position of an amino acid can be indicated by prepended or postpended numbers in a variety of ways routinely employed in the art. For example, the terms $^{14}$Leu, Leu14, 14Leu, Leu$^{14}$ and the like, are synonymous in referring to leucine at position 14.

It is understood that in some embodiments a C-terminal amide, or other C-terminal capping moiety can be present in compounds described herein.

Although the exendins have some sequence similarity to several members of the glucagon-like peptide family, with the highest homology, 53%, being to GLP-1(7-36)NH$_2$ (Goke et al, 1993, *J. Biol. Chem.*, 268:19650-55) [sequence of GLP-1(7-37)NH$_2$: HAEGTFTSDVSSYLEGQAAKEFI-AWLVKGRG (SEQ ID NO:5], also sometimes referred to as "GLP-1") which has an insulinotropic effect stimulating insulin secretion from pancreatic beta-cells, exendins are not GLP-1 homologs.

Pharmacological studies have led to reports that exendin-4 can act at GLP-1 receptors in vitro on certain insulin-secreting cells, however, it has also been reported that exendin-4 may act at receptors not acted upon by GLP-1. Further, exendin-4 shares some but not all biological properties in vivo with GLP-1, and it has a significantly longer duration of action than GLP-1. Based on their insulinotropic activities, the use of exendin-3 and exendin-4 for the treatment of diabetes mellitus and the prevention of hyperglycemia has been proposed (Eng, U.S. Pat. No. 5,424,286, incorporated herein by reference in its entirety and for all purposes), and in fact, exendin-4 has been approved in the United States and in Europe for use as a therapeutic for treating type 2 diabetes.

Indeed, it is believed that exendins are not the species homolog of mammalian GLP-1 as was reported by Chen and Drucker who cloned the exendin gene from the Gila monster (*J. Biol. Chem.* 272:4108-15 (1997)). The observation that the Gila monster also has separate genes for proglucagons (from which GLP-1 is processed), that are more similar to mammalian proglucagon than exendin, indicated that exendins are not merely species homologs of GLP-1.

Methods for regulating gastrointestinal motility using exendin agonists are described in U.S. Pat. No. 6,858,576 (i.e., based on U.S. application Ser. No. 08/908,867 filed Aug. 8, 1997, which is a continuation-in-part of U.S. application Ser. No. 08/694,954 filed Aug. 8, 1996). Methods for reducing food intake using exendin agonists are described in U.S. Pat. No. 6,956,026 (i.e., based on U.S. application Ser. No. 09/003,869, filed Jan. 7, 1998, which claims the benefit of U.S. Application Nos. 60/034,905 filed Jan. 7, 1997, 60/055,404 filed Aug. 7, 1997, 60/065,442 filed Nov. 14, 1997, and 60/066,029 filed Nov. 14, 1997.

Novel exendin agonist compound sequences useful in the engineered polypeptides described herein are described in WO 99/07404 (i.e., PCT/US98/16387 filed Aug. 6, 1998), in WO 99/25727 (i.e., PCT/US98/24210, filed Nov. 13, 1998), in WO 99/25728 (i.e., PCT/US98/24273, filed Nov. 13, 1998), in WO 99/40788, in WO 00/41546, and in WO 00/41548, which are incorporated herein by reference and for all purposes along with their granted U.S. patent counterparts. Methods to assay for exendin activities in vitro and in vivo, as known in the art, including insulinotropic, food intake inhibition activity and weight loss activity, are described herein and also in the above references and other references recited herein.

Certain exemplary exendins, exendin agonists, and exendin analog agonists include: exendin fragments exendin-4 (1-30) (His Gly Glu Gly Thr Phe Thr Ser Asp Leu Ser Lys Gln Met Glu Glu Glu Ala Val Arg Leu Phe Ile Glu Trp Leu Lys Asn Gly Gly); exendin-4(1-28), exendin-4(1-29), exendin-4(1-30), exendin-4(1-31) and exendin-4(1-32). Analogs include substitution at the $^{14}$Met position (i.e., $^{14}$Met) with a non-oxidizing amino acid such as leucine. Examples include [$^{14}$Leu]exendin-4, [$^{14}$Leu]exendin-4(1-30), [$^{14}$Leu]exendin-4(1-28) and [$^{14}$Leu,$^{25}$Phe]exendin-4.

Exendin analog agonists for use in the engineered polypeptides described herein include those described in U.S. Pat. No. 7,223,725 (incorporated herein by reference and for all purposes), such as compounds of the formula: Xaa$_1$ Xaa$_2$ Xaa$_3$ Gly Xaa$_5$ Xaa$_6$ Xaa$_7$ Xaa$_8$ Xaa$_9$ Xaa$_{10}$ Xaa$_{11}$ Xaa$_{12}$ Xaa$_{13}$ Xaa$_{14}$ Xaa$_{15}$ Xaa$_{16}$ Xaa$_{17}$ Ala Xaa$_{19}$ Xaa$_{20}$ Xaa$_{21}$ Xaa$_{22}$ Xaa$_{23}$ Xaa$_{24}$ Xaa$_{25}$ Xaa$_{26}$ Xaa$_{27}$ Xaa$_{28}$-Z$_1$; wherein Xaa$_1$ is His, Arg or Tyr; Xaa$_2$ is Ser, Gly, Ala or Thr; Xaa$_3$ is Ala, Asp or Glu; Xaa$_5$ is Ala or Thr; Xaa$_6$ is Ala, Phe, Tyr; Xaa$_7$ is Thr or Ser; Xaa$_8$ is Ala, Ser or Thr; Xaa$_9$ is Asp or Glu; Xaa$_{10}$ is Ala, Leu, Ile, Val, or Met; Xaa$_{11}$ is Ala or Ser; Xaa$_{12}$ is Ala or Lys; Xaa$_{13}$ is Ala or Gln; Xaa$_{14}$ is Ala, Leu, Ile, Val or Met; Xaa$_{15}$ is Ala or Glu; Xaa$_{16}$ is Ala or Glu; Xaa$_{17}$ is Ala or Glu; Xaa$_{19}$ is Ala or Val; Xaa$_{20}$ is Ala or Arg; Xaa$_{21}$ is Ala or Leu; Xaa$_{22}$ is Ala, Phe, Tyr; Xaa$_{23}$ is Ile, Val, Leu, or Met; Xaa$_{24}$ is Ala, Glu or Asp; Xaa$_{25}$ is Ala, Trp, Phe, Tyr; Xaa$_{26}$ is Ala or Leu; Xaa$_{27}$ is Ala or Lys; Xaa$_{28}$ is Ala or Asn; Z$_1$ is —OH, —NH$_2$, Gly-Z$_2$, Gly Gly-Z$_2$, Gly Gly Xaa$_{31}$-Z$_2$, Gly Gly Xaa$_{31}$ Ser-Z$_2$, Gly Gly Xaa$_{31}$ Ser Ser-Z$_2$, Gly Gly Xaa$_{31}$ Ser Ser Gly Gly Xaa$_{31}$ Ser Ser Gly Gly Gly Xaa$_{31}$ Ser Ser Gly Ala Xaa$_{36}$-Z$_2$, Gly Gly Xaa$_{31}$ Ser Ser Gly Ala Xaa$_{36}$ Xaa$_{37}$-Z$_2$ or Gly Gly Xaa$_{31}$ Ser Ser Gly Ala Xaa$_{36}$ Xaa$_{37}$ Xaa$_{38}$-Z$_2$; Xaa$_{31}$, Xaa$_{36}$, Xaa$_{37}$ and Xaa$_{38}$ are independently Pro or are absent; and Z$_2$ is —OH or —NH$_2$. In any and each of the exendin analogs described above, also specifically contemplated are those wherein a replacement for the histidine corresponding to Xaa1 is made with any of D-histidine, desamino-histidine, 2-amino-histidine, beta-hydroxy-histidine, homohistidine. N-alpha-acetyl-histidine, alpha-fluoromethyl-histidine, alpha-methyl-histidine, 3-pyridylalanine, 2-pyridylalanine, 4-pyridylalanine, 4-imidazoacetyl, des-amino-histidyl (imidazopropionyl), beta-hydroxy-imidazopropionyl, N-dimethyl-histidyl or beta-carboxy-imidazopropionyl. Further specifically contemplated herein are exendin analogs described herein wherein a replacement for the glycine at Xaa2 is made with any of D-Ala, Val, Leu, Lys, Aib, (1-amino cyclopropyl) carboxylic acid, (1-aminocyclobutyl)carboxylic acid, 1-aminocyclopentyl)carboxylic acid, (1-aminocyclohexyl)carboxylic acid, (1-aminocycloheptyl)carboxylic acid, or (1-amino cyclooctyl)carboxylic acid.

According to one embodiment, exemplary compounds include those of the above formula wherein: Xaa$_1$ is His or Arg; Xaa$_2$ is Gly or Ala; Xaa$_3$ is Asp or Glu; Xaa$_5$ is Ala or Thr; Xaa$_6$ is Ala or Phe; Xaa$_7$ is Thr or Ser; Xaa$_8$ is Ala, Ser or Thr; Xaa$_9$ is Asp or Glu; Xaa$_{10}$ is Ala, or Leu; Xaa$_{11}$ is Ala or Ser; Xaa$_{12}$ is Ala or Lys; Xaa$_{13}$ is Ala or Gln; Xaa$_{14}$ is Ala or Leu; Xaa$_{15}$ is Ala or Glu; Xaa$_{16}$ is Ala or Glu; Xaa$_{17}$ is Ala or Glu; Xaa$_{19}$ is Ala or Val; Xaa$_{20}$ is Ala or Arg; Xaa$_{21}$ is Ala or Leu; Xaa$_{22}$ is Phe; Xaa$_{23}$ is Ile, Val; Xaa$_{24}$ is Ala, Glu or Asp; Xaa$_{25}$ is Ala, Trp or Phe; Xaa$_{26}$ is Ala or Leu; Xaa$_{27}$ is Ala or Lys; Xaa$_{28}$ is Ala or Asn; Z$_1$ is —OH, —NH$_2$, Gly-Z$_2$, Gly Gly-Z$_2$, Gly Gly Xaa$_{31}$-Z$_2$, Gly Gly Xaa$_{31}$ Ser-Z$_2$, Gly Gly Xaa$_{31}$ Ser Ser-Z$_2$, Gly Gly Xaa$_{31}$ Ser Ser Gly-Z$_2$, Gly Gly Xaa$_{31}$ Ser Ser Gly Ala-Z$_2$, Gly Gly Xaa$_{31}$ Ser Ser Gly Ala Xaa$_{36}$-Z$_2$, Gly Gly Xaa$_{31}$ Ser Ser Gly Ala Xaa$_{36}$ Xaa$_{37}$-Z$_2$, Gly Gly Xaa$_{31}$ Ser Ser Gly Ala Xaa$_{36}$ Xaa$_{37}$ Xaa$_{38}$-Z$_2$; Xaa$_{31}$, Xaa$_{36}$, Xaa$_{37}$ and Xaa$_{38}$ being independently Pro or is absent and Z$_2$ being —OH or —NH$_2$; provided that no more than three of Xaa$_3$, Xaa$_5$, Xaa$_6$, Xaa$_8$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, Xaa$_{27}$ and Xaa$_{28}$ are Ala. In any and each of the exendin analogs described above, also specifically contemplated are those wherein a replacement for the histidine corresponding to position Xaa1 is made with any of D-histidine, desamino-histidine, 2-amino-histidine, beta-hydroxy-histidine, homohistidine. N-alpha-acetyl-histidine, alpha-fluoromethyl-histidine, alpha-methyl-histidine, 3-pyridylalanine, 2-pyridylalanine, 4-pyridylalanine, 4-imidazoacetyl, des-amino-histidyl (imidazopropionyl), beta-hydroxy-imidazopropionyl, N-dimethyl-histidyl or beta-carboxy-imidazopropionyl. Further specifically contemplated herein are exendin analogs described herein wherein a replacement for the glycine at Xaa 2 is made with any of D-Ala, Val, Leu, Lys, Aib, (1-aminocyclopropyl) carboxylic acid, (1-amino cyclobutyl) carboxylic acid, 1-aminocyclopentyl)carboxylic acid, (1-aminocyclohexyl)carboxylic acid, (1-amino cycloheptyl) carboxylic acid, or (1-aminocyclooctyl)carboxylic acid.

Other exemplary compounds include those set forth in WO 99/25727 identified therein as compounds 2-23. According to another embodiment, provided are compounds where Xaa$_{14}$ is Leu, Ile, or Val more preferably Leu, and/or Xaa$_{25}$ is Trp, Phe or Tyr, more preferably Trp or Phe. These compounds will be less susceptive to oxidative degradation, both in vitro and in vivo, as well as during synthesis of the compound.

Additional examples of exendin analogs suitable for use in the present fusion polypeptides include those described in U.S. Pat. No. 6,528,486 published Mar. 4, 2003 (incorporated herein by reference and for all purposes). Specifically, exendin analogs include those consisting of an exendin or exendin analog having at least 90% homology to exendin-4 having optionally between one and five deletions at positions 34-39, and a C-terminal extension of a peptide sequence of 4-20 amino acid units covalently bound to said exendin wherein each amino acid unit in said peptide extension sequence is selected from the group consisting of Ala, Leu, Ser, Thr, Tyr, Asn, Gln, Asp, Glu, Lys, Arg, His, and Met. More preferably the extension is a peptide sequence of 4-20 amino acid residues, e.g., in the range of 4-15, more preferably in the range of 4-10 in particular in the range of 4-7 amino acid residues, e.g., of 4, 5, 6, 7, 8 or 10 amino acid residues, where 6 amino acid residues are preferred. Most preferably, according to U.S. Pat. No. 6,528,486 the extension peptide contains at least one Lys residue, and is even more preferably from 3 to 7 lysines and even most preferably 6 lysines.

For example, one analog is HGEGTFTSDLSKQMEEE-AVRLFIEWLKNGG PSSGAPP SKKKKKK (SEQ ID NO:118) (also designated ([des-$^{36}$Pro]exendin-4(1-39)-Lys$_6$). Additional exemplary analogs include Lys$_6$-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-(Lys)$_6$ (H-Lys$_6$-des Pro $^{36}$exendin-4(1-39)-Lys$_6$) (SEQ ID NO:184); His-Gly-Glu-Gly-Thr-Phe-Thr-Ser-Asp-Leu-Ser-Lys-Gln-Met-Glu-Glu-Ala-Val-Arg-Leu-Phe-Ile-Glu-Trp-Leu-Trp-Leu-Lys-Asn-Gly-Gly-Pro-Ser-Ser-Gly-Ala-Ser (H-[des $^{36}$Pro, $^{37,38}$Pro]exendin-4(1-39)-NH$_2$) (SEQ ID NO:185); Lys-Lys-Lys-Lys-Lys-Lys-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys- Asn-Gly-Gly-Pro-Ser-Ser-Gly-Ala-Ser (H-(Lys)$_6$-[des $^{36}$Pro, $^{37,38}$Pro]exendin-4(1-39) (SEQ ID NO:186); Asn-Glu-Glu-Glu-Glu-Glu-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser (H-Asn-(Glu)$_5$-[des $^{36}$Pro, $^{37,38}$Pro]exendin-4(1-39) (SEQ ID NO:187); His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu- Lys-Asn-Gly-Gly-Pro-Ser-Ser-Gly-Ala-Ser-(Lys)$_6$ ([des $^{36}$Pro, $^{37,38}$Pro]exendin-4(1-39)-(Lys)$_6$) (SEQ ID NO:188); (Lys)$_6$-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser- (Lys)$_6$ (H-(Lys)$_6$-[des $^{36}$Pro, $^{37,38}$Pro]exendin-4(1-39)-(Lys)$_6$) (SEQ ID NO:189); and Asp-Glu-Glu-Glu-Glu-Glu-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser-(Lys)$_6$ (Asn-(Glu)$_5$-[des $^{36}$Pro, $^{37,38}$Pro]exendin-4(1-39)-(Lys)$_6$) (SEQ ID NO:190). As customary in the art, repetition of an amino acid can be indicated by a subscripted number setting forth the number of repetitions; i.e., Lys$_6$, (Lys)$_6$ and the like refer to hexalysyl (SEQ ID NO:191). In any and each of the exendin analogs described above, specifically contemplated are those wherein a replacement for the histidine corresponding to position 1 is made with any of D-histidine, desamino-histidine, 2-amino-histidine, beta-hydroxy-histidine, homo-histidine. N-alpha-acetyl-histidine, alpha-fluoromethyl-histidine, alpha-methyl-histidine, 3-pyridylalanine, 2-pyridylalanine, 4-pyridylalanine, 4-imidazoacetyl, des-amino-histidyl (or imidazopropionyl), beta-hydroxy-imidazopropionyl, N-dimethyl-histidyl or beta-carboxy-imidazopropionyl. Further specifically contemplated herein are exendin analogs described herein wherein a replacement for the glycine at position 2 is made with any of D-Ala, Val, Leu, Lys, Aib, (1-aminocyclopropyl)carboxylic acid, (1-aminocyclobutyl)carboxylic acid, 1-aminocyclopentyl) carboxylic acid, (1-amino cyclohexyl)carboxylic acid, (1-aminocycloheptyl) carboxylic acid, or (1-aminocyclooctyl) carboxylic acid.

Further examples of exendin analogs suitable for use in the engineered polypeptide constructs are those described in published PCT application WO2004035623 (incorporated herein by reference and for all purposes), particularly those comprised of naturally-occurring amino acids, which describes exendin analogs having at least one modified amino acid residue particularly at positions $^{13}$Gln, $^{14}$Met, $^{25}$Trp or $^{28}$Asn with reference to the corresponding positions of exendin-4(1-39). According to that publication are additional such analogs further comprising a 1-7 amino acid C-terminal extension that comprises at least one Lys amino acid and more preferably at least five Lys amino acid units such as six or seven Lys amino acid units.

Yet further examples of exendin analogs suitable for use in the engineered polypeptide constructs are those described in published PCT application WO/2010/120476, entitled "N-Terminus Conformationally Constrained GLP-1 Receptor Agonist Compounds" (incorporated herein by reference and for all purposes), which describes exendin analogs having modified amino acid residues in the N-terminal portion of an exendin or exendin analog to create a high beta-turn characteristic in that region. For example, analogs are designed to mimic amino acid residues His1 Gly2 Glu3 by creating a conformationally constrained region, include exendin analogs containing a thiazolidine-proline peptide mimetic at His1 Gly2 Glu3 (see for example compounds described in FIGS. 17A-17F therein), which can be used as a modification in exendin-4, lixisenatide, or other analogs described herein.

In any and each of the exendins, exendin analogs and formulas described herein, specifically contemplated are those wherein a replacement for the histidine corresponding to position 1 is made with any of L-histidine, D-histidine, desamino-histidine, 2-amino-histidine, beta-hydroxy-histidine, homohistidine. N-alpha-acetyl-histidine, alpha-fluoromethyl-histidine, alpha-methyl-histidine, 3-pyridylalanine, 2-pyridylalanine, 4-pyridylalanine, 4-imidazoacetyl, des-amino-histidyl (imidazopropionyl), beta-hydroxy-imidazopropionyl, N-dimethyl-histidyl or beta-carboxy-imidazopropionyl. For example, preferred exendin analogs for use in engineered polypeptide conjugates as described herein wherein the His1 position is modified are (4-imidazoacetyl) exendin-4, (des-amino-histidyl) exendin-4 (or (imidazopropionyl) exendin-4), (beta-hydroxy-imidazopropionyl) exendin-4, (N-dimethyl-histidyl) exendin-4 and (beta-carboxy-imidazopropionyl) exendin-4. Further specifically contemplated herein are exendins or exendin analogs described herein wherein a replacement for the glycine at position 2 is made with any of D-Ala, Val, Leu, Lys, Aib, (1-aminocyclopropyl)carboxylic acid, (1-aminocyclobutyl) carboxylic acid, 1-aminocyclopentyl)carboxylic acid, (1-amino cyclohexyl)carboxylic acid, (1-aminocycloheptyl) carboxylic acid, or (1-aminocyclooctyl) carboxylic acid.

Any of the above exendin analogs or their active fragments are suitable for use in the present engineered polypeptides, with or without a linker to the ABD.

Albumin Binding Domain (ABD) Peptides.

Albumin binding domain (ABD) peptides for use in the invention are those with comparably high affinity for albumin and derive from albumin-binding domains of bacterial protein G of *Streptococcus* strain G148. As such, ABD peptides contemplated for the engineered polypeptides described herein include those having the albumin binding motifs as described by Jonsson et al. (*Protein Eng. Design & Selection*, 2008, 21:515-527) as well as the ABD peptides described therein, and those motifs and ABD peptides further described in PCT Published Appl. No. WO2009/016043, as well as analogs thereof, particularly those having at least 85% amino acid identity. In one embodiment the ABD peptide can include an albumin binding motif ("ABM") that includes the amino acid sequence GVSD $X_5$ YK $X_8$ $X_9$ I $X_{11}$ $X_{12}$ A $X_{14}$ TVEGV $X_{20}$ AL $X_{23}$ $X_{24}$ $X_{25}$ I (SEQ ID NO:119) wherein, independently of each other, $X_5$ is selected from Y and F;
$X_8$ is selected from N, R and S;
$X_9$ is selected from V, I, L, M, F and Y;
$X_{11}$ is selected from N, S, E and D;
$X_{12}$ is selected from R, K and N;
$X_{14}$ is selected from K and R;
$X_{20}$ is selected from D, N, Q, E, H, S, R and K;
$X_{23}$ is selected from K, I and T;
$X_{24}$ is selected from A, S, T, G, H, L and D; and
$X_{25}$ is selected from H, E and D.

Preferably the ABD peptide binds to albumin with a $K_D$ value of the interaction that is at most $1\times10^{-6}$ M, and even more preferably at most $1\times10^{-9}$ M (even tighter affinity). The term "$K_D$" refers to a dissociation constant, as customary in the art. More preferably the $K_D$ value of the interaction that is at most $1\times10^{-10}$ M, even more preferably is at most $1\times10^{-11}$ M, yet even more preferably is at most $1\times10^{-12}$ M, and even further is at most $1\times10^{-13}$ M. For example, a Kd value of $1\times10^{-14}$ M is a $K_D$ value of the interaction that is at most $1\times10^{-13}$ M. The $K_D$ values can be determined as described in PCT Published Appl. No. WO 2009/016043, preferably to human serum albumin. In one embodiment is contemplated the above genus with the proviso that the amino acid sequence is not GVSDYYKNLINNAKTVEGVKALIDEI (SEQ ID NO:120).

As demonstrated herein and in the cited references, the albumin binding capacity of the ABD peptide can be retained despite amino acid changes so long as such changes retain sufficient tertiary structure of the ABD peptide. Such changes include, for example, a substitution where an amino acid residue belonging to a certain functional grouping of amino acid residues (e.g. hydrophobic, hydrophilic, polar etc.) is exchanged for another amino acid residue from the same functional group. Accordingly, in one such embodiment of the ABD peptide, the motif $X_5$ is Y. In one embodiment of the ABD $X_8$ is selected from N and R, and may in particular be R. In one embodiment $X_9$ is L. In one embodiment $X_{11}$ is selected from N and S, and may in particular be N. In one embodiment $X_{12}$ is selected from R and K, such as $X_{12}$ being R or $X_{12}$ being K. In one embodiment $X_{14}$ is K. In one embodiment $X_{20}$ is selected from D, N, Q, E, H, S and R, and may in particular be E. In one embodiment $X_{23}$ is selected from K and I, and may in particular be K. In one embodiment $X_{24}$ is selected from A, S, T, G, H and L. In a more specific embodiment $X_{24}$ is L. In an even more specific embodiment "$X_{23}$ $X_{24}$" is KL. In another even more specific embodiment "$X_{23}$ $X_{24}$" is TL. In one embodiment $X_{24}$ is selected from A, S, T, G and H. In a more specific embodiment $X_{24}$ is selected from A, S, T, G and H and $X_{23}$ is I. In one embodiment $X_{25}$ is H.

The sequences of individual albumin binding motifs within the above formula include those presented as SEQ ID NOs:1-257 in PCT Published Appl. No. WO 2009/016043, incorporated herein by reference and for all purposes. In certain embodiments of the albumin binding polypeptide the albumin binding motif consists of an amino acid sequence selected from SEQ ID NO:1-257. In a more specific embodiment of this aspect of the invention, the motif sequence is selected from SEQ ID NO:2, SEQ ID NO:3, SEQ ID NO:9, SEQ ID NO:15, SEQ ID NO:25, SEQ ID NO:27, SEQ ID NO:46, SEQ ID NO:49, SEQ ID NO:53, SEQ ID NO:54, SEQ ID NO:55, SEQ ID NO:1 55, SEQ ID NO:239, SEQ ID NO:240, SEQ ID NO:241, SEQ ID NO:242, SEQ ID NO:243, SEQ ID NO:244 and SEQ ID NO:245 of PCT Published Appl. No. WO 2009/016043. In yet more specific embodiments of this aspect of the invention, the motif sequence is selected from SEQ ID NO:3, SEQ ID NO:53 and SEQ ID NO:239 of PCT Published Appl. No. WO 2009/016043. Albumin binding polypeptides, containing these albumin binding motifs and thus suitable for conjugation or fusion to a hormone domain as described herein are further described herein and below and exemplified in Table 1 and the Examples. Not to be bound by theory but it is believed that the albumin binding motif can form part of a three-helix bundle protein domain. For example, the motif may essentially constitute or form part of two alpha helices with an interconnecting loop, within the three-helix bundle protein domain. Accordingly, in particular embodiments of the invention, such a three-helix bundle protein domain is selected from the group of three-helix domains of bacterial receptor protein G from *Streptococcus* strain G148. In different variants of this embodiment, the three-helix bundle protein domain of which the motif forms a part is selected from the group of domain GA1, domain GA2 and domain GA3 of protein G from *Streptococcus* strain G148, in particular domain GA3.

In embodiments of the present invention wherein the motif "forms part of a three-helix bundle protein domain," this is understood to mean that the sequence of the albumin binding motif is "inserted" into or "grafted" onto or "fused" to the sequence of the naturally occurring (or otherwise original) three-helix bundle domain, such that the motif replaces a similar structural motif in the original domain. For example and without wishing to be bound by theory, the motif is thought to constitute two of the three helices of a three-helix bundle, and can replace such a two-helix motif within any three-helix bundle. The replacement of two helices of the three-helix bundle domain by the two motif helices disclosed herein is performed so as not to affect the basic structure of the polypeptide. That is, the overall folding of the backbone of the polypeptide according to this embodiment of the invention will be substantially the same as that of the three-helix bundle protein domain of which it forms a part, e.g. having the same elements of secondary structure in the same order etc. Thus, a motif useful to the engineered polypeptides herein can "form part" of a three-helix bundle domain if the polypeptide according to this embodiment has the same fold as the original domain, implying that the basic structural properties are shared, those properties e.g. resulting in similar CD spectra.

Accordingly, in one embodiment the albumin binding domain polypeptide is a three-helix bundle protein domain, which includes the albumin binding motif as defined above and additional sequences making up the remainder of the three-helix configuration. To such an albumin binding domain polypeptide can be fused an exendin or analogs or active fragments thereof to create the engineered polypeptides as described herein. An albumin binding domain polypeptide suitable for conjugation or fusion to an exendin compound can includes the amino acid sequence: LAEAK $X_a$ $X_b$ A X, $X_d$ EL $X_e$ KY (SEQ ID NO:182) covalently linked to an albumin binding motif (ABM) which is further covalently linked to the amino acid sequence LAALP (SEQ ID NO:183), wherein ABM is an albumin binding motif as defined herein, $X_a$ is selected from V and E; $X_b$ is selected from L, E and D; $X_c$ is selected from N, L and I; $X_d$ is selected from R and K; and $X_e$ is selected from D and K. In some embodiments, an albumin binding domain polypeptide suitable for conjugation or fusion to an exendin compound is the amino acid sequence: LAEAK $X_a$ $X_b$ A $X_c$ $X_d$ EL $X_e$ KY (SEQ ID NO:182) covalently linked to an albumin binding motif (ABM) which is further covalently linked to the amino acid sequence LAALP (SEQ ID NO:183), as described above.

In some embodiments, the albumin binding domain polypeptide includes the amino acid sequence LAEAK $X_a$ $X_b$ A $X_c$ $X_d$ EL $X_e$ KY GVSD $X_5$ YK $X_8$ $X_9$ I $X_{11}$ $X_{12}$ A $X_{14}$ TVEGV $X_{20}$ AL $X_{23}$ $X_{24}$ $X_{25}$ I LAALP (SEQ ID NO:121), wherein $X_a$ is selected from V and E; $X_b$ is selected from L, E and D; $X_c$ is selected from N, L and I; $X_d$ is selected from R and K; $X_e$ is selected from D and K; $X_5$ is selected from Y and F; $X_8$ is selected from N, R and S; $X_9$ is selected from V, I, L, M, F and Y; $X_{11}$ is selected from N, S, E and D; $X_{12}$ is selected from R, K and N; $X_{14}$ is selected from K and R; $X_{20}$ is selected from D, N, Q, E, H, S, R and K; $X_{23}$ is selected from K, I and T; $X_{24}$ is selected from A, S, T, G, H, L and D; and $X_{25}$ is selected from H, E and D.

Further for each of the embodiments herein of the ABD sequence, the C-terminal proline (corresponding to position 46 above) can be optionally absent. Even further for each embodiment of the ABD sequence, the leucine at position 45 can be optionally present or absent. "ABD sequence" is a sequence of an ABD compound that is monovalent or divalent, as appropriate, that forms part of an engineered polypeptide disclosed herein. "Peptide hormone domain (HD1) sequence" is a sequence of a peptide hormone domain (HD1) compound that is monovalent or divalent, as appropriate, that forms part of an engineered polypeptide disclosed herein. "Exendin sequence" is a sequence of an exendin compound that is monovalent or divalent, as appropriate, that forms part of an engineered polypeptide disclosed herein. "Exendin analog sequence" is a sequence of an exendin analog compound that is monovalent or divalent, as appropriate, that forms part of an engineered polypeptide disclosed herein. "Exendin active fragment sequence" is a sequence of an exendin active fragment compound that is monovalent or divalent, as appropriate, that forms part of an engineered polypeptide disclosed herein. "Exendin analog active fragment sequence" is a sequence of an exendin analog active fragment compound that is monovalent or divalent, as appropriate, that forms part of an engineered polypeptide disclosed herein. "Albumin binding motif (ABM) sequence" is a sequence of an ABM that is monovalent or divalent, as appropriate, that forms part of an engineered polypeptide disclosed herein. Unless stated otherwise, it is understood that where an engineered polypeptide "comprises" a compound (e.g., an ABD or HD1), the sequence of the engineered polypeptide includes the sequence of the compound (e.g. an ABD sequence or an HD1 sequence).

Because of the presence of an albumin binding motif, the ABD peptide binds to albumin with a $K_D$ value of the interaction that is at most $1 \times 10^{-6}$ M and even more preferably at most $1 \times 10^{-9}$ M (even tighter affinity). More preferably the $K_D$ value of the interaction that is at most $1 \times 10^{-10}$ M, even more preferably is at most $1 \times 10^{-11}$ M, yet even more preferably is at most $1 \times 10^{-12}$ M, and even further is at most $1 \times 10^{-13}$ M. The values are most preferably for affinity to human serum albumin ("HSA").

In one embodiment of this albumin binding polypeptide $X_a$ is V. In one embodiment of this polypeptide $X_b$ is L. In one embodiment of this polypeptide $X_c$ is N. In one embodiment of this polypeptide $X_d$ is R. In one embodiment of this polypeptide $X_e$ is D.

In certain embodiments, $X_a$ is E. In certain embodiments $X_b$ is D. In certain embodiments, $X_c$ is I. In certain embodiments, $X_d$ is K. In certain embodiments, $X_a$ independently is E, and/or independently $X_b$ is D, and/or independently $X_c$ is I, and/or independently $X_d$ is K. In certain embodiments, the albumin binding domain polypeptide is LAEAKEDAIKELDKYGVSDYYKRLISKAKTVEGVKALISEILAALP (SEQ ID NO:122). In certain embodiments, the albumin binding domain polypeptide is LAEAKEDAIKELDKYGVSDYYKNLINKAKTVEGVEALTLHILAALP (SEQ ID NO:123). In certain embodiments, the albumin binding domain polypeptide is LAEAKEDAIKELDKYGVSDYYKNLINKAKTVEGVEALISEILAALP (SEQ ID NO:124).

Sequences of individual albumin binding domain polypeptides suitable for fusion with the active hormone domain peptides as described herein are presented in Jonsson et al. (Id.) and as SEQ ID NOs:258-514 in PCT Published Appl. No. WO 2009/016043, incorporated herein by reference. Selected sequences are disclosed in Table 1 below. Also encompassed by the present invention is an albumin binding polypeptide having an amino acid sequence with 85% or greater identity to a sequence selected from SEQ ID NOs: 258-514. In particular embodiments, the sequence of the albumin binding polypeptide is selected from SEQ ID NO:259, SEQ ID NO:260, SEQ ID NO:266, SEQ ID NO:272, SEQ ID NO:282, SEQ ID NO:284, SEQ ID NO:303, SEQ ID NO:306, SEQ ID NO:310, SEQ ID NO:311, SEQ ID NO:312, SEQ ID NO:412, SEQ ID NO:496, SEQ ID NO:497, SEQ ID NO:498, SEQ ID NO:499, SEQ ID NO:500, SEQ ID NO:501 and SEQ ID NO:502 in PCT Published Appl. No. WO 2009/016043, and sequences having 85% or greater identity thereto. In more specific embodiments of this aspect of the invention, the sequence of the albumin binding polypeptide is selected from SEQ ID NO:260, SEQ ID NO:310 and SEQ ID NO:496 in PCT Published Appl. No. WO 2009/016043 and sequences having 85% or greater identity thereto. In yet further embodiments, the sequence of the albumin binding polypeptide is selected from SEQ ID NO:260, SEQ ID NO:270, SEQ ID NO:272, SEQ ID NO:291, SEQ ID NO:294, SEQ ID NO:298, SEQ ID NO:299, SEQ ID NO:300, SEQ ID NO:400, SEQ ID NO:484, SEQ ID NO:485, SEQ ID NO:486, SEQ ID NO:487, SEQ ID NO:488, SEQ ID NO:489 and SEQ ID NO:490 in PCT Published Appl. No. WO 2009/016043, and sequences having 85% or greater identity thereto.

Exemplary ABD species include, but are not limited to, the compounds with sequence set forth in Table 1 following and the Examples. See also PCT Published Appl. No. WO 2009/016043, incorporated herein by reference in its entirety and for all purposes. An ABD peptide sequence useful in compounds, methods and pharmaceuticals compositions described herein can be a fragment or analog of an ABD peptide sequence disclosed herein or known in the art so long as it contains an albumin binding motif sequence and binds albumin with the affinity described herein.

TABLE 1

Selected ABD peptides

| ABD peptide sequence | SEQ ID NO: |
|---|---|
| LAEAKVLANRELDKYGVSDYYKNLINNAKTVEGVKALIDEI LAALP | 23 |
| LAEAKVLANRELDKYGVSDFYKSYINRAKTVEGVHTLIGHI LAALP | 24 |
| LAEAKVLANRELDKYGVSDFYKRLINKAKTVEGVNALTHHI LAALP | 25 |
| LAEAKVLANRELDKYGVSDYYKNLINRARTVEGVHALIDHI LAALP | 26 |
| LAEAKVLANRELDKYGVSDYYKNIINRAKTVEGVRALKLHI LAALP | 27 |
| LAEAKVLANRELDKYGVSDFYKNLINRAKTVEGVSSLKGHI LAALP | 28 |
| LAEAKVLANRELDKYGVSDYYKNLINKAKTVEGVEALTLHI LAALP | 29 |
| LAEAKVLANRELDKYGVSDFYKNLINRAKTVEGVDALIAHI LAALP | 30 |
| LAEAKVLANRELDKYGVSDFYKSLINRAKTVEGVDALTSHI LAALP | 31 |
| LAEAKVLANRELDKYGVSDFYKNLINRAKTVEGVNSLTSHI LAALP | 32 |
| LAEAKVLANRELDKYGVSDFYKNVINKAKTVEGVEALIADI LAALP | 33 |
| LAEAKVLANRELDKYGVSDYYKNLINKAKTVEGVQALIAHI LAALP | 34 |

TABLE 1-continued

Selected ABD peptides

| ABD peptide sequence | SEQ ID NO: |
|---|---|
| LAEAKVLANRELDKYGVSDFYKRLINKAKTVEGVEALKLHI LAALP | 35 |
| LAEAKEDAIKELDKYGVSDYYKRLISKAKTVEGVKALISEI LAALP | 122 |
| LAEAKEDAIKELDKYGVSDYYKNLINKAKTVEGVEALTLHI LAALP | 123 |
| LAEAKEDAIKELDKYGVSDYYKNLINKAKTVEGVEALISEI LAALP | 124 |

The terms "albumin binding" and "binding affinity for albumin" as used herein refer to a property of a polypeptide which may be tested for example by the use of surface plasmon resonance technology, such as in a Biacore instrument as known in the art. For example, as described in the examples below, albumin binding affinity may be tested in an experiment in which albumin, or a fragment thereof, is immobilized on a sensor chip of the instrument, and the sample containing the polypeptide to be tested is passed over the chip. Alternatively, the polypeptide to be tested is immobilized on a sensor chip of the instrument, and a sample containing albumin, or a fragment thereof, is passed over the chip. Albumin may, in this regard, be a serum albumin from a mammal, such as human serum albumin. The skilled person may then interpret the results obtained by such experiments to establish at least a qualitative measure of the binding affinity of the polypeptide for albumin. If a quantitative measure is desired, for example to determine a $K_D$ value for the interaction, surface plasmon resonance methods may also be used. Binding values may for example be defined in a Biacore2000 instrument (GE Healthcare). Albumin is suitably immobilized on a sensor chip of the measurement, and samples of the polypeptide whose affinity is to be determined are prepared by serial dilution and injected. $K_D$ values may then be calculated from the results using for example the 1:1 Langmuir binding model of the BIAevaluation 4.1 software provided by the instrument manufacturer (GE Healthcare).

In one embodiment, the albumin binding polypeptide according to this aspect binds to albumin such that the $k_{off}$ value of the interaction is at most $5 \times 10^{-5}$ $s^{-1}$, such as at most $5 \times 10^{-6}$ $s^{-1}$.

In another preferred embodiment of the ABD used in the engineered polypeptides described herein, the amino acid sequence of the albumin binding polypeptide portion of an engineered polypeptide includes an ABD selected from any one of the sequences described herein, including those from Table 1 or the listing herein and further including their des-Pro46 forms.

In one embodiment, the albumin binding polypeptide according to this aspect further includes one or more additional amino acid residues positioned at the N- and/or the C-terminal of the ABD sequence defined or exemplified herein. These additional amino acid residues may play a role in further enhancing the binding of albumin by the polypeptide, and improving the conformational stability of the folded albumin binding domain, but may equally well serve other purposes, related for example to one or more of production, purification, stabilization in vivo or in vitro, coupling, labeling or detection of the polypeptide, as well as any combination thereof. Such additional amino acid residues may include one or more amino acid residue(s) added for purposes of chemical coupling, e.g. to the HD1.

For example, the amino acids directly preceding or following the alpha helix at the N- or C-terminus of the ABD amino acid sequence may thus in one embodiment affect the conformational stability. One example of an amino acid residue which may contribute to improved conformational stability is a serine residue positioned at the N-terminal of the ABD amino acid sequence as defined above. The N-terminal serine residue may in some cases form a canonical S-X-X-E capping box, by involving hydrogen bonding between the gamma oxygen of the serine side chain and the polypeptide backbone NH of the glutamic acid residue. This N-terminal capping may contribute to stabilization of the first alpha helix of the three helix domain constituting the albumin binding polypeptide according to the first aspect of the disclosure.

Thus, in one embodiment, the additional amino acids include at least one serine residue at the N-terminal of the polypeptide. The ABD amino acid sequence is in other words preceded by one or more serine residue(s). In another embodiment of the albumin binding polypeptide, the additional amino acids include a glycine residue at the N-terminal of the ABD sequence. It is understood that the ABD amino acid sequence may be preceded by one, two, three, four or any suitable number of amino acid residues. Thus, the ABD amino acid sequence may be preceded by a single serine residue, a single glycine residue or a combination of the two, such as a glycine-serine (GS) combination or a glycine-serine-serine (GSS) combination. An example of one such ABD having a N-terminal serine is SLAEAKVLANRELDKYGVSDFYKRLINKAKTVEGVEALKLHILAALP (SEQ ID NO:176). The corresponding des-proline form would be SLAEAKVLANRELDKYGVSDFYKRLINKAKTVEGVEALKLHILAAL (SEQ ID NO:177).

In yet another embodiment, the additional amino acid residues include an alanine acid at the N-terminal of the ABD polypeptide defined herein, or in combination with serine as an alanine-serine sequence at the N-terminal of the ABD sequences above. In yet another embodiment, the additional amino acid residues include a glutamic acid at the N-terminal of the ABD polypeptide defined herein.

Similarly, C-terminal capping may be exploited to improve stability of the third alpha helix of the three helix domain constituting the albumin binding polypeptide. The C-terminal proline residue present at the C-terminal of the ABD amino acid sequence defined above may at least partly function as a capping residue. A lysine residue following the proline residue at the C-terminal may contribute to further stabilization of the third helix of the albumin binding polypeptide, by hydrogen bonding between the epsilon amino group of the lysine residue and the carbonyl groups of the amino acids located two and three residues before the lysine in the polypeptide backbone, e.g. the carbonyl groups of the leucine and alanine residues of the ABD amino acid sequence defined above. Thus, in one embodiment, the additional amino acids include a lysine residue at the C-terminal of the polypeptide.

As discussed above, the additional amino acids may be related to the production of the albumin binding polypeptide. In particular, one or more optional amino acid residues following the C-terminal proline may provide advantages when the albumin binding polypeptide according to the first aspect is produced by chemical peptide synthesis. Such additional amino acid residues may for example prevent formation of undesired substances, such as diketopiperazine at the dipeptide stage of the synthesis. One example of such an amino acid residue is glycine. Thus, in one embodiment, the additional amino acids include a glycine residue at the C-terminal of the polypeptide, directly following the proline residue or following an additional lysine and/or glycine residue as accounted for above. Alternatively, polypeptide production may benefit from amidation of the C-terminal proline residue of the ABD amino acid sequence. In this case, the C-terminal proline includes an additional amine group at the carboxyl carbon.

The skilled person is aware of methods for accomplishing C-terminal modification, such as by different types of pre-made matrices for peptide synthesis.

In another embodiment, the additional amino acid residues includes a cysteine residue at the N- and/or C-terminal of the polypeptide. Such a cysteine residue may directly precede and/or follow the ABD amino acid sequence as defined herein or may precede and/or follow any other additional amino acid residues as described above. By the addition of a cysteine residue to the polypeptide chain, a thiol group for site directed conjugation of the albumin binding polypeptide may be obtained. Alternatively, a selenocysteine residue may be introduced at the C-terminal of the polypeptide chain, in a similar fashion as for the introduction of a cysteine residue, to facilitate site-specific conjugation (Cheng et al, Nat Prot 1:2, 2006).

In one embodiment, the albumin binding polypeptide includes no more than two cysteine residues. In another embodiment, the albumin binding polypeptide includes no more than one cysteine residue.

In another embodiment, the additional amino acid residues of the albumin binding polypeptide includes a "tag" for purification or detection of the polypeptide, such as a hexahistidyl ($His_6$) tag, or a "myc" ("c-Myc") tag or a "FLAG" tag for interaction with antibodies specific to the tag and/or to be used in purification. The skilled person is aware of other alternatives.

For example, in preferred engineered polypeptide embodiments the ABD includes LAEAKVLANRELDKYGVSDFYKRLINKAKTVEGVEALKLHILAALP (SEQ ID NO:35), and its N-terminally extended ABD sequence forms including SLAEAKVLANRELDKYGVSDFYKRLINKAKTVEGVEALKLHILAALP (SEQ ID NO:176) and GSLAEAKVLANRELDKYGVSDFYKRLINKAKTVEGVEALKLHILAALP (SEQ ID NO:178). The serine in position 2 is capping the sequence, raising Tm approximately 2° C. compared to having a glycine or an alanine in this position. An alanine can also immediately precede the serine as in ASLAEAKVLANRELDKYGVSDFYKR LINKAKTVEGVEALKLHILAALP (SEQ ID NO:179). Also preferred are the corresponding polypeptides where the C-terminal proline, glycine or both is absent in each of the above ABD sequences. Accordingly, also preferred are sequences where the ABD includes the des-proline forms, which can improve yields compared to the parent forms LAEAKVLANRELDKYGVSDFYKRLINKAKTVEGVEALKLHILAAL (SEQ ID NO:35), and its N-terminally extended ABD sequence forms including SLAEAKVLANRELD KYGVSDFYKRLINKAKTVEGVEALKLHILAAL (SEQ ID NO:177) and GSLAEAKVLANRELDKYGVSDFYKRLINKAKTVEGVEALKLHILAAL (SEQ ID NO:180) and ASLAEAKVLANRELDKYGVSDFYKRLINKAKTVEGVEALKLHILAAL (SEQ ID NO: 181). In one aspect with any of the ABD sequences disclosed herein, the linker to exendin-4 or exendin analog is a glycine including linker as disclosed herein, for example G, GGG, GGS, GGGS (SEQ ID NO:192), TGGGGAS (SEQ ID NO:193), TGGGGGAS (SEQ ID NO:194), or TGGGGSAS (SEQ ID NO:195).

In one aspect with any of the ABD sequences disclosed herein, the linker to the C-terminus of exendin-4 or exendin analog is a glycine including linker as disclosed herein, for example G, GGG, GGS, GGGS, TGGGGAS, TGGGGGAS, and TGGGGSAS.

In one embodiment of the engineered polypeptides described herein, particularly those ending at its C-terminus with proline or other amino acid known to racemize during peptide synthesis, a glycine can be added to the C-terminus to counter potential problems with racemization of the C-terminal amino acid residue. Alternatively the C-terminal amino acid can in its (alpha-amino group) amidated form, e.g. proline versus proline amide, rather than ending with a glycine. However, if the amidated polypeptide is desired to be produced by recombinant rather than chemical synthesis, then amidation of the C-terminal amino acid can be performed by several methods known in the art, e.g. use of amidating PAM enzyme.

Another aspect of the engineered polypeptides is that the ABD can provide an increase in the solubility in aqueous solution of a poor or low soluble exendin variant. This property can be imparted by the ABD itself or because of the ensuing complex of the engineered polypeptide bound to highly soluble albumin in vivo or in vitro, which association increases the solubility of the engineered polypeptide in aqueous solution. Thus, in an embodiment of this further aspect, there is provided a composition, including an exendin compound which per se has a solubility in water of no more than 1 mg/ml, or no more than 2 mg/ml or no more than 5 mg/ml, covalently coupled to an albumin binding domain as a fusion protein or conjugate as described herein, wherein the compound and the albumin binding polypeptide, fusion protein or conjugate are covalently coupled and the solubility of the engineered polypeptide is greater than that of the unfused (or not conjugated) native exendin compound.

Binding to Albumin.

Serum albumin is the most abundant protein in mammalian sera (40 g/L; approximately 0.7 mM in humans) where it binds a variety of molecules including but not limited to lipids and bilirubin (Peters T, 1985, *Advances in Protein Chemistry* 37:161). It has been observed that the half-life of serum albumin is directly proportional to the size of the animal, where for example human serum albumin (HSA) has a half-life of 19 days and rabbit serum albumin has a half-life of about 5 days (McCurdy T R et al., *J. Lab. Clin. Med.* 143:115, 2004). Human serum albumin is widely distributed throughout the body, in particular in the intestinal and blood compartments, where it is mainly involved in the maintenance of osmolarity. Structurally, albumins are single-chain proteins including three homologous domains and totaling 584 or 585 amino acids (Dugaiczyk L et al., 1982, *Proc. Natl. Acad. Sci. USA* 79:71). Albumins contain 17 disulfide bridges and a single reactive thiol, C34, but lack N-linked and O-linked carbohydrate moieties (Peters, 1985, Id.; Nicholson J P et al., 2000, *Br J Anaesth* 85:599). The lack of glycosylation simplifies recombinant expression of albumin. This property of albumin, together with the fact that its three-dimensional structure is known (He, X M and Carter, D C, *Nature* 358:209 1992), has made it an attractive candidate for use in recombinant fusion proteins. Such fusion proteins generally combine a therapeutic protein (which would be rapidly cleared from the body upon administration of the protein per se) and a plasma protein (which exhibits a natural slow clearance) in a single polypeptide chain (Sheffield W P, *Curr. Drug Targets Cardiovacs. Haematol. Disord.* 1:1 2001). Such fusion proteins may provide clinical benefits in requiring less frequent injection and higher levels of therapeutic protein in vivo. However, the engineered polypeptides herein are not conjugated to albumin, but instead contain motifs that allow non-covalent binding to albumin.

Albumin Half-Life.

It has been observed that the half-life of albumin in different species generally adheres to allometric scaling based on animal weight. For example, the albumin half-life in mouse, rat, rabbit and human has been estimated as 1, 1.9, 5.6 and 19 days, respectively. Indeed, power fitting analysis (Davies & Morris, 1993, *Pharm. Res.* (N. Y.) 10:1093-1095) provides the equation:

$$\text{Albumin half-life(days)}=3.75*\text{body weight (kg)}^{0.368}.$$

Further Embodiments

It is understood that each of the polypeptides disclosed herein are also contemplated to include a methionine at the N-terminus in frame with the naturally-occurring first amino acid thereof, e.g., Met-exendin-4, which is exendin-4 with an added N-terminal methionine. It is further understood that where a C-terminal Gly appears in a engineered polypeptide sequence set forth herein, the residue may be lost during subsequent amidation. Some embodiments are intermediates in synthesis, for example, such as those having a "His tag" which is used for affinity purification as is known in the art, and that can optionally be subsequently removed to yield a mature engineered polypeptide suitable for therapeutic use.

In some embodiments of any of the engineered polypeptides described herein, an exendin analog can have at least 70%, for example 70%, 75%, 80%, 85%, 90%, 95%, 98% or even higher, sequence identity relative to a parent exendin sequence. In some embodiments, the parent exendin is exendin-4, and the exendin analog may have at least 70%, for example 70%, 75%, 80%, 85%, 90%, 95%, 98% or even higher, sequence identity relative to exendin-4. As known the art, GLP-1 (glucagon-like peptide 1) is not an exendin; and the sequence of GLP-1 is specifically excluded from exendin sequences suitable for the engineered polypeptides described herein.

In some embodiments, compounds are provided having a linker, for example L1, as described herein, covalently linking a polypeptide hormone domain with an ABD peptide. In some embodiments, a first linker (L1) covalently links HD1 within the engineered polypeptide. In some embodiments, L1 is a bond. In some embodiments, the polypeptide hormone domain (e.g., HD1 as described herein) can be covalently linked to the ABD peptide via a peptide linker. Any linker is optional; i.e., any linker may simply be a bond. When present the chemical structure of a linker is not critical because it serves mainly a spacer function. In one embodiment the linker includes from 1 to 30 amino acids linked by peptide bonds. The amino acids can be selected from the 20 naturally occurring (i.e., physiological) amino acids. Alternatively, non-natural amino acids can be incorporated either by chemical synthesis, post-translational chemical modification or by in vivo incorporation by recombinant expression in a host cell. Some of these amino acids may be glycosylated. In another embodiment the 1 to 30 amino acids are selected from glycine, alanine, proline, asparagine, glutamine, and lysine, and further from aspartate and glutamate. In a further embodiment the linker is made up of a majority of amino acids that are sterically unhindered, such as glycine, alanine and/or serine. "Sterically unhindered" refers, in the customary sense, to a amino acid having a small side chain, e.g., 0-2 non-hydrogen atoms, such that steric hindrance is minimized relative to amino acids having larger side chains, e.g., Leu, Trp, Tyr, Phe, and the like. Polyglycines are particularly useful, e.g. $(Gly)_3$, $(Gly)_4$ (SEQ ID NO:125), $(Gly)_5$ (SEQ ID NO:126), as are polyalanines, poly(Gly-Ala) and poly(Gly-Ser). Charged polyglycines can be useful, and include e.g., poly $(Gly_n\text{-Glu})$ (SEQ ID NO:127), poly$(Gly_n\text{-Lys})$ (SEQ ID NO:128), poly $(Gly_n\text{-Asp})$ (SEQ ID NO:129), and poly$(Gly_n\text{-Arg})$ (SEQ ID NO:130) motifs (where n can be 1 to 6). Other specific examples of linkers are $(Gly)_3Lys(Gly)_4$ (SEQ ID NO:131); $(Gly)_3AsnGlySer(Gly)_2$ (SEQ ID NO:132); $(Gly)_3Cys(Gly)_4$ (SEQ ID NO:133); and GlyProAsnGlyGly (SEQ ID NO:134). Combinations of Gly and Ala are particularly useful as are combination of Gly and Ser. Thus, in a further embodiment the peptide linker is selected from the group of a glycine rich peptide, e.g., Gly-Gly-Gly; the sequences $[Gly\text{-}Ser]_n$(SEQ ID NO:135), $[Gly\text{-}Gly\text{-}Ser]_n$(SEQ ID NO:136), $[Gly\text{-}Gly\text{-}Gly\text{-}Ser]_n$ (SEQ ID NO:137) and $[Gly\text{-}Gly\text{-}Gly\text{-}Gly\text{-}Ser]_n$ (SEQ ID NO:138), where n is 1, 2, 3, 4, 5 or 6, for example $[Gly\text{-}Gly\text{-}Gly\text{-}Gly\ Ser]_3$. "Glycine rich peptide" refers to a polypeptide which includes a plurality of glycine residues, preferably a majority of glycine residues, more preferably a preponderance of glycine residues.

In certain embodiments, charged linkers may be used. Such charges linkers may be contain a significant number of acidic residues (e.g., Asp, Glu, and the like), or may contain a significant number of basic residues (e.g., Lys, Arg, and the like), such that the linker has a pI lower than 7 or greater than 7, respectively. As understood by the artisan, and all other things being equal, the greater the relative amount of acidic or basic residues in a given linker, the lower or higher, respectively, the pI of that linker will be. Such linkers may impart advantageous properties to the engineered polypeptides disclosed herein, such as modifying the peptides pI (isoelectric point) which can in turn improve solubility and/or stability characteristics of such polypeptides at a particular pH, such as at physiological pH (e.g., between pH 7.2 and pH 7.6, inclusive), or in a pharmaceutical composition including such polypeptides. As is known in the art, solubility for a peptide can be improved by formulation in a composition having a pH that is at least or more than plus or minus one pH unit from the pI of the peptide.

For example, an "acidic linker" is a linker that has a pI of less than 7; between 6 and 7, inclusive; between 5 and 6, inclusive; between 4 and 5, inclusive; between 3 and 4, inclusive; between 2 and 3, inclusive; or between 1 and 2, inclusive. Similarly, a "basic linker" is a linker that has a pI of greater than 7; between 7 and 8, inclusive; between 8 and 9, inclusive; between 9 and 10, inclusive; between 10 and 11, inclusive; between 11 and 12 inclusive, or between 12 and 13, inclusive. In certain embodiments, an acidic linker will contain a sequence that is selected from the group of $[Gly\text{-}Glu]_n$ (SEQ ID NO:139); $[Gly\text{-}Gly\text{-}Glu]_n$ (SEQ ID NO:140); $[Gly\text{-}Gly\text{-}Gly\text{-}Glu]_n$ (SEQ ID NO:141); $[Gly\text{-}Gly\text{-}Gly\text{-}Gly\text{-}Glu]_n$ (SEQ ID NO:142), $[Gly\text{-}Asp]_n$ (SEQ ID NO:143); $[Gly\text{-}Gly\text{-}Asp]_n$ (SEQ ID NO:144); $[Gly\text{-}Gly\text{-}Gly\text{-}Asp]_n$ (SEQ ID NO:145); $[Gly\text{-}Gly\text{-}Gly\text{-}Gly\text{-}Asp]_n$ (SEQ ID NO:146), where n is 1, 2, 3, 4, 5, 6, 7, 8, 9, 10, or more; for example, $[Gly\text{-}Gly\text{-}Glu]_6$. In certain embodiments, a basic linker will contain a sequence that is selected from the group of $[Gly\text{-}Lys]_n$ (SEQ ID NO:147); $[Gly\text{-}Gly\text{-}Lys]_n$ (SEQ ID NO:148); $[Gly\text{-}Gly\text{-}Gly\text{-}Lys]_n$ (SEQ ID NO:149); $[Gly\text{-}Gly\text{-}Gly\text{-}Gly\text{-}Lys]_n$ (SEQ ID NO:150), $[Gly\text{-}Arg]_n$ (SEQ ID NO:151); $[Gly\text{-}Gly\text{-}Arg]_n$ (SEQ ID NO:152); $[Gly\text{-}Gly\text{-}Gly\text{-}Arg]_n$ (SEQ ID NO:153); $[Gly\text{-}Gly\text{-}Gly\text{-}Gly\text{-}Arg]_n$ (SEQ ID NO:154) where n is 1, 2, 3, 4, 5, 6, 7, 8, 9, 10, or more; for example, $[Gly\text{-}Gly\text{-}Lys]_6$.

Additionally, linkers may be prepared which possess certain structural motifs or characteristics, such as an alpha helix. For example, such a linker may contain a sequence that is selected from the group of $[Glu\text{-}Ala\text{-}Ala\text{-}Ala\text{-}Lys]_n$ (SEQ ID NO:155), where n is 1, 2, 3, 4, 5, 6, 7, 8, 9, 10, or more; for example, $[Glu\text{-}Ala\text{-}Ala\text{-}Ala\text{-}Lys]_3$, $[Glu\text{-}Ala\text{-}Ala\text{-}Ala\text{-}Lys]_4$, or $[Glu\text{-}Ala\text{-}Ala\text{-}Ala\text{-}Lys]_5$. One in the art can readily determine helix content of any particular linker sequence.

A biocompatible linker other than a peptide linker may be used to covalently attach the C-terminus of an exendin to the N-terminus of the ABD or ABM sequence. The linker can be a biocompatible polymer, preferably water soluble, and more preferably about 50 kD to about 5000 kD, or about 50 KD to 500 kD, or about 100 kD to 500 kD. An exemplary biocompatible, water soluble polymer linker is a PEG linker, such as $-(CH_2-CH_2-O)_n-$ where n is such that the PEG linker can have a molecular weight of 100 to 5000 kD, preferably 100 to 500 kD. Such a linker may be $-NH-CH_2-CH_2-(O-CH_2-CH_2)_n-O-CH_2-CO-$, where n is such that the PEG linker molecular weight is 100 kD to 5000 kD, preferably 10 kD to 500 kD. Other biocompatible polymers can be used, such as including but not limited to polysaccharides, polypropylene glycol, and co-polymers of propylene and ethylene glycols. Typically such a linker will include a reactive group at each end that can be the same or different reactive group. Such linkers with reactive groups are known and available. Preferably the reactive group is reactive with either an N-terminal amino or C-terminal carboxy group of a peptide. For example, a reactive group can be an a butylaldehyde, a propionaldehyde, an aldehyde, a succinimide or a maleimide moiety, as is known in the art. Less preferred are alkyl linkers such as $-NH-(CH_2)_n-C(O)-$, wherein n=2-20, and which can be further substituted by any group that does not sterically-hinder peptide function, such as a lower alkyl (e.g., $C_1\text{-}C_6$), lower acyl, halogen, CN, and $NH_2$.

It is also to be understood that linkers suitable for use in accordance with the invention may possess one or more of the characteristics and motifs described above and herein. For example, a linker may include an acidic linker as well as a structural motif, such as an alpha helix. Similarly, a linker may include a basic linker and a structural motif, such as an alpha helix. A linker may include an acidic linker, a basic linker, and a structural motif, such as an alpha helix. Additionally, it is also to be understood that engineered polypeptides in accordance with the invention may possess more than one linker, and each such linker may possess one or more of the characteristics described herein.

The linkers described herein are exemplary, and linkers within the scope of this invention may be much longer and may include other residues. In one embodiment, expressly excluded are engineered polypeptides in which the exendin sequence is linked directly to the ABD sequence without a linker.

In some embodiments, the engineered polypeptide includes an ABD sequence at the C-terminal, and a HD1 sequence at the N-terminal. In certain preferred embodiments, the N-terminal is an exendin sequence, an exendin fragment sequence or an exendin analog sequence. Further to embodiments which include an ABD and a HD1, the engineered polypeptide can have the structure HD1-ABD.

It is understood that absent an express indication of the N-terminus and/or C-terminus of a engineered polypeptide set forth herein, the engineered polypeptide is to be read in the N-terminus to C-terminus orientation. For example, where HD1 has the sequence of an exendin compound or analog thereof, the terms HD1-ABD, HD1-L1-ABD, HD1-ABD, and the like mean, in the absence of an express indication of the N-terminus and/or the C-terminus, that the exendin sequence or analog thereof resides at the N-terminus of the engineered polypeptide, and the ABD resides at the C-terminus. Conversely, if the N-terminus and/or C-terminus is expressly indicated, then the engineered polypeptide is to be read according to the express indication of the termini. For example, the terms $HD1_{C\text{-}term}$-ABD, HD1-L1-$ABD_{N\text{-}term}$ and the like mean that the ABD resides at the N-terminus of the engineered polypeptide, and HD1 resides at the C-terminus.

In some embodiments, the engineered polypeptide described herein has an affinity for serum albumin which is different than the affinity of the ABD polypeptide alone, i.e., in the absence of a fused hormone domain. In order to obtain effective association, the engineered polypeptide can have a binding affinity for serum albumin such that the dissociation constant $K_D$ is, for example, less than about $10^{-6}$ M, $10^{-7}$ M, $10^{-8}$ M, $10^{-9}$ M, $10^{-10}$ M, $10^{-11}$ M, $10^{-12}$ M, $10^{-13}$ M, $10^{-14}$ M or even $10^{-15}$ M. In some embodiments, the affinity is not excessively tight such that the engineered polypeptide can dissociate from the albumin and elicit a biological response, for example binding to a receptor, for example, an exendin receptor. The affinity can be measured as described in PCT Published Appl. No. WO 2009/016043, preferably to human serum albumin, which is incorporated herein by reference in its entirety and for all purposes, including without limitation assays and synthesis methods.

In some embodiments, a engineered polypeptide described herein is superior to a corresponding compound having a different moiety that can extend plasma half-life (e.g., PEG or of Fc or albumin) conjugated with a hormone domain(s). In this context, the term "superior" refers to a variety of functional properties which could be weighed in the evaluation of a treatment for a disease or disorder. For example, the engineered polypeptide described herein could require less biologically active (hormone domain) component, for example 1×, 2×, 3×, 4×, 5×, or even less, than the corresponding compound having a different moiety conjugated with the hormone domain(s). For further example, the engineered polypeptide described herein could have higher potency, for example, 1.5×, 2×, 3×, 4×, 5×, 10×, 20×, 50×, or even higher potency.

Engineered polypeptide compounds contemplated herein include the compounds as set forth in Table 2 following. One preferred compound is Cmpd 31.

TABLE 2

Selected exemplary engineered polypeptides

| Cmpd | Sequence |
|---|---|
| 5 | HGEGTFTSDLSKQLEEEAVRLFIEWLKNGGPSSGAPPPSTGGGGSASLAEAKVLANRELDKYGVSDFYKRLINKAKTVEGVEALKLHILAALP (SEQ ID NO: 40) |
| 6 | HGEGTFTSDLSKQLEEEAVRLFIEWLKNGGPSSGAPPPSTGGGGSGGGSGGGSGGGSASLAEAKVLANRELDKYGVSDFYKRLINKAKTVEGVEALKLHILAALP (SEQ ID NO: 41) |

TABLE 2-continued

Selected exemplary engineered polypeptides

| Cmpd | Sequence |
|---|---|
| 7 | HGEGTFTSDLSKQLEEEAVRLFIEWLKQGGPSKEIISTGGGGGASLAEAKVLANRELDKYGVSDFYKRLINKAKTVEGVEALKLHILAALP (SEQ ID NO: 42) |
| 8 | HGEGTFTSDLSKQLEEEAVRLFIEWLKQGGPSKEIISTGGGGSGGGSGGGSGGGSASLAEAKVLANRELDKYGVSDFYKRLINKAKTVEGVEALKLHILAALP (SEQ ID NO: 43) |
| 10 | HGEGTFTSDLSKQMEEEAVRLFIEWLKNTGGGGSASLAEAKVLANRELDKYGVSDFYKRLINKAKTVEGVEALKLHILAALP (SEQ ID NO: 51) |
| 15 | HGEGTFTSDLSKQLEEEAVRLFIEWLKQGGPSKEIISTGGGGSASLAEAKVLANRELDKYGVSDFYKRLINKAKTVEGVEALKLHILAALP (SEQ ID NO: 163) |
| 21 | HGEGTFTSDLSKQMEEEAVRLFIEWLKNGGPSSGAPPPSGGSLAEAKVLANRELDKYGVSDFYKRLINKAKTVEGVEALKLHILAALP (SEQ ID NO: 99) |
| 23 | HGEGTFTSDLSKQMEEEAVRLFIEWLKNGGPSSGAPPPSGGSLSEAKEMAIRELDANGVSDFYKDKIDDAKTVEGVVALKDLILNSLP (SEQ ID NO: 169) |
| 24 | HGEGTFTSDLSKQMEEEAVRLFIEWLKNGGPSSGAPPPSGGSLAKAKADAIEILKKYGIGDYYIKLINNGKTAEGVTALKDEILASLP (SEQ ID NO: 170) |
| 31 | HGEGTFTSDLSKQLEEEAVRLFIEWLKNGGPSSGAPPPSGGSLAEAKVLANRELDKYGVSDFYKRLINKAKTVEGVEALKLHILAALP (SEQ ID NO: 95) |
| 32 | HGEGTFTSDLSKQMEEEAVRLFIEWLKNGGSLAEAKVLANRELDKYGVSDFYKRLINKAKTVEGVEALKLHILAALP (SEQ ID NO: 97) |
| 33 | HGEGTFTSDLSKQLEEEAVRLFIEWLKQGGPSKEIISGGSLAEAKVLANRELDKYGVSDFYKRLINKAKTVEGVEALKLHILAALP (SEQ ID NO: 96) |
| 34 | HGEGTFTSDLSKQMEEEAVRLFIEWLKNGGPSSGAPPPSTGGGGSASLAEAKVLANRELDKYGVSDFYKRLINKAKTVEGVEALKLHILAALP (SEQ ID NO: 55); |

Additional polypeptide compounds contemplated herein include the compounds as set forth in Table 3A following:

TABLE 3A

Selected exemplary engineered polypeptides

| Cmpd | Sequence |
|---|---|
| 9 | HGEGTFTSDLSKQMEEEAVRLFIEWLKNTGGGGSGGGSGGGSGGGSASLAEAKVLANRELDKYGVSDFYKRLINKAKTVEGVEALKLHILAALP (SEQ ID NO: 53) |
| 11 | HGEGTFTSDLSKQMEEEAVRLFIEWLKNTGGGGSGGGSGGGSGGGSASLAEAKVLANRELDKYGVSDYYKNIINRAKTVEGVRALKLHILAALP (SEQ ID NO: 62) |
| 12 | HGEGTFTSDLSKQMEEEAVRLFIEWLKNTGGGGSASLAEAKVLANRELDKYGVSDYYKNIINRAKTVEGVRALKLHILAALP (SEQ ID NO: 67) |
| 19 | HGEGTFTSDLSKQMEEEAVRLFIEWLKNGGPSSGAPPPSTGGGGSASYGVSDFYKRLINKAKTVEGVEALKLHILAALP (SEQ ID NO: 166) |
| 20 | HGEGTFTSDLSKQMEEEAVRLFIEWLKNGGPSSGAPPPSGYGVSDFYKRLINKAKTVEGVEALKLHILAALP (SEQ ID NO: 167) |

Specifically contemplated are compounds of the above sequences in which any N-terminal methionine is absent. The N-terminal methionine can be present primarily as a convenience for bacterial expression. However, engineered peptides of the present invention can be expressed in a eukaryotic host cell (e.g. yeast (e.g. *Pichia*), mammalian, baculovirus) or other host cell having post-translational N-terminal proteolytic processing to yield an N-terminal amino acid as found in a naturally occurring mature peptide counterpart of the desired hormone or ABD sequence, i.e. without the added methionine or other leader sequence. Alternatively, an N-terminal sequence used for expression and/or secretion (and even purification) can be one that can be removed post-translationally, e.g. as by use of a protease such as TEV.

Additional engineered polypeptide compounds contemplated herein, having a variety of HD1, L1 and ABD components, include the compounds having the structure of any of the engineered polypeptides of the tables and listing herein, including those disclosed in Table 3B following.

TABLE 3B

Selected exemplary engineered polypeptides

Sequence

HGEGTFTSDLSKQMEEEAVRLFIEWLKNTGGGGSASLAEAKVLANR
ELDKYGVSDFYKRLINKAKTVEGVEALKLHILAALP
(SEQ ID NO: 51)

HGEGTFTSDLSKQLEEEAVRLFIEWLKNTGGGGSASLAEAKVLANR
ELDKYGVSDFYKRLINKAKTVEGVEALKLHILAALP
(SEQ ID NO: 52)

HGEGTFTSDLSKQMEEEAVRLFIEWLKNTGGGGSGGGSGGGSGGGS
ASLAEAKVLANRELDKYGVSDFYKRLINKAKTVEGVEALKLHILAA
LP (SEQ ID NO: 53)

HGEGTFTSDLSKQLEEEAVRLFIEWLKNTGGGGSGGGSGGGSGGGS
ASLAEAKVLANRELDKYGVSDFYKRLINKAKTVEGVEALKLHILAA
LP (SEQ ID NO: 54)

HGEGTFTSDLSKQMEEEAVRLFIEWLKNGGPSSGAPPPSTGGGGSA
SLAEAKVLANRELDKYGVSDFYKRLINKAKTVEGVEALKLHILAAL
P (SEQ ID NO: 55)

HGEGTFTSDLSKQMEEEAVRLFIEWLKNGGPSSGAPPPSTGGGGSG
GGSGGGSGGGSASLAEAKVLANRELDKYGVSDFYKRLINKAKTVEG
VEALKLHILAALP (SEQ ID NO: 56)

HGEGTFTSDLSKQMEEEAVRLFIEWLKQGGPSKEIISTGGGGSASL
AEAKVLANRELDKYGVSDFYKRLINKAKTVEGVEALKLHILAALP
(SEQ ID NO: 57)

HGEGTFTSDLSKQMEEEAVRLFIEWLKQGGPSKEIISTGGGGSGGG
SGGGSGGGSASLAEAKVLANRELDKYGVSDFYKRLINKAKTVEGVE
ALKLHILAALP (SEQ ID NO: 58)

HGEGTFTSDLSKQMEEEAVRLFIEWLKNGGPSSGAPPSKKKKKKTG
GGGSASLAEAKVLANRELDKYGVSDFYKRLINKAKTVEGVEALKLH
ILAALP (SEQ ID NO: 59)

HGEGTFTSDLSKQMEEEAVRLFIEWLKNGGPSSGAPPSKKKKKKTG
GGGSGGGSGGGGGGSASLAEAKVLANRELDKYGVSDFYKRLINKAK
TVEGVEALKLHILAALP (SEQ ID NO: 60)

HGEGTFTSDLSKQLEEEAVRLFIEWLKNGGPSSGAPPPSGGGLAEA
KVLANRELDKYGVSDFYKRLINKAKTVEGVEALKLHILAALP
(SEQ ID NO: 61)

HGEGTFTSDLSKQMEEEAVRLFIEWLKNTGGGGSGGGSGGGSGGGS
ASLAEAKVLANRELDKYGVSDYYKNIINRAKTVEGVRALKLHILAA
LP (SEQ ID NO: 62)

TABLE 3B-continued

Selected exemplary engineered polypeptides

Sequence

HGEGTFTSDLSKQLEEEAVRLFIEWLKNGGPSSGAPPPSTGGGGSA
SLAEAKVLANRELDKYGVSDYYKNIINRAKTVEGVRALKLHILAAL
P (SEQ ID NO: 63)

HGEGTFTSDLSKQLEEEAVRLFIEWLKNGGPSSGAPPPSTGGGGSG
GGSGGGSGGGSASLAEAKVLANRELDKYGVSDYYKNIINRAKTVEG
VRALKLHILAALP (SEQ ID NO: 64)

HGEGTFTSDLSKQLEEEAVRLFIEWLKQGGPSKEIISTGGGGSASL
AEAKVLANRELDKYGVSDYYKNIINRAKTVEGVRALKLHILAALP
(SEQ ID NO: 65)

HGEGTFTSDLSKQLEEEAVRLFIEWLKQGGPSKEIISTGGGGSGGG
SGGGSGGGSASLAEAKVLANRELDKYGVSDYYKNIINRAKTVEGVR
ALKLHILAALP (SEQ ID NO: 66)

HGEGTFTSDLSKQMEEEAVRLFIEWLKNTGGGGSASLAEAKVLANR
ELDKYGVSDYYKNIINRAKTVEGVRALKLHILAALP
(SEQ ID NO: 67)

HGEGTFTSDLSKQLEEEAVRLFIEWLKNTGGGGSASLAEAKVLANR
ELDKYGVSDYYKNIINRAKTVEGVRALKLHILAALP
(SEQ ID NO: 68)

HGEGTFTSDLSKQLEEEAVRLFIEWLKNTGGGGSGGGSGGGSGGGS
ASLAEAKVLANRELDKYGVSDYYKNIINRAKTVEGVRALKLHILAA
LP (SEQ ID NO: 70)

HGEGTFTSDLSKQMEEEAVRLFIEWLKNGGPSSGAPPPSTGGGGSA
SLAEAKVLANRELDKYGVSDYYKNIINRAKTVEGVRALKLHILAAL
P (SEQ ID NO: 71)

HGEGTFTSDLSKQMEEEAVRLFIEWLKNGGPSSGAPPPSTGGGGSG
GGSGGGSGGGSASLAEAKVLANRELDKYGVSDYYKNIINRAKTVEG
VRALKLHILAALP (SEQ ID NO: 72)

HGEGTFTSDLSKQMEEEAVRLFIEWLKQGGPSKEIISTGGGGSASL
AEAKVLANRELDKYGVSDYYKNIINRAKTVEGVRALKLHILAALP
(SEQ ID NO: 73)

HGEGTFTSDLSKQMEEEAVRLFIEWLKQGGPSKEIISTGGGGSGGG
SGGGSGGGSASLAEAKVLANRELDKYGVSDYYKNIINRAKTVEGVR
ALKLHILAALP (SEQ ID NO: 74)

HGEGTFTSDLSKQMEEEAVRLFIEWLKNGGPSSGAPPSKKKKKKTG
GGGSASLAEAKVLANRELDKYGVSDYYKNIINRAKTVEGVRALKLH
ILAALP (SEQ ID NO: 75)

HGEGTFTSDLSKQMEEEAVRLFIEWLKNGGPSSGAPPSKKKKKKTG
GGGSGGGSGGGSGGGSASLAEAKVLANRELDKYGVSDYYKNIINRA
KTVEGVRALKLHILAALP (SEQ ID NO: 76)

HGEGTFTSDLSKQLEEEAVRLFIEWLKNGGPSSGAPPPSGGGLAEA
KVLANRELDKYGVSDYYKNIINRAKTVEGVRALKLHILAALP
(SEQ ID NO: 77)

HGEGTFTSDLSKQLEEEAVRLFIEWLKNGGPSSGAPPPSGGGLAEA
KVLANRELDKYGVSDFYKRLINKAKTVEGVEALKLHILAALP
(SEQ ID NO: 78)

HGEGTFTSDLSKQLEEEAVRLFIEWLKQGGPSKEIISGGGLAEAKV
LANRELDKYGVSDFYKRLINKAKTVEGVEALKLHILAALP
(SEQ ID NO: 79)

HGEGTFTSDLSKQMEEEAVRLFIEWLKNGGGLAEAKVLANRELDKY
GVSDFYKRLINKAKTVEGVEALKLHILAALP
(SEQ ID NO: 80)

HGEGTFTSDLSKQLEEEAVRLFIEWLKNGGGLAEAKVLANRELDKY
GVSDFYKRLINKAKTVEGVEALKLHILAALP (SEQ ID NO: 81)

HGEGTFTSDLSKQMEEEAVRLFIEWLKNGGPSSGAPPPSGGGLAEA
KVLANRELDKYGVSDFYKRLINKAKTVEGVEALKLHILAALP
(SEQ ID NO: 82)

TABLE 3B-continued

Selected exemplary engineered polypeptides

Sequence

HGEGTFTSDLSKQMEEEAVRLFIEWLKQGGPSKEIISGGGLAEAKV
LANRELDKYGVSDFYKRLINKAKTVEGVEALKLHILAALP
(SEQ ID NO: 83)

HGEGTFTSDLSKQMEEEAVRLFIEWLKNGGPSSGAPPSKKKKKGG
GLAEAKVLANRELDKYGVSDFYKRLINKAKTVEGVEALKLHILAAL
P
(SEQ ID NO: 84)

HGEGTFTSDLSKQLEEEAVRLFIEWLKNGGPSSGAPPPSGGGLAEA
KVLANRELDKYGVSDFYKRLINKAKTVEGVEALKLHILAALP
(SEQ ID NO: 85)

HGEGTFTSDLSKQMEEEAVRLFIEWLKNGGGLAEAKVLANRELDKY
GVSDYYKNIINRAKTVEGVRALKLHILAALP (SEQ ID NO: 86)

HGEGTFTSDLSKQLEEEAVRLFIEWLKNGGPSSGAPPPSGGGLAEA
KVLANRELDKYGVSDYYKNIINRAKTVEGVRALKLHILAALP
(SEQ ID NO: 87)

HGEGTFTSDLSKQLEEEAVRLFIEWLKQGGPSKEIISGGGLAEAKV
LANRELDKYGVSDYYKNIINRAKTVEGVRALKLHILAALP
(SEQ ID NO: 88)

HGEGTFTSDLSKQLEEEAVRLFIEWLKNGGGLAEAKVLANRELDKY
GVSDYYKNIINRAKTVEGVRALKLHILAALP (SEQ ID NO: 89)

HGEGTFTSDLSKQLEEEAVRLFIEWLKNGGGLAEAKVLANRELDKY
GVSDYYKNIINRAKTVEGVRALKLHILAALP (SEQ ID NO: 90)

HGEGTFTSDLSKQMEEEAVRLFIEWLKNGGPSSGAPPPSGGGLAEA
KVLANRELDKYGVSDYYKNIINRAKTVEGVRALKLHILAALP
(SEQ ID NO: 91)

HGEGTFTSDLSKQMEEEAVRLFIEWLKQGGPSKEIISGGGLAEAKV
LANRELDKYGVSDYYKNIINRAKTVEGVRALKLHILAALP
(SEQ ID NO: 92)

HGEGTFTSDLSKQMEEEAVRLFIEWLKNGGPSSGAPPSKKKKKGG
GLAEAKVLANRELDKYGVSDYYKNIINRAKTVEGVRALKLHILAAL
P (SEQ ID NO: 93)

HGEGTFTSDLSKQLEEEAVRLFIEWLKNGGPSSGAPPPSGGSLAEA
KVLANRELDKYGVSDYYKNIINRAKTVEGVRALKLHILAALP
(SEQ ID NO: 94)

HGEGTFTSDLSKQLEEEAVRLFIEWLKNGGPSSGAPPPSGGSLAEA
KVLANRELDKYGVSDFYKRLINKAKTVEGVEALKLHILAALP
(SEQ ID NO: 95)

HGEGTFTSDLSKQLEEEAVRLFIEWLKQGGPSKEIISGGSLAEAKV
LANRELDKYGVSDFYKRLINKAKTVEGVEALKLHILAALP
(SEQ ID NO: 96)

HGEGTFTSDLSKQMEEEAVRLFIEWLKNGGSLAEAKVLANRELDKY
GVSDFYKRLINKAKTVEGVEALKLHILAALP (SEQ ID NO: 97)

HGEGTFTSDLSKQLEEEAVRLFIEWLKNGGSLAEAKVLANRELDKY
GVSDFYKRLINKAKTVEGVEALKLHILAALP (SEQ ID NO: 98)

HGEGTFTSDLSKQMEEEAVRLFIEWLKNGGPSSGAPPPSGGSLAEA
KVLANRELDKYGVSDFYKRLINKAKTVEGVEALKLHILAALP
(SEQ ID NO: 99)

HGEGTFTSDLSKQMEEEAVRLFIEWLKQGGPSKEIISGGSLAEAKV
LANRELDKYGVSDFYKRLINKAKTVEGVEALKLHILAALP
(SEQ ID NO: 100)

HGEGTFTSDLSKQMEEEAVRLFIEWLKNGGPSSGAPPSKKKKKGG
SLAEAKVLANRELDKYGVSDFYKRLINKAKTVEGVEALKLHILAAL
P (SEQ ID NO: 101)

HGEGTFTSDLSKQMEEEAVRLFIEWLKNGGSLAEAKVLANRELDKY
GVSDYYKNIINRAKTVEGVRALKLHILAALP (SEQ ID NO: 102)

HGEGTFTSDLSKQLEEEAVRLFIEWLKNGGPSSGAPPPSGGSLAEA
KVLANRELDKYGVSDYYKNIINRAKTVEGVRALKLHILAALP
(SEQ ID NO: 103)

HGEGTFTSDLSKQLEEEAVRLFIEWLKQGGPSKEIISGGSLAEAKV
LANRELDKYGVSDYYKNIINRAKTVEGVRALKLHILAALP
(SEQ ID NO: 104)

HGEGTFTSDLSKQLEEEAVRLFIEWLKNGGSLAEAKVLANRELDKY
GVSDYYKNIINRAKTVEGVRALKLHILAALP
(SEQ ID NO: 105)

HGEGTFTSDLSKQLEEEAVRLFIEWLKNGGSLAEAKVLANRELDKY
GVSDYYKNIINRAKTVEGVRALKLHILAALP (SEQ ID NO: 106)

HGEGTFTSDLSKQMEEEAVRLFIEWLKNGGPSSGAPPPSGGSLAEA
KVLANRELDKYGVSDYYKNIINRAKTVEGVRALKLHILAALP
(SEQ ID NO: 107)

HGEGTFTSDLSKQMEEEAVRLFIEWLKQGGPSKEIISGGSLAEAKV
LANRELDKYGVSDYYKNIINRAKTVEGVRALKLHILAALP
(SEQ ID NO: 108)

HGEGTFTSDLSKQMEEEAVRLFIEWLKNGGPSSGAPPSKKKKKGG
SLAEAKVLANRELDKYGVSDYYKNIINRAKTVEGVRALKLHILAAL
P (SEQ ID NO: 109)

III. Methods of Design and Production

Design of Constructs

The engineered polypeptides described herein can be designed at the amino acid level. These sequences can then be back translated using a variety of software products known in the art such that the nucleotide sequence is optimized for the desired expression host, e.g. based protein expression, codon optimization, restriction site content. For example, the nucleotide sequence can be optimized for *E. coli* based protein expression and for restriction site content. Based on the nucleotide sequence of interest, overlapping oligonucleotides can be provided for multistep PCR, as known in the art. These oligonucleotides can be used in multiple PCR reactions under conditions well known in the art to build the cDNA encoding the protein of interest. For one example is 1× Amplitaq Buffer, 1.3 mM $MgCl_2$, 200 uM dNTPs, 4 U Amplitaq Gold, 0.2 uM of each primer (Ampli-Taq Gold, ABI), with cycling parameters: (94 C:30 s, 58 C:1 min, 72 C:1 min), 35 cycles.

Restriction sites can be added to the ends of the PCR products for use in vector ligation as known in the art. Specific sites can include Nde1 and Xho1, such that the cDNA can then be in the proper reading frame in a pET45b expression vector (Novagen). By using these sites, any N-terminal His Tag that are in this vector can be removed as the translation start site would then be downstream of the tag. Once expression constructs are completed, verification can be conduct by sequencing using e.g., T7 promoter primer, T7 terminator primer and standard ABI BigDye Term v 3.1 protocols as known in the art. Sequence information can be obtained from e.g., an ABI 3730 DNA Analyzer and can be analyzed using Vector NTI v. 10 software (Invitrogen). Expression constructs can be designed in a modular manner such that linker sequences can be easily cut out and changed, as known in the art.

Protease recognition sites, known in the art or described herein, can be incorporated into constructs useful for the design, construction, manipulation and production of recombinant engineering polypeptides described herein.

Exemplary Constructs.

Constructs useful in the production of engineered polypeptides contemplated herein include constructs encoding the polypeptides set forth in Table 4 following.

TABLE 4

Selected exemplary constructs for production of engineered polypeptides

| Cmpd | Sequence |
|---|---|
| P1 | MAHHHHHHVGTGSNENLYFQHGEGTFTSDLSKQMEEEAVRLF IEWLKNTGGGGSGGGSGGGSGGGSASLAEAKVLANRELDKYG VSDFYKRLINKAKTVEGVEALKLHILAALP (SEQ ID NO: 156) |
| P2 | MAHHHHHHVGTGSNENLYFQHGEGTFTSDLSKQMEEEAVRLF IEWLKNTGGGGSASLAEAKVLANRELDKYGVSDFYKRLINKA KTVEGVEALKLHILAALP (SEQ ID NO: 157) |
| P3 | MAHHHHHHVGTGSNENLYFQHGEGTFTSDLSKQMEEEAVRLF IEWLKNTGGGGSGGGSGGGSGGGSASLAEAKVLANRELDKYG VSDYYKNIINRAKTVEGVRALKLHILAALP (SEQ ID NO: 158) |
| P4 | MAHHHHHHVGTGSNENLYFQHGEGTFTSDLSKQMEEEAVRLF IEWLKNTGGGGSASLAEAKVLANRELDKYGVSDYYKNIINRA KTVEGVRALKLHILAALP (SEQ ID NO: 159) |
| P5 | MSDKIIHLTDDSFDTDVLKADGAILVDFWAEWCGPCKMIAPI LDEIADEYQGKLTVAKLNIDQNPGTAPKYGIRGIPTLLLFKN GEVAATKVGALSKGQLKEFLDANLAGSGSGHMHHHHHSSGL VPRGSGMKETAAAKFERQHMDSPDLGTENLYFQHGEGTFTSD LSKQLEEEAVRLFIEWLKNGGPSSGAPPPSTGGGGSGGGSGG GSGGGSASLAEAKVLANRELDKYGVSDFYKRLINKAKTVEGV EALKLHILAALP (SEQ ID NO: 160) |
| P6 | MSDKIIHLTDDSFDTDVLKADGAILVDFWAEWCGPCKMIAPI LDEIADEYQGKLTVAKLNIDQNPGTAPKYGIRGIPTLLLFKN GEVAATKVGALSKGQLKEFLDANLAGSGSGHMHHHHHSSGL VPRGSGMKETAAAKFERQHMDSPDLGTENLYFQHGEGTFTSD LSKQMEEEAVRLFIEWLKNTGGGGSGGGSGGGSGGGSASLAE AKVLANRELDKYGVSDYYKNIINRAKTVEGVRALKLHILAAL P (SEQ ID NO: 161) |
| P7 | MSDKIIHLTDDSFDTDVLKADGAILVDFWAEWCGPCKMIAPI LDEIADEYQGKLTVAKLNIDQNPGTAPKYGIRGIPTLLLFKN GEVAATKVGALSKGQLKEFLDANLAGSGSGHMHHHHHSSGL VPRGSGMKETAAAKFERQHMDSPDLGTENLYFQHGEGTFTSD LSKQMEEEAVRLFIEWLKNTGGGGSASLAEAKVLANRELDKY GVSDYYKNIINRAKTVEGVRALKLHILAALP (SEQ ID NO: 162) |

General Methods of Production.

The engineered polypeptide compounds described herein may be prepared using biological, chemical, and/or recombinant DNA techniques that are known in the art. Exemplary methods are described herein and in U.S. Pat. No. 6,872,700; WO 2007/139941; WO 2007/140284; WO 2008/082274; WO 2009/011544; and US Publication No. 2007/0238669, the disclosures of which are incorporated herein by reference in their entireties and for all purposes. Other methods for preparing the compounds are set forth herein.

The engineered polypeptides compounds described herein may be prepared using standard solid-phase peptide synthesis techniques, such as an automated or semiautomated peptide synthesizer. Briefly and generally, the ABD and therapeutic hormonal peptide can be made separately and then conjugated together or can be made as a single polypeptide. Thus, the albumin binding polypeptide, therapeutic hormone or engineered polypeptide may alternatively be produced by non-biological peptide synthesis using amino acids and/or amino acid derivatives having reactive side-chains protected, the non-biological peptide synthesis including step-wise coupling of the amino acids and/or the amino acid derivatives to form a polypeptide according to the first aspect having reactive side-chains protected, removing the protecting groups from the reactive side-chains of the polypeptide, and folding of the polypeptide in aqueous solution. Thus, normal amino acids (e.g. glycine, alanine, phenylalanine, isoleucine, leucine and valine) and pre-protected amino acid derivatives are used to sequentially build a polypeptide sequence, in solution or on a solid support in an organic solvent. When a complete polypeptide sequence is built, the protecting groups are removed and the polypeptide is allowed to fold in an aqueous solution.

Each polypeptide according to the present disclosure reversibly folds, with the ABD domain reversibly folding into a three helix bundle domain without added factors, and hence folds spontaneously. The engineered conjugate may be produced by a method including producing an albumin binding polypeptide according to any method, e.g. as described herein, such as by non-biological peptide synthesis, and conjugating the produced ABD polypeptide with the therapeutic hormone defined herein, the ABDs herein folding completely reversibly. This was assessed by circular dichroism spectra analysis; one spectrum taken at 20° C. and a second spectrum after heating to 90° C. followed by return to 20° C. During this procedure the Tm, as known in the art, was determined and found to be unchanged after the folding of the denatured polypeptide.

Typically, using such techniques, an alpha-N-carbamoyl protected amino acid and an amino acid attached to the growing peptide chain on a resin are coupled at RT in an inert solvent (e.g., dimethylformamide, N-methylpyrrolidinone, methylene chloride, and the like) in the presence of coupling agents (e.g., dicyclohexylcarbodiimide, 1-hydroxybenzo-triazole, and the like) in the presence of a base (e.g., diisopropylethylamine, and the like). The alpha-N-carbamoyl protecting group is removed from the resulting peptide-resin using a reagent (e.g., trifluoroacetic acid, piperidine, and the like) and the coupling reaction repeated with the next desired N-protected amino acid to be added to the peptide chain. Suitable N-protecting groups are well known in the art, such as t-butyloxycarbonyl (tBoc) fluorenylmethoxycarbonyl (Fmoc), and the like. The solvents, amino acid derivatives and 4-methylbenzhydryl-amine resin used in the peptide synthesizer may be purchased from Applied Biosystems Inc. (Foster City, Calif.).

For chemical synthesis solid phase peptide synthesis can be used for the engineered polypeptides, since in general solid phase synthesis is a straightforward approach with excellent scalability to commercial scale, and is generally compatible with relatively long engineered polypeptides. Solid phase peptide synthesis may be carried out with an automatic peptide synthesizer (Model 430A, Applied Biosystems Inc., Foster City, Calif.) using the NMP/HOBt (Option 1) system and tBoc or Fmoc chemistry (See APPLIED BIOSYSTEMS USER'S MANUAL FOR THE ABI 430A PEPTIDE SYNTHESIZER, Version 1.3B Jul. 1, 1988, section 6, pp. 49-70, Applied Biosystems, Inc., Foster City, Calif.) with capping. Boc-peptide-resins may be cleaved with HF (−5° C. to 0° C., 1 hour). The peptide may be extracted from the resin with alternating water and acetic acid, and the filtrates lyophilized. The Fmoc-peptide resins may be cleaved according to standard methods (e.g., Introduction to Cleavage Techniques, Applied Biosystems, Inc., 1990, pp. 6-12). Peptides may also be assembled using an Advanced Chem Tech Synthesizer (Model MPS 350, Louisville, Ky.).

The compounds (exendins, ABDs, linkers, engineered polypeptides) described herein may also be prepared using recombinant DNA techniques using methods known in the art, such as Sambrook et al., 1989, MOLECULAR CLONING: A LABORATORY MANUAL, 2d Ed., Cold Spring Harbor. Non-peptide compounds may be prepared by art-known methods. For example, phosphate-containing amino acids and peptides containing such amino acids, may be prepared using methods known in the art, such as described in Bartlett et al, 1986, Biorg. Chem., 14:356-377. Compounds can be conjugated using art methods or as described herein The engineered polypeptides may alternatively be produced by recombinant techniques well known in the art. See, e.g., Sambrook et al., 1989 (Id.). These engineered polypeptides produced by recombinant technologies may be expressed from a polynucleotide. One skilled in the art will appreciate that the polynucleotides, including DNA and RNA, that encode such engineered polypeptides may be obtained from the wild-type cDNA, e.g. exendin-4, taking into consideration the degeneracy of codon usage, and may further engineered as desired to incorporate the indicated substitutions. These polynucleotide sequences may incorporate codons facilitating transcription and translation of mRNA in microbial hosts. Such manufacturing sequences may readily be constructed according to the methods well known in the art. See, e.g., WO 83/04053, incorporated herein by reference in its entirety and for all purposes. The polynucleotides above may also optionally encode an N-terminal methionyl residue. Non-peptide compounds useful in the present invention may be prepared by art-known methods. For example, phosphate-containing amino acids and peptides containing such amino acids may be prepared using methods known in the art. See, e.g., Bartlett and Landen, 1986, Bioorg. Chem. 14: 356-77.

A variety of expression vector/host systems may be utilized to contain and express a engineered polypeptide coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells that are useful in recombinant protein productions include but are not limited to VERO cells, HeLa cells, Chinese hamster ovary (CHO) cell lines, COS cells (such as COS-7), WI 38, BHK, HepG2, 3T3, RIN, MDCK, A549, PC12, K562 and 293 cells. Exemplary protocols for the recombinant expression of the protein are described herein and/or are known in the art.

As such, polynucleotide sequences are useful in generating new and useful viral and plasmid DNA vectors, new and useful transformed and transfected prokaryotic and eucaryotic host cells (including bacterial, yeast, and mammalian cells grown in culture), and new and useful methods for cultured growth of such host cells capable of expression of the present engineered polypeptides. The polynucleotide sequences encoding engineered polypeptides herein may be useful for gene therapy in instances where underproduction of engineered polypeptides would be alleviated, or the need for increased levels of such would be met.

The present invention also provides for processes for recombinant DNA production of the present engineered polypeptides. Provided is a process for producing the engineered polypeptides from a host cell containing nucleic acids encoding the engineered polypeptide including: (a) culturing the host cell containing polynucleotides encoding the engineered polypeptide under conditions facilitating the expression of the DNA molecule; and (b) obtaining the engineered polypeptides.

Host cells may be prokaryotic or eukaryotic and include bacteria, mammalian cells (such as Chinese Hamster Ovary (CHO) cells, monkey cells, baby hamster kidney cells, cancer cells or other cells), yeast cells, and insect cells.

Mammalian host systems for the expression of the recombinant protein also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing, which cleaves a "prepro" form of the protein, may also be important for correct insertion, folding and/or function. Different host cells, such as CHO, HeLa, MDCK, 293, WI38, and the like, have specific cellular machinery and characteristic mechanisms for such post-translational activities, and may be chosen to ensure the correct modification and processing of the introduced foreign protein.

Alternatively, a yeast system may be employed to generate the engineered polypeptides of the present invention. The coding region of the engineered polypeptides DNA is amplified by PCR. A DNA encoding the yeast pre-pro-alpha leader sequence is amplified from yeast genomic DNA in a PCR reaction using one primer containing nucleotides 1-20 of the alpha mating factor gene and another primer complementary to nucleotides 255-235 of this gene (Kurjan and Herskowitz, 1982, Cell, 30: 933-43). The pre-pro-alpha leader coding sequence and engineered polypeptide coding sequence fragments are ligated into a plasmid containing the yeast alcohol dehydrogenase (ADH2) promoter, such that the promoter directs expression of a fusion protein consisting of the pre-pro-alpha factor fused to the mature engineered polypeptide. As taught by Rose and Broach, (Rose & Broach, 1990, Meth. Enz., 185: 234-79, Goeddel ed., Academic Press, Inc., San Diego, Calif.), the vector further includes an ADH2 transcription terminator downstream of the cloning site, the yeast "2-micron" replication origin, the yeast leu-2d gene, the yeast REP1 and REP2 genes, the E. coli beta-lactamase gene, and an E. coli origin of replication. The beta-lactamase and leu-2d genes provide for selection in bacteria and yeast, respectively. The leu-2d gene also facilitates increased copy number of the plasmid in yeast to induce higher levels of expression. The REP1 and REP2 genes encode proteins involved in regulation of the plasmid copy number.

The DNA construct described in the preceding paragraph is transformed into yeast cells using a known method, e.g., lithium acetate treatment (Steams et al., 1990, Meth. Enz. 185: 280-297). The ADH2 promoter is induced upon exhaustion of glucose in the growth media (Price et al., 1987, Gene 55:287). The pre-pro-alpha sequence effects secretion of the fusion protein from the cells. Concomitantly, the yeast KEX2 protein cleaves the pre-pro sequence from the mature engineered polypeptides (Bitter et al., 1984, Proc. Natl. Acad. Sci. USA 81:5330-5334).

Engineered polypeptides of the invention may also be recombinantly expressed in yeast, e.g. Pichia, using a commercially available expression system, e.g., the *Pichia* Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol. The secreted engineered polypeptide is purified from the yeast growth medium by, e.g., the methods used to purify said engineered polypeptide from bacterial and mammalian cell supernatants.

Alternatively, the DNA encoding a engineered polypeptide may be cloned into a baculovirus expression vector, e.g. pVL1393 (PharMingen, San Diego, Calif.). This engineered-polypeptide-encoding vector is then used according to the manufacturer's directions (PharMingen) or known techniques to infect *Spodoptera frugiperda* cells, grown for example in sF9 protein-free media, and to produce recombinant protein. The protein is purified and concentrated from the media using methods known in the art, e.g. a heparin-Sepharose column (Pharmacia, Piscataway, N.J.) and sequential molecular sizing columns (Amicon, Beverly, Mass.), and resuspended in appropriate solution, e.g. PBS. SDS-PAGE analysis can be used to characterize the protein, for example by showing a single band that confirms the size of the desired engineered polypeptide, as can full amino acid amino acid sequence analysis, e.g. Edman sequencing on a Proton 2090 Peptide Sequencer, or confirmation of its N-terminal sequence.

For example, the DNA sequence encoding the predicted mature engineered polypeptide may be cloned into a plasmid containing a desired promoter and, optionally, a leader sequence (see, e.g., Better et al., 1988, *Science* 240:1041-1043). The sequence of this construct may be confirmed by automated sequencing. The plasmid is then transformed into *E. coli*, strain MC1061, using standard procedures employing CaCl2 incubation and heat shock treatment of the bacteria (Sambrook et al., Id.). The transformed bacteria are grown in LB medium supplemented with carbenicillin, and production of the expressed protein is induced by growth in a suitable medium. If present, the leader sequence will affect secretion of the mature engineered polypeptide and be cleaved during secretion. The secreted recombinant engineered polypeptide is purified from the bacterial culture media by the method described herein.

Alternatively, the engineered polypeptides may be expressed in an insect system. Insect systems for protein expression are well known to those of skill in the art. In one such system, Autographa californica nuclear polyhedrosis virus (AcNPV) is used as a vector to express foreign genes in *Spodoptera frugiperda* cells or in *Trichoplusia* larvae. The engineered polypeptide coding sequence is cloned into a nonessential region of the virus, such as the polyhedrin gene, and placed under control of the polyhedrin promoter. Successful insertion of a engineered polypeptide will render the polyhedrin gene inactive and produce recombinant virus lacking coat protein coat. The recombinant viruses are then used to infect *S. frugiperda* cells or *Trichoplusia* larvae in which engineered polypeptide of the present invention is expressed (Smith et al., 1983, *J. Virol.* 46:584; Engelhard et al., 1994, *Proc. Natl. Acad. Sci. USA* 91:3224-3227).

In another example, the DNA sequence encoding the engineered polypeptides may be amplified by PCR and cloned into an appropriate vector, for example, pGEX-3x (Pharmacia, Piscataway, N.J.). The pGEX vector is designed to produce a fusion protein including glutathione-S-transferase (GST), encoded by the vector, and a protein encoded by a DNA fragment inserted into the vector's cloning site. The primers for the PCR may be generated to include, for example, an appropriate cleavage site. The recombinant fusion protein may then be cleaved from the GST portion of the fusion protein. The pGEX-3x/engineered polypeptide construct is transformed into *E. coli* XL-1 Blue cells (Stratagene, La Jolla, Calif.), and individual transformants are isolated and grown at 37 degrees C. in LB medium (supplemented with carbenicillin) to an optical density at wavelength 600 nm of 0.4, followed by further incubation for 4 hours in the presence of 0.5 mM Isopropyl beta-D-Thiogalactopyranoside (Sigma Chemical Co., St. Louis, Mo.). Plasmid DNA from individual transformants is purified and partially sequenced using an automated sequencer to confirm the presence of the desired engineered polypeptide-encoding gene insert in the proper orientation.

The fusion protein, when expected to be produced as an insoluble inclusion body in the bacteria, may be purified as described above or as follows. Cells are harvested by centrifugation; washed in 0.15 M NaCl, 10 mM Tris, pH 8, 1 mM EDTA; and treated with 0.1 mg/mL lysozyme (Sigma Chemical Co.) for 15 min. at RT. The lysate is cleared by sonication, and cell debris is pelleted by centrifugation for 10 min. at 12,000×g. The fusion protein-containing pellet is resuspended in 50 mM Tris, pH 8, and 10 mM EDTA, layered over 50% glycerol, and centrifuged for 30 min. at 6000×g. The pellet is resuspended in standard phosphate buffered saline solution (PBS) free of $Mg^{++}$ and $Ca^{++}$. The fusion protein is further purified by fractionating the resuspended pellet in a denaturing SDS polyacrylamide gel (Sambrook et al., supra). The gel is soaked in 0.4 M KCl to visualize the protein, which is excised and electroeluted in gel-running buffer lacking SDS. If the GST/engineered polypeptide fusion protein is produced in bacteria as a soluble protein, it may be purified using the GST Purification Module (Pharmacia Biotech).

The fusion protein may be subjected to digestion to cleave the GST from the mature engineered polypeptide. The digestion reaction (20-40 μg fusion protein, 20-30 units human thrombin (4000 U/mg (Sigma) in 0.5 mL PBS) is incubated 16-48 hrs. at RT and loaded on a denaturing SDS-PAGE gel to fractionate the reaction products. The gel is soaked in 0.4 M KCl to visualize the protein bands. The identity of the protein band corresponding to the expected molecular weight of the engineered polypeptide may be confirmed by partial amino acid sequence analysis using an automated sequencer (Applied Biosystems Model 473A, Foster City, Calif.).

In a particularly exemplary method of recombinant expression of the engineered polypeptides of the present invention, mammalian 293 cells may be co-transfected with plasmids containing the engineered polypeptides cDNA in the pCMV vector (5' CMV promoter, 3' HGH poly A sequence) and pSV2neo (containing the neo resistance gene) by the calcium phosphate method. In one embodiment, the vectors should be linearized with ScaI prior to transfection. Similarly, an alternative construct using a similar pCMV vector with the neo gene incorporated can be used. Stable cell lines are selected from single cell clones by limiting dilution in growth media containing 0.5 mg/mL G418 (neomycin-like antibiotic) for 10-14 days. Cell lines are screened for engineered polypeptides expression by ELISA or Western blot, and high-expressing cell lines are expanded for large scale growth.

It is preferable that the transformed cells are used for long-term, high-yield protein production and as such stable expression is desirable. Once such cells are transformed with vectors that contain selectable markers along with the desired expression cassette, the cells may be allowed to grow for 1-2 days in an enriched media before they are switched to selective media. The selectable marker is designed to confer resistance to selection, and its presence allows growth and recovery of cells that successfully express the introduced sequences. Resistant clumps of stably transformed cells can be proliferated using tissue culture techniques appropriate to the cell.

A number of selection systems may be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to methotrexate; gpt, that confers resistance to mycophenolic acid; neo, that confers resistance to the aminoglycoside, G418; also, that confers resistance to chlorsulfuron; and hygro, that confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, beta-glucuronidase and its substrate, GUS, and luciferase and its substrate, luciferin.

The engineered polypeptides of the present invention may be produced using a combination of both automated peptide synthesis and recombinant techniques. For example, either or both the exendin compound and the ABD, and optionally a linker, can be made synthetically or recombinantly and then ligated together using methods known in the art, such as "native chemical ligation" and known variations thereof in which an amide bond is formed joining the parent compounds. See, e.g., U.S. Pat. No. 6,326,468, which is incorporated herein by reference and for all purposes. Alternatively, for example, an engineered polypeptide of the present invention may contain a combination of modifications including deletion, substitution, insertion and derivatization by PEGylation (or other moiety, e.g. polymer, fatty acyl chain, C-terminal amidation). Such an engineered polypeptide may be produced in stages. In the first stage, an intermediate engineered polypeptide containing the modifications of deletion, substitution, insertion, and any combination thereof, may be produced by recombinant techniques as described. Then after an optional purification step as described herein, the intermediate engineered polypeptide is PEGylated (or subjected to other chemical derivatization, e.g., acylation, C-terminal amidation) through chemical modification with an appropriate PEGylating reagent (e.g., from NeKtar Transforming Therapeutics, San Carlos, Calif.) to yield the desired engineered polypeptide derivative. One skilled in the art will appreciate that the above-described procedure may be generalized to apply to a engineered polypeptide containing a combination of modifications selected from deletion, substitution, insertion, derivation, and other means of modification well known in the art and contemplated by the present invention.

C-terminal amidation can be achieved by use of a glycine amino acid-C-terminally extended precursor, synthesized for example in yeast (e.g. *Pichia*) as alpha-factor fusion protein that will be secreted into culture medium. After purification, the C-terminal glycine of the engineered polypeptide precursor can be converted to amide by enzymatic amidation, e.g. peptidylglycine alpha-amidating monooxygenase (PAM). See e.g., Cooper et al., 1989, *Biochem. Biophys. Acta*, 1014:247-258. See also U.S. Pat. No. 6,319, 685, which is incorporated herein by reference in its entirety and for all purposes, which teaches methods for enzymatic amidation, including an alpha-amidating enzyme from rat being sufficiently pure in alpha-amidating enzyme to exhibit a specific activity of at least about 25 mU per mg of protein, and being sufficiently free of proteolytic impurities to be suitable for use with substrates purified from natural sources or produced by recombinant DNA techniques.

Peptides may be purified by any number of methods known in the art, including as described herein In one method peptides are purified by RP-HPLC (preparative and analytical) using a Waters Delta Prep 3000 system. A C4, C8 or C18 preparative column (10μ, 2.2×25 cm; Vydac, Hesperia, Calif.) may be used to isolate peptides, and purity may be determined using a C4, C8 or C18 analytical column (5μ, 0.46×25 cm; Vydac). Solvents (A=0.1% TFA/water and B=0.1% TFA/$CH_3CN$) may be delivered to the analytical column at a flow rate of 1.0 ml/min and to the preparative column at 15 ml/min. Amino acid analyses may be performed on the Waters Pico Tag system and processed using the Maxima program. Peptides may be hydrolyzed by vapor-phase acid hydrolysis (115° C., 20-24 h). Hydrolysates may be derivatized and analyzed by standard methods (Cohen et al, THE PICO TAG METHOD: A MANUAL OF ADVANCED TECHNIQUES FOR AMINO ACID ANALYSIS, pp. 11-52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer.

Engineered Polypeptide Expression Assay.

Methods are available for assaying the level of protein expression by a host cell. Procedures useful for assaying the level of protein expression by a host cell are exemplified in the following typical protocol. About 25 ul BL21 *E. coli* cells are transformed with 2 ul plasmid DNA (expression vector for the engineered polynucleotide). Cells can be plated and incubated overnight at 37 degrees C. or at room temperature (RT) over a 48-hr period. A single colony can be selected and used to grow starter culture in 4 ml LB media with appropriate antibiotic for ~6 hrs. Glycerol stocks can be prepared by adding 100 ul 80% sterile glycerol to 900 ul stock, which can then be mixed gently and stored at −80 C. A 250 ul sample can be removed for TCP uninduced sample. An aliquot, for example, 2 ml of Magic media containing appropriate antibiotic can be inoculated with 5 ul starter culture, which can then be incubated overnight (up to 24 hrs) at 37 C, 300 rpm. As known in the art, Magic Media is autoinducing. Alternatively, 60 ml Magic Media containing appropriate antibiotic can be inoculated with 60 ul starter culture in a 250 ml or 125 ml Thompson flask, which can then be incubated overnight (up to 24 hrs) at 30 C, 300 rpm. After incubation, 250 ul culture can be removed from each tube and the cells pelleted. The cell can be resuspended in 1 ml 50 mM Tris pH 8, 150 mM NaCl, to which can be added 0.1 volumes (100 ul) POP culture reagent and 1 ul r-lysozyme (1:750 dilution in r-lysozyme buffer). The mixture can be mixed well and incubated at least 10 min at RT. The preparation can then be centrifuge 10 min at 14000×G. The supernatant (soluble fraction) can be removed and retained, and samples can be prepared for gel analysis (15 ul+5 ul LDS). The remaining inclusion body pellet can be resuspended in 1 ml 1% SDS with sonication. The sample can be prepared for gel analysis (15 ul+5 ul LDS). For uninduced samples, 1.0 volumes POP culture reagent and 1 ul r-lysozyme (1:750 dilution in r-lysozyme buffer) can be added. The mixture can be mixed well and incubated at least 10 min at RT. These samples may not need to be centrifuged. The sample can then be prepared for gel analysis (15 ul+5 ul LDS). NU-PAGE gels (4-12%) non-reduced in 1×MES buffer can be run and stained with SimplyBlue microwave protocol. Destaining can be conducted overnight, as known in the art. A gel image can be retained, and analyzed to determine protein expression levels.

Engineered polypeptides can be and were expressed and isolated as follows. A protein sequence of the desired engineered polypeptide was designed and back translated using commercial software to a DNA sequence for cloning into an E. coli expression vector. Nucleic acid sequences were either obtained as oligonucleotides and ligated using standard PCR amplification techniques, or were digested from existing expression constructs using standard restriction enzymes and then ligated together. Sequences expressing the protein of interest were placed in plasmid pET45 with a T7 promoter for inducible expression. After constructs were verified by sequencing, the vector DNA was purified and transformed into an expression host, typically BL21(DE3). A single colony was selected to grow a starter culture in 4 ml LB media for ~6 hrs. Glycerol stocks were prepared by adding 100 ul 80% glycerol to 900 ul stock and stored at –80 C. Optionally, 500 ul of un-induced sample was retained for gel analysis. A 60 ml culture (e.g. Magic-Media™ E. coli Expression Medium; Invitrogen, USA; see Glenn et al., J. Biol. Chem. 2008, 283(19):12717-29) was inoculated using 60 ul starter culture in a 125 ml Thompson flask and incubated at 30 degrees C. overnight. Removed 250 ul sample for analysis. The cells were collected as a pellet by centrifuging, and frozen for later processing. Preparation of cell extract and first pass purification with Nickel resin was performed as follows. E. coli cell pellets were completely resuspended in a volume of lysis buffer (50 mM TrisHCl, 150 mM NaCl, pH 8.0) equal to the starting culture volume. Cells were then subjected to a microfluidizer (Microfluidics, MA) at 100 psi for three times. Cell extracts were centrifuged for 30 minutes at 16,000×g to remove debris. EGTA (150 mM stock) was added to the cell extract to a final concentration of 3 mM EGTA. The lysate was then applied to a Ni-NTA Superflow column that had been washed and pre-equilibrated. Protein bound to the column was then washed with lysis buffer plus EGTA (50 mM TrisHCl, 150 mM NaCl, pH8.0, 3 mM EGTA) before the bound protein was eluted with 50 mL of elution buffer (25 mM TrisHCl, 50 mM NaCl, 250 mM Imidazol, pH8.0). Cleavage of His-Tag and subsequent purification was as follows. The eluted protein was concentrated with Amicon-Ultra15 centrifugal filter unit (Millipore, USA) and then diluted with 25 mM TrisHCl, pH8.0, 50 mM NaCl to prepare for protease digestion which removes the HisTag from the N-terminus of the desired protein. Added was 0.1% of β-mercaptoethanol and 1% of Turbo TEV protease (2 mg/mL, 10,000 units/mg; Excellgen, USA) to the protein solution, which was mixed and incubated at room temperature for 4 hours and then at 4° C. over night. An Ni-NTA Superflow column (Qiagen, USA) was pre-equilibrated with 50 mM TrisHCl, 100 mM NaCl, 45 mM imidazole, pH8.0. The TEV digest reaction was diluted 2-fold with 50 mM TrisHCl, 150 mM NaCl, pH8.0. The diluted digest reaction was carefully applied to the top of Ni-NTA column and flow-through was collected. To the column was added 10 mL of 50 mM trisHCl, 100 mM NaCl, 45 mM imidazole, pH8.0 to elute any unbound protein. The eluted proteins from the column were collected and combined, and then polished using size exclusion chromatography (2× with Superdex 75 HiLoad 26/60 column; GE Healthcare Biosciences, USA). Any remaining bacterial endotoxin was removed using EndoTrap Red (Lonza, Switzerland) according to manufacturer's instructions.

Inclusion Body Preparation.

For engineered polypeptides that are found in the inclusion body fraction, the following procedure can be beneficial. The cell pellet can be resuspended in a minimum of 100 ml Lysis buffer for each 50 ml culture. Upon the addition of 30 ml, a 10 ml pipette can be used to resuspend, then the tube can be washed out with an additional 70 ml. The resuspended cell solution can be multiply run, e.g., 4 passes, through a microfluidizer@ 100 PSI (min) taking care to keep chamber in ice water through the entire process. The fluidized slurry can be centrifuged at 14000×g, 20 min (e.g., JLA 10.5, 10,000 rpm, using 250 ml nalgene bottles). The inclusion body pellet can be resuspended on ice in chilled lysis buffer with stir bar and stir plate for 1 hour at 4 C after disruption with pipette tip. The pellet can be resuspended a second time in distilled $H_2O$ with stir bar and stir plate for 1 hour at 4 C after disruption with pipette tip, followed by centrifugation at 14000×g, 15 min. The supernatant can be removed and discarded. The resultant can be stored at –80 C.

Protein Purification.

As described herein, numerous methods are known for isolation of expressed polypeptides. Preferred are secreted engineered polypeptides. However, the following is one example if inclusion bodies are formed. Inclusion body pellets can be solubilized in appropriate volume of solubilization buffer (8M urea or 8M guanidine, 50 mM Tris, 10 mM DTT, pH 7.75) for 1 hour at RT. The solubilized pellets can be centrifuged for 20 min at 27 000 g. Filtered (e.g., 0.4 um) supernatant can be transferred drop by drop into appropriate volume of refolding buffer (50 mM Tris-HCl, 1 M urea, 0.8 M arginine, 4 mM cysteine, 1 mM cystamine; pH 8) at RT. The result can then be placed at 4° C. overnight or longer with gentle mixing. Samples can be concentrated and run on a gel filtration column (Superdex75 26/60) at 1-2 ml/min in 4 C environment using a GE Healthsciences AKTA FPLC. Appropriate protein containing fractions can be identified via SDS-PAGE, pooled and run through a second gel filtration column. Pooled protein can then be concentrated in Amicon filter to appropriate concentration and assayed for endotoxin levels using, e.g., Endosafe PTS Reader (Charles River), as known in the art. Once a protein sample has passed the endotoxin criteria, it can be sterile filtered, dispensed into aliquots and run through quality control assays. Quality control assays can include analytical HPLC-SEC, non reducing SDS PAGE and RP HPLC-MS to obtain approximate mass. Proteins can be obtained in 1×PBS (137 mM sodium chloride, 2.7 mM potassium chloride, 4.3 mM disodium phosphate, 1.4 mM monopotassium phosphate, pH7.2), distributed into aliquots and flash frozen for storage at –70 to –80° C.

IV. Methods of Use and Treating Disease

Indications.

A variety of diseases and disorders are contemplated to be beneficially treated by the polypeptide compounds and methods described herein.

Obesity and Overweight.

Obesity and its associated disorders including overweight are common and serious public health problems in the United States and throughout the world. Upper body obesity is the strongest risk factor known for type 2 diabetes mellitus and is a strong risk factor for cardiovascular disease. Obesity is a recognized risk factor for hypertension, atherosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia. See, e.g., Kopelman, 2000, *Nature* 404:635-43.

Obesity reduces life-span and carries a serious risk of the co-morbidities listed above, as well disorders such as infections, varicose veins, acanthosis nigricans, eczema, exercise intolerance, insulin resistance, hypertension hypercholesterolemia, cholelithiasis, orthopedic injury, and thromboembolic disease. See e.g., Rissanen et al, 1990, *Br. Med. J.*, 301:835-7. Obesity is also a risk factor for the group of conditions called insulin resistance syndrome, or "Syndrome X" and metabolic syndrome. The worldwide medical cost of obesity and associated disorders is enormous.

The pathogenesis of obesity is believed to be multifactoral. A problem is that, in obese subjects, nutrient availability and energy expenditure do not come into balance until there is excess adipose tissue. The central nervous system (CNS) controls energy balance and coordinates a variety of behavioral, autonomic and endocrine activities appropriate to the metabolic status of the animal. The mechanisms or systems that control these activities are broadly distributed across the forebrain (e.g., hypothalamus), hindbrain (e.g., brainstem), and spinal cord. Ultimately, metabolic (i.e., fuel availability) and cognitive (i.e., learned preferences) information from these systems is integrated and the decision to engage in appetitive (food seeking) and consummatory (ingestion) behaviors is either turned on (meal procurement and initiation) or turned off (meal termination). The hypothalamus is thought to be principally responsible for integrating these signals and then issuing commands to the brainstem. Brainstem nuclei that control the elements of the consummatory motor control system (e.g., muscles responsible for chewing and swallowing). As such, these CNS nuclei have literally been referred to as constituting the "final common pathway" for ingestive behavior.

Neuroanatomical and pharmacological evidence support that signals of energy and nutritional homeostasis integrate in forebrain nuclei and that the consummatory motor control system resides in brainstem nuclei, probably in regions surrounding the trigeminal motor nucleus. There are extensive reciprocal connection between the hypothalamus and brainstem. A variety of CNS-directed anti-obesity therapeutics (e.g., small molecules and peptides) focus predominantly upon forebrain substrates residing in the hypothalamus and/or upon hindbrain substrates residing in the brainstem.

Obesity remains a poorly treatable, chronic, essentially intractable metabolic disorder. Accordingly, a need exists for new therapies useful in weight reduction and/or weight maintenance in a subject. Such therapies would lead to a profound beneficial effect on the subject's health.

Diabetes and Cardiovascular Disease.

Diabetes mellitus is recognized as a complex, chronic disease in which 60% to 70% of all case fatalities among diabetic patients are a result of cardiovascular complications. Diabetes is not only considered a coronary heart disease risk equivalent but is also identified as an independent predictor of adverse events, including recurrent myocardial infarction, congestive heart failure, and death following a cardiovascular incident. The adoption of tighter glucose control and aggressive treatment for cardiovascular risk factors would be expected to reduce the risk of coronary heart disease complications and improve overall survival among diabetic patients. Yet, diabetic patients are two to three times more likely to experience an acute myocardial infarction than non-diabetic patients, and diabetic patients live eight to thirteen years less than non-diabetic patients.

Understanding the high risk nature of diabetic/acute myocardial infarction patients, the American College of Cardiology/American Heart Association ("ACC/AHA") clinical practice guidelines for the management of hospitalized patients with unstable angina or non-ST-elevation myocardial infarction (collectively referred to as "ACS") recently recognized that hospitalized diabetic patients are a special population requiring aggressive management of hyperglycemia. Specifically, the guidelines state that glucose-lowering therapy for hospitalized diabetic/ACS patients should be targeted to achieve preprandial glucose less than 10 mg/dL, a maximum daily target than 180 mg/dL, and a post-discharge hemoglobin A1c less than 7%.

In a nationwide sample of elderly ACS patients, it was demonstrated that an increase in 30-day mortality in diabetic patients corresponded with the patients having higher glucose values upon admission to the hospital. See "Diabetic Coronary Artery Disease & Intervention," *Coronary Therapeutics* 2002, Oak Brook, Ill., Sep. 20, 2002. There is increasing evidence that sustained hyperglycemia rather than transient elevated glucose upon hospital admission is related to serious adverse events. Although the ideal metric for hyperglycemia and vascular risk in patients is not readily known, it appears that the mean glucose value during hospitalization is most predictive of mortality. In a separate study of ACS patients form over forty hospitals in the United States, it was found that persistent hyperglycemia, as opposed to random glucose values upon admission to the hospital, was more predictive of in-hospital mortality. See *Acute Coronary Syndrome Summit: A State of the Art Approach*, Kansas City, Mo., Sep. 21, 2002. Compared with glucose values upon admission, a logistic regression model of glucose control over the entire hospitalization was most predictive of mortality. There was nearly a two-fold increased risk of mortality during hospitalization for each 10 mg/dL increase in glucose over 120 mg/dL. In a smaller cohort of consecutive diabetic/ACS patients, there was a graded increase in mortality at one year with increasing glucose levels upon hospital admission. In the hospital setting, the ACC/AHA guidelines suggest initiation of aggressive insulin therapy to achieve lower blood glucose during hospitalization.

Lipid Regulation Diseases.

Dyslipidemia is a disruption in the normal lipid component in the blood. It is believed that prolonged elevation of insulin levels can lead to dyslipidemia. Hyperlipidemia is the presence of raised or abnormal levels of lipids and/or lipoproteins in the blood. Fatty liver disease, e.g., nonalcoholic fatty liver disease (NAFLD) refers to a wide spectrum of liver disease ranging from simple fatty liver (steatosis), to nonalcoholic steatohepatitis (NASH), to cirrhosis (irreversible, advanced scarring of the liver). All of the stages of NAFLD have in common the accumulation of fat (fatty infiltration) in the liver cells (hepatocytes).

Additionally, without wishing to be bound by any theory, it is believed that relative insulin deficiency in type 2 diabetes, glucose toxicity, and increased hepatic free fatty acid burden through elevated delivery from intra-abdominal adipose tissue via the portal vein, are implicated as possible causes in fatty liver disorders. Indeed, it has been hypothesized that eating behavior is the key factor driving the metabolic syndrome of obesity with its many corollaries, including NASH. Accordingly, treatments aimed at decreasing food intake and increasing the number of small meals, as has already been demonstrated in type 2 diabetes, may effectively treat and prevent NASH. Drugs that promote insulin secretion and weight loss, and delay gastric emptying are also effective at improving glucose tolerance and thus may improve fatty liver with its attendant hyperinsulinemia. Thus, use of exendins, exendin analog agonists, exendin derivative agonists, particularly exendin-4, can be well suited as a treatment modality for this condition. Accordingly, engineered polypeptides described herein which include an exendin or biologically active (hormone domain) peptide component, or fragment or analog thereof, can be useful in the treatment of fatty liver disorders.

Alzheimer's Disease.

Alzheimer's disease (AD), as known in the art, is associated with plaques and tangles in the brain which include dysregulation of the A-beta protein. Stimulation of neuronal GLP-1 receptors has been reported to play an important role in regulating neuronal plasticity and cell survival. GLP-1 has been reported to induce neurite outgrowth and to protect against excitotoxic cell death and oxidative injury in cultured neuronal cells. GLP-1 and exendin-4 were reported to reduce endogenous levels of amyloid-beta peptide (A-beta protein) in mouse brain and to reduce levels of beta-amyloid precursor protein (beta-APP) in neurons. See, e.g., Perry et al., 2004, *Curr. Drug Targets* 5(6):565-571. Treatment with the engineered compounds disclosed herein can provide benefit to the therapeutic targets associated with Alzheimer's disease.

Parkinson's Disease.

Parkinson's disease (PD) is the synonym of "primary parkinsonism", i.e. isolated parkinsonism due to a neurodegenerative process without any secondary systemic cause. Parkinsonism is characterized by symptoms of tremor, stiffness, and slowing of movement caused by loss of dopamine. Without wishing to be bound by any theory, it is believed that exendin-4 may act as a survival factor for dopaminergic neurons by functioning as a microglia-deactivating factor and suggest that exendin-4 may be a valuable therapeutic agent for neurodegenerative diseases such as PD.

Metabolic Syndrome X.

Metabolic Syndrome X is characterized by insulin resistance, dyslipidemia, hypertension, and visceral distribution of adipose tissue, and plays a pivotal role in the pathophysiology of type 2 diabetes. It has also been found to be strongly correlated with NASH, fibrosis, and cirrhosis of the liver. Accordingly, engineered polypeptides described herein can be useful in the treatment of metabolic syndrome X.

Steroid Induced Diabetes.

Glucocorticoids are well known to affect carbohydrate metabolism. In response to exogenous glucocorticoid administration, increased hepatic glucose production and reduced insulin secretion and insulin-stimulated glucose uptake in peripheral tissues is observed. Furthermore, glucocorticoid treatment alters the proinsulin (P1)/immunoreactive insulin (IRI) ratio, as known in the art. Typical characteristics of the hyperglycemia induced by glucocorticoids in subjects without diabetes include a minimal elevation of fasting blood glucose, exaggerated postprandial hyperglycemia, insensitivity to exogenous insulin, and non-responsiveness to metformin or sulfonylurea therapy. Accordingly, engineered polypeptides described herein which include an exendin biologically active (hormone domain) peptide component, or fragment or analog thereof, can be useful in the treatment of steroid induced diabetes.

Human Immunodeficiency Virus (HIV) Treatment-Induced Diabetes.

Shortly after the introduction of human immunodeficiency virus (HIV)-1 protease inhibitors (PIs) into routine clinical use, reports linking PT use with the development of hyperglycemia began to appear. While approximately 1% to 6% of HIV-infected subjects who are treated with PIs will develop diabetes mellitus, a considerably larger proportion will develop insulin resistance and impaired glucose tolerance. Accordingly, engineered polypeptides described herein which include an exendin biologically active (hormone domain) peptide component, or fragment or analog thereof, can be useful in the treatment of HIV treatment-induced diabetes.

Latent Autoimmune Diabetes in Adults (LADA).

Progressive autoimmune diabetes, also known as latent autoimmune diabetes in adults (LADA), is thought to be present in approximately 10% of patients diagnosed with type 2 diabetes. LADA patients have circulating antibodies to either islet cell cytoplasmic antigen or, more frequently, glutamic acid decarboxylase. These subjects exhibit clinical features characteristic of both type 1 and type 2 diabetes. Although insulin secretion is better preserved in the slowly progressing than in the rapidly progressing form of autoimmune diabetes, insulin secretion tends to deteriorate with time in LADA subjects. Accordingly, engineered polypeptides described herein which include an exendin biologically active (hormone domain) peptide component, or fragment or analog thereof, can be useful in the treatment of LADA.

Hypoglycemia Unawareness (HU).

Defective glucose counterregulation can occur even after only a single recent episode of hypoglycemia. Subjects who experience repeated episodes of hypoglycemia often lose their capacity to recognize the symptoms typically associated with hypoglycemia or impending insulin shock, a condition called "hypoglycemia unawareness". Because the patient doesn't appreciate his or her own status, blood glucose levels can then fall so low that serious neurological problems ensue, including coma and seizure. Accordingly, engineered polypeptides described herein which include an exendin biologically active (hormone domain) peptide component, or fragment or analog thereof, can be useful in the treatment of HU.

Restrictive Lung Disease.

GLP 1 receptor has been localized in the lung. Exendins can elicit a biological response via GLP-1 receptor. In particular, sarcoidosis is a systemic granulomatous disease that frequently involves the lung. Although classically thought of as a restrictive lung disease, airway obstruction has become a recognized feature of the disease in the past years. Sarcoidosis can affect the airway at any level and when the involvement includes small airways, it can resemble more common obstructive airway diseases, such as asthma and chronic bronchitis. Accordingly, engineered polypeptides described herein which include an exendin biologically active (hormone domain) peptide component, or fragment or analog thereof, can be useful in the treatment of restrictive lung disease because such hormone domain peptide can improve elasticity of lung or delay rigidity.

Short Bowel Syndrome (SBS).

Exendin-4 has been reported as effective for the treatment of short bowel syndrome. See Kunkel et al. Neurogastroenterol. Motil. (2011). SBS is a serious clinical disorder characterized by diarrhea and nutritional deprivation. Glucagon-like peptide-1 (GLP-1), produced by L-cells in the ileum, regulates proximal gut transit. When extensive ileal resection occurs, as in SBS, GLP-1 levels may be deficient.

Exenatide improved the nutritional state and intestinal symptoms of patients with SBS. Accordingly, SBS patients are amenable to treatment with the engineered polypeptides described herein. Improvement in bowel frequency and form and obtaining bowel movements that are no longer meal-related can be achieved. An additional benefit is that total parenteral nutrition can be stopped. These compounds herein will provide substantial improvement in the bowel habits, nutritional status and quality of life of SBS patients, and further may reduce the need for parenteral nutrition and small bowel transplant.

Accordingly, in one aspect, there is provided a method for treating a disease or disorder in a subject. The subject is in need of treatment for the disease or disorder. In some embodiments, the subject is need of treatment is obese. The disease or disorder is diabetes, overweight, obesity, Alzheimer's disease, fatty liver disease, dyslipidemia, coronary artery disease, stroke, SBS or hyperlipidemia, or other diseases discussed herein. Diabetes can include type I, type II, gestational or pre-diabetes as well as HIV or steroid induced diabetes. The method of treatment includes administration to the subject of a engineered polypeptide as described herein in an amount effective to treatment the disease or disorder. Particularly useful for these diseases are compounds described herein having glucose lowering activity (e.g. exendin-4 or its fragments or analogs linked to an ABD), having reduction of body weight or reduction of food intake activity, lowering of HbA1c, delaying of gastric emptying, lowering of plasma glucagon, and/or intestinal motility benefit.

In some embodiments, the disease or disorder is diabetes, overweight or obesity, or dyslipidemia or hyperlipidemia. The engineered polypeptide can include ABD and HD1 polypeptides, and optionally a linker K1, where HD1 is an exendin or fragment or analog thereof. Accordingly, the engineered polypeptide can have one of the following structures: HD1-ABD or HD1-L1-ABD.

In some embodiments, the disease or disorder is diabetes, overweight, obesity, dyslipidemia, Alzheimer's disease, fatty liver disease, SBS or hyperlipidemia. The engineered polypeptide may include an exendin or fragment or analog thereof. Accordingly, the engineered polypeptide can have one of the following structures: HD1-ABD or HD1-L1-ABD. In some embodiments, the exendin in the engineered polypeptide is exendin-4. In some embodiments, the exendin fragment is a fragment of exendin-4. In some embodiments, the exendin analog has at least 70%, for example 70%, 75%, 80%, 85%, 90%, 95% or even higher, identity with exendin-4. Particularly useful for these diseases are compounds described herein having glucose lowering activity (e.g. exendin-4 or its fragments or analogs linked to an ABD), having reduction of body weight or reduction of food intake activity, lowering of HbA1c, delaying of gastric emptying, lowering of plasma glucagon, or intestinal motility benefit.

In some embodiments, the disease or disorder is diabetes, overweight, obesity, dyslipidemia, Alzheimer's disease, fatty liver disease, SBS or hyperlipidemia. The engineered polypeptide may include an exendin or fragment or analog thereof. Accordingly, the engineered polypeptide can have one of the following structures: HD1 ABD or HD1 L1 ABD. In some embodiments, the exendin is exendin-4. In some embodiments, the exendin fragment is a fragment of exendin-4. In some embodiments, the exendin analog has at least 70%, for example 70%, 75%, 80%, 85%, 90%, 95% or even higher, identity with exendin-4. Particularly useful for these diseases are compounds described herein having glucose lowering activity (e.g. exendin-4 or its fragments or analogs linked to an ABD), having reduction of body weight or reduction of food intake activity, delaying of gastric emptying, lowering of plasma glucagon, or intestinal motility benefit. The engineered polypeptide can include only exendin, or analog or fragment thereof, as a hormone domain.

The disease or disorder can be diabetes, overweight, obesity, dyslipidemia, Alzheimer's disease, fatty liver disease, SBS, hyperlipidemia, Parkinson's disease or cardiovascular disease or other diseases described herein. The engineered polypeptide may include an exendin or fragment or analog thereof. Accordingly, the engineered polypeptide can have one of the following structures: HD1 ABD or HD1 L1 ABD. In some embodiments, the exendin is exendin-4. In some embodiments, the exendin fragment is a fragment of exendin-4. In some embodiments, the exendin analog has at least 70%, for example 70%, 75%, 80%, 85%, 90%, 95% or even higher, identity with exendin-4. Particularly useful for these diseases are compounds described herein having glucose lowering activity (e.g. exendin-4 or its fragments or analogs linked to an ABD), having reduction of body weight or reduction of food intake activity, a lowering of HbA1c, delaying of gastric emptying, lowering of plasma glucagon, or intestinal motility benefit.

Additional diseases and disorders which can be treated by the compounds and methods described herein include steroid-induced diabetes, HIV treatment-induced diabetes, latent autoimmune diabetes in adults (LADA), Nonalcoholic steatohepatitis (NASH) and nonalcoholic fatty liver disease (NAFLD), hypoglycemia unawareness (HU), restrictive lung disease including sarcoidosis, and metabolic syndrome X. The engineered polypeptide may include an exendin or fragment or analog thereof. Accordingly, the engineered polypeptide can have one of the following structures: HD1-ABD or HD1-L1-ABD. In some embodiments, the exendin is exendin-4. In some embodiments, the exendin fragment is a fragment of exendin-4. In some embodiments, the exendin analog has at least 70%, for example 70%, 75%, 80%, 85%, 90%, 95% or even higher, identity with exendin-4. Particularly useful for these diseases are compounds described herein having glucose lowering activity (e.g. exendin-4 or its fragments or analogs linked to an ABD), having reduction of body weight or reduction of food intake activity, delaying of gastric emptying, lowering of HbA1c, lowering of plasma glucagon, or intestinal motility benefit. The engineered polypeptide can include only exendin, or analog or fragment thereof, as a hormone domain. The disease or disorder can be diabetes, overweight, obesity, dyslipidemia, Alzheimer's disease, fatty liver disease, hyperlipidemia, Parkinson's disease or cardiovascular disease or other diseases described herein.

Additional diseases and disorders which can be treated by the compounds and methods described herein include steroid-induced diabetes, HIV treatment-induced diabetes, latent autoimmune diabetes in adults (LADA), Nonalcoholic steatohepatitis (NASH) and nonalcoholic fatty liver disease (NAFLD), hypoglycemia unawareness (HU), restrictive lung disease including sarcoidosis, and metabolic syndrome X. Particularly useful for these diseases are compounds described herein having glucose lowering activity (e.g. exendin-4 or its fragments or analogs linked to an ABD).

V. Assays

Methods for production and assay of engineered polypeptides described herein are generally available to the skilled artisan. Further, specific methods are described herein as well as in the patent publications and other references cited herein, which are incorporated by reference for this additional purpose.

GLP-1 Receptor Binding and Functional Assays:

GLP-1 receptor binding activity and affinity may be measured in any number of known methods. For example, in one method binding activity is measured using a binding displacement assay in which the receptor source is RINm5F cell membranes, and the ligand is [$^{125}$I]GLP-1 or iodinated exendin(1-39) or iodinated exendin(9-39). Homogenized RINm5F cell membranes are incubated in 20 mM HEPES buffer with 40,000 cpm [$^{125}$I]GLP-1 (or exendin) tracer, and varying concentrations of test compound for 2 hours at 23° C. with constant mixing. Reaction mixtures are filtered through glass filter pads presoaked with 0.3% PEI solution and rinsed with ice-cold phosphate buffered saline. Bound counts are determined using a scintillation counter. Binding affinities are calculated using GraphPad Prism® software (GraphPad Software, Inc., San Diego, Calif.).

In vitro assays for functional GLP-1 receptor activation can be performed using known methods and cells and tissues. For example, exendin-4 stimulation of GLP-1 receptor bearing cells can induce an increase in adenylate cyclase activation, cAMP synthesis, membrane depolarization, rise in intracellular calcium and increase in glucose-induced insulin secretion. See e.g., Holz et al., 1995, *J. Biol. Chem.* 270(30):17749-57. Cell-based assays using the rMTC 6-23 (clone 6) cell line can be used to determine GLP-1 receptor agonist activity of a compound based on the cAMP generated. In one embodiment of the bioassay the GLP-1 receptor agonist activity of a compound is quantitatively determined by correlations to cAMP production in cell-based assays with 6-23 (clone 6) cells. The cell-based assay uses living 6-23 (clone 6) cells. The 6-23 (clone 6) cells are available from the American Type Culture Collection as ATCC® No. CRL-1607™ and the European Collection of Cell Cultures as ECACC No. 87042206. In another embodiment the cell-based assay is a homogeneous time-resolved fluorescence assay (HTRF®). HTRF® kits are commercially available from Cisbio International (Bedford, Mass.). Methods for using HTRF® kits are known in the art and the kits generally include instruction manuals, e.g., on how to prepare samples, standards, calibration curves, and conduct experiments. Homogeneous time-resolved fluorescence cell-based assays are described in U.S. Pat. No. 5,527,684, the disclosure of which is incorporated by reference herein, and Document Reference No. 62AM4PEB rev02 (August 2007) available from Cisbio HTRF® Product Center. See www.htrf.com/products/gper/camp/, the disclosure of which is incorporated by reference herein. In a preferred method the bioassay uses the rat thyroid carcinoma 6-23 (clone 6) cells in a cell-based assay using the HTRF® cAMP dynamic 2 1,000 assay kit, available from Cisbio as Catalog No. 62AM4PEB. The HTRF® standards and calibrations are prepared following the instructions in the kit. Assays may be performed with or without the presence of albumin.

In vivo assays for activity and duration of action and pharmacokinetics can be done using known methods. For example, duration can be performed using an oral glucose tolerance test (OGTT) in which the drug is administered to the subject at a desired time point before the glucose is administered orally (to measure drug duration of action; OGTT DOA) and glucose blood levels are measured (e.g. readily done in mice). Activity and duration can also be measured using an intravenous glucose tolerance test (IVGTT) in which the drug is administered to the subject at a desired time point before the glucose is administered IV (IVGTT DOA) and blood glucose levels are measured (e.g. can readily be done in rats). Preferred engineered compounds have a desired effect on blood glucose of at least 24 hours duration after a single dose of drug, preferably at least 3 days, at least 4 days, at least 5 days, at least 6 days, and at least 1 week after the single dose of drug is given.

For example, test polypeptide is injected subcutaneously at t=0 immediately following a baseline sample into NIH/Swiss female mice. Blood samples are taken at desired time periods such as t=2, 4, and 8 hours during day 1 and then daily through day 5 or through to day 7 or longer. Blood glucose is measured with a OneTouch® Ultra® (LifeScan, Inc., a Johnson & Johnson Company, Milpitas, Calif.). For a duration of activity (DOA) determination, such as for glucose control activity of a drug, an OGTT or IVGTT can be performed at the desired point after drug administration. Body weight can also be measured, as well as food intake, or other pharmacological or pharmacokinetic parameter. For example, female NIH/Swiss mice (8-20 weeks old) are group housed with a 12:12 hour light:dark cycle with lights on at 0600. Water and a standard pelleted mouse chow diet were available ad libitum, except as noted. The morning of the experiment, animals are divided into experimental groups and fasted starting at approximately 0630 hrs. In a typical study, n=2 cages with 3 mice/cage. At time=0 min, a blood glucose sample is taken and immediately followed by an intraperitoneal injection of vehicle or compound in an amount ranging from about 1 nmol/kg to 25 nmol/kg. Blood glucose can be measured at 30, 60, 120, 180, and 240 min and daily for a week or longer after the single dose. In a variation of the experiment, doses are provided daily or even weekly over a longer period such as 14 or 28 days. Percent pre-treatment is calculated by dividing the blood glucose at the measured time point, e.g. 60 minutes or 1 day, by the blood glucose at time=0 min. Significant treatment effects were identified by ANOVA ($p<0.05$). Where a significant difference exists, test means are compared to the control mean using Dunnett's test (Prism® v. 4.01, GraphPad Software Inc., San Diego, Calif.). Blood glucose can measured with a OneTouch® Ultra® (LifeScan, Inc., a Johnson & Johnson Company, Milpitas, Calif.). * $p<0.05$ vs. vehicle control; ANOVA, Dunnett's test. Other parameters can also be measured.

In Vivo Assay for Food Intake Inhibition:

The engineered polypeptides may be tested for their duration and extent of appetite suppression and for their duration and extent of effect on body weight loss in various known methods. For example, the polypeptides may be tested for appetite suppression in the mouse food intake assay and for their effect on body weight gain in diet-induced obesity (DIO) mice. An experimental protocol for such assays are described below.

For example, female NIH/Swiss mice (8-24 weeks old) are group housed with a 12:12 hour light:dark cycle with lights on at 0600. Water and a standard pelleted mouse chow diet are available ad libitum, except as noted. Animals are fasted starting at approximately 1500 hrs, 1 day prior to experiment. The morning of the experiment, animals are divided into experimental groups. In a typical study, n=4 cages with 3 mice/cage. At time=0 min, all animals are given an intraperitoneal injection of vehicle or test compound, typically in an amount ranging from about 2 nmol/kg to 75 nmol/kg, and immediately given a pre-weighed amount (10-15 g) of standard chow. Food is removed and weighed at various times, typically 30, 60, and 120 minutes or longer, such as daily, to determine the amount of food consumed (Morley, Flood et al., 1994, *Am. J. Physiol.* 267: R178-

R184). Food intake is calculated by subtracting the weight of the food remaining at the e.g., 30 or 60 minute time point, from the weight of the food provided initially at time=0. Significant treatment effects are identified by ANOVA (p<0.05). Where a significant difference exists, test means are compared to the control mean using Dunnett's test (Prism® v. 2.01, GraphPad Software Inc., San Diego, Calif.). Body weight can also be measured.

Body Weight, Fat Redistribution, and Lean Body Mass Assays:

Assays for body weight and related effects can also be performed as follows. Diet-induced obesity (DIO) in the in the Sprague-Dawley rat is a valuable model for the study of obesity and regulation of energy homeostasis. These rats were developed from a line of (Crl:CD®(SD)BR) rats that are prone to become obese on a diet relatively high in fat and energy. See, for example, Levin, 1994, *Am. J. Physiol.* 267:R527-R535, Levin et al., 1997, *Am. J. Physiol.* 273: R725-R730. DIO male rats are obtained from Charles River Laboratories, Inc. (Wilmington, Mass.). The rats are housed individually in shoebox cages at 22° C. in a 12/12-hour light dark cycle. Rats are maintained ad-libitum on a moderately high fat diet (32% kcal from fat; Research Diets D1226B). The animals typically achieve a mean body weight of about 500 g. Levin DIO rats are habituated to caging environment for 7 days. During the 3 nights of habituation, animals receive a single intraperitoneal (IP) injection of vehicle. On test day, rats are administered a single IP injection of compound or vehicle (e.g. 10% DMSO) at the onset of the dark cycle. Food intake is measured by an automated food intake measuring system (BioDAQ, Research Diets) at 5 sec intervals throughout the course of the study. Body weight is recorded nightly.

Body composition can be measured prior to and after drug treatment using NMR (Echo Medical Systems, Houston, Tex.). For body composition measurements, rats are briefly placed (~1 min) in a well-ventilated plexiglass tube that was then inserted into a specialized rodent NMR machine. This enabled the calculation of changes in actual grams of fat and dry lean tissue (e.g., grams of body fat after treatment-grams of body fat at baseline=change in grams of body fat) and changes in % body composition for fat and dry lean tissue (e.g., % body fat after treatment-% body fat at baseline=change in % body fat). All data are represented as mean±SEM. Analysis of variance (ANOVA) and post-hoc tests are used to test for group difference. A P-value<0.05 is considered significant. Statistical analysis and graphing are performed using PRISM® 4 for Windows (GraphPad Software, Inc., San Diego, Calif.). Graphs and results are typically presented as vehicle-corrected changes in percent body weight, body fat and changes in body protein VI. Pharmaceutical Compositions In one aspect, there are provided pharmaceutical compositions including compounds described herein in combination with a pharmaceutically acceptable excipient (e.g., carrier). The term "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (e.g., Ringer's solution and the like), alcohols, oils, gelatins, and carbohydrates such as lactose, amylose or starch, fatty acid esters, hydroxymethylcellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

In a further aspect, there is provided a pharmaceutical composition which includes a engineered polypeptide as described herein in combination with a pharmaceutically acceptable excipient. In one embodiment, the pharmaceutical composition is an oral pharmaceutical composition, as described herein. In some embodiments, the pharmaceutical composition is a long lasting pharmaceutical composition. The term "long lasting" in the context of administration of a pharmaceutical composition refers to duration of action. Accordingly, a long lasting pharmaceutical composition may be administered at intervals of, for example, 1 hr, 2 hr, 4 hr, 8 hr, 12 hr, 1 day, 2 days, 3 days, 4 days, 5 days, 6 days, 1 week, 2 weeks, 3 weeks, 1 month or even longer. In one embodiment, administration is twice a day (i.e., "twice daily"). In a preferred embodiment, administration is once a day (i.e., "once daily"). In a more preferred embodiments, administration is once a week (i.e., "once weekly"). In some embodiments, the engineered polypeptide is selected from the engineered polypeptides set forth in Tables 2, 3A and 3B herein. In some embodiments, the engineered polypeptide is selected from the engineered polypeptides set forth in Tables 2 and 3A herein. In some embodiments, the engineered polypeptide is selected from the engineered polypeptides set forth in Table 2 herein.

A. Formulations

The engineered polypeptides described herein can be administered alone or can be co-administered to a subject. Co-administration is meant to include simultaneous or sequential administration of the compounds individually or in combination (more than one compound). For example, it has been found that obesity can be beneficially treated with a combination therapy including leptin (e.g., metreleptin) and an amylin (e.g., pramlintide). See e.g., U.S. Published Appl. No. 2008/0207512. Accordingly, an engineered polypeptide described herein including an ABD and an exendin compound useful for treatment of e.g., obesity and overweight, can be administered alone to achieve such treatment or co-administered with either a leptin or leptin agonist, e.g. metreleptin, and/or an amylin or amylin agonist, e.g. pramlintide.

In some embodiments, the formulations and methods described herein further provide that the exendin, exendin analog or exendin analog agonist engineered polypeptide is co-administered with one or more anti-diabetic agents, such as anti-hyperglycemia agents, e.g. insulin (including regular, short acting, long-acting, and basal insulins), amylins, pramlintide, metformin and thiazolidinediones (including rosiglitazone and pioglitazone).

In some embodiments, the formulations and methods described herein further provide that the exendin, exendin analog or exendin analog agonist engineered polypeptide is co-administered with one or more cholesterol and/or triglyceride lowering agents. Exemplary agents include HMG CoA reductase inhibitors (e.g., atorvastatin, fluvastatin, lovastatin, pravastatin, rosuvastatin, simvastatin); bile ace sequestrants (e.g., colesevelam, cholestyramine, colestipol); fibrates (e.g., fenofibrate, clofibrate, gemfibrozil); ezetimibe, nicotinic acid, probucol, a lovastatin/niacin combination; an atorvastatin/amlodipine combination; and a simvastatin/ezetimibe combination.

The present disclosure provides the composition for use as a medicament, i.e. for use in therapy, since the exendin compound is a therapeutically active compound, and surprisingly retains activity when fused to ABD. Compositions including an engineered polypeptide, either liquid or dry form, and optionally at least one pharmaceutically acceptable carrier and/or excipient are also specifically contemplated and are exemplified herein.

The composition has an ability to associate with albumin in vivo or in vitro. In certain cases, it may be of benefit to form a complex of the composition with albumin outside of a living organism, i.e. to add exogenous albumin to the composition. Such a composition may be lyophilized, providing a formulation that is suitable for storage at ambient temperature. Thus, the present disclosure also provides a composition as defined above which further includes albumin, such as human serum albumin, and which may optionally be in dry form.

Co-administration can be achieved by separately administering the exendin, exendin agonist, or exendin analog agonist engineered polypeptide with the second agent, or by administering a single pharmaceutical formulation including the exendin, exendin agonist, or exendin analog agonist engineered polypeptide and the second agent. Appropriate dosage regimens for the second agents are generally known in the art.

The preparations can also be co-administered, when desired, with other active substances (e.g. to reduce metabolic degradation) as known in the art or other therapeutically active agents. An exendin engineered polypeptide described herein can be administered with other active anti-diabetes or anti-obesity agents, such as leptin or leptin agonists and amylin or amylin agonist compounds, e.g. the amylins, including davalintide and their analogs.

Amylins.

Amylin is a peptide hormone synthesized by pancreatic β-cells that is co-secreted with insulin in response to nutrient intake. The sequence of amylin is highly preserved across mammalian species, with structural similarities to calcitonin gene-related peptide (CGRP), the calcitonins, the intermedins, and adrenomedullin, as known in the art. The glucoregulatory actions of amylin complement those of insulin by regulating the rate of glucose appearance in the circulation via suppression of nutrient-stimulated glucagon secretion and slowing gastric emptying. In insulin-treated patients with diabetes, pramlintide, a synthetic and equipotent analogue of human amylin, reduces postprandial glucose excursions by suppressing inappropriately elevated postprandial glucagon secretion and slowing gastric emptying. The sequences of rat amylin, human amylin and pramlintide follow:
KCNTATCATQRLANFLVRSSNNLGPVLPPTNVGSNTY (SEQ ID NO:6);
KCNTATCATQRLANFLVHSSNNFGAILSSTNVGSNTY (SEQ ID NO:7);
KCNTATCATQRLANFLVHSSNNFGPILPPTNVGSNTY (SEQ ID NO:8).

Davalintide.

Davalintide, also known as "AC-2307" is a potent amylin agonist useful in the treatment of a variety of disease indications. See WO 2006/083254 and WO 2007/114838, each of which is incorporated by reference herein in its entirety and for all purposes. Davalintide is a chimeric peptide, having an N-terminal loop region of amylin or calcitonin and analogs thereof, an alpha-helical region of at least a portion of an alpha-helical region of calcitonin or analogs thereof or an alpha-helical region having a portion of an amylin alpha-helical region and a calcitonin alpha-helical region or analog thereof, and a C-terminal tail region of amylin or calcitonin. The sequences of human calcitonin, salmon calcitonin and davalintide follow:
CGNLSTCMLGTYTQDFNKFHTFPQTAIGVGAP (SEQ ID NO:9);
CSNLSTCVLGKLSQELHKLQTYPRTNTGSGTP (SEQ ID NO:10);
KCNTATCVLGRLSQELHRLQTYPRTNTGSNTY (SEQ ID NO:11).

Without wishing to be bound by any theory, it is believed that amylins and davalintide, and fragment and analogs thereof, can require C-terminal amidation to elicit a full biological response. It is understood that amylin compounds such as those described herein which include amylins and/or davalintide, and fragment and analogs thereof, can be amidated at the C-terminal.

"Amylin agonist compounds" include native amylin peptides, amylin analog peptides, and other compounds (e.g., small molecules) that have amylin agonist activity. The "amylin agonist compounds" can be derived from natural sources, can be synthetic, or can be derived from recombinant DNA techniques. Amylin agonist compounds have amylin agonist receptor binding activity and may include amino acids (e.g., natural, unnatural, or a combination thereof), peptide mimetics, chemical moieties, and the like. The skilled artisan will recognize amylin agonist compounds using amylin receptor binding assays or by measuring amylin agonist activity in soleus muscle assays. In one embodiment, amylin agonist compounds will have an $IC_{50}$ of about 200 nM or less, about 100 nM or less, or about 50 nM or less, in an amylin receptor binding assay, such as that described herein, in U.S. Pat. No. 5,686,411, and US Publication No. 2008/0176804, the disclosures of which are incorporated by reference herein in their entireties and for all purposes. In one embodiment, amylin agonist compounds will have an $EC_{50}$ of about 20 nM or less, about nM 15 or less, about nM 10 or less, or about nM 5 or less in a soleus muscle assay, such as that described herein and in U.S. Pat. No. 5,686,411. In one embodiment, the amylin agonist compound has at least 90% or 100% sequence identity to $^{25,28,29}$Pro-human-amylin. In one embodiment, the amylin agonist compound is a peptide chimera of amylin (e.g., human amylin, rat amylin, and the like) and calcitonin (e.g., human calcitonin, salmon calcitonin, and the like). Suitable and exemplary amylin agonist compounds are also described in US Publication No. 2008/0274952, the disclosure of which is incorporated by reference herein in its entirety and for all purposes.

When co-administered with another active agent, the compounds can be administered simultaneously or sequentially, together or separately formulated. Since the engineered compounds herein are inherently long-acting, they are suitable for once daily, once weekly or longer administration. Accordingly, the other agent may be administered either in one or multiple doses, e.g. once daily, twice daily, three times daily, once weekly, as needed, during the period of dosing for the exendin engineered polypeptide, e.g. once weekly.

Single and multiple-use formulations of other agents such as amylin compounds have been reported. For example, pramlintide has been formulated for and successfully administered for once, twice and three times daily administration for treating diabetes and for treating obesity.

These pharmaceutical compounds may be formulated with pharmaceutically acceptable carriers or diluents as well as any other known adjuvants and excipients in accordance with conventional techniques such as those disclosed in *Remington's Pharmaceutical Sciences* by E. W. Martin. See also Wang et al. (1988) *J. of Parenteral Sci.* and Tech., Technical Report No. 10, Supp. 42:2 S.

In general, the engineered polypeptides may be formulated into a stable, safe pharmaceutical composition for administration to a patient. Pharmaceutical formulations contemplated for use in the methods of the invention may include approximately 0.01 to 1.0% (w/v), in certain cases 0.05 to 1.0%, of the engineered polypeptide, approximately 0.02 to 0.5% (w/v) of an acetate, phosphate, citrate or glutamate buffer allowing a pH of the final composition of from about 3.0 to about 7.0; approximately 1.0 to 10% (w/v) of a carbohydrate or polyhydric alcohol tonicifier and, optionally, approximately 0.005 to 1.0% (w/v) of a preservative selected from the group of m-cresol, benzyl alcohol, methyl, ethyl, propyl and butyl parabens and phenol. Such a preservative is generally included if the formulated peptide is to be included in a multiple use product.

In particular embodiments, a pharmaceutical formulation of the present engineered polypeptides may contain a range of concentrations of the compound(s), e.g., between about 0.01% to about 98% w/w, or between about 1 to about 98% w/w, or preferably between 80% and 90% w/w, or preferably between about 0.01% to about 50% w/w, or more preferably between about 10% to about 25% w/w in these embodiments. A sufficient amount of water for injection may be used to obtain the desired concentration of solution.

Additional tonicifying agents such as sodium chloride, as well as other known excipients, may also be present, if desired. In some cases, such excipients are useful in maintenance of the overall tonicity of the compound. An excipient may be included in the presently described formulations at various concentrations. For example, an excipient may be included in the concentration range from about 0.02% to about 20% w/w, preferably between about 0.02% and 0.5% w/w, about 0.02% to about 10% w/v, or about 1% to about 20% w/w. In addition, similar to the present formulations themselves, an excipient may be included in solid (including powdered), liquid, semi-solid or gel form.

The pharmaceutical formulations may be composed in various forms, e.g., solid, liquid, semisolid or liquid. The term "solid", as used herein, is meant to encompass all normal uses of this term including, for example, powders and lyophilized formulations. The presently described formulations may be lyophilized.

The terms buffer, buffer solution and buffered solution, when used with reference to hydrogen-ion concentration or pH, refer to the ability of a system, particularly an aqueous solution, to resist a change of pH on adding acid or alkali, or on dilution with a solvent. Characteristic of buffered solutions, which undergo small changes of pH on addition of acid or base, is the presence either of a weak acid and a salt of the weak acid, or a weak base and a salt of the weak base. An example of the former system is acetic acid and sodium acetate. The change of pH is slight as long as the amount of hydronium or hydroxyl ion added does not exceed the capacity of the buffer system to neutralize it.

As described herein, a variety of liquid vehicles are suitable for use in the formulations of engineered polypeptides, for example, water or an aqueous/organic solvent mixture or suspension.

The stability of a engineered polypeptide formulation for use as described herein is enhanced by maintaining the pH of the formulation in a range determined by methods known in the art. In certain embodiments, the pH of the formulation is maintained in the range of about 3.5 to 5.0, or about 3.5 to 6.5, in some embodiments from about 3.7 to 4.3, or about 3.8 to 4.2. In some embodiments, pH may be about 4.0, about 5.0, about 6.0, about 7.0, about 8.0, about 9.0, or even higher. In some embodiments, pH may be in the physiological range, pH 6-8, preferably pH 7-7.6.

In certain embodiments, the buffer with the engineered polypeptide is an acetate buffer (preferably at a final formulation concentration of from about 1-5 to about 60 mM), phosphate buffer (preferably at a final formulation concentration of from about 1-5 to about to about 30 mM) or glutamate buffer (preferably at a final formulation concentration of from about 1-5 to about to about 60 mM). In some embodiments, the buffer is acetate (preferably at a final formulation concentration of from about 5 to about 30 mM).

A stabilizer may be included in the formulations but is not necessarily needed. If included, however, a stabilizer useful in the practice of the present invention is a carbohydrate or a polyhydric alcohol. A suitable stabilizer useful in the practice of the present invention is approximately 1.0 to 10% (w/v) of a carbohydrate or polyhydric alcohol. The polyhydric alcohols and carbohydrates share the same feature in their backbones, i.e., —CHOH—CHOH—, which is responsible for stabilizing the proteins. The polyhydric alcohols include such compounds as sorbitol, mannitol, glycerol, and polyethylene glycols (PEGs). These compounds are straight-chain molecules. The carbohydrates, such as mannose, ribose, sucrose, fructose, trehalose, maltose, inositol, and lactose, on the other hand, are cyclic molecules that may contain a keto or aldehyde group. These two classes of compounds have been demonstrated to be effective in stabilizing protein against denaturation caused by elevated temperature and by freeze-thaw or freeze-drying processes. Suitable carbohydrates include: galactose, arabinose, lactose or any other carbohydrate which does not have an adverse affect on a diabetic patient, i.e., the carbohydrate is not metabolized to form unacceptably large concentrations of glucose in the blood. Such carbohydrates are well known in the art as suitable for diabetics. Sucrose and fructose are suitable for use with the compound in non-diabetic applications (e.g. treating obesity).

In certain embodiments, if a stabilizer is included, the compound is stabilized with a polyhydric alcohol such as sorbitol, mannitol, inositol, glycerol, xylitol, and polypropylene/ethylene glycol copolymer, as well as various polyethylene glycols (PEG) of molecular weight 200, 400, 1450, 3350, 4000, 6000, 8000 and even higher). Mannitol is the preferred polyhydric alcohol in some embodiments. Another useful feature of the lyophilized formulations of the present invention is the maintenance of the tonicity of the lyophilized formulations described herein with the same formulation component that serves to maintain their stability. In some embodiments, mannitol is the preferred polyhydric alcohol used for this purpose.

The United States Pharmacopeia (USP) states that antimicrobial agents in bacteriostatic or fungistatic concentrations must be added to preparations contained in multiple dose containers. They must be present in adequate concentration at the time of use to prevent the multiplication of microorganisms inadvertently introduced into the preparation while withdrawing a portion of the contents with a hypodermic needle and syringe, or using other invasive means for delivery, such as pen injectors. Antimicrobial agents should be evaluated to ensure compatibility with all other components of the formula, and their activity should be evaluated in the total formula to ensure that a particular agent that is effective in one formulation is not ineffective in another. It is not uncommon to find that a particular antimicrobial agent will be effective in one formulation but not effective in another formulation.

A preservative is, in the common pharmaceutical sense, a substance that prevents or inhibits microbial growth and may be added to pharmaceutical formulations for this purpose to avoid consequent spoilage of the formulation by microorganisms. While the amount of the preservative is not great, it may nevertheless affect the overall stability of the peptide.

While the preservative for use in the pharmaceutical compositions can range from 0.005 to 1.0% (w/v), in some embodiments range for each preservative, alone or in combination with others, is: benzyl alcohol (0.1-1.0%), or m-cresol (0.1-0.6%), or phenol (0.1-0.8%) or combination of methyl (0.05-0.25%) and ethyl or propyl or butyl (0.005%-0.03%) parabens. The parabens are lower alkyl esters of para-hydroxybenzoic acid. A detailed description of each preservative is set forth in *Remington's Pharmaceutical Sciences* (Id.)

Engineered polypeptides may not have a tendency to adsorb onto the glass in a glass container when in a liquid form, therefore, a surfactant may not be required to further stabilize the pharmaceutical formulation. However, with regard to compounds which do have such a tendency when in liquid form, a surfactant should be used in their formulation. These formulations may then be lyophilized. Surfactants frequently cause denaturation of protein, both of hydrophobic disruption and by salt bridge separation. Relatively low concentrations of surfactant may exert a potent denaturing activity, because of the strong interactions between surfactant moieties and the reactive sites on proteins. However, judicious use of this interaction can stabilize proteins against interfacial or surface denaturation. Surfactants which could further stabilize the engineered polypeptide may optionally be present in the range of about 0.001 to 0.3% (w/v) of the total formulation and include polysorbate 80 (i.e., polyoxyethylene (20) sorbitan monooleate), CHAPS® (i.e., 3-[(3-cholamidopropyl) dimethylammonio] 1-propanesulfonate), Brij® (e.g., Brij® 35, which is (polyoxyethylene (23) lauryl ether), poloxamer, or another nonionic surfactant.

It may also be desirable to add sodium chloride or other salt to adjust the tonicity of the pharmaceutical formulation, depending on the tonicifier selected. However, this is optional and depends on the particular formulation selected. Parenteral formulations preferably may be isotonic or substantially isotonic.

A preferred vehicle for parenteral products is water. Water of suitable quality for parenteral administration can be prepared either by distillation or by reverse osmosis. Water for injection is the preferred aqueous vehicle for use in the pharmaceutical formulations.

It is possible that other ingredients may be present in the pharmaceutical formulations. Such additional ingredients may include, e.g., wetting agents, emulsifiers, oils, antioxidants, bulking agents, tonicity modifiers, chelating agents, metal ions, oleaginous vehicles, proteins (e.g., human serum albumin, gelatin or proteins) and a zwitterion (e.g., an amino acid such as betaine, taurine, arginine, glycine, lysine and histidine). Additionally, polymer solutions, or mixtures with polymers provide the opportunity for controlled release of the peptide. Such additional ingredients, of course, should not adversely affect the overall stability of the pharmaceutical formulation of the present invention.

Containers are also an integral part of the formulation of an injection and may be considered a component, for there is no container that is totally inert, or does not in some way affect the liquid it contains, particularly if the liquid is aqueous. Therefore, the selection of a container for a particular injection must be based on a consideration of the composition of the container, as well as of the solution, and the treatment to which it will be subjected. Adsorption of the peptide to the glass surface of the vial can also be minimized, if necessary, by use of borosilicate glass, for example, Wheaton Type I borosilicate glass #33 (Wheaton Type I-33) or its equivalent (Wheaton Glass Co.). Other vendors of similar borosilicate glass vials and cartridges acceptable for manufacture include Kimbel Glass Co., West Co., Bunder Glas GMBH and Form a Vitrum. The biological and chemical properties of the compound may be stabilized by formulation and lyophilization in a Wheaton Type I-33 borosilicate serum vial to a final concentration of 0.1 mg/ml and 10 mg/ml of the compound in the presence of 5% mannitol, and 0.02% Tween 80.

For formulations to be delivered by injection, in order to permit introduction of a needle from a hypodermic syringe into a multiple-dose vial and provide for resealing as soon as the needle is withdrawn, the open end of each vial is preferably sealed with a rubber stopper closure held in place by an aluminum band.

Stoppers for glass vials, such as, West 4416/50, 4416/50 (Teflon faced) and 4406/40, Abbott 5139 or any equivalent stopper can be used as the closure for pharmaceutical for injection. For formulations including peptidic anti-obesity agents, these stoppers are compatible with the peptide as well as the other components of the formulation. The inventors have also discovered that these stoppers pass the stopper integrity test when tested using patient use patterns, e.g., the stopper can withstand at least about 100 injections. Alternatively, the peptide can be lyophilized in to vials, syringes or cartridges for subsequent reconstitution. Liquid formulations of the present invention can be filled into one or two chambered cartridges, or one or two chamber syringes.

Each of the components of the pharmaceutical formulation described above is known in the art and is described in *Pharmaceutical Dosage Forms: Parenteral Medications*, Vol. 1, 2nd ed., Avis et al. Ed., Mercel Dekker, New York, N.Y. 1992, which is incorporated by reference in its entirety herein.

The manufacturing process for the above liquid formulations generally involves compounding, sterile filtration and filling steps. The compounding procedure involves dissolution of ingredients in a specific order (preservative followed by stabilizer/tonicity agents, buffers and peptide) or dissolving at the same time.

Alternative formulations, e.g., non-parenteral, may not require sterilization. However, if sterilization is desired or necessary, any suitable sterilization process can be used in developing the peptide pharmaceutical formulation of the present invention. Typical sterilization processes include filtration, steam (moist heat), dry heat, gases (e.g., ethylene oxide, formaldehyde, chlorine dioxide, propylene oxide, beta-propiolactone, ozone, chloropicrin, peracetic acid methyl bromide and the like), exposure to a radiation source, and aseptic handling. Filtration is the preferred method of sterilization for liquid formulations of the present invention. The sterile filtration involves filtration through 0.45 um and 0.22 um (1 or 2) which may be connected in series. After filtration, the solution is filled into appropriate vials or containers.

In certain embodiments, the engineered polypeptides described herein are administered peripherally to the subjects. In some embodiments, the liquid pharmaceutical formulations of the present invention are intended for parenteral administration. Suitable routes of administration include intramuscular, intravenous, subcutaneous, intradermal, intraarticular, intrathecal and the like. In some embodiments, the subcutaneous route of administration is preferred. In certain embodiments, mucosal delivery is also preferred. These routes include, but are not limited to, oral, nasal, sublingual, pulmonary and buccal routes which may include administration of the peptide in liquid, semi-solid or solid form. For formulations including engineered polypeptides, administration via these routes can require substantially more compound to obtain the desired biological effects due to decreased bioavailability compared to parenteral delivery.

In addition, parenteral controlled release delivery can be achieved by forming polymeric microcapsules, matrices, solutions, implants and devices and administering them parenterally or by surgical means. Examples of controlled release formulations are described in U.S. Pat. Nos. 6,368,630, 6,379,704, and 5,766,627, which are incorporated herein by reference. These dosage forms may have a lower bioavailability due to entrapment of some of the peptide in the polymer matrix or device. See e.g., U.S. Pat. Nos. 6,379,704, 6,379,703, and 6,296,842, each of which is incorporated herein by reference in its entirety and for all purposes.

The compounds may be provided in dosage unit form containing an amount of the engineered polypeptide that will be effective in one or multiple doses.

As will be recognized by those in the field, an effective amount of the engineered polypeptide will vary with many factors including the age and weight of the subject, the subject's physical condition, the condition to be treated, and other factors known in the art. An effective amount of the engineered polypeptides will also vary with the particular combination administered. As described herein, administration of the engineered polypeptides in combination may allow for a reduced amount of any of the administered engineered polypeptides to be an effective amount.

Administration can be by oral route, including transcellular, paracellular or receptor-mediated routes. Without wishing to be bound by any theory, the engineered polypeptides containing an exendin as described herein are orally available, in part because of their relatively small size and relative stability to gut enzymes. It has been reported that tight junctions between intestinal cells opened by absorption/permeation enhancers are less than 20 nm wide. See e.g., Chao et al., 1998, *J. Drug Targeting*, 6:37-43. Accordingly, a sufficiently small (for example, less than 10 kD or 15 kD) engineered polypeptide as described herein can transit the gut wall and bind albumin in the portal system, thereby gaining access to the circulation. Oral delivery of the engineered polypeptides of the present invention may be twice daily, once daily, once other day, once every three days, once weekly, once in two weeks, one in three weeks, or even once a month. Oral delivery systems suitable for other peptides can be used. In one embodiment the oral delivery system may have a relatively rapid uptake profile, e.g. from 1 to 4 hours, in which case the inherently long-duration of action of the engineered polypeptide provides the extended duration of action desired, such as for once daily or once weekly administration. The duration of action can be selected, for example, by choice of ABD and its affinity for albumin. While not wishing to be bound by theory, it is believed that higher affinity to albumin will yield longer circulation times providing longer duration of action. Oral delivery can be tested using known in vitro and in vivo methods. For example, a mouse can be orally gavaged with a solution containing an engineered polypeptide formulated with or without a permeation/absorption enhancer and/or protease inhibitor in order to test orally availability and effect of any added excipient. Either or both pharmacodynamic (therapeutic effects) and pharmacokinetic (drug properties) can be measured over time, such as drug plasma levels, acute or chronic glucose and/or HbA1c lowering, insulin plasma levels, food intake inhibition, weight loss, and/or lipid levels.

B. Effective Dosages

Pharmaceutical compositions provided herein include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat diabetes, such compositions will contain an amount of active ingredient effective to achieve the desired result (e.g. decreasing fasting blood glucose in a subject). When administered in methods to treat obesity, such compositions will contain an amount of active ingredient effective to achieve the desired result (e.g. decrease the body mass).

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., the disease responsive to compounds described herein; fasting blood glucose); presence of other diseases or other health-related problems; kind of concurrent treatment; and complications from any disease or treatment regimen. Other therapeutic regimens or agents can be used in conjunction with the methods and compounds of the invention.

Therapeutically effective amounts for use in humans may be determined from animal models. For example, a dose for humans can be formulated to achieve a concentration that has been found to be effective in animals. The dosage in humans can be adjusted by monitoring one or more physiological parameters, including but not limited to blood sugar and body mass, and adjusting the dosage upwards or downwards, as described above and known in the art.

Dosages may be varied depending upon the requirements of the patient and the compound being employed. The dose administered to a patient, in the context of the present invention, should be sufficient to affect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In one embodiment of the invention, the dosage range is 0.001% to 10% w/v. In another embodiment, the dosage range is 0.1% to 5% w/v.

However, typical doses may contain from a lower limit of about 1 ug, 5 ug, 10 ug, 50 ug, 100 ug to 150 ug per day to an upper limit of about to 50 ug, to 100 ug, to 150 ug, to 200 ug or even to 300 ug of the pharmaceutical compound per week in view of the extended half-life of the engineered polypeptides herein. The doses may be delivered in discrete unit doses at the desired interval, e.g. daily or weekly.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

The surprising dose-sparing property of the engineered polypeptides of the present invention, along with their surprisingly long plasma half-life and duration of pharmacological action, provides for a superior pharmaceutical agent. Also surprising in the case of the exendin-containing engineered polypeptides are their oral availability. The superior properties including dose-sparing, allow for lower dosing, thus less or less severe side-effects and improved cost of goods, and/or more cost-effective and simpler formulations for once daily or once weekly administration not currently achieved by the parent compounds alone.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

Without wishing to be bound by any theory, it is believed that fusion of an ABD albumin binding domain with a hormone domain as described herein, can provide decreased immunogenicity as judged by a reduction in immune response relative to the hormone domain without ABD fusion. See e.g., WO 2009/016043, incorporated herein by reference in its entirety and for all purposes.

VII. Examples

Peptides useful in the examples following include: HaPGTFTSDLSKQMEEE AVRLFIEWLKNGGPSSGAPPPSTGGGGSASLAEAKVLANRELDKYGVSDFYKRLINKAK TVEGVEALKLHILAALP; HAEGTFTSDVSSYLEGQAAKEFIAWLVKLAEAKVLANRELDKYGVSDFYKRLINKAKTVEGVEALKLHILAALP (SEQ ID NO:164); HGEGTFTSDLSKQMEEEAVRLFIEWLKLAEAKVLANRELDKYGVSDFYKRLINKAKTV EGVEALKLHILAALP (SEQ ID NO:165); HGEGTFTSDLSKQMEEEAVRLFIEW LKNGGPSSGAPPPSGGSLKNAKEDAIAELKKAGITSDFYFNAVNKAKTVEEVNALKNEI LKALP (Cmpd 22) (SEQ ID NO:168); H(Aib)QGTFTSDYSKYLDEQAAKEFIAWLMN TYGVSDFYKRLINKAKTVEGVEALKLHILAALP (SEQ ID NO:171); HSQGTFTSDYSKYLDEQAAKEFIAWLMNTYGVSDFYKRLINKAKT VEGVEALKLHILA ALP (SEQ ID NO:172); HSQGTFTSDYSKYLDEQAAKEFIAWLMNTGGGSYGVSD FYKRLINKAKTVEGVEALKLHILAALP (SEQ ID NO:173); HaPGTFTSDLSKQMEEE AVRLFIEWLKNGGPSSGAPPPSTGGGGSASLAEAKVLANRELDKYGVSDFYKRLINKAK TVEGVEALKLHILAALP (Cmpd 14), and [[Lys27#]HGEGTFTSDLSKQMEEEAVRLFIEWLKNGGPSSGAPPPS] [LAEAKVLANRELDKYGVSDFYKRLINKAKTVEGVEAL KLHILAALP-GGG-#] (Cmpd 30). As customary in the art, a lower case single-letter amino acid abbreviation (e.g., "a") indicates a D-amino acid (e.g., D-Ala). In the nomenclature of side chain linked peptide compounds, square brackets ("[ ]") indicate separate fragments and crosshatch ("#") indicates linking positions.

Example 1

Purification of Exendin Analog-ABD Engineered Polypeptide

Method.

Exemplary Cmpd 15 (SEQ ID NO:163) was initially produced having an N-terminal extension which incorporates a $His_6$ (SEQ ID NO:49) "tag" as known in the art, with sequence: MAHHHHHHVGTGSNENLYFQHGEGTFTSDLSKQLEEEAVRLFIEW LKQGGPSKEIISTGGGGSASLAEAKVLANRELDKYGVSDFYKRLINKAKTVEGVEALKL HILAALP (SEQ ID NO:50).

Preparation of Cell Extract.

In order to prepare the cell extract, cell pellets from 50 mL of cell cultures were completely resuspended in 60 mL of lysis buffer (50 mM TrisHCl, 150 mM NaCl, pH 8.0). Resuspended cells were run through a microfluidizer (Microfluidics, MA) at 100 PSI three times. Cell extracts were centrifuged for 30 min at 16,000×g to remove debris. EGTA (150 mM stock) was added to cell extract to a final concentration of 3 mM.

Ni-NTA Chromatography.

Ten mL of 50% suspension of Ni-NTA superflow was packed to a 15 mL empty column. The column was washed with 10 mL of water, 50 mL of lysis buffer, and 20 mL of lysis buffer with 3 mM EGTA (50 mM TrisHCl, 150 mM NaCl, pH8.0, 3 mM EGTA). Cell extract was carefully added on the top of Ni-NTA column, and the flow-through was collected. The column was washed with 30 mL of lysis buffer with EGTA (50 mM TrisHCl, 150 mM NaCl, pH8.0, 3 mM EGTA). Ten mL of elution buffer (25 mM TrisHCl, 50 mM NaCl, 250 mM imidazole, pH8.0) was added to the top of column, and the elution fractions (2 mL/fraction) were collected. SDS-PAGE was run to check the flow through and each fraction. Fractions containing the His-tagged compound were pooled.

TEV Protease Digestion.

$His_6$-tagged compound was diluted three fold with 25 mM TrisHCl, 50 mM NaCl, pH8.0. β-mercaptoethanol (0.1%) and 2% of Turbo TEV protease (2 mg/mL, 10,000 units/mg, Accelagen), were added, and the result was mixed and incubated at RT for 2 hours and at 4° C. over night.

Removal of Cleaved his-Tag and Turbo TEV with Ni-NTA.

Six mL of 50% suspension of Ni-NTA superflow was packed to a 15 mL empty column. The column was washed with 20 mL of water and 20 mL of 50 mM TrisHCl, 100 mM NaCl, 45 mM imidazole, pH8.0. The TEV digest reaction was diluted 2-fold with 50 mM TrisHCl, 150 mM NaCl, pH8.0. Diluted digest reaction was carefully added to the top of Ni-NTA column, and the flow-through was collected. Ten mL of 50 mM TrisHCl, 100 mM NaCl, 45 mM imidazole, pH8.0, was added to the column to elute any unbound protein. The flow-throughs were collected and combined.

First Size Exclusion Chromatography (SEC).

The Ni-NTA flow-through was filtered with 0.2 um filter. Superdex 75 HiLoad 26/60 column was pre-equilibrated with 390 mL of PBS. Filtered flow-through was injected to the HiLoad 26/60 column with a sample pump. Protein was eluted with 1.5 CV of PBS, and the monomer peak was pooled.

Second Size Exclusion Chromatograph.

The first SEC pool was filtered with 0.2 um filter. A Superdex 75 HiLoad 26/60 column was pre-equilibrated with 390 mL of PBS. Filtered flow-through was injected to the column HiLoad 26/60 with a sample pump. Protein was eluted with 1.5 CV of PBS, and the monomer peak was pooled.

Third Size Exclusion Chromatography.

The second SEC pool was filtered with 0.2 um filter. A Superdex 75 HiLoad 26/60 column was pre-equilibrated with 390 mL of PBS. Filtered flow-through was injected to the column HiLoad 26/60 with a sample pump. Protein was eluted with 1.5 CV of PBS, and the monomer peak was pooled.

Removal of Residual Endotoxin with EndoTrap Red.

The third SEC pool still contained ~20 EU/mg of endotoxin, which was removed by the use of EndoTrap Red. Briefly, 0.5 mL of gel slurry was activated by adding 1 mL of Regeneration Buffer to the slurry and mix by gently shaking the tube for approximately 5 seconds. The supernatant was centrifuged and aspirated. This step was repeated two additional times. One mL of Equilibration Buffer was added, and mixing was conducted by gently shaking the tube for approximately 5 seconds. The supernatant was centrifuged and aspirated. This step was repeated two additional times. Protein sample (5.5 mL) was added to the resin and incubated for 90 minutes at RT, with gentle rocking or rotating of the tube while incubating. The result was centrifuged at 1200×g for 5 minutes, and the supernatant was transferred to a clean tube.

Results.

The final purified protein migrated on SDS-PAGE gel as approximately a 6 kD protein under the conditions employed. The LC-MS showed a correct molecular weight of 9827 dalton. The protein yield was 3.3 mg from 50 mL of cell culture.

Example 2

Activities of Exendin-ABD Engineered Polypeptides

Exendin-ABD engineered polypeptides of the invention retained sufficient exendin activity in an in vitro cell activation assay. Additionally, the engineered polypeptides provided dramatically improved duration of action for blood glucose lowering and body weight loss, as when compared to exendin-4, when administered as a single dose to a mammal. Surprisingly, duration of action can be extended to at least 1 day, even at least 4 days, and even at least 7 days, or longer, in a rodent model, which translates to at least one week duration of action in a human subject, thus suitable for twice daily, once daily, three times weekly, twice weekly or even once weekly administration.

Functional activity of the compounds disclosed herein can be determined using a cell line expressing GLP-1 receptor. See e.g., United States Patent Application Publication US20110097751A1, incorporated by reference for the assay method. In this example, functional activity was determined using cells that endogenously express GLP-1R, and cAMP induction is detected as a measure of exendin activity. An HTRF assay kit was used (Cisbio International (Bedford, Mass.). The bioassay used the rat thyroid carcinoma 6-23 (clone 6) cells in the cell-based assay using the HTRF® cAMP dynamic 2 1,000 assay kit, available from Cisbio as Catalog No. 62AM4PEB. The HTRF® standards and calibrations are prepared following the instructions in the kit. Accumulation of cAMP is measured following 30 minutes of compound treatment using the HTRF (CisBio) cell-based cAMP assay kit in 384-well format. Efficacy of peptides is determined relative to cell treatment with 10 uM forskolin (a constitutive activator of adenylate cyclase), and potency ($EC_{50}$) of peptides is determined by the analysis of a concentration-response curve using non-linear regression analysis fitted to a 4-parameter model. The results of the GLP-1 receptor functional activity (cAMP induction) for potency ($EC_{50}$) are provided in the following Table 5, where values normalized to an exendin-4 standard. The ABD domain did not bind nor activate the GLP-1 receptor.

TABLE 5

GLP-1R Functional Activity

| Description | GLP-1R Functional activity ($EC_{50}$) in nM |
|---|---|
| Exendin-4 (SEQ ID NO: 2) | 0.004 |
| [Leu$^{14}$,Gln$^{28}$]Exendin-4(1-32)-fGLP-1)33-37) (SEQ ID NO: 4) | 0.016 |
| Exendin-4 (1-28) amide | 0.011 |
| Cmpd 5 (SEQ ID NO: 40) | 0.982 |
| Cmpd 6 (SEQ ID NO: 41) | 0.0325 |
| Cmpd 15 (SEQ ID NO: 163) | 0.091 |
| Cmpd 8 (SEQ ID NO: 43) | 0.048 |
| Cmpd 10 (SEQ ID NO: 51) | 0.146 |
| Cmpd 21 (SEQ ID NO: 99) | 0.131 |
| Cmpd 31 (SEQ ID NO: 95) | 0.62 |
| Cmpd 32 (SEQ ID NO: 97) | 2.043 |
| Cmpd 33 (SEQ ID NO: 96) | 0.77 |

Example 3

OGTT DOA Activity

Figure 1A:
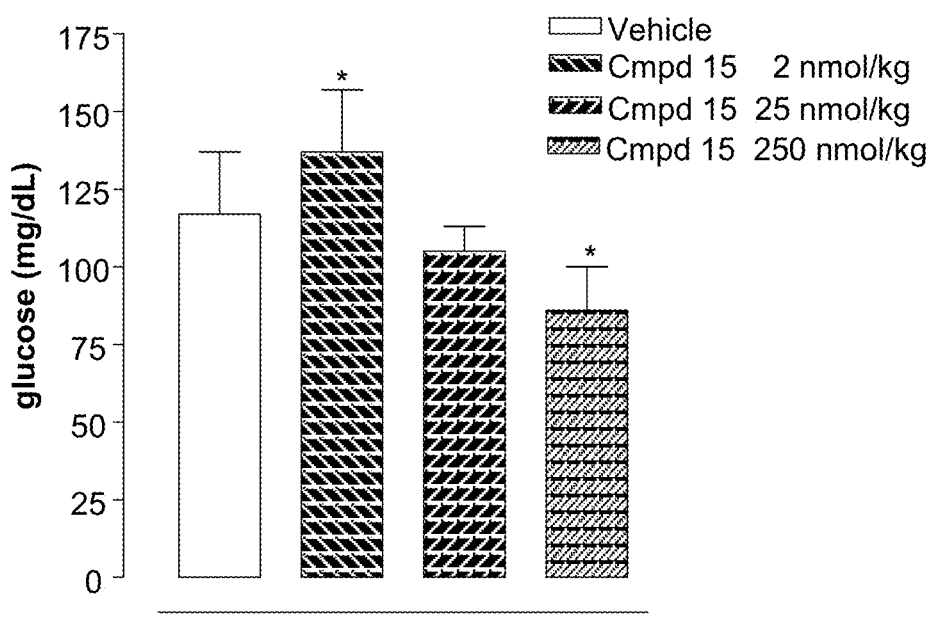
FIG. 1A: Blood glucose level (BGL) data histogram prior to gavage at 1-day post dosage of Cmpd 15 in OGTT DOA test. Vehicle mean pre-gavage glucose: 117 mg/dL. Legend (left to right): vehicle (open), 2 nmol/kg (diagonal upper left to lower right); 25 nmol/kg (diagonal lower left to upper right); 250 nmol/kg (fine diagonal).
Figure 1B:
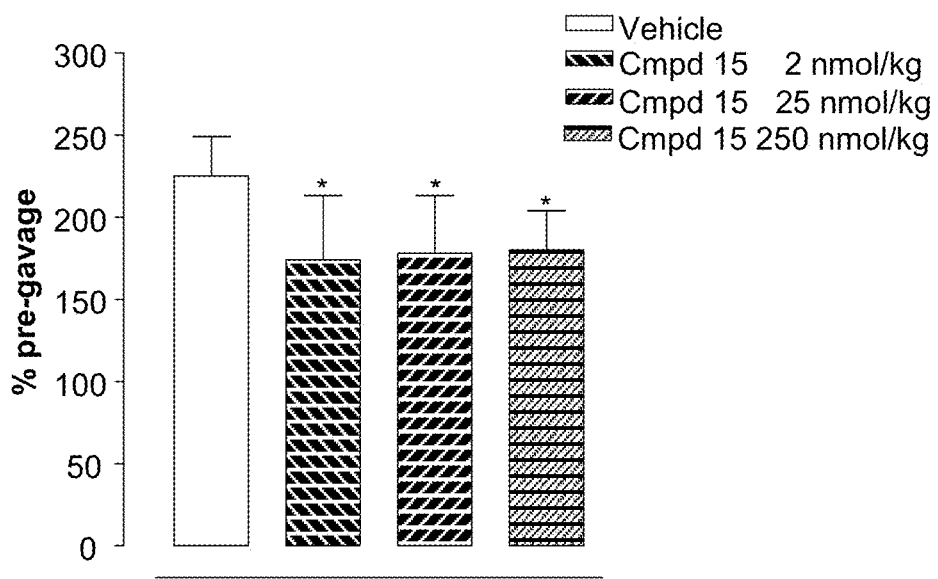
FIG. 1B: Change in blood glucose at 30 min. Vehicle mean pre-gavage glucose: 117 mg/dL. Legend: same as in FIG. 1A. *$p<0.5$ vs. vehicle control; ANOVA, Dunnett's test.

The effects on blood glucose prior to glucose gavage (1.5 k/kg dextrose) and at 30 minutes post-glucose gavage were investigated 1 day post dose of peptide compound with varying amounts of Cmpd 15, with results shown in FIGS. 1A-1B. Cmpd 31 at 25 nmol/kg also demonstrated activity at 24 hours post dosing, as shown in FIG. 9. Drug was administered to 4-hr fasted NIH/Swiss mice at the doses indicated in the figures. Bars represent mean±sd. Peptide was injected IP at t=−1 day. Glucose gavage (1.5 g/kg) given at t=0 to 4-hour fasted NIH/Swiss female mice. Blood glucose was measured with a OneTouch® Ultra® (LifeScan, Inc., a Johnson & Johnson Company, Milpitas, Calif.) * $p<0.05$ vs. vehicle control; ANOVA, Dunnett's test. This OGTT DOA indicates drug activity is present at least 24 hours after drug was administered. Exendin-4 (unconjugated) was ineffective in this assay when dosed at t-24 hours (1 day prior to the glucose assay), and even at higher doses.

Example 4

OGTT DOA Activity

Figure 2A:
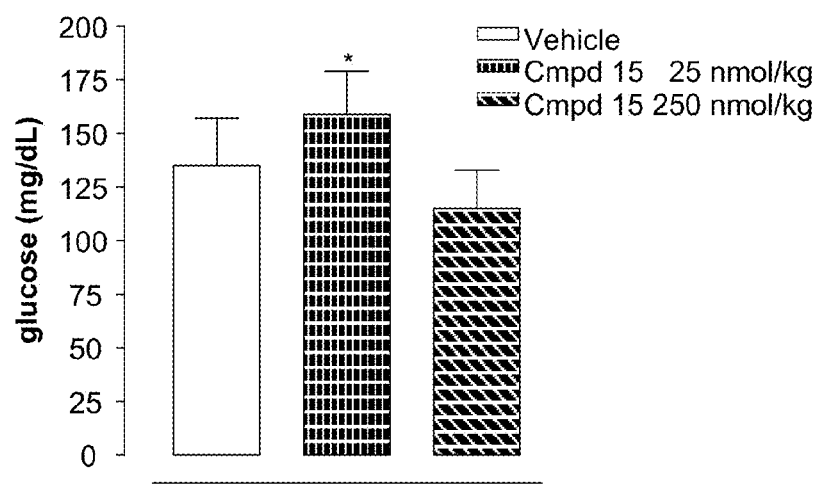
FIG. 2A: Blood glucose level (BGL) data histogram prior to gavage at 2-day post dosage of Cmpd 15 in OGTT DOA test. Vehicle mean pre-gavage glucose: 135 mg/dL. Legend (left to right): vehicle (open), 25 nmol/kg (vertical lines); 250 nmol/kg (diagonal lines).
Figure 2B:
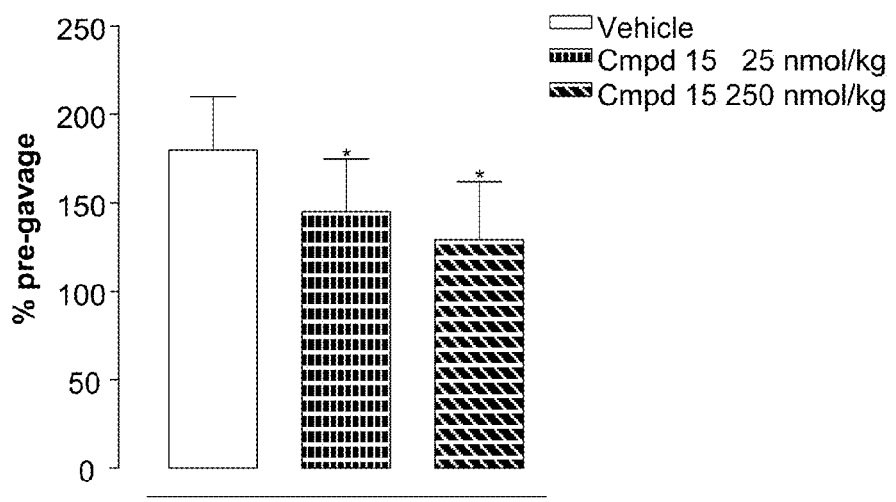
FIG. 2B: Change in blood glucose at 30 min. Vehicle mean pre-gavage glucose: 135 mg/dL. Legend: same as FIG. 2A. * p<0.5 vs. vehicle control; ANOVA, Dunnett's test.

The effects on blood glucose prior to gavage (1.5 k/kg dextrose) and at 30 min were investigated 2 day post dose with varying amounts of Cmpd 15, with results shown in FIGS. 2A-2B. Drug was administered to 4-hr fasted NIH/Swiss mice at the doses indicated in the figures. This OGTT DOA indicates drug activity is present at least 48 hours after drug was administered.

Example 5

OGTT DOA Activity

A comparison of the effects of Cmpds 15 and 8 on blood glucose was conducted, with results depicts in FIGS. 3A-3B. Drug was administered to 4-hr fasted NIH/Swiss mice at the doses indicated in the figures. This OGTT DOA indicates drug activity is present at least 24 hours after drug was administered.

Example 6

Effect of Cmpd 15 on HSD Fed Anesthetized Rats

The effects of treatment with Cmpd 15 (240 nmol/kg) were investigated in Sprague Dawley fed anesthetized rats 5 days post dose. The time course of plasma glucose after IVGTT is depicted in FIG. 4A. Integrated ($AUC_{0-60}$) glucose levels are depicted in the histogram of FIG. 4B. The time course of the change in insulin levels in the test subjects was depicted in FIG. 4C. The integrated insulin levels ($AUC_{0-30}$) are depicted in FIG. 4D. The time course of body weight change (% change from baseline) is depicted for the test subjects in FIG. 4E. A histogram depiction of daily food intake for the test subjects is provided in FIG. 4F. This IVGTT DOA indicates drug activity is present at least 5 days hours after drug was administered, particularly for effects on body weight and daily food intake.

Example 7

Effect of Cmpd 15 in ob/ob Mice

The time course of the effect of Cmpd 15 on body weight, glucose and $HbA_{1c}$ in ob/ob mice was investigated post dose. As depicted in FIG. 5A, significant body weight loss attends treatment with 250 nmol/kg Cmpd 15. Changes in glucose (% pre-treatment) and in HbA1c (% pre-treatment) are depicted in FIGS. 5B-5C. Points represent mean±s.d. (standard deviation). Cmpd 15 was injected sc on day=0 immediately following baseline sample collection in non-fasted male ob/ob mice. Unless indicated otherwise, blood glucose measures described herein employed a OneTouch® Ultra® device (LifeScan, Inc. Miliptas, Calif.). Cmpd 21 also demonstrated body weight loss and reduction of HbA1c.

Example 8

Activity of Cmpd 15 in Zucker Diabetic Fatty (ZDF) Rats

To assess the combined body weight and glucose lowering efficacy of exemplary compounds described herein, the dose dependent effects of Cmpd 15 in ~14 week old male ZDF rats was investigated. Baseline glucose was 426 mg/dL, and baseline body weight was 431 g. Group size n=8. FIG. 6A depicts the time course of the change in body weight (% vehicle corrected) after treatment. FIG. 6B depicts the time course of plasma glucose.

Example 9

Activity of Cmpds 15, 8 and 10 on OGTT DOA (Duration of Action)

The effects of Cmpds 15, 8 and 10 on the change in blood glucose at 30 min (% pre-gavage) was investigated, as depicted in FIG. 7. In the figure, bars represent mean±s.d. Test compound was injected IP at t=−1 day. Glucose gavage (1.5 g/kg) given at t=0 to 4 hr fasted NIH/Swiss female mice. Blood glucose was measured as described herein. This OGTT DOA indicates drug activity is present at least 24 hours after drug was administered.

Example 10

Activity of Cmpds on OGTT DOA (Duration of Action) at 24 Hours

The effects of compounds disclosed herein on the change in blood glucose at 30 min (% pre-gavage) were investigated as described above. Test compound was injected IP at t=−1 day at 25 nmol/kg. Glucose gavage (1.5 g/kg) given at t=0 to 4 hr fasted NIH/Swiss female mice. Blood glucose was measured as described herein. This OGTT DOA indicates drug activity is present at least 24 hours after drug was administered. Results are presented in the following Table 6. Cmpd 30 (Lysine 27-linked) and Cmpd 32 gave no glucose lowering, indicating a lack of presence at 24 hours under these conditions. Exendin-4 (unconjugated) was ineffective in this assay when dosed at t-24 hours, and even at higher doses. Cmpd 14 with proline at position 3 was essentially inactive in the in vitro functional assay and inactive (and perhaps weight promoting) in the glucose lowering OGTT assay (data not shown). Cmpd 22 with an albumin binding sequence the PAB protein from *P. magnus* had little if any weight lowering (3%) in the above assay. Cmpd 19 and Cmpd 20 with truncated ABDs still maintained in vitro activity, but with reduced duration, having 6% and 8% glucose lowering in the OGTT DOA assays, respectively.

TABLE 6

Glucose Lowering in OGTT at 24 Hours Post Dose

| Description | % Glucose Lowering Compared to Vehicle |
|---|---|
| Cmpd 5 (SEQ ID NO: 40) | −28 |
| Cmpd 6 (SEQ ID NO: 41) | −18 |
| Cmpd 15 (SEQ ID NO: 163) | −21 |
| Cmpd 8 (SEQ ID NO: 43) | −21 |
| Cmpd 10 (SEQ ID NO: 51) | −22 |
| Cmpd 21 (SEQ ID NO: 99) | −23 |
| Cmpd 23 (SEQ ID NO: 169) | −23 |
| Cmpd 24 (SEQ ID NO: 170) | −17 |
| Cmpd 31 (SEQ ID NO: 95) | −22 |
| Cmpd 33 (SEQ ID NO: 96) | −19 |

Example 11

Serum Albumin Binding

Characterization of the binding of engineered polypeptide compounds to albumin can be performed by any number of methods, including that of Biacore described herein. In this example binding measurements were conducted with a BioRad ProteOn XPR36 system (BioRad Laboratories, Hercules Calif., USA; ProteOn XPR36 Protein Interaction Array System catalog number #176-0100), using a GLC sensor chip at 25 degrees C. For amine coupling the GLC chip was activated for 5 minutes using a 1:1 mixture of sulfo-NHS/EDC diluted 30-fold from the initial stock in water as shown below. Each albumin sample was diluted to 25 ug/ml in 10 mM Na acetate pH 5.0 and injected for 5 minutes over separate sensor surfaces. Each surface was then blocked with 1 M ethanolamine pH 8.5. Each albumin was coupled at a density of 2000-5000 in resonance units. The binding of an engineered polypeptide was tested using 5 nM as the highest concentration in a three-fold dilution series. The running buffer contained 10 mM HEPES pH 7.4, 150 mM NaCl, 3 mM EDTA and 0.005% tween-20. All samples were tested using a 3-fold dilution series. Each concentration series was tested in duplicate. The dissociation phase for the highest concentration was monitored for 3 hours.

The relative $K_D$ measured for the engineered polypeptides are presented in Table 7 below. The results show that the albumin binding polypeptides associate with serum albumins with high affinity. The number in parentheses represents the standard deviation in the last significant digit. As seen from the following table the exendin polypeptides fused to albumin binding domains of SEQ ID NO:35 retain extremely high affinity for serum albumin from various species, especially human serum albumin, even compared to the unconjugated ABD peptide itself.

TABLE 7

| Cmpd | Human SA | Dog SA | Monkey SA | Mouse SA | Rat SA |
|---|---|---|---|---|---|
| SEQ ID NO: 35 | 16 (4) pM | 201 (2) pM | 123 (1) pM | 1.24 (1) nM | 18 (5) pM |
| Cmpd 15 | 68 pM | 513 pM | 91 pM | 1.25 nM | 200 pM |
| Cmpd 21 | 85 pM | 397 pM | 78 pM | 1.33 nM | 16 pM |

Example 12

Activity in the Presence of Serum Albumin

Characterization of the in vitro activity of the engineered polypeptide compounds in the presence of serum albumin was demonstrated. Assays can be run in the presence and absence of an albumin, particularly human serum albumin. The data above was determined in the presence of about 0.1% bovine serum albumin (BSA). The following table presents functional activity of receptor activation (cAMP induction) assay described above, but in the presence of serum albumin from various species. As can be seen, surprisingly, even when compounds are bound to serum albumin, such as to human serum albumin, despite the presence of the large serum albumin, with its potential for steric hindrance and even a change in the apparent Stoke's radius of the compounds resulting from albumin binding, the engineered polypeptide retains GLP-1 receptor agonist activity. Given the picomolar affinity of ABD and the engineered polypeptides to some species of serum albumin, e.g. human serum albumin, the engineered polypeptide is believed to be effectively fully bound to albumin present in the assay (and thus also in vivo in circulating blood). Because of the extremely high affinity of compound binding to albumin (as above) and the presence of high concentration of serum albumin in the blood, it is expected that the compounds will exist essentially in the bound state in vivo yet surprisingly provide sufficient exendin functions (as demonstrated herein).

TABLE 8

| Cmpd | 0.1% Bovine Albumin | 1% Bovine Albumin | 1% Human Albumin | 1% Rat Albumin |
|---|---|---|---|---|
| GLP-1(7-36) amide (SEQ ID NO: 5) | 0.0306 | 0.0058 | 0.0112 | 0.0179 |
| Cmpd 15 (SEQ ID NO: 163) | 0.7854 | 0.2204 | 0.185 | 0.2473 |
| Cmpd 21 (SEQ ID NO: 99) | 1.1013 | 0.2234 | 0.2022 | 0.2164 |
| Cmpd 31 (SEQ ID NO: 95) | 1.1408 | 0.2313 | 0.2139 | 0.2358 |
| GLP-1(7-36) amide normal assay conditions | 0.0256 | 0.0224 | 0.0165 | 0.0153 |

Example 13

Compounds are Stable to Human Plasma and Human Plasma Enzymes

Compounds were examined for stability to human plasma and human cell membrane proteases. Stability of representative peptides in human plasma was performed as follows. 10 µg/ml of compound in human plasma was prepared at sufficient volume to remove 100 µL samples every 10 minutes for the time period (5 hours), starting at the zero time point. Following the addition of compound to the human plasma, the sample is mixed gently and a 100 µL sample of the mixture was transferred to a microcentrifuge tube to represent the zero time point. The remainder of the sample was placed in an incubator at 37 degrees C., mixing at 600 RPM for sixty minutes. At 10 minute intervals, a 100 µl sample of the mixture was removed and transferred to a separate microcentrifuge tubes. Following the transfer of the 100 µL sample at the zero time point and each 10 minute interval, each collected sample was extracted by slow addition of 100 µl cold 0.2% formic acid:acetonitrile, while mixing. After addition of the acetonitrile solution, the sample was vortex mixed at high speed for 15 seconds. The extracted samples were stored at −20° C. for at least 20 minutes and then centrifuged at 11,000×g for 10 minutes at 5 degrees C. The supernatant of each sample was transferred to a new microcentrifuge tube, centrifuged again, and finally transferred for LC/MS analysis. Sample analysis was done on an Agilent HLPC (LC/MS 1200) using gradient 5-95% acetonitrile in water containing 0.1% trifluoroacetic acid. Table 9 present results normalized to a standard (100%).

FIG. 8 presents a time profile of percent of compound remaining in Human Plasma over the 5 hour time course.

TABLE 9

| Cmpd | Percent Stable in Human Plasma |
| --- | --- |
| GLP-1(7-37) amide (SEQ ID NO: 5) | 41.7 |
| HGEGTFTSDLSKQLEEEAVRLFIEWLKQ GGPSKEIIS (SEQ ID NO: 4) | 100 |
| Cmpd 15 (SEQ ID NO: 163) | 96.0 |
| Cmpd 21 (SEQ ID NO: 99) | 89.5 |
| Cmpd 31 (SEQ ID NO: 95) | 93.7 |

Relative stability of representative peptides in a human kidney brush border membrane (KBBM) assay was performed as follows. Human kidney brush border membrane protein extracts are rich in various peptidases. Protein extract preparation (hKBBMP), 5 microL (approximately 7 micrograms/mL of protein) was diluted with 625 microL of HEPES buffer (25 mM, pH 7.4) in a polypropylene micro centrifuge tube with an O-ring seal to avoid solvent evaporation. In a separate vial, peptide stock solution (300 microM in 50% acetonitrile in water) was prepared and 70 microL of this solution was added to the above hKBBMP solution. The solution was gently mixed by manual shaking so that the final peptide concentration is 30 microM. Then 100 microL of this solution was aliquoted into six different tubes and into one tube 200 microL of enzyme stop solution (50% acetonitrile in water with 0.1% TFA) was added. This tube was used for the measurement of the initial peptide concentration at time t=0 minute while all other 5 tubes were incubated at 37 degrees C. using a water bath. At intervals of 1, 2, 3, 4 and 5 hour, each tube was taken out and quenched with 200 microL of stop solution. Finally, all six tubes were centrifuged at 1800×g for 10 min to remove any precipitated proteins. The supernatant (10 microL) was transferred into an HPLC auto sampler, and by using selected ion count method AUC was measured. Each sample was run in triplicates and average AUC was calculated for data analysis. Sample analysis was done on Agilent HPLC with mass detector with an acetonitrile with 0.1% TFA gradient. Percentage of parent peptide remaining from time t=0 to 5 hours of enzymatic digestion was plotted using GraphPad Prism® 5 software. The data was reported as relative peptide stability versus positive control for each peptide. As noted samples were run as n=6, and CV was within 20%. Results from the hKBBM stability assay are presented in Table 10.

TABLE 10

| Cmpd | Percent Stable |
| --- | --- |
| GLP-1(7-37) amide (SEQ ID NO: 5) | 16 |
| HGEGTFTSDLSKQLEEEAVRLFIEWLKQGGPS KEIIS (SEQ ID NO: 4) | 100 |
| Cmpd 21 (SEQ ID NO: 99) | 103 |

Example 14

Lack of Vacuolization

With some drugs, such as some pegylated proteins, undesirable vacuoles can form in cytoplasm of epithelial cells lining the proximal convoluted tubules, which is an undesirable toxicity measure. The engineered albumin binding compounds of the present application do not form kidney vacuoles. C57BL6 female mice (n=2 cages, 3 mice/cage) were weighed daily 3 hours prior to lights out. Immediately after weighing, on days 0-6 mice were injected subcutaneously with test compound. Mice were sacrificed on day 7 and kidneys submitted for histopathology. Severity score for cytoplasmic vacuolation of renal cortical tubular epithelial cells was as follows: score 1=minimal (8-15%); 2=mild (16-35%); 3=moderate (36-60%); 4=marked (>60%). A positive control compound known to cause vacuole formation was scored as 3. The ABD polypeptide itself scored 0. Cmpd 15 scored 0.

Example 15

Effect on Inhibiting Food Intake in Normal Mice

The time course of the effect of test compounds on inhibition of food intake of normal mice was determined. As depicted in FIG. 10A, dose-dependent, significant body weight loss attends treatment with Cmpd 31 over 6 hours. FIG. 10B demonstrates a dose-dependent, sustained inhibition of food intake after a single dose of compound, for at least 54 hours in normal mice. Effect of exendin analog is gone within 24 hours. Cmpd 31 still significantly inhibits food intake even at 3 days at the highest dose. Points represent mean±sd of n=4 cages (3 mice/cage). Peptide was injected IP at t=0. Food was introduced immediately after injection and amount consumed measured at t=30, 60, 120, 180, 240, 300, 360 min, 24 h, 30 h, 48 h, and 54 h. *p<0.05 vs. vehicle control; ANOVA, Dunnett's test. ED50's were ~10 nmol/kg for Cmpd 31 and 2 nmol/kg for [Leu14] exendin-4.

Example 16

Effect of an Exendin-Albumin Binding Domain Polypeptide in Diabetic Ob/Ob Mice

To demonstrate the effect of chronic exposure of an exendin-albumin binding domain engineered polypeptide described herein on glucose lowering, HbA1c lowering, and body weight reduction, diabetic ob/ob/ mice were treated with Cmpd 15 and Cmpd 21. The time course of the effect of the test compound on body weight, glucose lowering and HbA$_{1c}$ lowering in ob/ob mice was investigated post dose, with values at 4 weeks presented in FIGS. 11A, 11B, 11C and 11D. FIGS. 11A (Cmpd 15) and 11B (Cmpd 21) depict changes in blood glucose compared to liraglutide, all given twice weekly (BIW). and FIG. 11C depicts lowering of HbA1c (% change from baseline) for Cmpd 15 and Cmpd 21 given twice weekly (BIW), compared to exendin-4 given by continuous subcutaneous infusion (CSI). FIG. 11D depicts reduction in body weight (% change from baseline) for Cmpd 15 and Cmpd 21 given twice weekly (BIW), compared to exendin-4 given by continuous subcutaneous infusion (CSI). Surprisingly, as seen from FIGS. 11A and 11B, each compound is superior to liraglutide at equimolar dosing for glucose lowering upon chronic exposure. Further, at equimolar dosing to liraglutide, Cmpd 15 and Cmpd 21 were each more effective than liraglutide [N-epsilon-(gamma-Glu (N-alpha-hexadecanoyl))-Lys26,Arg34]-GLP-1-(7-37)-acid, a long-acting albumin binding GLP-1 derivative, in HbA1c lowering and body weight loss (data not shown). As depicted in FIG. 11C significant HbA1c lowering attends treatment and in FIG. 11D significant body weight loss attends treatment, with 25 and 250 nmol/kg of each compound provided intraperitoneally (IP) twice each week for 28 days. Points represent mean±s.d. (standard deviation). Each test compound was injected IP on day=0 immediately following baseline sample collection in non-fasted male ob/ob mice. The effects observed for the 25 nmol/kg biw (twice weekly) dose was greater than that observed for exendin-4 given at ~7.2 nmol/kg/d by continuous infusion (CSI), a dose known to provide a maximal efficacy for exendin-4. Thus at a comparable equimolar dose, Cmpd 15 and Cmpd 21 exceeded the glycemic and body weight loss effects of the maximally efficacious dose of exendin-4. At 250 nmol/kg, Cmpd 15 was significantly greater and Cmpd 21 was twice as effective, as the maximally efficacious dose of exendin-4. Unless indicated otherwise, blood glucose measures described herein employed a OneTouch® Ultra® device (LifeScan, Inc. Miliptas, Calif.).

Surprisingly, despite the reduced in vitro potency compared to unconjugated exendin-4 as observed above, the acute (within 6 hours) in vivo activity of an exendin fused to an albumin binding polypeptide disclosed herein is similar to that of unconjugated exendin with regard to maximum efficacy and only slightly less (several fold) with regard to potency (ED50 for example), such as when measured by reduction of food intake in mice (data not shown). Even more surprisingly, the effect of chronic exposure demonstrates that an exendin fused to the albumin binding polypeptides disclosed herein is as potent or even has greater potency as exendin-4 (continuously infused) but is able to provide a greater maximal effect. Furthermore, in light of the very high affinity for mouse or rat albumin and low off rates, all of the engineered compounds are effectively bound to albumin in the in vivo assays (as well as in the in vitro assays). Thus the engineered polypeptides retained GLP-1R functional activity even when bound to albumin. This is surprising in part because albumin compounds, e.g. liraglutide, have been reported as significantly active only when dissociated from albumin. And others have reported a need to remove proteolytically an exendin from an albumin binding peptide to which it was conjugated in order to obtain exendin function. Accordingly, the in vivo activities as shown herein are even more impressive.

Example 17

Long Duration and Action of the Engineered Polypeptides In Vivo

To further demonstrate the long half-life and long duration of activity of the engineered polypeptides described herein, the pharmacokinetic (PK) and pharmacodynamic (PD) properties were determined using rats. Pharmacokinetic profile and biological activity of exemplary engineered polypeptides Cmpd 15 and Cmpd 21 subcutaneously dosed in normal Harlan Sprague-Dawley (HSD) rats is presented. The recombinant engineered compounds Cmpd 21 and Cmpd 15 were injected subcutaneously at t=0 at 25 nmol/kg into normal HSD rats. Blood was collected via tail bleed at t=1 hour, 3 hours, 6 hours, 24 hours, 48 hours, 72 hours, 96 hours and 168 hours from fed HSD male rats. Food and body weights were measured daily. FIG. 12A depicts effect of Cmpd 15 and Cmpd 21 to reduce food intake. FIG. 12B depicts effect of Cmpd 15 and Cmpd 21 to reduce body weight. FIG. 12C depicts a PK profile of Cmpd 15 and Cmpd 21 after a single dose. Points represent mean±sd.

Exposure of at least up to seven (7) days was observed for both exemplary engineered polypeptides. Cmpd 15 has an apparent half-life of 54 hours and Cmpd 21 has an apparent half-life of 61 hours, in rats by this subcutaneous delivery. By allometric scaling and in view of the strong affinity of the engineered polypeptides for human albumin, physical and biological activity duration at least as long and even longer is expected in human subjects. Accordingly, the compounds have use for at least twice daily (e.g. morning and night), at least daily, twice weekly, and even once weekly administration, especially in human subjects.

Pharmacokinetic profile and biological activity of an exemplary engineered polypeptide intravenously dosed in normal Harlan Sprague-Dawley (HSD) rats is presented. The recombinant engineered compound Cmpd 31 was injected intravenously at t=0 at 2 nmol/kg into normal HSD rats. Blood was collected via tail bleed at t=1 hour, 3 hours, 6 hours, 24 hours, 48 hours, 72 hours, 96 hours and 168 hours from fed HSD male rats. Food and body weights were measured daily. FIG. 13A depicts effect of Cmpd 31 to reduce food intake. FIG. 13B depicts effect of Cmpd 31 to reduce body weight. FIG. 13C depicts a PK profile of Cmpd 31 after a single IV dose. Half-life is estimated at about at least 14 hours, Points represent mean±sd.

Exposure of up to seven (7) days was observed for this exemplary engineered polypeptide, even at these relatively low doses. By allometric scaling and in view of the strong affinity of the engineered polypeptides for human albumin, physical and biological activity duration at least as long and even longer is expected in human subjects. Accordingly, the compounds have use for at least twice daily (e.g. morning and night), at least daily, twice weekly, and even once weekly administration, especially in human subjects.

Example 18

Oral Delivery of Engineered Polypeptides Achieves Systemic Distribution

Oral delivery with intestinal uptake was investigated using a representative engineered compound. Diabetic db/db mice were dosed orally (peroral via gavage) with 240 nmol/kg of the following compounds, an exendin analog [Leu14,Gln28]Exendin-4-(1-32)-fGLP-1-(33-37) acid and Cmpd 15. The data demonstrate that the engineered peptides are orally bioavailable, even in a formulation PBS/propylene glycol (50:50) absent other specific excipients that might enhance delivery and uptake. Compared to the exendin analog, Cmpd 15 (both at 1 mg/kg dose) at more than twice the molecular weight of the exendin analog is also orally bioavailable in the same formulation. The results indicate that both compounds were active when dosed orally, and equally efficacious under the conditions tested to 120 minutes. The results are presented in FIG. 14. Points represent mean+/−sd. Peptides were dosed peroral by gavage at t=0 immediately following the taking of a baseline sample. Mice were 2-hour fasted db/db mice. Accordingly, the compounds presented herein have use for at least twice daily (e.g. morning and night), at least daily, thrice weekly, twice weekly, and even once weekly oral administration, especially in human subjects.

VIII. Embodiments

Embodiment 1

An engineered polypeptide comprising: an albumin binding domain polypeptide (ABD) sequence and a first peptide hormone domain (HD1) sequence selected from an exendin sequence, an exendin analog sequence, an exendin active fragment sequence or an exendin analog active fragment sequence.

Embodiment 2

The engineered polypeptide according to embodiment 1, further comprising a first linker (L1) covalently linking said ABD sequence and said HD1 sequence.

Embodiment 3

The engineered polypeptide according to any one of embodiments 1 to 2, wherein said engineered polypeptide comprises said ABD sequence as a C-terminal moiety and said HD1 sequence as an N-terminal moiety.

Embodiment 4

The engineered polypeptide according to embodiment 3, having the structure HD1-ABD.

Embodiment 5

The engineered polypeptide according to embodiment 3, having the structure HD1-L1-ABD.

Embodiment 6

The engineered polypeptide according to any one of the embodiments 1 to 5, wherein said HD1 sequence consists of said exendin sequence or said exendin analog sequence.

Embodiment 7

The engineered polypeptide according to embodiment 6, wherein said exendin sequence is exendin-4 sequence.

Embodiment 8

The engineered polypeptide according to embodiment 6, wherein said exendin active fragment sequence is the sequence of exendin-4(1-28), exendin-4(1-29), exendin-4(1-30), exendin-4(1-31) or exendin-4(1-32) (SEQ ID NO:2).

Embodiment 9

The engineered polypeptide according to claim 6, wherein the sequence of said exendin or exendin analog comprises a sequence selected from the group consisting of (SEQ ID NO:3), (SEQ ID NO:4), (SEQ ID NO:2), (SEQ ID NO:111), (SEQ ID NO:112), (SEQ ID NO:113), (SEQ ID NO:114), (SEQ ID NO:115), (SEQ ID NO:116), (SEQ ID NO:117), and (SEQ ID NO:118).

Embodiment 10

The engineered polypeptide according to any one of embodiments 1 to 9, wherein said exendin analog sequence has at least 70% identity with exendin-4 sequence or to an exendin analog sequence selected from the group consisting of any one of sequences (SEQ ID NO:3), (SEQ ID NO:4), (SEQ ID NO:2), (SEQ ID NO:111), (SEQ ID NO:112), (SEQ ID NO:113), (SEQ ID NO:114), (SEQ ID NO:115), (SEQ ID NO:116), (SEQ ID NO:117), and (SEQ ID NO:118).

Embodiment 11

The engineered polypeptide according to any one of embodiments 1 to 10, wherein said exendin analog sequence comprises from 1 to 5 amino acid modifications relative to exendin-4 sequence, or to an exendin analog with sequence selected from the group consisting of (SEQ ID NO:3), (SEQ ID NO:4), (SEQ ID NO:2), (SEQ ID NO:111), (SEQ ID NO:112), (SEQ ID NO:113), (SEQ ID NO:114), (SEQ ID NO:115), (SEQ ID NO:116), (SEQ ID NO:117), and (SEQ ID NO:118), said modifications independently selected from any one or combination of an insertion, deletion, addition and substitution.

Embodiment 12

The engineered polypeptide according to any one of embodiments 1 to 11, wherein said ABD sequence comprises an albumin binding motif (ABM) sequence.

Embodiment 13

The engineered polypeptide according to any one of embodiments 1 to 11, wherein said ABD sequence comprises an albumin binding motif (ABM) sequence that consists of amino acid sequence: GVSD X5 YK X8 X9 I X11 X12 A X14 TVEGV X20 AL X23 X24 X25 I (SEQ ID NO:119), wherein, X5 is selected from Y and F; X8 is selected from N, R and S; X9 is selected from V, I, L, M, F and Y; X11 is selected from N, S, E and D; X12 is selected from R, K and N; X14 is selected from K and R; X20 is selected from D, N, Q, E, H, S, R and K; X23 is selected from K, I and T; X24 is selected from A, S, T, G, H, L and D; and X25 is selected from H, E and D.

Embodiment 14

The engineered polypeptide according to any one of embodiments 1 to 13, wherein said ABD sequence comprises an albumin binding motif (ABM) sequence that does not consist of the amino acid sequence GVSDYYKNLINNAKTVEGVKALIDEI (SEQ ID NO:120).

Embodiment 15

The engineered polypeptide according to any one of embodiments 1 to 14, wherein said ABD sequence comprises the amino acid sequence: LAEAK Xa Xb A Xc Xd EL Xe KY (SEQ ID NO:182) covalently linked to an albumin binding motif (ABM) sequence which is further covalently linked to amino acid sequence LAALP (SEQ ID NO:183), wherein Xa is selected from V and E; Xb is selected from L, E and D; Xc is selected from N, L and I; Xd is selected from R and K; and Xe is selected from D and K.

Embodiment 16

The engineered polypeptide according to any one embodiments 1 to 15, wherein said ABD sequence comprises the amino acid sequence: LAEAK Xa Xb A Xc Xd EL Xe KY GVSD X5 YK X8 X9 I X11 X12 A X14 TVEGV X20 AL X23 X24 X25 I LAALP (SEQ ID NO:121), wherein Xa is selected from V and E; Xb is selected from L, E and D; Xc is selected from N, L and I; Xd is selected from R and K; Xe is selected from D and K; X5 is selected from Y and F; X8 is selected from N, R and S; X9 is selected from V, I, L, M, F and Y; X11 is selected from N, S, E and D; X12 is selected from R, K and N; X14 is selected from K and R; X20 is selected from D, N, Q, E, H, S, R and K; X23 is selected from K, I and T; X24 is selected from A, S, T, G, H, L and D; and X25 is selected from H, E and D.

Embodiment 17

The engineered polypeptide according to embodiment 16, wherein in said ABD sequence the C-terminal proline is absent.

Embodiment 18

The engineered polypeptide according to any one of embodiments 16 to 17, wherein in said ABD sequence the leucine at position 45 is absent.

Embodiment 19

The engineered polypeptide according to any one of embodiments 16 to 18, wherein said ABD sequence further comprises an N-terminal addition selected from A, AS, G or GS.

Embodiment 20

The engineered polypeptide according to embodiment 16, wherein said ABD sequence comprises the amino acid sequence LAEAKVLANRELDKYGVSDFYKRLINKAK-TVEGVEALKLHILAALP (SEQ ID NO:35).

Embodiment 21

The engineered polypeptide according to embodiment 16, wherein said ABD sequence comprises a sequence selected from the group consisting of: (SEQ ID NO: 23), (SEQ ID NO: 24), (SEQ ID NO: 25), (SEQ ID NO: 26), (SEQ ID NO: 27), (SEQ ID NO: 28), (SEQ ID NO: 29), (SEQ ID NO: 30), (SEQ ID NO: 31), (SEQ ID NO: 32), (SEQ ID NO: 33), (SEQ ID NO: 34), (SEQ ID NO: 35), (SEQ ID NO:122), (SEQ ID NO:123) and (SEQ ID NO:124).

Embodiment 22

The engineered polypeptide according to any one of embodiments 1 to 11, wherein the sequence of said ABD has at least 85% identity with the sequence of an ABD with sequence selected from the group consisting of (SEQ ID NO:23), (SEQ ID NO:24), (SEQ ID NO:25), (SEQ ID NO:26), (SEQ ID NO:27), (SEQ ID NO:28), (SEQ ID NO:29), (SEQ ID NO:30), (SEQ ID NO:31), (SEQ ID NO:32), (SEQ ID NO:33), (SEQ ID NO:34), (SEQ ID NO:35), (SEQ ID NO:122), (SEQ ID NO:123) and (SEQ ID NO:124).

Embodiment 23

The engineered polypeptide according to any one of embodiments 16 to 22, wherein in said ABD sequence the C-terminal proline is absent.

Embodiment 24

The engineered polypeptide according to any one of embodiments 16 to 23, wherein in said ABD sequence the leucine at position 45 is absent.

Embodiment 25

The engineered polypeptide according to any one of embodiments 2 to 24, wherein said linker L1 is a peptide linker of from 1 to 30 amino acids.

Embodiment 26

The engineered polypeptide according to any one of embodiments 2 to 25, wherein said linker L1 is selected from the 20 naturally occurring amino acids.

Embodiment 27

The engineered polypeptide according to any one of embodiments 2 to 25, wherein said linker L1 comprises a non-natural amino acid incorporated by chemical synthesis, post-translational chemical modification or by in vivo incorporation by recombinant expression in a host cell.

Embodiment 28

The engineered polypeptide according to any one of embodiments 2 to 27, wherein said linker L1 amino acids are selected from glycine, alanine, proline, asparagine, glutamine, and lysine.

Embodiment 29

The engineered polypeptide according to any one of embodiments 2 to 28, wherein said linker L1 comprises a majority of amino acids that are sterically unhindered.

Embodiment 30

The engineered polypeptide according to any one of embodiments 2 to 29, wherein said linker L1 comprises polyglycine, polyalanine, poly(Gly-Ala) or poly(Gly-Ser).

Embodiment 31

The engineered polypeptide according to embodiment 30, wherein said linker L1 comprises the sequence (Gly)3, (Gly)4 (SEQ ID NO:196), or (Gly)5 (SEQ ID NO:197).

Embodiment 32

The engineered polypeptide according to any one of embodiments 2 to 29, wherein said linker L1 comprises the sequence (Gly)3Lys(Gly)4 (SEQ ID NO:131); (Gly)3AsnGlySer(Gly)2 (SEQ ID NO:132); (Gly)3Cys(Gly)4 (SEQ ID NO:133); or GlyProAsnGlyGly (SEQ ID NO:134).

Embodiment 33

The engineered polypeptide according to any one of embodiments 2 to 32, wherein said linker L1 comprises combinations of Gly and Ala.

Embodiment 34

The engineered polypeptide according to any one of embodiments 2 to 32, wherein said linker L1 comprises combination of Gly and Ser.

Embodiment 35

The engineered polypeptide according to any one of embodiments 2 to 34, wherein said linker L1 is selected from the group consisting of a glycine rich peptide.

Embodiment 36

The engineered polypeptide according to any one of the embodiments 2 to 35, wherein said linker L1 comprises an N-terminal TG dipeptide.

Embodiment 37

The engineered polypeptide according to any one of embodiments 2 to 36, wherein said linker L1 comprises a C-terminal AS dipeptide.

Embodiment 38

The engineered polypeptide according to any one of embodiments 2 to 37, wherein said linker L1 comprises an N-terminal TG dipeptide and a C-terminal AS dipeptide.

Embodiment 39

The engineered polypeptide according to any one of embodiments 2 to 38, wherein said linker L1 comprises a sequence selected from the group consisting of TG-(GGGS)1 (SEQ ID NO:198), TG-(GGGS)2 (SEQ ID NO:199), TG (GGGS)3 (SEQ ID NO:200), TG-(GGGS)4 (SEQ ID NO:201), TG-(GGGS)5 (SEQ ID NO:202), (GGGS)1-AS (SEQ ID NO:203), (GGGS)2-AS (SEQ ID NO:204), (GGGS)3-AS (SEQ ID NO:205), (GGGS)4-AS (SEQ ID NO:206), (GGGS)5-AS (SEQ ID NO:207), TG-(GGGS)1-AS (SEQ ID NO:208), TG-(GGGS)2-AS (SEQ ID NO:209), TG-(GGGS)3-AS (SEQ ID NO:210), TG (GGGS)4-AS (SEQ ID NO:211), and TG-(GGGS)5-AS (SEQ ID NO:212).

Embodiment 40

The engineered polypeptide according to embodiment 39, wherein said linker L1 TG dipeptide or AS dipeptide are absent or are replaced by a pair of amino acids selected from T, A, S, and G.

Embodiment 41

The engineered polypeptide according to any one of embodiments 1 to 40, which binds to serum albumin with a dissociation constant less than about 10-6 mol/L.

Embodiment 42

The engineered polypeptide according to embodiment 41, which binds to serum albumin with a dissociation constant less than about 10-9 mol/L.

Embodiment 43

The engineered polypeptide according to embodiment 42, which binds to serum albumin with a dissociation constant less than about 10-12 mol/L.

Embodiment 44

The engineered polypeptide according to any one of embodiments 1 to 43, wherein the polypeptide has a duration of action of at least 1 day.

Embodiment 45

The engineered polypeptide according to embodiment 44, wherein the polypeptide has a duration of action of at least 3 days.

Embodiment 46

The engineered polypeptide according to embodiment 45, wherein the polypeptide has a duration of action of at least 6 days.

Embodiment 47

The engineered polypeptide according to any one of embodiments 1 to 46, wherein the polypeptide has a duration of action of at least 6 days in a human subject.

Embodiment 48

The engineered polypeptide of any one of embodiments 1 to 47 comprising (SEQ ID NO:40), (SEQ ID NO:41), (SEQ ID NO:42), (SEQ ID NO:43), (SEQ ID NO:51), (SEQ ID NO:163), (SEQ ID NO:99), (SEQ ID NO:169), (SEQ ID NO:170), (SEQ ID NO: 95), (SEQ ID NO: 97), (SEQ ID NO: 96), (SEQ ID NO:55), (SEQ ID NO:53), (SEQ ID NO:62), (SEQ ID NO:67), (SEQ ID NO:166), (SEQ ID NO:167), (SEQ ID NO:51), (SEQ ID NO:52), (SEQ ID NO:53), (SEQ ID NO:54), (SEQ ID NO:55), (SEQ ID NO:56), (SEQ ID NO:57), (SEQ ID NO:58), (SEQ ID NO:59), (SEQ ID NO:60), (SEQ ID NO:61), (SEQ ID NO:62), (SEQ ID NO:63), (SEQ ID NO:64), (SEQ ID NO:65), (SEQ ID NO:66), (SEQ ID NO:67), (SEQ ID NO:68), (SEQ ID NO:70), (SEQ ID NO:71), (SEQ ID NO:72), (SEQ ID NO:73), (SEQ ID NO:74), (SEQ ID NO:75), (SEQ ID NO:76), (SEQ ID NO:77), (SEQ ID NO:78), (SEQ ID NO:79), (SEQ ID NO:80), (SEQ ID NO:81), (SEQ ID NO:82), (SEQ ID NO:83), (SEQ ID NO:84), (SEQ ID NO:85), (SEQ ID NO:86), (SEQ ID NO:87), (SEQ ID NO:88), (SEQ ID NO:89), (SEQ ID NO:90), (SEQ ID NO:91), (SEQ ID NO:92), (SEQ ID NO:93), (SEQ ID NO:94), (SEQ ID NO:95), (SEQ ID NO:96), (SEQ ID NO:97), (SEQ ID NO:98), (SEQ ID NO:99), (SEQ ID NO:100) (SEQ ID NO:101), (SEQ ID NO:102), (SEQ ID NO:103), (SEQ ID NO:104), (SEQ ID NO:105), (SEQ ID NO:106), (SEQ ID NO:107), (SEQ ID NO:108) or (SEQ ID NO:109).

Embodiment 49

The engineered polypeptide of any one of embodiments 1 to 47 comprising (SEQ ID NO:40), (SEQ ID NO:41), (SEQ ID NO:42), (SEQ ID NO:43), (SEQ ID NO:51), (SEQ ID NO:163), (SEQ ID NO:99), (SEQ ID NO:169), (SEQ ID NO:170), (SEQ ID NO: 95), (SEQ ID NO: 97), (SEQ ID NO: 96), (SEQ ID NO:55), (SEQ ID NO:53), (SEQ ID NO:62), (SEQ ID NO:67), (SEQ ID NO:166) or (SEQ ID NO:167).

Embodiment 50

The engineered polypeptide of any one of embodiments 1 to 47 comprising (SEQ ID NO:40), (SEQ ID NO:41), (SEQ ID NO:42), (SEQ ID NO:43), (SEQ ID NO:51), (SEQ ID NO:163), (SEQ ID NO:99), (SEQ ID NO:169), (SEQ ID NO:170), (SEQ ID NO: 95), (SEQ ID NO: 97), (SEQ ID NO: 96) or (SEQ ID NO:55).

Embodiment 51

A method for treating a disease or disorder in a subject, comprising administering a engineered polypeptide according to any one of embodiments 1-50 to a subject in need thereof in an amount effective to treat said disease or disorder.

Embodiment 52

The method according to embodiment 51, wherein said disease or disorder is diabetes, overweight, obesity, Alzheimer's disease, short bowel syndrome, fatty liver disease, dyslipidemia, coronary artery disease, stroke, hyperlipidemia or Parkinson's disease.

Embodiment 53

The method according to embodiment 52, wherein said disease or disorder is diabetes, overweight, obesity, short bowel syndrome or Parkinson's disease.

Embodiment 54

The method according to embodiment 53, wherein said disease or disorder is type I diabetes, type II diabetes or prediabetes.

Embodiment 55

The method according to embodiment 52, wherein said disease or disorder is type II diabetes.

Embodiment 56

The method according to embodiment 52, wherein said disease or disorder is dyslipidemia or hyperlipidemia.

Embodiment 57

The method according to embodiment 52, wherein the subject in need of such treatment is obese.

Embodiment 58

A pharmaceutical composition comprising an engineered polypeptide according to any one of embodiments 1-50 and a pharmaceutically acceptable excipient.

Embodiment 59

The pharmaceutical composition according to embodiment 58, wherein said pharmaceutical composition is an oral pharmaceutical composition.

Embodiment 60

The pharmaceutical composition according to any one of embodiments 58 to 59, wherein said pharmaceutical composition is a sustained release or long lasting pharmaceutical composition.

Embodiment 61

The pharmaceutical composition according to any one of embodiments 58 to 60, wherein said pharmaceutical composition is a once daily pharmaceutical composition.

Embodiment 62

The pharmaceutical composition according to any one of embodiment 58 to 60, wherein said pharmaceutical composition is a twice daily pharmaceutical composition.

Embodiment 63

The pharmaceutical composition according to any one of embodiments 58 to 60, wherein said pharmaceutical composition is a once weekly pharmaceutical composition.

Embodiment 64

The pharmaceutical composition according to any one of embodiments 58 to 63 for treating a disease or disorder in a subject.

Embodiment 65

The pharmaceutical composition of embodiment 64 wherein the disease or disorder is diabetes, overweight, obesity, Alzheimer's disease, fatty liver disease, short bowel syndrome, dyslipidemia, coronary artery disease, stroke, hyperlipidemia or Parkinson's disease.

Embodiment 66

The pharmaceutical composition of embodiment 65 wherein said disease or disorder is diabetes, overweight, obesity, short bowel syndrome, or Parkinson's disease.

Embodiment 67

The pharmaceutical composition of embodiment 66, wherein said disease or disorder is type I diabetes, type II diabetes or prediabetes.

Embodiment 68

The engineered polypeptide or pharmaceutical composition of any one of embodiments 1 to 67, wherein the engineered polypeptide or pharmaceutical composition provides once weekly administration.

Embodiment 69

The engineered polypeptide or pharmaceutical composition of any one of embodiments 1 to 67, wherein the engineered polypeptide or pharmaceutical composition provides once daily administration.

Embodiment 70

The engineered polypeptide or pharmaceutical composition of any one of embodiments 1 to 67, wherein the engineered polypeptide or pharmaceutical composition provides twice daily administration.

Embodiment 71

The pharmaceutical composition of any one of embodiments 58 to 70, wherein the engineered polypeptide comprises (SEQ ID NO:40), (SEQ ID NO:41), (SEQ ID NO:42), (SEQ ID NO:43), (SEQ ID NO:51), (SEQ ID NO:163), (SEQ ID NO:99), (SEQ ID NO:169), (SEQ ID NO:170), (SEQ ID NO: 95), (SEQ ID NO: 97), (SEQ ID NO: 96), (SEQ ID NO:55), (SEQ ID NO:53), (SEQ ID NO:62), (SEQ ID NO:67), (SEQ ID NO:166), (SEQ ID NO:167), (SEQ ID NO:51), (SEQ ID NO:52), (SEQ ID NO:53), (SEQ ID NO:54), (SEQ ID NO:55), (SEQ ID NO:56), (SEQ ID NO:57), (SEQ ID NO:58), (SEQ ID NO:59), (SEQ ID NO:60), (SEQ ID NO:61), (SEQ ID NO:62), (SEQ ID NO:63), (SEQ ID NO:64), (SEQ ID NO:65), (SEQ ID NO:66), (SEQ ID NO:67), (SEQ ID NO:68), (SEQ ID NO:70), (SEQ ID NO:71), (SEQ ID NO:72), (SEQ ID NO:73), (SEQ ID NO:74), (SEQ ID NO:75), (SEQ ID NO:76), (SEQ ID NO:77), (SEQ ID NO:78), (SEQ ID NO:79), (SEQ ID NO:80), (SEQ ID NO:81), (SEQ ID NO:82), (SEQ ID NO:83), (SEQ ID NO:84), (SEQ ID NO:85), (SEQ ID NO:86), (SEQ ID NO:87), (SEQ ID NO:88), (SEQ ID NO:89), (SEQ ID NO:90), (SEQ ID NO:91), (SEQ ID NO:92), (SEQ ID NO:93), (SEQ ID NO:94), (SEQ ID NO:95), (SEQ ID NO:96), (SEQ ID NO:97), (SEQ ID NO:98), (SEQ ID NO:99), (SEQ ID NO:100) (SEQ ID NO:101), (SEQ ID NO:102), (SEQ ID NO:103), (SEQ ID NO:104), (SEQ ID NO:105), (SEQ ID NO:106), (SEQ ID NO:107), (SEQ ID NO:108) or (SEQ ID NO:109).

Embodiment 72

The pharmaceutical composition of any one of embodiments 58 to 71, wherein the engineered polypeptide comprises (SEQ ID NO:40), (SEQ ID NO:41), (SEQ ID NO:42), (SEQ ID NO:43), (SEQ ID NO:51), (SEQ ID NO:163), (SEQ ID NO:99), (SEQ ID NO:169), (SEQ ID NO:170), (SEQ ID NO: 95), (SEQ ID NO: 97), (SEQ ID NO: 96), (SEQ ID NO:55), (SEQ ID NO:53), (SEQ ID NO:62), (SEQ ID NO:67), (SEQ ID NO:166) or (SEQ ID NO:167).

Embodiment 73

The pharmaceutical composition of any one of embodiments 58 to 71, wherein the engineered polypeptide comprises (SEQ ID NO:40), (SEQ ID NO:41), (SEQ ID NO:42), (SEQ ID NO:43), (SEQ ID NO:51), (SEQ ID NO:163), (SEQ ID NO:99), (SEQ ID NO:169), (SEQ ID NO:170), (SEQ ID NO: 95), (SEQ ID NO: 97), (SEQ ID NO: 96) or (SEQ ID NO:55).

Embodiment 74

The pharmaceutical composition of any one of embodiments 58 to 67 wherein the engineered polypeptide comprises the sequence of (SEQ ID NO:95).

---

What is claimed is:

1. A polypeptide comprising the amino acid sequence of SEQ ID NO:95.

2. A polypeptide comprising the amino acid sequence of SEQ ID NO:42.

3. A polypeptide comprising the amino acid sequence of SEQ ID NO:51.

4. A polypeptide comprising the amino acid sequence of SEQ ID NO:99.

5. A polypeptide comprising the amino acid sequence of SEQ ID NO:163.

6. A pharmaceutical composition comprising the polypeptide of claim 1 and a pharmaceutically acceptable excipient.

7. A pharmaceutical composition comprising the polypeptide of claim 2 and a pharmaceutically acceptable excipient.

8. A pharmaceutical composition comprising the polypeptide of claim 3 and a pharmaceutically acceptable excipient.

9. A pharmaceutical composition comprising the polypeptide of claim 4 and a pharmaceutically acceptable excipient.

10. A pharmaceutical composition comprising the polypeptide of claim 5 and a pharmaceutically acceptable excipient.

* * * * *

SEQUENCE LISTING

```
<160> NUMBER OF SEQ ID NOS: 212

<210> SEQ ID NO 1
<211> LENGTH: 39
<212> TYPE: PRT
<213> ORGANISM: Heloderma horridum

<400> SEQUENCE: 1

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Heloderma suspectum

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: Artificial sequence
```

```
<220> FEATURE:
<223> OTHER INFORMATION: Synthetic polypeptide

<400> SEQUENCE: 3

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 4
<211> LENGTH: 37
<212> TYPE: PRT
<213> ORGANISM: Artificial sequence
<220> FEATURE:
<223> OTHER INFORMATION: Synthetic polypeptide

<400> SEQUENCE: 4

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser
        35

<210> SEQ ID NO 5
<211> LENGTH: 31
<212> TYPE: PRT
<213> ORGANISM: Homo sapiens

<400> SEQUENCE: 5

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 6
<211> LENGTH: 37
<212> TYPE: PRT
<213> ORGANISM: Rattus Norvegicus

<400> SEQUENCE: 6

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
            20                  25                  30

Gly Ser Asn Thr Tyr
        35

<210> SEQ ID NO 7
<211> LENGTH: 37
<212> TYPE: PRT
<213> ORGANISM: Homo sapiens

<400> SEQUENCE: 7

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
```

<210> SEQ ID NO 8
<211> LENGTH: 37
<212> TYPE: PRT
<213> ORGANISM: Artificial sequence
<220> FEATURE:
<223> OTHER INFORMATION: Synthetic polypeptide

<400> SEQUENCE: 8

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 9
<211> LENGTH: 32
<212> TYPE: PRT
<213> ORGANISM: Homo sapiens

<400> SEQUENCE: 9

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 10
<211> LENGTH: 32
<212> TYPE: PRT
<213> ORGANISM: Oncorhynchus gorbuscha

<400> SEQUENCE: 10

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 11
<211> LENGTH: 32
<212> TYPE: PRT
<213> ORGANISM: Artificial sequence
<220> FEATURE:
<223> OTHER INFORMATION: Synthetic polypeptide

<400> SEQUENCE: 11

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 12
<211> LENGTH: 28
<212> TYPE: PRT
<213> ORGANISM: Artificial sequence
<220> FEATURE:
<223> OTHER INFORMATION: Synthetic polypeptide

<400> SEQUENCE: 12

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn

```
            20              25
```

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23
<211> LENGTH: 46
<212> TYPE: PRT
<213> ORGANISM: Artificial sequence
<220> FEATURE:
<223> OTHER INFORMATION: Synthetic polypeptide

<400> SEQUENCE: 23

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Asn Ala Lys Thr Val Glu
            20                  25                  30

Gly Val Lys Ala Leu Ile Asp Glu Ile Leu Ala Ala Leu Pro
        35                  40                  45

<210> SEQ ID NO 24
<211> LENGTH: 46
<212> TYPE: PRT
<213> ORGANISM: Artificial sequence
<220> FEATURE:
<223> OTHER INFORMATION: Synthetic polypeptide

<400> SEQUENCE: 24

Leu Ala Glu Ala Lys Val Leu Ala Asn Arg Glu Leu Asp Lys Tyr Gly
1               5                   10                  15

Val Ser Asp Phe Tyr Lys Ser Tyr Ile Asn Arg Ala Lys Thr Val Glu
            20                  25                  30

Gly Val His Thr Leu Ile Gly His Ile Leu Ala Ala Leu Pro
        35                  40                  45

<210> SEQ ID NO 25
<211> LENGTH: 46
<212> TYPE: PRT
<213> ORGANISM: Artificial sequence
<220> FEATURE:
<223> OTHER INFORMATION: Synthetic polypeptide

<400> SEQUENCE: 25

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

Gly Val Asn Ala Leu Thr His His Ile Leu Ala Ala Leu Pro
        35                  40                  45

<210> SEQ ID NO 26
<211> LENGTH: 46
<212> TYPE: PRT
<213> ORGANISM: Artificial sequence
<220> FEATURE:
<223> OTHER INFORMATION: Synthetic polypeptide

<400> SEQUENCE: 26

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Arg Ala Arg Thr Val Glu
            20                  25                  30

Gly Val His Ala Leu Ile Asp His Ile Leu Ala Ala Leu Pro
        35                  40                  45

<210> SEQ ID NO 27
<211> LENGTH: 46
<212> TYPE: PRT
<213> ORGANISM: Artificial sequence
<220> FEATURE:
<223> OTHER INFORMATION: Synthetic polypeptide

<400> SEQUENCE: 27

```
Leu Ala Glu Ala Lys Val Leu Ala Asn Arg Glu Leu Asp Lys Tyr Gly
1               5                   10                  15

Val Ser Asp Tyr Tyr Lys Asn Ile Ile Asn Arg Ala Lys Thr Val Glu
            20                  25                  30

Gly Val Arg Ala Leu Lys Leu His Ile Leu Ala Ala Leu Pro
            35                  40                  45

<210> SEQ ID NO 28
<211> LENGTH: 46
<212> TYPE: PRT
<213> ORGANISM: Artificial sequence
<220> FEATURE:
<223> OTHER INFORMATION: Synthetic polypeptide

<400> SEQUENCE: 28

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Ser Ser Leu Lys Gly His Ile Leu Ala Ala Leu Pro
            35                  40                  45

<210> SEQ ID NO 29
<211> LENGTH: 46
<212> TYPE: PRT
<213> ORGANISM: Artificial sequence
<220> FEATURE:
<223> OTHER INFORMATION: Synthetic polypeptide

<400> SEQUENCE: 29

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Lys Ala Lys Thr Val Glu
            20                  25                  30

Gly Val Glu Ala Leu Thr Leu His Ile Leu Ala Ala Leu Pro
            35                  40                  45

<210> SEQ ID NO 30
<211> LENGTH: 46
<212> TYPE: PRT
<213> ORGANISM: Artificial sequence
<220> FEATURE:
<223> OTHER INFORMATION: Synthetic polypeptide

<400> SEQUENCE: 30

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Asp Ala Leu Ile Ala His Ile Leu Ala Ala Leu Pro
            35                  40                  45

<210> SEQ ID NO 31
<211> LENGTH: 46
<212> TYPE: PRT
<213> ORGANISM: Artificial sequence
<220> FEATURE:
<223> OTHER INFORMATION: Synthetic polypeptide

<400> SEQUENCE: 31

Leu Ala Glu Ala Lys Val Leu Ala Asn Arg Glu Leu Asp Lys Tyr Gly
1               5                   10                  15
```

Val Ser Asp Phe Tyr Lys Ser Leu Ile Asn Arg Ala Lys Thr Val Glu
            20                  25                  30

Gly Val Asp Ala Leu Thr Ser His Ile Leu Ala Ala Leu Pro
        35                  40                  45

<210> SEQ ID NO 32
<211> LENGTH: 46
<212> TYPE: PRT
<213> ORGANISM: Artificial sequence
<220> FEATURE:
<223> OTHER INFORMATION: Synthetic polypeptide

<400> SEQUENCE: 32

Leu Ala Glu Ala Lys Val Leu Ala Asn Arg Glu Leu Asp Lys Tyr Gly
1               5                   10                  15

Val Ser Asp Phe Tyr Lys Asn Leu Ile Asn Arg Ala Lys Thr Val Glu
            20                  25                  30

Gly Val Asn Ser Leu Thr Ser His Ile Leu Ala Ala Leu Pro
        35                  40                  45

<210> SEQ ID NO 33
<211> LENGTH: 46
<212> TYPE: PRT
<213> ORGANISM: Artificial sequence
<220> FEATURE:
<223> OTHER INFORMATION: Synthetic polypeptide

<400> SEQUENCE: 33

Leu Ala Glu Ala Lys Val Leu Ala Asn Arg Glu Leu Asp Lys Tyr Gly
1               5                   10                  15

Val Ser Asp Phe Tyr Lys Asn Val Ile Asn Lys Ala Lys Thr Val Glu
            20                  25                  30

Gly Val Glu Ala Leu Ile Ala Asp Ile Leu Ala Ala Leu Pro
        35                  40                  45

<210> SEQ ID NO 34
<211> LENGTH: 46
<212> TYPE: PRT
<213> ORGANISM: Artificial sequence
<220> FEATURE:
<223> OTHER INFORMATION: Synthetic polypeptide

<400> SEQUENCE: 34

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Lys Ala Lys Thr Val Glu
            20                  25                  30

Gly Val Gln Ala Leu Ile Ala His Ile Leu Ala Ala Leu Pro
        35                  40                  45

<210> SEQ ID NO 35
<211> LENGTH: 46
<212> TYPE: PRT
<213> ORGANISM: Artificial sequence
<220> FEATURE:
<223> OTHER INFORMATION: Synthetic polypeptide

<400> SEQUENCE: 35

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

```
Gly Val Glu Ala Leu Lys Leu His Ile Leu Ala Ala Leu Pro
        35                  40                  45
```

<210> SEQ ID NO 36
<211> LENGTH: 46
<212> TYPE: PRT
<213> ORGANISM: Artificial sequence
<220> FEATURE:
<223> OTHER INFORMATION: Synthetic polypeptide

<400> SEQUENCE: 36

```
Leu Ala Glu Ala Lys Val Leu Ala Asn Arg Glu Leu Asp Lys Tyr Gly
1               5                   10                  15

Val Ser Asp Tyr Tyr Lys Asn Ile Ile Asn Arg Ala Lys Thr Val Glu
            20                  25                  30

Gly Val Arg Ala Leu Lys Leu His Ile Leu Ala Ala Leu Pro
        35                  40                  45
```

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40
<211> LENGTH: 93
<212> TYPE: PRT
<213> ORGANISM: Artificial sequence
<220> FEATURE:
<223> OTHER INFORMATION: Synthetic polypeptide

<400> SEQUENCE: 40

```
His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Thr Gly Gly Gly Ser Ala Ser Leu
        35                  40                  45

Ala Glu Ala Lys Val Leu Ala Asn Arg Glu Leu Asp Lys Tyr Gly Val
    50                  55                  60

Ser Asp Phe Tyr Lys Arg Leu Ile Asn Lys Ala Lys Thr Val Glu Gly
65                  70                  75                  80

Val Glu Ala Leu Lys Leu His Ile Leu Ala Ala Leu Pro
                85                  90
```

<210> SEQ ID NO 41
<211> LENGTH: 105
<212> TYPE: PRT
<213> ORGANISM: Artificial sequence
<220> FEATURE:
<223> OTHER INFORMATION: Synthetic polypeptide

<400> SEQUENCE: 41

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Thr Gly Gly Gly Gly Ser Gly Gly Gly Gly
        35                  40                  45

Ser Gly Gly Gly Ser Gly Gly Gly Ser Ala Ser Leu Ala Glu Ala Lys
50                  55                  60

Val Leu Ala Asn Arg Glu Leu Asp Lys Tyr Gly Val Ser Asp Phe Tyr
65                  70                  75                  80

Lys Arg Leu Ile Asn Lys Ala Lys Thr Val Glu Gly Val Glu Ala Leu
                85                  90                  95

Lys Leu His Ile Leu Ala Ala Leu Pro
                100                 105

<210> SEQ ID NO 42
<211> LENGTH: 91
<212> TYPE: PRT
<213> ORGANISM: Artificial sequence
<220> FEATURE:
<223> OTHER INFORMATION: Synthetic polypeptide

<400> SEQUENCE: 42

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Thr Gly Gly Gly Gly Ala Ser Leu Ala Glu
        35                  40                  45

Ala Lys Val Leu Ala Asn Arg Glu Leu Asp Lys Tyr Gly Val Ser Asp
50                  55                  60

Phe Tyr Lys Arg Leu Ile Asn Lys Ala Lys Thr Val Glu Gly Val Glu
65                  70                  75                  80

Ala Leu Lys Leu His Ile Leu Ala Ala Leu Pro
                85                  90

<210> SEQ ID NO 43
<211> LENGTH: 103
<212> TYPE: PRT
<213> ORGANISM: Artificial sequence
<220> FEATURE:
<223> OTHER INFORMATION: Synthetic polypeptide

<400> SEQUENCE: 43

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Thr Gly Gly Gly Gly Ser Gly Gly Gly Ser Gly
        35                  40                  45

Gly Gly Ser Gly Gly Gly Ser Ala Ser Leu Ala Glu Ala Lys Val Leu
50                  55                  60

Ala Asn Arg Glu Leu Asp Lys Tyr Gly Val Ser Asp Phe Tyr Lys Arg
65                  70                  75                  80

Leu Ile Asn Lys Ala Lys Thr Val Glu Gly Val Glu Ala Leu Lys Leu
                85                  90                  95

```
His Ile Leu Ala Ala Leu Pro
            100

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 49

His His His His His His
1               5

<210> SEQ ID NO 50
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 50

Met Ala His His His His His His Val Gly Thr Gly Ser Asn Glu Asn
1               5                   10                  15

Leu Tyr Phe Gln His Gly Glu Gly Thr Phe Thr Ser Asp Leu Ser Lys
            20                  25                  30

Gln Leu Glu Glu Glu Ala Val Arg Leu Phe Ile Glu Trp Leu Lys Gln
        35                  40                  45

Gly Gly Pro Ser Lys Glu Ile Ile Ser Thr Gly Gly Gly Ser Ala
    50                  55                  60

Ser Leu Ala Glu Ala Lys Val Leu Ala Asn Arg Glu Leu Asp Lys Tyr
65                  70                  75                  80

Gly Val Ser Asp Phe Tyr Lys Arg Leu Ile Asn Lys Ala Lys Thr Val
                85                  90                  95
```

Glu Gly Val Glu Ala Leu Lys Leu His Ile Leu Ala Ala Leu Pro
            100                 105                 110

<210> SEQ ID NO 51
<211> LENGTH: 82
<212> TYPE: PRT
<213> ORGANISM: Artificial sequence
<220> FEATURE:
<223> OTHER INFORMATION: Synthetic polypeptide

<400> SEQUENCE: 51

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Thr Gly Gly Gly
            20                  25                  30

Gly Ser Ala Ser Leu Ala Glu Ala Lys Val Leu Ala Asn Arg Glu Leu
        35                  40                  45

Asp Lys Tyr Gly Val Ser Asp Phe Tyr Lys Arg Leu Ile Asn Lys Ala
    50                  55                  60

Lys Thr Val Glu Gly Val Glu Ala Leu Lys Leu His Ile Leu Ala Ala
65                  70                  75                  80

Leu Pro

<210> SEQ ID NO 52
<211> LENGTH: 82
<212> TYPE: PRT
<213> ORGANISM: Artificial sequence
<220> FEATURE:
<223> OTHER INFORMATION: Synthetic polypeptide

<400> SEQUENCE: 52

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Thr Gly Gly Gly
            20                  25                  30

Gly Ser Ala Ser Leu Ala Glu Ala Lys Val Leu Ala Asn Arg Glu Leu
        35                  40                  45

Asp Lys Tyr Gly Val Ser Asp Phe Tyr Lys Arg Leu Ile Asn Lys Ala
    50                  55                  60

Lys Thr Val Glu Gly Val Glu Ala Leu Lys Leu His Ile Leu Ala Ala
65                  70                  75                  80

Leu Pro

<210> SEQ ID NO 53
<211> LENGTH: 94
<212> TYPE: PRT
<213> ORGANISM: Artificial sequence
<220> FEATURE:
<223> OTHER INFORMATION: Synthetic polypeptide

<400> SEQUENCE: 53

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Thr Gly Gly Gly
            20                  25                  30

Gly Ser Gly Gly Gly Ser Gly Gly Gly Ser Gly Gly Ser Ala Ser
        35                  40                  45

Leu Ala Glu Ala Lys Val Leu Ala Asn Arg Glu Leu Asp Lys Tyr Gly
    50                  55                  60

```
Val Ser Asp Phe Tyr Lys Arg Leu Ile Asn Lys Ala Lys Thr Val Glu
 65                  70                  75                  80

Gly Val Glu Ala Leu Lys Leu His Ile Leu Ala Ala Leu Pro
                 85                  90

<210> SEQ ID NO 54
<211> LENGTH: 94
<212> TYPE: PRT
<213> ORGANISM: Artificial sequence
<220> FEATURE:
<223> OTHER INFORMATION: Synthetic polypeptide

<400> SEQUENCE: 54

His Gly Glu Gly Thr Phe Thr Ser Asp Leu Ser Lys Gln Leu Glu Glu
  1               5                  10                  15

Glu Ala Val Arg Leu Phe Ile Glu Trp Leu Lys Asn Thr Gly Gly Gly
                 20                  25                  30

Gly Ser Gly Gly Gly Ser Gly Gly Gly Ser Gly Gly Gly Ser Ala Ser
             35                  40                  45

Leu Ala Glu Ala Lys Val Leu Ala Asn Arg Glu Leu Asp Lys Tyr Gly
 50                  55                  60

Val Ser Asp Phe Tyr Lys Arg Leu Ile Asn Lys Ala Lys Thr Val Glu
 65                  70                  75                  80

Gly Val Glu Ala Leu Lys Leu His Ile Leu Ala Ala Leu Pro
                 85                  90

<210> SEQ ID NO 55
<211> LENGTH: 93
<212> TYPE: PRT
<213> ORGANISM: Artificial sequence
<220> FEATURE:
<223> OTHER INFORMATION: Synthetic polypeptide

<400> SEQUENCE: 55

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
                 20                  25                  30

Ser Gly Ala Pro Pro Ser Thr Gly Gly Gly Gly Ser Ala Ser Leu
             35                  40                  45

Ala Glu Ala Lys Val Leu Ala Asn Arg Glu Leu Asp Lys Tyr Gly Val
 50                  55                  60

Ser Asp Phe Tyr Lys Arg Leu Ile Asn Lys Ala Lys Thr Val Glu Gly
 65                  70                  75                  80

Val Glu Ala Leu Lys Leu His Ile Leu Ala Ala Leu Pro
                 85                  90

<210> SEQ ID NO 56
<211> LENGTH: 105
<212> TYPE: PRT
<213> ORGANISM: Artificial sequence
<220> FEATURE:
<223> OTHER INFORMATION: Synthetic polypeptide

<400> SEQUENCE: 56

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
                 20                  25                  30

Ser Gly Ala Pro Pro Ser Thr Gly Gly Gly Gly Ser Gly Gly Gly
```

```
              35                  40                  45
Ser Gly Gly Ser Gly Gly Gly Ser Ala Ser Leu Ala Glu Ala Lys
 50                  55                  60

Val Leu Ala Asn Arg Glu Leu Asp Lys Tyr Gly Val Ser Asp Phe Tyr
 65                  70                  75                  80

Lys Arg Leu Ile Asn Lys Ala Lys Thr Val Glu Gly Val Glu Ala Leu
                 85                  90                  95

Lys Leu His Ile Leu Ala Ala Leu Pro
                100                 105

<210> SEQ ID NO 57
<211> LENGTH: 91
<212> TYPE: PRT
<213> ORGANISM: Artificial sequence
<220> FEATURE:
<223> OTHER INFORMATION: Synthetic polypeptide

<400> SEQUENCE: 57

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Gln Gly Gly Pro Ser
                20                  25                  30

Lys Glu Ile Ile Ser Thr Gly Gly Gly Ser Ala Ser Leu Ala Glu
             35                  40                  45

Ala Lys Val Leu Ala Asn Arg Glu Leu Asp Lys Tyr Gly Val Ser Asp
 50                  55                  60

Phe Tyr Lys Arg Leu Ile Asn Lys Ala Lys Thr Val Glu Gly Val Glu
 65                  70                  75                  80

Ala Leu Lys Leu His Ile Leu Ala Ala Leu Pro
                85                  90

<210> SEQ ID NO 58
<211> LENGTH: 103
<212> TYPE: PRT
<213> ORGANISM: Artificial sequence
<220> FEATURE:
<223> OTHER INFORMATION: Synthetic polypeptide

<400> SEQUENCE: 58

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Gln Gly Gly Pro Ser
                20                  25                  30

Lys Glu Ile Ile Ser Thr Gly Gly Gly Ser Gly Gly Gly Ser Gly
             35                  40                  45

Gly Gly Ser Gly Gly Ser Ala Ser Leu Ala Glu Ala Lys Val Leu
 50                  55                  60

Ala Asn Arg Glu Leu Asp Lys Tyr Gly Val Ser Asp Phe Tyr Lys Arg
 65                  70                  75                  80

Leu Ile Asn Lys Ala Lys Thr Val Glu Gly Val Glu Ala Leu Lys Leu
                85                  90                  95

His Ile Leu Ala Ala Leu Pro
                100

<210> SEQ ID NO 59
<211> LENGTH: 98
<212> TYPE: PRT
<213> ORGANISM: Artificial sequence
<220> FEATURE:
```

<223> OTHER INFORMATION: Synthetic polypeptide

<400> SEQUENCE: 59

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Thr Gly Gly Gly
        35                  40                  45

Gly Ser Ala Ser Leu Ala Glu Ala Lys Val Leu Ala Asn Arg Glu Leu
    50                  55                  60

Asp Lys Tyr Gly Val Ser Asp Phe Tyr Lys Arg Leu Ile Asn Lys Ala
65                  70                  75                  80

Lys Thr Val Glu Gly Val Glu Ala Leu Lys Leu His Ile Leu Ala Ala
                85                  90                  95

Leu Pro

<210> SEQ ID NO 60
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 60

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Thr Gly Gly Gly
        35                  40                  45

Gly Ser Gly Gly Ser Gly Gly Gly Gly Gly Ser Ala Ser Leu
    50                  55                  60

Ala Glu Ala Lys Val Leu Ala Asn Arg Glu Leu Asp Lys Tyr Gly Val
65                  70                  75                  80

Ser Asp Phe Tyr Lys Arg Leu Ile Asn Lys Ala Lys Thr Val Glu Gly
                85                  90                  95

Val Glu Ala Leu Lys Leu His Ile Leu Ala Ala Leu Pro
            100                 105

<210> SEQ ID NO 61
<211> LENGTH: 88
<212> TYPE: PRT
<213> ORGANISM: Artificial sequence
<220> FEATURE:
<223> OTHER INFORMATION: Synthetic polypeptide

<400> SEQUENCE: 61

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Gly Gly Leu Ala Glu Ala Lys Val
        35                  40                  45

Leu Ala Asn Arg Glu Leu Asp Lys Tyr Gly Val Ser Asp Phe Tyr Lys
    50                  55                  60

Arg Leu Ile Asn Lys Ala Lys Thr Val Glu Gly Val Glu Ala Leu Lys
65                  70                  75                  80

```
Leu His Ile Leu Ala Ala Leu Pro
            85

<210> SEQ ID NO 62
<211> LENGTH: 94
<212> TYPE: PRT
<213> ORGANISM: Artificial sequence
<220> FEATURE:
<223> OTHER INFORMATION: Synthetic polypeptide

<400> SEQUENCE: 62

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Thr Gly Gly Gly
            20                  25                  30

Gly Ser Gly Gly Gly Ser Gly Gly Ser Gly Gly Ser Ala Ser
        35                  40                  45

Leu Ala Glu Ala Lys Val Leu Ala Asn Arg Glu Leu Asp Lys Tyr Gly
    50                  55                  60

Val Ser Asp Tyr Tyr Lys Asn Ile Ile Asn Arg Ala Lys Thr Val Glu
65                  70                  75                  80

Gly Val Arg Ala Leu Lys Leu His Ile Leu Ala Ala Leu Pro
                85                  90

<210> SEQ ID NO 63
<211> LENGTH: 93
<212> TYPE: PRT
<213> ORGANISM: Artificial sequence
<220> FEATURE:
<223> OTHER INFORMATION: Synthetic polypeptide

<400> SEQUENCE: 63

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Thr Gly Gly Gly Ser Ala Ser Leu
        35                  40                  45

Ala Glu Ala Lys Val Leu Ala Asn Arg Glu Leu Asp Lys Tyr Gly Val
    50                  55                  60

Ser Asp Tyr Tyr Lys Asn Ile Ile Asn Arg Ala Lys Thr Val Glu Gly
65                  70                  75                  80

Val Arg Ala Leu Lys Leu His Ile Leu Ala Ala Leu Pro
                85                  90

<210> SEQ ID NO 64
<211> LENGTH: 105
<212> TYPE: PRT
<213> ORGANISM: Artificial sequence
<220> FEATURE:
<223> OTHER INFORMATION: Synthetic polypeptide

<400> SEQUENCE: 64

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Thr Gly Gly Gly Ser Gly Gly Gly
        35                  40                  45
```

```
Ser Gly Gly Ser Gly Gly Gly Ser Ala Ser Leu Ala Glu Ala Lys
    50              55                  60

Val Leu Ala Asn Arg Glu Leu Asp Lys Tyr Gly Val Ser Asp Tyr Tyr
 65                  70                  75                  80

Lys Asn Ile Ile Asn Arg Ala Lys Thr Val Glu Gly Val Arg Ala Leu
                 85                  90                  95

Lys Leu His Ile Leu Ala Ala Leu Pro
            100                 105

<210> SEQ ID NO 65
<211> LENGTH: 91
<212> TYPE: PRT
<213> ORGANISM: Artificial sequence
<220> FEATURE:
<223> OTHER INFORMATION: Synthetic polypeptide

<400> SEQUENCE: 65

His Gly Glu Gly Thr Phe Thr Ser Asp Leu Ser Lys Gln Leu Glu Glu
  1               5                  10                  15

Glu Ala Val Arg Leu Phe Ile Glu Trp Leu Lys Gln Gly Gly Pro Ser
                 20                  25                  30

Lys Glu Ile Ile Ser Thr Gly Gly Gly Ser Ala Ser Leu Ala Glu
                 35                  40                  45

Ala Lys Val Leu Ala Asn Arg Glu Leu Asp Lys Tyr Gly Val Ser Asp
     50                  55                  60

Tyr Tyr Lys Asn Ile Ile Asn Arg Ala Lys Thr Val Glu Gly Val Arg
 65                  70                  75                  80

Ala Leu Lys Leu His Ile Leu Ala Ala Leu Pro
                 85                  90

<210> SEQ ID NO 66
<211> LENGTH: 103
<212> TYPE: PRT
<213> ORGANISM: Artificial sequence
<220> FEATURE:
<223> OTHER INFORMATION: Synthetic polypeptide

<400> SEQUENCE: 66

His Gly Glu Gly Thr Phe Thr Ser Asp Leu Ser Lys Gln Leu Glu Glu
  1               5                  10                  15

Glu Ala Val Arg Leu Phe Ile Glu Trp Leu Lys Gln Gly Gly Pro Ser
                 20                  25                  30

Lys Glu Ile Ile Ser Thr Gly Gly Gly Ser Gly Gly Gly Ser Gly
                 35                  40                  45

Gly Gly Ser Gly Gly Gly Ser Ala Ser Leu Ala Glu Ala Lys Val Leu
     50                  55                  60

Ala Asn Arg Glu Leu Asp Lys Tyr Gly Val Ser Asp Tyr Tyr Lys Asn
 65                  70                  75                  80

Ile Ile Asn Arg Ala Lys Thr Val Glu Gly Val Arg Ala Leu Lys Leu
                 85                  90                  95

His Ile Leu Ala Ala Leu Pro
                100

<210> SEQ ID NO 67
<211> LENGTH: 82
<212> TYPE: PRT
<213> ORGANISM: Artificial sequence
<220> FEATURE:
<223> OTHER INFORMATION: Synthetic polypeptide
```

```
<400> SEQUENCE: 67

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Thr Gly Gly Gly
            20                  25                  30

Gly Ser Ala Ser Leu Ala Glu Ala Lys Val Leu Ala Asn Arg Glu Leu
        35                  40                  45

Asp Lys Tyr Gly Val Ser Asp Tyr Tyr Lys Asn Ile Ile Asn Arg Ala
    50                  55                  60

Lys Thr Val Glu Gly Val Arg Ala Leu Lys Leu His Ile Leu Ala Ala
65                  70                  75                  80

Leu Pro

<210> SEQ ID NO 68
<211> LENGTH: 82
<212> TYPE: PRT
<213> ORGANISM: Artificial sequence
<220> FEATURE:
<223> OTHER INFORMATION: Synthetic polypeptide

<400> SEQUENCE: 68

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Thr Gly Gly Gly
            20                  25                  30

Gly Ser Ala Ser Leu Ala Glu Ala Lys Val Leu Ala Asn Arg Glu Leu
        35                  40                  45

Asp Lys Tyr Gly Val Ser Asp Tyr Tyr Lys Asn Ile Ile Asn Arg Ala
    50                  55                  60

Lys Thr Val Glu Gly Val Arg Ala Leu Lys Leu His Ile Leu Ala Ala
65                  70                  75                  80

Leu Pro

<210> SEQ ID NO 69

<400> SEQUENCE: 69

000

<210> SEQ ID NO 70
<211> LENGTH: 94
<212> TYPE: PRT
<213> ORGANISM: Artificial sequence
<220> FEATURE:
<223> OTHER INFORMATION: Synthetic polypeptide

<400> SEQUENCE: 70

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Thr Gly Gly Gly
            20                  25                  30

Gly Ser Gly Gly Gly Ser Gly Gly Ser Gly Gly Ser Ala Ser
        35                  40                  45

Leu Ala Glu Ala Lys Val Leu Ala Asn Arg Glu Leu Asp Lys Tyr Gly
    50                  55                  60

Val Ser Asp Tyr Tyr Lys Asn Ile Ile Asn Arg Ala Lys Thr Val Glu
65                  70                  75                  80

Gly Val Arg Ala Leu Lys Leu His Ile Leu Ala Ala Leu Pro
```

<210> SEQ ID NO 71
<211> LENGTH: 93
<212> TYPE: PRT
<213> ORGANISM: Artificial sequence
<220> FEATURE:
<223> OTHER INFORMATION: Synthetic polypeptide

<400> SEQUENCE: 71

His Gly Glu Gly Thr Phe Thr Ser Asp Leu Ser Lys Gln Met Glu Glu
1               5                   10                  15
Glu Ala Val Arg Leu Phe Ile Glu Trp Leu Lys Asn Gly Gly Pro Ser
                20                  25                  30
Ser Gly Ala Pro Pro Pro Ser Thr Gly Gly Gly Gly Ser Ala Ser Leu
            35                  40                  45
Ala Glu Ala Lys Val Leu Ala Asn Arg Glu Leu Asp Lys Tyr Gly Val
        50                  55                  60
Ser Asp Tyr Tyr Lys Asn Ile Ile Asn Arg Ala Lys Thr Val Glu Gly
65                  70                  75                  80
Val Arg Ala Leu Lys Leu His Ile Leu Ala Ala Leu Pro
                85                  90

<210> SEQ ID NO 72
<211> LENGTH: 105
<212> TYPE: PRT
<213> ORGANISM: Artificial sequence
<220> FEATURE:
<223> OTHER INFORMATION: Synthetic polypeptide

<400> SEQUENCE: 72

His Gly Glu Gly Thr Phe Thr Ser Asp Leu Ser Lys Gln Met Glu Glu
1               5                   10                  15
Glu Ala Val Arg Leu Phe Ile Glu Trp Leu Lys Asn Gly Gly Pro Ser
                20                  25                  30
Ser Gly Ala Pro Pro Pro Ser Thr Gly Gly Gly Gly Ser Gly Gly Gly
            35                  40                  45
Ser Gly Gly Gly Ser Gly Gly Gly Ser Ala Ser Leu Ala Glu Ala Lys
        50                  55                  60
Val Leu Ala Asn Arg Glu Leu Asp Lys Tyr Gly Val Ser Asp Tyr Tyr
65                  70                  75                  80
Lys Asn Ile Ile Asn Arg Ala Lys Thr Val Glu Gly Val Arg Ala Leu
                85                  90                  95
Lys Leu His Ile Leu Ala Ala Leu Pro
            100                 105

<210> SEQ ID NO 73
<211> LENGTH: 91
<212> TYPE: PRT
<213> ORGANISM: Artificial sequence
<220> FEATURE:
<223> OTHER INFORMATION: Synthetic polypeptide

<400> SEQUENCE: 73

His Gly Glu Gly Thr Phe Thr Ser Asp Leu Ser Lys Gln Met Glu Glu
1               5                   10                  15
Glu Ala Val Arg Leu Phe Ile Glu Trp Leu Lys Gln Gly Gly Pro Ser
                20                  25                  30
Lys Glu Ile Ile Ser Thr Gly Gly Gly Gly Ser Ala Ser Leu Ala Glu
            35                  40                  45

```
Ala Lys Val Leu Ala Asn Arg Glu Leu Asp Lys Tyr Gly Val Ser Asp
         50                  55                  60

Tyr Tyr Lys Asn Ile Ile Asn Arg Ala Lys Thr Val Glu Gly Val Arg
 65                  70                  75                  80

Ala Leu Lys Leu His Ile Leu Ala Ala Leu Pro
                 85                  90
```

<210> SEQ ID NO 74
<211> LENGTH: 103
<212> TYPE: PRT
<213> ORGANISM: Artificial sequence
<220> FEATURE:
<223> OTHER INFORMATION: Synthetic polypeptide

<400> SEQUENCE: 74

```
His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Gln Gly Gly Pro Ser
                 20                  25                  30

Lys Glu Ile Ile Ser Thr Gly Gly Gly Ser Gly Gly Gly Ser Gly
             35                  40                  45

Gly Gly Ser Gly Gly Gly Ser Ala Ser Leu Ala Glu Ala Lys Val Leu
         50                  55                  60

Ala Asn Arg Glu Leu Asp Lys Tyr Gly Val Ser Asp Tyr Tyr Lys Asn
 65                  70                  75                  80

Ile Ile Asn Arg Ala Lys Thr Val Glu Gly Val Arg Ala Leu Lys Leu
                 85                  90                  95

His Ile Leu Ala Ala Leu Pro
                100
```

<210> SEQ ID NO 75
<211> LENGTH: 98
<212> TYPE: PRT
<213> ORGANISM: Artificial sequence
<220> FEATURE:
<223> OTHER INFORMATION: Synthetic polypeptide

<400> SEQUENCE: 75

```
His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
                 20                  25                  30

Ser Gly Ala Pro Pro Ser Lys Lys Lys Lys Lys Thr Gly Gly Gly
             35                  40                  45

Gly Ser Ala Ser Leu Ala Glu Ala Lys Val Leu Ala Asn Arg Glu Leu
         50                  55                  60

Asp Lys Tyr Gly Val Ser Asp Tyr Tyr Lys Asn Ile Ile Asn Arg Ala
 65                  70                  75                  80

Lys Thr Val Glu Gly Val Arg Ala Leu Lys Leu His Ile Leu Ala Ala
                 85                  90                  95

Leu Pro
```

<210> SEQ ID NO 76
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 76

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Thr Gly Gly Gly
        35                  40                  45

Gly Ser Gly Gly Ser Gly Gly Gly Ser Gly Gly Ser Ala Ser
    50                  55                  60

Leu Ala Glu Ala Lys Val Leu Ala Asn Arg Glu Leu Asp Lys Tyr Gly
65                  70                  75                  80

Val Ser Asp Tyr Tyr Lys Asn Ile Ile Asn Arg Ala Lys Thr Val Glu
                85                  90                  95

Gly Val Arg Ala Leu Lys Leu His Ile Leu Ala Ala Leu Pro
            100                 105                 110

<210> SEQ ID NO 77
<211> LENGTH: 88
<212> TYPE: PRT
<213> ORGANISM: Artificial sequence
<220> FEATURE:
<223> OTHER INFORMATION: Synthetic polypeptide

<400> SEQUENCE: 77

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Gly Gly Leu Ala Glu Ala Lys Val
        35                  40                  45

Leu Ala Asn Arg Glu Leu Asp Lys Tyr Gly Val Ser Asp Tyr Tyr Lys
    50                  55                  60

Asn Ile Ile Asn Arg Ala Lys Thr Val Glu Gly Val Arg Ala Leu Lys
65                  70                  75                  80

Leu His Ile Leu Ala Ala Leu Pro
                85

<210> SEQ ID NO 78
<211> LENGTH: 88
<212> TYPE: PRT
<213> ORGANISM: Artificial sequence
<220> FEATURE:
<223> OTHER INFORMATION: Synthetic polypeptide

<400> SEQUENCE: 78

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Gly Gly Leu Ala Glu Ala Lys Val
        35                  40                  45

Leu Ala Asn Arg Glu Leu Asp Lys Tyr Gly Val Ser Asp Phe Tyr Lys
    50                  55                  60

Arg Leu Ile Asn Lys Ala Lys Thr Val Glu Gly Val Glu Ala Leu Lys
65                  70                  75                  80

Leu His Ile Leu Ala Ala Leu Pro
                85

<210> SEQ ID NO 79
<211> LENGTH: 86
<212> TYPE: PRT
<213> ORGANISM: Artificial sequence
<220> FEATURE:
<223> OTHER INFORMATION: Synthetic polypeptide

<400> SEQUENCE: 79

```
His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Gly Gly Leu Ala Glu Ala Lys Val Leu Ala
        35                  40                  45

Asn Arg Glu Leu Asp Lys Tyr Gly Val Ser Asp Phe Tyr Lys Arg Leu
    50                  55                  60

Ile Asn Lys Ala Lys Thr Val Glu Gly Val Glu Ala Leu Lys Leu His
65                  70                  75                  80

Ile Leu Ala Ala Leu Pro
                85
```

<210> SEQ ID NO 80
<211> LENGTH: 77
<212> TYPE: PRT
<213> ORGANISM: Artificial sequence
<220> FEATURE:
<223> OTHER INFORMATION: Synthetic polypeptide

<400> SEQUENCE: 80

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly Leu
            20                  25                  30

Ala Glu Ala Lys Val Leu Ala Asn Arg Glu Leu Asp Lys Tyr Gly Val
        35                  40                  45

Ser Asp Phe Tyr Lys Arg Leu Ile Asn Lys Ala Lys Thr Val Glu Gly
    50                  55                  60

Val Glu Ala Leu Lys Leu His Ile Leu Ala Ala Leu Pro
65                  70                  75
```

<210> SEQ ID NO 81
<211> LENGTH: 77
<212> TYPE: PRT
<213> ORGANISM: Artificial sequence
<220> FEATURE:
<223> OTHER INFORMATION: Synthetic polypeptide

<400> SEQUENCE: 81

```
His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Gly Leu
            20                  25                  30

Ala Glu Ala Lys Val Leu Ala Asn Arg Glu Leu Asp Lys Tyr Gly Val
        35                  40                  45

Ser Asp Phe Tyr Lys Arg Leu Ile Asn Lys Ala Lys Thr Val Glu Gly
    50                  55                  60

Val Glu Ala Leu Lys Leu His Ile Leu Ala Ala Leu Pro
65                  70                  75
```

```
<210> SEQ ID NO 82
<211> LENGTH: 88
<212> TYPE: PRT
<213> ORGANISM: Artificial sequence
<220> FEATURE:
<223> OTHER INFORMATION: Synthetic polypeptide

<400> SEQUENCE: 82

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Gly Gly Leu Ala Glu Ala Lys Val
        35                  40                  45

Leu Ala Asn Arg Glu Leu Asp Lys Tyr Gly Val Ser Asp Phe Tyr Lys
    50                  55                  60

Arg Leu Ile Asn Lys Ala Lys Thr Val Glu Gly Val Glu Ala Leu Lys
65                  70                  75                  80

Leu His Ile Leu Ala Ala Leu Pro
                85

<210> SEQ ID NO 83
<211> LENGTH: 86
<212> TYPE: PRT
<213> ORGANISM: Artificial sequence
<220> FEATURE:
<223> OTHER INFORMATION: Synthetic polypeptide

<400> SEQUENCE: 83

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Gly Gly Gly Leu Ala Glu Ala Lys Val Leu Ala
        35                  40                  45

Asn Arg Glu Leu Asp Lys Tyr Gly Val Ser Asp Phe Tyr Lys Arg Leu
    50                  55                  60

Ile Asn Lys Ala Lys Thr Val Glu Gly Val Glu Ala Leu Lys Leu His
65                  70                  75                  80

Ile Leu Ala Ala Leu Pro
                85

<210> SEQ ID NO 84
<211> LENGTH: 93
<212> TYPE: PRT
<213> ORGANISM: Artificial sequence
<220> FEATURE:
<223> OTHER INFORMATION: Synthetic polypeptide

<400> SEQUENCE: 84

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Gly Gly Gly Leu
        35                  40                  45

Ala Glu Ala Lys Val Leu Ala Asn Arg Glu Leu Asp Lys Tyr Gly Val
    50                  55                  60

Ser Asp Phe Tyr Lys Arg Leu Ile Asn Lys Ala Lys Thr Val Glu Gly
65                  70                  75                  80
```

Val Glu Ala Leu Lys Leu His Ile Leu Ala Ala Leu Pro
            85                  90

<210> SEQ ID NO 85
<211> LENGTH: 88
<212> TYPE: PRT
<213> ORGANISM: Artificial sequence
<220> FEATURE:
<223> OTHER INFORMATION: Synthetic polypeptide

<400> SEQUENCE: 85

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Leu Ala Glu Ala Lys Val
        35                  40                  45

Leu Ala Asn Arg Glu Leu Asp Lys Tyr Gly Val Ser Asp Phe Tyr Lys
50                  55                  60

Arg Leu Ile Asn Lys Ala Lys Thr Val Glu Gly Val Glu Ala Leu Lys
65                  70                  75                  80

Leu His Ile Leu Ala Ala Leu Pro
            85

<210> SEQ ID NO 86
<211> LENGTH: 77
<212> TYPE: PRT
<213> ORGANISM: Artificial sequence
<220> FEATURE:
<223> OTHER INFORMATION: Synthetic polypeptide

<400> SEQUENCE: 86

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly Leu
            20                  25                  30

Ala Glu Ala Lys Val Leu Ala Asn Arg Glu Leu Asp Lys Tyr Gly Val
        35                  40                  45

Ser Asp Tyr Tyr Lys Asn Ile Ile Asn Arg Ala Lys Thr Val Glu Gly
    50                  55                  60

Val Arg Ala Leu Lys Leu His Ile Leu Ala Ala Leu Pro
65                  70                  75

<210> SEQ ID NO 87
<211> LENGTH: 88
<212> TYPE: PRT
<213> ORGANISM: Artificial sequence
<220> FEATURE:
<223> OTHER INFORMATION: Synthetic polypeptide

<400> SEQUENCE: 87

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Leu Ala Glu Ala Lys Val
        35                  40                  45

Leu Ala Asn Arg Glu Leu Asp Lys Tyr Gly Val Ser Asp Tyr Tyr Lys
50                  55                  60

Asn Ile Ile Asn Arg Ala Lys Thr Val Glu Gly Val Arg Ala Leu Lys
 65                  70                  75                  80

Leu His Ile Leu Ala Ala Leu Pro
                 85

<210> SEQ ID NO 88
<211> LENGTH: 86
<212> TYPE: PRT
<213> ORGANISM: Artificial sequence
<220> FEATURE:
<223> OTHER INFORMATION: Synthetic polypeptide

<400> SEQUENCE: 88

His Gly Glu Gly Thr Phe Thr Ser Asp Leu Ser Lys Gln Leu Glu Glu
 1               5                  10                  15

Glu Ala Val Arg Leu Phe Ile Glu Trp Leu Lys Gln Gly Gly Pro Ser
                 20                  25                  30

Lys Glu Ile Ile Ser Gly Gly Gly Leu Ala Glu Ala Lys Val Leu Ala
             35                  40                  45

Asn Arg Glu Leu Asp Lys Tyr Gly Val Ser Asp Tyr Tyr Lys Asn Ile
         50                  55                  60

Ile Asn Arg Ala Lys Thr Val Glu Gly Val Arg Ala Leu Lys Leu His
 65                  70                  75                  80

Ile Leu Ala Ala Leu Pro
                 85

<210> SEQ ID NO 89
<211> LENGTH: 77
<212> TYPE: PRT
<213> ORGANISM: Artificial sequence
<220> FEATURE:
<223> OTHER INFORMATION: Synthetic polypeptide

<400> SEQUENCE: 89

His Gly Glu Gly Thr Phe Thr Ser Asp Leu Ser Lys Gln Leu Glu Glu
 1               5                  10                  15

Glu Ala Val Arg Leu Phe Ile Glu Trp Leu Lys Asn Gly Gly Gly Leu
                 20                  25                  30

Ala Glu Ala Lys Val Leu Ala Asn Arg Glu Leu Asp Lys Tyr Gly Val
             35                  40                  45

Ser Asp Tyr Tyr Lys Asn Ile Ile Asn Arg Ala Lys Thr Val Glu Gly
         50                  55                  60

Val Arg Ala Leu Lys Leu His Ile Leu Ala Ala Leu Pro
 65                  70                  75

<210> SEQ ID NO 90
<211> LENGTH: 77
<212> TYPE: PRT
<213> ORGANISM: Artificial sequence
<220> FEATURE:
<223> OTHER INFORMATION: Synthetic polypeptide

<400> SEQUENCE: 90

His Gly Glu Gly Thr Phe Thr Ser Asp Leu Ser Lys Gln Leu Glu Glu
 1               5                  10                  15

Glu Ala Val Arg Leu Phe Ile Glu Trp Leu Lys Asn Gly Gly Gly Leu
                 20                  25                  30

Ala Glu Ala Lys Val Leu Ala Asn Arg Glu Leu Asp Lys Tyr Gly Val
             35                  40                  45

Ser Asp Tyr Tyr Lys Asn Ile Ile Asn Arg Ala Lys Thr Val Glu Gly

Val Arg Ala Leu Lys Leu His Ile Leu Ala Ala Leu Pro
65                  70                  75

<210> SEQ ID NO 91
<211> LENGTH: 88
<212> TYPE: PRT
<213> ORGANISM: Artificial sequence
<220> FEATURE:
<223> OTHER INFORMATION: Synthetic polypeptide

<400> SEQUENCE: 91

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Gly Gly Leu Ala Glu Ala Lys Val
        35                  40                  45

Leu Ala Asn Arg Glu Leu Asp Lys Tyr Gly Val Ser Asp Tyr Tyr Lys
        50                  55                  60

Asn Ile Ile Asn Arg Ala Lys Thr Val Glu Gly Val Arg Ala Leu Lys
65                  70                  75                  80

Leu His Ile Leu Ala Ala Leu Pro
                85

<210> SEQ ID NO 92
<211> LENGTH: 86
<212> TYPE: PRT
<213> ORGANISM: Artificial sequence
<220> FEATURE:
<223> OTHER INFORMATION: Synthetic polypeptide

<400> SEQUENCE: 92

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Gly Gly Gly Leu Ala Glu Ala Lys Val Leu Ala
        35                  40                  45

Asn Arg Glu Leu Asp Lys Tyr Gly Val Ser Asp Tyr Tyr Lys Asn Ile
        50                  55                  60

Ile Asn Arg Ala Lys Thr Val Glu Gly Val Arg Ala Leu Lys Leu His
65                  70                  75                  80

Ile Leu Ala Ala Leu Pro
                85

<210> SEQ ID NO 93
<211> LENGTH: 93
<212> TYPE: PRT
<213> ORGANISM: Artificial sequence
<220> FEATURE:
<223> OTHER INFORMATION: Synthetic polypeptide

<400> SEQUENCE: 93

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Gly Gly Gly Leu
        35                  40                  45

Ala Glu Ala Lys Val Leu Ala Asn Arg Glu Leu Asp Lys Tyr Gly Val
            50                  55                  60

Ser Asp Tyr Tyr Lys Asn Ile Ile Asn Arg Ala Lys Thr Val Glu Gly
 65                  70                  75                  80

Val Arg Ala Leu Lys Leu His Ile Leu Ala Ala Leu Pro
                85                  90

<210> SEQ ID NO 94
<211> LENGTH: 88
<212> TYPE: PRT
<213> ORGANISM: Artificial sequence
<220> FEATURE:
<223> OTHER INFORMATION: Synthetic polypeptide

<400> SEQUENCE: 94

His Gly Glu Gly Thr Phe Thr Ser Asp Leu Ser Lys Gln Leu Glu Glu
 1               5                  10                  15

Glu Ala Val Arg Leu Phe Ile Glu Trp Leu Lys Asn Gly Gly Pro Ser
                20                  25                  30

Ser Gly Ala Pro Pro Pro Ser Gly Gly Ser Leu Ala Glu Ala Lys Val
            35                  40                  45

Leu Ala Asn Arg Glu Leu Asp Lys Tyr Gly Val Ser Asp Tyr Tyr Lys
 50                  55                  60

Asn Ile Ile Asn Arg Ala Lys Thr Val Glu Gly Val Arg Ala Leu Lys
 65                  70                  75                  80

Leu His Ile Leu Ala Ala Leu Pro
                85

<210> SEQ ID NO 95
<211> LENGTH: 88
<212> TYPE: PRT
<213> ORGANISM: Artificial sequence
<220> FEATURE:
<223> OTHER INFORMATION: Synthetic polypeptide

<400> SEQUENCE: 95

His Gly Glu Gly Thr Phe Thr Ser Asp Leu Ser Lys Gln Leu Glu Glu
 1               5                  10                  15

Glu Ala Val Arg Leu Phe Ile Glu Trp Leu Lys Asn Gly Gly Pro Ser
                20                  25                  30

Ser Gly Ala Pro Pro Pro Ser Gly Gly Ser Leu Ala Glu Ala Lys Val
            35                  40                  45

Leu Ala Asn Arg Glu Leu Asp Lys Tyr Gly Val Ser Asp Phe Tyr Lys
 50                  55                  60

Arg Leu Ile Asn Lys Ala Lys Thr Val Glu Gly Val Glu Ala Leu Lys
 65                  70                  75                  80

Leu His Ile Leu Ala Ala Leu Pro
                85

<210> SEQ ID NO 96
<211> LENGTH: 86
<212> TYPE: PRT
<213> ORGANISM: Artificial sequence
<220> FEATURE:
<223> OTHER INFORMATION: Synthetic polypeptide

<400> SEQUENCE: 96

His Gly Glu Gly Thr Phe Thr Ser Asp Leu Ser Lys Gln Leu Glu Glu
 1               5                  10                  15

```
Glu Ala Val Arg Leu Phe Ile Glu Trp Leu Lys Gln Gly Gly Pro Ser
            20                  25                  30

Lys Glu Ile Ile Ser Gly Gly Ser Leu Ala Glu Ala Lys Val Leu Ala
        35                  40                  45

Asn Arg Glu Leu Asp Lys Tyr Gly Val Ser Asp Phe Tyr Lys Arg Leu
 50                  55                  60

Ile Asn Lys Ala Lys Thr Val Glu Gly Val Glu Ala Leu Lys Leu His
 65                  70                  75                  80

Ile Leu Ala Ala Leu Pro
                85

<210> SEQ ID NO 97
<211> LENGTH: 77
<212> TYPE: PRT
<213> ORGANISM: Artificial sequence
<220> FEATURE:
<223> OTHER INFORMATION: Synthetic polypeptide

<400> SEQUENCE: 97

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Ser Leu
            20                  25                  30

Ala Glu Ala Lys Val Leu Ala Asn Arg Glu Leu Asp Lys Tyr Gly Val
        35                  40                  45

Ser Asp Phe Tyr Lys Arg Leu Ile Asn Lys Ala Lys Thr Val Glu Gly
    50                  55                  60

Val Glu Ala Leu Lys Leu His Ile Leu Ala Ala Leu Pro
65                  70                  75

<210> SEQ ID NO 98
<211> LENGTH: 77
<212> TYPE: PRT
<213> ORGANISM: Artificial sequence
<220> FEATURE:
<223> OTHER INFORMATION: Synthetic polypeptide

<400> SEQUENCE: 98

His Gly Glu Gly Thr Phe Thr Ser Asp Leu Ser Lys Gln Leu Glu Glu
 1               5                  10                  15

Glu Ala Val Arg Leu Phe Ile Glu Trp Leu Lys Asn Gly Gly Ser Leu
            20                  25                  30

Ala Glu Ala Lys Val Leu Ala Asn Arg Glu Leu Asp Lys Tyr Gly Val
        35                  40                  45

Ser Asp Phe Tyr Lys Arg Leu Ile Asn Lys Ala Lys Thr Val Glu Gly
    50                  55                  60

Val Glu Ala Leu Lys Leu His Ile Leu Ala Ala Leu Pro
65                  70                  75

<210> SEQ ID NO 99
<211> LENGTH: 88
<212> TYPE: PRT
<213> ORGANISM: Artificial sequence
<220> FEATURE:
<223> OTHER INFORMATION: Synthetic polypeptide

<400> SEQUENCE: 99

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
```

```
                 20                  25                  30

Ser Gly Ala Pro Pro Ser Gly Gly Ser Leu Ala Glu Ala Lys Val
            35                  40                  45

Leu Ala Asn Arg Glu Leu Asp Lys Tyr Gly Val Ser Asp Phe Tyr Lys
 50                  55                  60

Arg Leu Ile Asn Lys Ala Lys Thr Val Glu Gly Val Glu Ala Leu Lys
 65                  70                  75                  80

Leu His Ile Leu Ala Ala Leu Pro
                85

<210> SEQ ID NO 100
<211> LENGTH: 86
<212> TYPE: PRT
<213> ORGANISM: Artificial sequence
<220> FEATURE:
<223> OTHER INFORMATION: Synthetic polypeptide

<400> SEQUENCE: 100

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Gln Gly Gly Pro Ser
            20                  25                  30

Lys Glu Ile Ile Ser Gly Gly Ser Leu Ala Glu Ala Lys Val Leu Ala
            35                  40                  45

Asn Arg Glu Leu Asp Lys Tyr Gly Val Ser Asp Phe Tyr Lys Arg Leu
 50                  55                  60

Ile Asn Lys Ala Lys Thr Val Glu Gly Val Glu Ala Leu Lys Leu His
 65                  70                  75                  80

Ile Leu Ala Ala Leu Pro
                85

<210> SEQ ID NO 101
<211> LENGTH: 93
<212> TYPE: PRT
<213> ORGANISM: Artificial sequence
<220> FEATURE:
<223> OTHER INFORMATION: Synthetic polypeptide

<400> SEQUENCE: 101

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Gly Gly Ser Leu
            35                  40                  45

Ala Glu Ala Lys Val Leu Ala Asn Arg Glu Leu Asp Lys Tyr Gly Val
 50                  55                  60

Ser Asp Phe Tyr Lys Arg Leu Ile Asn Lys Ala Lys Thr Val Glu Gly
 65                  70                  75                  80

Val Glu Ala Leu Lys Leu His Ile Leu Ala Ala Leu Pro
                85                  90

<210> SEQ ID NO 102
<211> LENGTH: 77
<212> TYPE: PRT
<213> ORGANISM: Artificial sequence
<220> FEATURE:
<223> OTHER INFORMATION: Synthetic polypeptide

<400> SEQUENCE: 102
```

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Ser Leu
            20                  25                  30

Ala Glu Ala Lys Val Leu Ala Asn Arg Glu Leu Asp Lys Tyr Gly Val
        35                  40                  45

Ser Asp Tyr Tyr Lys Asn Ile Ile Asn Arg Ala Lys Thr Val Glu Gly
    50                  55                  60

Val Arg Ala Leu Lys Leu His Ile Leu Ala Ala Leu Pro
65                  70                  75

<210> SEQ ID NO 103
<211> LENGTH: 88
<212> TYPE: PRT
<213> ORGANISM: Artificial sequence
<220> FEATURE:
<223> OTHER INFORMATION: Synthetic polypeptide

<400> SEQUENCE: 103

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Ser Leu Ala Glu Ala Lys Val
        35                  40                  45

Leu Ala Asn Arg Glu Leu Asp Lys Tyr Gly Val Ser Asp Tyr Tyr Lys
    50                  55                  60

Asn Ile Ile Asn Arg Ala Lys Thr Val Glu Gly Val Arg Ala Leu Lys
65                  70                  75                  80

Leu His Ile Leu Ala Ala Leu Pro
                85

<210> SEQ ID NO 104
<211> LENGTH: 86
<212> TYPE: PRT
<213> ORGANISM: Artificial sequence
<220> FEATURE:
<223> OTHER INFORMATION: Synthetic polypeptide

<400> SEQUENCE: 104

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Gly Gly Ser Leu Ala Glu Ala Lys Val Leu Ala
        35                  40                  45

Asn Arg Glu Leu Asp Lys Tyr Gly Val Ser Asp Tyr Tyr Lys Asn Ile
    50                  55                  60

Ile Asn Arg Ala Lys Thr Val Glu Gly Val Arg Ala Leu Lys Leu His
65                  70                  75                  80

Ile Leu Ala Ala Leu Pro
                85

<210> SEQ ID NO 105
<211> LENGTH: 77
<212> TYPE: PRT
<213> ORGANISM: Artificial sequence
<220> FEATURE:
<223> OTHER INFORMATION: Synthetic polypeptide

<400> SEQUENCE: 105

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Ser Leu
            20                  25                  30

Ala Glu Ala Lys Val Leu Ala Asn Arg Glu Leu Asp Lys Tyr Gly Val
        35                  40                  45

Ser Asp Tyr Tyr Lys Asn Ile Ile Asn Arg Ala Lys Thr Val Glu Gly
    50                  55                  60

Val Arg Ala Leu Lys Leu His Ile Leu Ala Ala Leu Pro
65                  70                  75

<210> SEQ ID NO 106
<211> LENGTH: 77
<212> TYPE: PRT
<213> ORGANISM: Artificial sequence
<220> FEATURE:
<223> OTHER INFORMATION: Synthetic polypeptide

<400> SEQUENCE: 106

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Ser Leu
            20                  25                  30

Ala Glu Ala Lys Val Leu Ala Asn Arg Glu Leu Asp Lys Tyr Gly Val
        35                  40                  45

Ser Asp Tyr Tyr Lys Asn Ile Ile Asn Arg Ala Lys Thr Val Glu Gly
    50                  55                  60

Val Arg Ala Leu Lys Leu His Ile Leu Ala Ala Leu Pro
65                  70                  75

<210> SEQ ID NO 107
<211> LENGTH: 88
<212> TYPE: PRT
<213> ORGANISM: Artificial sequence
<220> FEATURE:
<223> OTHER INFORMATION: Synthetic polypeptide

<400> SEQUENCE: 107

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Ser Leu Ala Glu Ala Lys Val
        35                  40                  45

Leu Ala Asn Arg Glu Leu Asp Lys Tyr Gly Val Ser Asp Tyr Tyr Lys
    50                  55                  60

Asn Ile Ile Asn Arg Ala Lys Thr Val Glu Gly Val Arg Ala Leu Lys
65                  70                  75                  80

Leu His Ile Leu Ala Ala Leu Pro
            85

<210> SEQ ID NO 108
<211> LENGTH: 86
<212> TYPE: PRT
<213> ORGANISM: Artificial sequence
<220> FEATURE:
<223> OTHER INFORMATION: Synthetic polypeptide -continued

<400> SEQUENCE: 108

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Gly Gly Ser Leu Ala Glu Ala Lys Val Leu Ala
        35                  40                  45

Asn Arg Glu Leu Asp Lys Tyr Gly Val Ser Asp Tyr Tyr Lys Asn Ile
50                  55                  60

Ile Asn Arg Ala Lys Thr Val Glu Gly Val Arg Ala Leu Lys Leu His
65                  70                  75                  80

Ile Leu Ala Ala Leu Pro
                85

<210> SEQ ID NO 109
<211> LENGTH: 93
<212> TYPE: PRT
<213> ORGANISM: Artificial sequence
<220> FEATURE:
<223> OTHER INFORMATION: Synthetic polypeptide

<400> SEQUENCE: 109

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Gly Gly Ser Leu
        35                  40                  45

Ala Glu Ala Lys Val Leu Ala Asn Arg Glu Leu Asp Lys Tyr Gly Val
50                  55                  60

Ser Asp Tyr Tyr Lys Asn Ile Ile Asn Arg Ala Lys Thr Val Glu Gly
65                  70                  75                  80

Val Arg Ala Leu Lys Leu His Ile Leu Ala Ala Leu Pro
                85                  90

<210> SEQ ID NO 110

<400> SEQUENCE: 110

000

<210> SEQ ID NO 111
<211> LENGTH: 37
<212> TYPE: PRT
<213> ORGANISM: Artificial sequence
<220> FEATURE:
<223> OTHER INFORMATION: Synthetic polypeptide

<400> SEQUENCE: 111

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Lys Glu Ile Ile Ser
        35

<210> SEQ ID NO 112
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 112

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 113
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 113

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 114
<211> LENGTH: 43
<212> TYPE: PRT
<213> ORGANISM: Artificial sequence
<220> FEATURE:
<223> OTHER INFORMATION: Synthetic polypeptide

<400> SEQUENCE: 114

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Lys Lys Lys Lys Lys Lys
        35                  40

<210> SEQ ID NO 115
<211> LENGTH: 45
<212> TYPE: PRT
<213> ORGANISM: Artificial sequence
<220> FEATURE:
<223> OTHER INFORMATION: Synthetic polypeptide

<400> SEQUENCE: 115

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys
        35                  40              45

<210> SEQ ID NO 116
<211> LENGTH: 43
<212> TYPE: PRT
<213> ORGANISM: Artificial sequence
<220> FEATURE:
<223> OTHER INFORMATION: Synthetic polypeptide -continued

```
<400> SEQUENCE: 116

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Lys Lys Lys Lys Lys
        35                  40

<210> SEQ ID NO 117
<211> LENGTH: 44
<212> TYPE: PRT
<213> ORGANISM: Artificial sequence
<220> FEATURE:
<223> OTHER INFORMATION: Synthetic polypeptide

<400> SEQUENCE: 117

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 118
<211> LENGTH: 44
<212> TYPE: PRT
<213> ORGANISM: Artificial sequence
<220> FEATURE:
<223> OTHER INFORMATION: Synthetic polypeptide

<400> SEQUENCE: 118

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 119
<211> LENGTH: 26
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (5)..(5)
<223> OTHER INFORMATION: Xaa can be Y or F
<220> FEATURE:
<221> NAME/KEY: MISC_FEATURE
<222> LOCATION: (8)..(8)
<223> OTHER INFORMATION: Xaa can be N, R or S
<220> FEATURE:
<221> NAME/KEY: MISC_FEATURE
<222> LOCATION: (9)..(9)
<223> OTHER INFORMATION: Xaa can be V, I, L, M, F or Y
<220> FEATURE:
<221> NAME/KEY: MISC_FEATURE
<222> LOCATION: (11)..(11)
<223> OTHER INFORMATION: Xaa can be N, S, E or D
<220> FEATURE:
<221> NAME/KEY: MISC_FEATURE
<222> LOCATION: (12)..(12)
<223> OTHER INFORMATION: Xaa can be R, K or N
<220> FEATURE:
<221> NAME/KEY: MISC_FEATURE
<222> LOCATION: (14)..(14)
```

```
<223> OTHER INFORMATION: Xaa can be K or R
<220> FEATURE:
<221> NAME/KEY: MISC_FEATURE
<222> LOCATION: (20)..(20)
<223> OTHER INFORMATION: Xaa can be D, N, Q, E, H, S, R or K
<220> FEATURE:
<221> NAME/KEY: MISC_FEATURE
<222> LOCATION: (23)..(23)
<223> OTHER INFORMATION: Xaa can be K, I or T
<220> FEATURE:
<221> NAME/KEY: MISC_FEATURE
<222> LOCATION: (24)..(24)
<223> OTHER INFORMATION: Xaa can be A, S, T, G, H, L or D
<220> FEATURE:
<221> NAME/KEY: MISC_FEATURE
<222> LOCATION: (25)..(25)
<223> OTHER INFORMATION: Xaa can be H, E or D

<400> SEQUENCE: 119

Gly Val Ser Asp Xaa Tyr Lys Xaa Xaa Ile Xaa Xaa Ala Xaa Thr Val
1               5                   10                  15

Glu Gly Val Xaa Ala Leu Xaa Xaa Xaa Ile
            20                  25

<210> SEQ ID NO 120
<211> LENGTH: 26
<212> TYPE: PRT
<213> ORGANISM: Artificial sequence
<220> FEATURE:
<223> OTHER INFORMATION: Synthetic polypeptide

<400> SEQUENCE: 120

Gly Val Ser Asp Tyr Tyr Lys Asn Leu Ile Asn Asn Ala Lys Thr Val
1               5                   10                  15

Glu Gly Val Lys Ala Leu Ile Asp Glu Ile
            20                  25

<210> SEQ ID NO 121
<211> LENGTH: 46
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (6)..(6)
<223> OTHER INFORMATION: Xaa can be V or E
<220> FEATURE:
<221> NAME/KEY: MISC_FEATURE
<222> LOCATION: (7)..(7)
<223> OTHER INFORMATION: Xaa can be L, E or D
<220> FEATURE:
<221> NAME/KEY: MISC_FEATURE
<222> LOCATION: (9)..(9)
<223> OTHER INFORMATION: Xaa can be N, L or I
<220> FEATURE:
<221> NAME/KEY: MISC_FEATURE
<222> LOCATION: (10)..(10)
<223> OTHER INFORMATION: Xaa can be R or K
<220> FEATURE:
<221> NAME/KEY: MISC_FEATURE
<222> LOCATION: (13)..(13)
<223> OTHER INFORMATION: Xaa can be D or K
<220> FEATURE:
<221> NAME/KEY: MISC_FEATURE
<222> LOCATION: (20)..(20)
<223> OTHER INFORMATION: Xaa can be Y or F
<220> FEATURE:
<221> NAME/KEY: MISC_FEATURE
<222> LOCATION: (23)..(23)
<223> OTHER INFORMATION: Xaa can be N, R or S
<220> FEATURE:
<221> NAME/KEY: MISC_FEATURE
```

```
<222> LOCATION: (24)..(24)
<223> OTHER INFORMATION: Xaa can be V, I, L, M, F or Y
<220> FEATURE:
<221> NAME/KEY: MISC_FEATURE
<222> LOCATION: (26)..(26)
<223> OTHER INFORMATION: Xaa can be N, S, E or D
<220> FEATURE:
<221> NAME/KEY: MISC_FEATURE
<222> LOCATION: (27)..(27)
<223> OTHER INFORMATION: Xaa can be R, K or N
<220> FEATURE:
<221> NAME/KEY: MISC_FEATURE
<222> LOCATION: (29)..(29)
<223> OTHER INFORMATION: Xaa can be K or R
<220> FEATURE:
<221> NAME/KEY: MISC_FEATURE
<222> LOCATION: (35)..(35)
<223> OTHER INFORMATION: Xaa can be D, N, Q, E, H, S, R or K
<220> FEATURE:
<221> NAME/KEY: MISC_FEATURE
<222> LOCATION: (38)..(38)
<223> OTHER INFORMATION: Xaa can be K, I or T
<220> FEATURE:
<221> NAME/KEY: MISC_FEATURE
<222> LOCATION: (39)..(39)
<223> OTHER INFORMATION: Xaa can be A, S, T, G, H, L or D
<220> FEATURE:
<221> NAME/KEY: MISC_FEATURE
<222> LOCATION: (40)..(40)
<223> OTHER INFORMATION: Xaa can be H, E or D

<400> SEQUENCE: 121

Leu Ala Glu Ala Lys Xaa Xaa Ala Xaa Xaa Glu Leu Xaa Lys Tyr Gly
1               5                   10                  15

Val Ser Asp Xaa Tyr Lys Xaa Xaa Ile Xaa Xaa Ala Xaa Thr Val Glu
            20                  25                  30

Gly Val Xaa Ala Leu Xaa Xaa Xaa Ile Leu Ala Ala Leu Pro
        35                  40                  45

<210> SEQ ID NO 122
<211> LENGTH: 46
<212> TYPE: PRT
<213> ORGANISM: Artificial sequence
<220> FEATURE:
<223> OTHER INFORMATION: Synthetic polypeptide

<400> SEQUENCE: 122

Leu Ala Glu Ala Lys Glu Asp Ala Ile Lys Glu Leu Asp Lys Tyr Gly
1               5                   10                  15

Val Ser Asp Tyr Tyr Lys Arg Leu Ile Ser Lys Ala Lys Thr Val Glu
            20                  25                  30

Gly Val Lys Ala Leu Ile Ser Glu Ile Leu Ala Ala Leu Pro
        35                  40                  45

<210> SEQ ID NO 123
<211> LENGTH: 46
<212> TYPE: PRT
<213> ORGANISM: Artificial sequence
<220> FEATURE:
<223> OTHER INFORMATION: Synthetic polypeptide

<400> SEQUENCE: 123

Leu Ala Glu Ala Lys Glu Asp Ala Ile Lys Glu Leu Asp Lys Tyr Gly
1               5                   10                  15

Val Ser Asp Tyr Tyr Lys Asn Leu Ile Asn Lys Ala Lys Thr Val Glu
            20                  25                  30

Gly Val Glu Ala Leu Thr Leu His Ile Leu Ala Ala Leu Pro
        35                  40                  45
```

<210> SEQ ID NO 124
<211> LENGTH: 46
<212> TYPE: PRT
<213> ORGANISM: Artificial sequence
<220> FEATURE:
<223> OTHER INFORMATION: Synthetic polypeptide

<400> SEQUENCE: 124

Leu Ala Glu Ala Lys Glu Asp Ala Ile Lys Glu Leu Asp Lys Tyr Gly
1               5                   10                  15

Val Ser Asp Tyr Tyr Lys Asn Leu Ile Asn Lys Ala Lys Thr Val Glu
            20                  25                  30

Gly Val Glu Ala Leu Ile Ser Glu Ile Leu Ala Ala Leu Pro
        35                  40                  45

<210> SEQ ID NO 125
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 125

Gly Gly Gly Gly
1

<210> SEQ ID NO 126
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 126

Gly Gly Gly Gly Gly
1               5

<210> SEQ ID NO 127
<211> LENGTH: 7
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (4)..(6)
<223> OTHER INFORMATION: Xaa can be Gly or absent

<400> SEQUENCE: 127

Gly Gly Gly Xaa Xaa Xaa Glu
1               5

<210> SEQ ID NO 128
<211> LENGTH: 7
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (4)..(6)
<223> OTHER INFORMATION: Xaa can be Gly or absent

<400> SEQUENCE: 128

Gly Gly Gly Xaa Xaa Xaa Lys
1               5

```
<210> SEQ ID NO 129
<211> LENGTH: 7
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (4)..(6)
<223> OTHER INFORMATION: Xaa can be Gly or absent

<400> SEQUENCE: 129

Gly Gly Gly Xaa Xaa Xaa Asp
1               5

<210> SEQ ID NO 130
<211> LENGTH: 7
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (4)..(6)
<223> OTHER INFORMATION: Xaa can be Gly or absent

<400> SEQUENCE: 130

Gly Gly Gly Xaa Xaa Xaa Arg
1               5

<210> SEQ ID NO 131
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 131

Gly Gly Gly Lys Gly Gly Gly Gly
1               5

<210> SEQ ID NO 132
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 132

Gly Gly Gly Asn Gly Ser Gly Gly
1               5

<210> SEQ ID NO 133
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 133

Gly Gly Gly Cys Gly Gly Gly Gly
1               5

<210> SEQ ID NO 134
<211> LENGTH: 5
<212> TYPE: PRT
<213> ORGANISM: Artificial sequence
```

```
<220> FEATURE:
<223> OTHER INFORMATION: Synthetic polypeptide

<400> SEQUENCE: 134

Gly Pro Asn Gly Gly
1               5

<210> SEQ ID NO 135
<211> LENGTH: 2
<212> TYPE: PRT
<213> ORGANISM: Artificial sequence
<220> FEATURE:
<223> OTHER INFORMATION: Synthetic polypeptide

<400> SEQUENCE: 135

Gly Ser
1

<210> SEQ ID NO 136
<211> LENGTH: 3
<212> TYPE: PRT
<213> ORGANISM: Artificial sequence
<220> FEATURE:
<223> OTHER INFORMATION: Synthetic polypeptide

<400> SEQUENCE: 136

Gly Gly Ser
1

<210> SEQ ID NO 137
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 137

Gly Gly Gly Ser
1

<210> SEQ ID NO 138
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 138

Gly Gly Gly Gly Ser
1               5

<210> SEQ ID NO 139
<211> LENGTH: 2
<212> TYPE: PRT
<213> ORGANISM: Artificial sequence
<220> FEATURE:
<223> OTHER INFORMATION: Synthetic polypeptide

<400> SEQUENCE: 139

Gly Glu
1

<210> SEQ ID NO 140
<211> LENGTH: 3
<212> TYPE: PRT
<213> ORGANISM: Artificial sequence
<220> FEATURE:
```

```
<223> OTHER INFORMATION: Synthetic polypeptide

<400> SEQUENCE: 140

Gly Gly Glu
1

<210> SEQ ID NO 141
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 141

Gly Gly Gly Glu
1

<210> SEQ ID NO 142
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 142

Gly Gly Gly Gly Glu
1               5

<210> SEQ ID NO 143
<211> LENGTH: 2
<212> TYPE: PRT
<213> ORGANISM: Artificial sequence
<220> FEATURE:
<223> OTHER INFORMATION: Synthetic polypeptide

<400> SEQUENCE: 143

Gly Asp
1

<210> SEQ ID NO 144
<211> LENGTH: 3
<212> TYPE: PRT
<213> ORGANISM: Artificial sequence
<220> FEATURE:
<223> OTHER INFORMATION: Synthetic polypeptide

<400> SEQUENCE: 144

Gly Gly Asp
1

<210> SEQ ID NO 145
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 145

Gly Gly Gly Asp
1

<210> SEQ ID NO 146
<211> LENGTH: 5
<212> TYPE: PRT
<213> ORGANISM: Artificial sequence
<220> FEATURE:
<223> OTHER INFORMATION: Synthetic polypeptide
```

```
<400> SEQUENCE: 146

Gly Gly Gly Gly Asp
1               5

<210> SEQ ID NO 147
<211> LENGTH: 2
<212> TYPE: PRT
<213> ORGANISM: Artificial sequence
<220> FEATURE:
<223> OTHER INFORMATION: Synthetic polypeptide

<400> SEQUENCE: 147

Gly Lys
1

<210> SEQ ID NO 148
<211> LENGTH: 3
<212> TYPE: PRT
<213> ORGANISM: Artificial sequence
<220> FEATURE:
<223> OTHER INFORMATION: Synthetic polypeptide

<400> SEQUENCE: 148

Gly Gly Lys
1

<210> SEQ ID NO 149
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 149

Gly Gly Gly Lys
1

<210> SEQ ID NO 150
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 150

Gly Gly Gly Gly Lys
1               5

<210> SEQ ID NO 151
<211> LENGTH: 2
<212> TYPE: PRT
<213> ORGANISM: Artificial sequence
<220> FEATURE:
<223> OTHER INFORMATION: Synthetic polypeptide

<400> SEQUENCE: 151

Gly Arg
1

<210> SEQ ID NO 152
<211> LENGTH: 3
<212> TYPE: PRT
<213> ORGANISM: Artificial sequence
<220> FEATURE:
<223> OTHER INFORMATION: Synthetic polypeptide
```

```
<400> SEQUENCE: 152

Gly Gly Arg
1

<210> SEQ ID NO 153
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 153

Gly Gly Gly Arg
1

<210> SEQ ID NO 154
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 154

Gly Gly Gly Gly Arg
1               5

<210> SEQ ID NO 155
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 155

Glu Ala Ala Ala Lys
1               5

<210> SEQ ID NO 156
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 156

Met Ala His His His His His His Val Gly Thr Gly Ser Asn Glu Asn
1               5                   10                  15

Leu Tyr Phe Gln His Gly Glu Gly Thr Phe Thr Ser Asp Leu Ser Lys
                20                  25                  30

Gln Met Glu Glu Glu Ala Val Arg Leu Phe Ile Glu Trp Leu Lys Asn
            35                  40                  45

Thr Gly Gly Gly Gly Ser Gly Gly Gly Ser Gly Gly Gly Ser Gly Gly
        50                  55                  60

Gly Ser Ala Ser Leu Ala Glu Ala Lys Val Leu Ala Asn Arg Glu Leu
65                  70                  75                  80

Asp Lys Tyr Gly Val Ser Asp Phe Tyr Lys Arg Leu Ile Asn Lys Ala
                85                  90                  95

Lys Thr Val Glu Gly Val Glu Ala Leu Lys Leu His Ile Leu Ala Ala
                100                 105                 110

Leu Pro

<210> SEQ ID NO 157
```

```
<211> LENGTH: 102
<212> TYPE: PRT
<213> ORGANISM: Artificial sequence
<220> FEATURE:
<223> OTHER INFORMATION: Synthetic polypeptide

<400> SEQUENCE: 157

Met Ala His His His His His Val Gly Thr Gly Ser Asn Glu Asn
1               5                   10                  15

Leu Tyr Phe Gln His Gly Glu Gly Thr Phe Thr Ser Asp Leu Ser Lys
            20                  25                  30

Gln Met Glu Glu Glu Ala Val Arg Leu Phe Ile Glu Trp Leu Lys Asn
        35                  40                  45

Thr Gly Gly Gly Gly Ser Ala Ser Leu Ala Glu Ala Lys Val Leu Ala
    50                  55                  60

Asn Arg Glu Leu Asp Lys Tyr Gly Val Ser Asp Phe Tyr Lys Arg Leu
65                  70                  75                  80

Ile Asn Lys Ala Lys Thr Val Glu Gly Val Glu Ala Leu Lys Leu His
                85                  90                  95

Ile Leu Ala Ala Leu Pro
            100

<210> SEQ ID NO 158
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 158

Met Ala His His His His His Val Gly Thr Gly Ser Asn Glu Asn
1               5                   10                  15

Leu Tyr Phe Gln His Gly Glu Gly Thr Phe Thr Ser Asp Leu Ser Lys
            20                  25                  30

Gln Met Glu Glu Glu Ala Val Arg Leu Phe Ile Glu Trp Leu Lys Asn
        35                  40                  45

Thr Gly Gly Gly Gly Ser Gly Gly Ser Gly Gly Ser Gly Gly
    50                  55                  60

Gly Ser Ala Ser Leu Ala Glu Ala Lys Val Leu Ala Asn Arg Glu Leu
65                  70                  75                  80

Asp Lys Tyr Gly Val Ser Asp Tyr Tyr Lys Asn Ile Asn Arg Ala
                85                  90                  95

Lys Thr Val Glu Gly Val Arg Ala Leu Lys Leu His Ile Leu Ala Ala
            100                 105                 110

Leu Pro

<210> SEQ ID NO 159
<211> LENGTH: 102
<212> TYPE: PRT
<213> ORGANISM: Artificial sequence
<220> FEATURE:
<223> OTHER INFORMATION: Synthetic polypeptide

<400> SEQUENCE: 159

Met Ala His His His His His Val Gly Thr Gly Ser Asn Glu Asn
1               5                   10                  15

Leu Tyr Phe Gln His Gly Glu Gly Thr Phe Thr Ser Asp Leu Ser Lys
            20                  25                  30

Gln Met Glu Glu Glu Ala Val Arg Leu Phe Ile Glu Trp Leu Lys Asn
```

```
                35                  40                  45
Thr Gly Gly Gly Ser Ala Ser Leu Ala Glu Ala Lys Val Leu Ala
 50                  55                  60
Asn Arg Glu Leu Asp Lys Tyr Gly Val Ser Asp Tyr Tyr Lys Asn Ile
 65                  70                  75                  80
Ile Asn Arg Ala Lys Thr Val Glu Gly Val Arg Ala Leu Lys Leu His
                 85                  90                  95
Ile Leu Ala Ala Leu Pro
                100

<210> SEQ ID NO 160
<211> LENGTH: 263
<212> TYPE: PRT
<213> ORGANISM: Artificial sequence
<220> FEATURE:
<223> OTHER INFORMATION: Synthetic polypeptide

<400> SEQUENCE: 160

Met Ser Asp Lys Ile Ile His Leu Thr Asp Asp Ser Phe Asp Thr Asp
  1               5                  10                  15
Val Leu Lys Ala Asp Gly Ala Ile Leu Val Asp Phe Trp Ala Glu Trp
                 20                  25                  30
Cys Gly Pro Cys Lys Met Ile Ala Pro Ile Leu Asp Glu Ile Ala Asp
                 35                  40                  45
Glu Tyr Gln Gly Lys Leu Thr Val Ala Lys Leu Asn Ile Asp Gln Asn
 50                  55                  60
Pro Gly Thr Ala Pro Lys Tyr Gly Ile Arg Gly Ile Pro Thr Leu Leu
 65                  70                  75                  80
Leu Phe Lys Asn Gly Glu Val Ala Ala Thr Lys Val Gly Ala Leu Ser
                 85                  90                  95
Lys Gly Gln Leu Lys Glu Phe Leu Asp Ala Asn Leu Ala Gly Ser Gly
                100                 105                 110
Ser Gly His Met His His His His His Ser Ser Gly Leu Val Pro
                115                 120                 125
Arg Gly Ser Gly Met Lys Glu Thr Ala Ala Ala Lys Phe Glu Arg Gln
130                 135                 140
His Met Asp Ser Pro Asp Leu Gly Thr Glu Asn Leu Tyr Phe Gln His
145                 150                 155                 160
Gly Glu Gly Thr Phe Thr Ser Asp Leu Ser Lys Gln Leu Glu Glu Glu
                165                 170                 175
Ala Val Arg Leu Phe Ile Glu Trp Leu Lys Asn Gly Gly Pro Ser Ser
                180                 185                 190
Gly Ala Pro Pro Pro Ser Thr Gly Gly Gly Ser Gly Gly Gly Ser
                195                 200                 205
Gly Gly Gly Ser Gly Gly Ser Ala Ser Leu Ala Glu Ala Lys Val
                210                 215                 220
Leu Ala Asn Arg Glu Leu Asp Lys Tyr Gly Val Ser Asp Phe Tyr Lys
225                 230                 235                 240
Arg Leu Ile Asn Lys Ala Lys Thr Val Glu Gly Val Glu Ala Leu Lys
                245                 250                 255
Leu His Ile Leu Ala Ala Leu
                260

<210> SEQ ID NO 161
<211> LENGTH: 253
<212> TYPE: PRT
```

<213> ORGANISM: Artificial sequence
<220> FEATURE:
<223> OTHER INFORMATION: Synthetic polypeptide

<400> SEQUENCE: 161

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
130                 135                 140

His Met Asp Ser Pro Asp Leu Gly Thr Glu Asn Leu Tyr Phe Gln His
145                 150                 155                 160

Gly Glu Gly Thr Phe Thr Ser Asp Leu Ser Lys Gln Met Glu Glu Glu
                165                 170                 175

Ala Val Arg Leu Phe Ile Glu Trp Leu Lys Asn Thr Gly Gly Gly Gly
            180                 185                 190

Ser Gly Gly Gly Ser Gly Gly Gly Ser Gly Gly Gly Ser Ala Ser Leu
        195                 200                 205

Ala Glu Ala Lys Val Leu Ala Asn Arg Glu Leu Asp Lys Tyr Gly Val
    210                 215                 220

Ser Asp Tyr Tyr Lys Asn Ile Ile Asn Arg Ala Lys Thr Val Glu Gly
225                 230                 235                 240

Val Arg Ala Leu Lys Leu His Ile Leu Ala Ala Leu Pro
                245                 250
```

<210> SEQ ID NO 162
<211> LENGTH: 241
<212> TYPE: PRT
<213> ORGANISM: Artificial sequence
<220> FEATURE:
<223> OTHER INFORMATION: Synthetic polypeptide

<400> SEQUENCE: 162

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80
```

```
Leu Phe Lys Asn Gly Glu Val Ala Ala Thr Lys Val Gly Ala Leu Ser
             85                  90                  95

Lys Gly Gln Leu Lys Glu Phe Leu Asp Ala Asn Leu Ala Gly Ser Gly
        100                 105                 110

Ser Gly His Met His His His His His Ser Ser Gly Leu Val Pro
        115                 120                 125

Arg Gly Ser Gly Met Lys Glu Thr Ala Ala Ala Lys Phe Glu Arg Gln
        130                 135                 140

His Met Asp Ser Pro Asp Leu Gly Thr Glu Asn Leu Tyr Phe Gln His
145                 150                 155                 160

Gly Glu Gly Thr Phe Thr Ser Asp Leu Ser Lys Gln Met Glu Glu
                165                 170                 175

Ala Val Arg Leu Phe Ile Glu Trp Leu Lys Asn Thr Gly Gly Gly
                180                 185                 190

Ser Ala Ser Leu Ala Glu Ala Lys Val Leu Ala Asn Arg Glu Leu Asp
            195                 200                 205

Lys Tyr Gly Val Ser Asp Tyr Tyr Lys Asn Ile Ile Asn Arg Ala Lys
        210                 215                 220

Thr Val Glu Gly Val Arg Ala Leu Lys Leu His Ile Leu Ala Ala Leu
225                 230                 235                 240

Pro

<210> SEQ ID NO 163
<211> LENGTH: 91
<212> TYPE: PRT
<213> ORGANISM: Artificial sequence
<220> FEATURE:
<223> OTHER INFORMATION: Synthetic polypeptide

<400> SEQUENCE: 163

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Thr Gly Gly Gly Ser Ala Ser Leu Ala Glu
        35                  40                  45

Ala Lys Val Leu Ala Asn Arg Glu Leu Asp Lys Tyr Gly Val Ser Asp
    50                  55                  60

Phe Tyr Lys Arg Leu Ile Asn Lys Ala Lys Thr Val Glu Gly Val Glu
65                  70                  75                  80

Ala Leu Lys Leu His Ile Leu Ala Ala Leu Pro
                85                  90

<210> SEQ ID NO 164
<211> LENGTH: 74
<212> TYPE: PRT
<213> ORGANISM: Artificial sequence
<220> FEATURE:
<223> OTHER INFORMATION: Synthetic polypeptide

<400> SEQUENCE: 164

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Leu Ala Glu Ala
            20                  25                  30

Lys Val Leu Ala Asn Arg Glu Leu Asp Lys Tyr Gly Val Ser Asp Phe
        35                  40                  45
```

```
Tyr Lys Arg Leu Ile Asn Lys Ala Lys Thr Val Glu Gly Val Glu Ala
 50                  55                  60

Leu Lys Leu His Ile Leu Ala Ala Leu Pro
 65                  70
```

<210> SEQ ID NO 165
<211> LENGTH: 73
<212> TYPE: PRT
<213> ORGANISM: Artificial sequence
<220> FEATURE:
<223> OTHER INFORMATION: Synthetic polypeptide

<400> SEQUENCE: 165

```
His Gly Glu Gly Thr Phe Thr Ser Asp Leu Ser Lys Gln Met Glu Glu
 1               5                   10                  15

Glu Ala Val Arg Leu Phe Ile Glu Trp Leu Lys Leu Ala Glu Ala Lys
                 20                  25                  30

Val Leu Ala Asn Arg Glu Leu Asp Lys Tyr Gly Val Ser Asp Phe Tyr
             35                  40                  45

Lys Arg Leu Ile Asn Lys Ala Lys Thr Val Glu Gly Val Glu Ala Leu
 50                  55                  60

Lys Leu His Ile Leu Ala Ala Leu Pro
 65                  70
```

<210> SEQ ID NO 166
<211> LENGTH: 79
<212> TYPE: PRT
<213> ORGANISM: Artificial sequence
<220> FEATURE:
<223> OTHER INFORMATION: Synthetic polypeptide

<400> SEQUENCE: 166

```
His Gly Glu Gly Thr Phe Thr Ser Asp Leu Ser Lys Gln Met Glu Glu
 1               5                   10                  15

Glu Ala Val Arg Leu Phe Ile Glu Trp Leu Lys Asn Gly Gly Pro Ser
                 20                  25                  30

Ser Gly Ala Pro Pro Pro Ser Thr Gly Gly Gly Ser Ala Ser Tyr
             35                  40                  45

Gly Val Ser Asp Phe Tyr Lys Arg Leu Ile Asn Lys Ala Lys Thr Val
 50                  55                  60

Glu Gly Val Glu Ala Leu Lys Leu His Ile Leu Ala Ala Leu Pro
 65                  70                  75
```

<210> SEQ ID NO 167
<211> LENGTH: 72
<212> TYPE: PRT
<213> ORGANISM: Artificial sequence
<220> FEATURE:
<223> OTHER INFORMATION: Synthetic polypeptide

<400> SEQUENCE: 167

```
His Gly Glu Gly Thr Phe Thr Ser Asp Leu Ser Lys Gln Met Glu Glu
 1               5                   10                  15

Glu Ala Val Arg Leu Phe Ile Glu Trp Leu Lys Asn Gly Gly Pro Ser
                 20                  25                  30

Ser Gly Ala Pro Pro Pro Ser Gly Tyr Gly Val Ser Asp Phe Tyr Lys
             35                  40                  45

Arg Leu Ile Asn Lys Ala Lys Thr Val Glu Gly Val Glu Ala Leu Lys
 50                  55                  60

Leu His Ile Leu Ala Ala Leu Pro
 65                  70
```

```
65                  70
```

<210> SEQ ID NO 168
<211> LENGTH: 89
<212> TYPE: PRT
<213> ORGANISM: Artificial sequence
<220> FEATURE:
<223> OTHER INFORMATION: Synthetic polypeptide

<400> SEQUENCE: 168

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Ser Leu Lys Asn Ala Lys Glu
        35                  40                  45

Asp Ala Ile Ala Glu Leu Lys Lys Ala Gly Ile Thr Ser Asp Phe Tyr
    50                  55                  60

Phe Asn Ala Val Asn Lys Ala Lys Thr Val Glu Glu Val Asn Ala Leu
65                  70                  75                  80

Lys Asn Glu Ile Leu Lys Ala Leu Pro
                85

<210> SEQ ID NO 169
<211> LENGTH: 88
<212> TYPE: PRT
<213> ORGANISM: Artificial sequence
<220> FEATURE:
<223> OTHER INFORMATION: Synthetic polypeptide

<400> SEQUENCE: 169

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Ser Leu Ser Glu Ala Lys Glu
        35                  40                  45

Met Ala Ile Arg Glu Leu Asp Ala Asn Gly Val Ser Asp Phe Tyr Lys
    50                  55                  60

Asp Lys Ile Asp Asp Ala Lys Thr Val Glu Gly Val Ala Leu Lys
65                  70                  75                  80

Asp Leu Ile Leu Asn Ser Leu Pro
                85

<210> SEQ ID NO 170
<211> LENGTH: 88
<212> TYPE: PRT
<213> ORGANISM: Artificial sequence
<220> FEATURE:
<223> OTHER INFORMATION: Synthetic polypeptide

<400> SEQUENCE: 170

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Ser Leu Ala Lys Ala Lys Ala
        35                  40                  45

Asp Ala Ile Glu Ile Leu Lys Lys Tyr Gly Ile Gly Asp Tyr Tyr Ile
    50                  55                  60

```
Lys Leu Ile Asn Asn Gly Lys Thr Ala Glu Gly Val Thr Ala Leu Lys
 65                  70                  75                  80

Asp Glu Ile Leu Ala Ser Leu Pro
                85
```

<210> SEQ ID NO 171
<211> LENGTH: 61
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: Aib

<400> SEQUENCE: 171

```
His Xaa Gln Gly Thr Phe Thr Ser Asp Tyr Ser Lys Tyr Leu Asp Glu
  1               5                  10                  15

Gln Ala Ala Lys Glu Phe Ile Ala Trp Leu Met Asn Thr Tyr Gly Val
             20                  25                  30

Ser Asp Phe Tyr Lys Arg Leu Ile Asn Lys Ala Lys Thr Val Glu Gly
         35                  40                  45

Val Glu Ala Leu Lys Leu His Ile Leu Ala Ala Leu Pro
     50                  55                  60
```

<210> SEQ ID NO 172
<211> LENGTH: 61
<212> TYPE: PRT
<213> ORGANISM: Artificial sequence
<220> FEATURE:
<223> OTHER INFORMATION: Synthetic polypeptide

<400> SEQUENCE: 172

```
His Ser Gln Gly Thr Phe Thr Ser Asp Tyr Ser Lys Tyr Leu Asp Glu
  1               5                  10                  15

Gln Ala Ala Lys Glu Phe Ile Ala Trp Leu Met Asn Thr Tyr Gly Val
             20                  25                  30

Ser Asp Phe Tyr Lys Arg Leu Ile Asn Lys Ala Lys Thr Val Glu Gly
         35                  40                  45

Val Glu Ala Leu Lys Leu His Ile Leu Ala Ala Leu Pro
     50                  55                  60
```

<210> SEQ ID NO 173
<211> LENGTH: 65
<212> TYPE: PRT
<213> ORGANISM: Artificial sequence
<220> FEATURE:
<223> OTHER INFORMATION: Synthetic polypeptide

<400> SEQUENCE: 173

```
His Ser Gln Gly Thr Phe Thr Ser Asp Tyr Ser Lys Tyr Leu Asp Glu
  1               5                  10                  15

Gln Ala Ala Lys Glu Phe Ile Ala Trp Leu Met Asn Thr Gly Gly Gly
             20                  25                  30

Ser Tyr Gly Val Ser Asp Phe Tyr Lys Arg Leu Ile Asn Lys Ala Lys
         35                  40                  45

Thr Val Glu Gly Val Glu Ala Leu Lys Leu His Ile Leu Ala Ala Leu
     50                  55                  60

Pro
 65
```

<210> SEQ ID NO 174

<400> SEQUENCE: 174

000

<210> SEQ ID NO 175

<400> SEQUENCE: 175

000

<210> SEQ ID NO 176
<211> LENGTH: 47
<212> TYPE: PRT
<213> ORGANISM: Artificial sequence
<220> FEATURE:
<223> OTHER INFORMATION: Synthetic polypeptide

<400> SEQUENCE: 176

```
Ser Leu Ala Glu Ala Lys Val Leu Ala Asn Arg Glu Leu Asp Lys Tyr
1               5                   10                  15
Gly Val Ser Asp Phe Tyr Lys Arg Leu Ile Asn Lys Ala Lys Thr Val
            20                  25                  30
Glu Gly Val Glu Ala Leu Lys Leu His Ile Leu Ala Ala Leu Pro
        35                  40                  45
```

<210> SEQ ID NO 177
<211> LENGTH: 46
<212> TYPE: PRT
<213> ORGANISM: Artificial sequence
<220> FEATURE:
<223> OTHER INFORMATION: Synthetic polypeptide

<400> SEQUENCE: 177

```
Ser Leu Ala Glu Ala Lys Val Leu Ala Asn Arg Glu Leu Asp Lys Tyr
1               5                   10                  15
Gly Val Ser Asp Phe Tyr Lys Arg Leu Ile Asn Lys Ala Lys Thr Val
            20                  25                  30
Glu Gly Val Glu Ala Leu Lys Leu His Ile Leu Ala Ala Leu
        35                  40                  45
```

<210> SEQ ID NO 178
<211> LENGTH: 48
<212> TYPE: PRT
<213> ORGANISM: Artificial sequence
<220> FEATURE:
<223> OTHER INFORMATION: Synthetic polypeptide

<400> SEQUENCE: 178

```
Gly Ser Leu Ala Glu Ala Lys Val Leu Ala Asn Arg Glu Leu Asp Lys
1               5                   10                  15
Tyr Gly Val Ser Asp Phe Tyr Lys Arg Leu Ile Asn Lys Ala Lys Thr
            20                  25                  30
Val Glu Gly Val Glu Ala Leu Lys Leu His Ile Leu Ala Ala Leu Pro
        35                  40                  45
```

<210> SEQ ID NO 179
<211> LENGTH: 48
<212> TYPE: PRT
<213> ORGANISM: Artificial sequence
<220> FEATURE:
<223> OTHER INFORMATION: Synthetic polypeptide

<400> SEQUENCE: 179

Ala Ser Leu Ala Glu Ala Lys Val Leu Ala Asn Arg Glu Leu Asp Lys
1               5                   10                  15

Tyr Gly Val Ser Asp Phe Tyr Lys Arg Leu Ile Asn Lys Ala Lys Thr
            20                  25                  30

Val Glu Gly Val Glu Ala Leu Lys Leu His Ile Leu Ala Ala Leu Pro
        35                  40                  45

<210> SEQ ID NO 180
<211> LENGTH: 47
<212> TYPE: PRT
<213> ORGANISM: Artificial sequence
<220> FEATURE:
<223> OTHER INFORMATION: Synthetic polypeptide

<400> SEQUENCE: 180

Gly Ser Leu Ala Glu Ala Lys Val Leu Ala Asn Arg Glu Leu Asp Lys
1               5                   10                  15

Tyr Gly Val Ser Asp Phe Tyr Lys Arg Leu Ile Asn Lys Ala Lys Thr
            20                  25                  30

Val Glu Gly Val Glu Ala Leu Lys Leu His Ile Leu Ala Ala Leu
        35                  40                  45

<210> SEQ ID NO 181
<211> LENGTH: 47
<212> TYPE: PRT
<213> ORGANISM: Artificial sequence
<220> FEATURE:
<223> OTHER INFORMATION: Synthetic polypeptide

<400> SEQUENCE: 181

Ala Ser Leu Ala Glu Ala Lys Val Leu Ala Asn Arg Glu Leu Asp Lys
1               5                   10                  15

Tyr Gly Val Ser Asp Phe Tyr Lys Arg Leu Ile Asn Lys Ala Lys Thr
            20                  25                  30

Val Glu Gly Val Glu Ala Leu Lys Leu His Ile Leu Ala Ala Leu
        35                  40                  45

<210> SEQ ID NO 182
<211> LENGTH: 15
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (6)..(6)
<223> OTHER INFORMATION: Xaa can be V or E
<220> FEATURE:
<221> NAME/KEY: MISC_FEATURE
<222> LOCATION: (7)..(7)
<223> OTHER INFORMATION: Xaa can be L, E or D
<220> FEATURE:
<221> NAME/KEY: MISC_FEATURE
<222> LOCATION: (9)..(9)
<223> OTHER INFORMATION: Xaa can be N, L or I
<220> FEATURE:
<221> NAME/KEY: MISC_FEATURE
<222> LOCATION: (10)..(10)
<223> OTHER INFORMATION: Xaa can be R or K
<220> FEATURE:
<221> NAME/KEY: MISC_FEATURE
<222> LOCATION: (13)..(13)
<223> OTHER INFORMATION: Xaa can be D or K

<400> SEQUENCE: 182

```
Leu Ala Glu Ala Lys Xaa Xaa Ala Xaa Xaa Glu Leu Xaa Lys Tyr
1               5                   10                  15

<210> SEQ ID NO 183
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 183

Leu Ala Ala Leu Pro
1               5

<210> SEQ ID NO 184
<211> LENGTH: 50
<212> TYPE: PRT
<213> ORGANISM: Artificial sequence
<220> FEATURE:
<223> OTHER INFORMATION: Synthetic polypeptide

<400> SEQUENCE: 184

Lys Lys Lys Lys Lys His Gly Glu Gly Thr Phe Thr Ser Asp Leu
1               5                   10                  15

Ser Lys Gln Met Glu Glu Ala Val Arg Leu Phe Ile Glu Trp Leu
                20                  25                  30

Lys Asn Gly Gly Pro Ser Ser Gly Ala Pro Pro Ser Lys Lys Lys
            35                  40                  45

Lys Lys
    50

<210> SEQ ID NO 185
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 185

His Gly Glu Gly Thr Phe Thr Ser Asp Leu Ser Lys Gln Met Glu
1               5                   10                  15

Glu Ala Val Arg Leu Phe Ile Glu Trp Leu Trp Leu Lys Asn Gly Gly
                20                  25                  30

Pro Ser Ser Gly Ala Ser
        35

<210> SEQ ID NO 186
<211> LENGTH: 42
<212> TYPE: PRT
<213> ORGANISM: Artificial sequence
<220> FEATURE:
<223> OTHER INFORMATION: Synthetic polypeptide

<400> SEQUENCE: 186

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
                20                  25                  30

Lys Asn Gly Gly Pro Ser Ser Gly Ala Ser
            35                  40

<210> SEQ ID NO 187
```

```
<211> LENGTH: 42
<212> TYPE: PRT
<213> ORGANISM: Artificial sequence
<220> FEATURE:
<223> OTHER INFORMATION: Synthetic polypeptide

<400> SEQUENCE: 187

Asn Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asn Gly Gly Pro Ser Ser Gly Ala Ser
        35                  40

<210> SEQ ID NO 188
<211> LENGTH: 42
<212> TYPE: PRT
<213> ORGANISM: Artificial sequence
<220> FEATURE:
<223> OTHER INFORMATION: Synthetic polypeptide

<400> SEQUENCE: 188

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Ser Lys Lys Lys Lys Lys Lys
        35                  40

<210> SEQ ID NO 189
<211> LENGTH: 48
<212> TYPE: PRT
<213> ORGANISM: Artificial sequence
<220> FEATURE:
<223> OTHER INFORMATION: Synthetic polypeptide

<400> SEQUENCE: 189

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asn Gly Gly Pro Ser Ser Gly Ala Ser Lys Lys Lys Lys Lys Lys
        35                  40                  45

<210> SEQ ID NO 190
<211> LENGTH: 48
<212> TYPE: PRT
<213> ORGANISM: Artificial sequence
<220> FEATURE:
<223> OTHER INFORMATION: Synthetic polypeptide

<400> SEQUENCE: 190

Asp Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asn Gly Gly Pro Ser Ser Gly Ala Ser Lys Lys Lys Lys Lys Lys
        35                  40                  45

<210> SEQ ID NO 191
<211> LENGTH: 6
<212> TYPE: PRT
<213> ORGANISM: Artificial sequence
```

```
<220> FEATURE:
<223> OTHER INFORMATION: Synthetic polypeptide

<400> SEQUENCE: 191

Lys Lys Lys Lys Lys Lys
1               5

<210> SEQ ID NO 192
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 192

Gly Gly Gly Ser
1

<210> SEQ ID NO 193
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 193

Thr Gly Gly Gly Gly Ala Ser
1               5

<210> SEQ ID NO 194
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 194

Thr Gly Gly Gly Gly Gly Ala Ser
1               5

<210> SEQ ID NO 195
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 195

Thr Gly Gly Gly Gly Ser Ala Ser
1               5

<210> SEQ ID NO 196
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 196

Gly Gly Gly Gly
1

<210> SEQ ID NO 197
<211> LENGTH: 5
<212> TYPE: PRT
<213> ORGANISM: Artificial sequence
<220> FEATURE:
```

-continued

```
<223> OTHER INFORMATION: Synthetic polypeptide

<400> SEQUENCE: 197

Gly Gly Gly Gly Gly
1               5

<210> SEQ ID NO 198
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 198

Thr Gly Gly Gly Gly Ser
1               5

<210> SEQ ID NO 199
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 199

Thr Gly Gly Gly Gly Ser Gly Gly Gly Ser
1               5                   10

<210> SEQ ID NO 200
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 200

Thr Gly Gly Gly Gly Ser Gly Gly Gly Ser Gly Gly Gly Ser
1               5                   10

<210> SEQ ID NO 201
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 201

Thr Gly Gly Gly Gly Ser Gly Gly Gly Ser Gly Gly Gly Ser Gly Gly
1               5                   10                  15

Gly Ser

<210> SEQ ID NO 202
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 202

Thr Gly Gly Gly Gly Ser Gly Gly Gly Ser Gly Gly Gly Ser Gly Gly
1               5                   10                  15

Gly Ser Gly Gly Gly Ser
                20

<210> SEQ ID NO 203
```

```
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 203

Gly Gly Gly Ser Ala Ser
1               5

<210> SEQ ID NO 204
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 204

Gly Gly Gly Ser Gly Gly Gly Ser Ala Ser
1               5                   10

<210> SEQ ID NO 205
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 205

Gly Gly Gly Ser Gly Gly Gly Ser Gly Gly Gly Ser Ala Ser
1               5                   10

<210> SEQ ID NO 206
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 206

Gly Gly Gly Ser Gly Gly Gly Ser Gly Gly Gly Ser Gly Gly Gly Ser
1               5                   10                  15

Ala Ser

<210> SEQ ID NO 207
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 207

Gly Gly Gly Ser Gly Gly Gly Ser Gly Gly Gly Ser Gly Gly Gly Ser
1               5                   10                  15

Gly Gly Gly Ser Ala Ser
            20

<210> SEQ ID NO 208
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 208

Thr Gly Gly Gly Gly Ser Ala Ser
```

<210> SEQ ID NO 209
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 209

Thr Gly Gly Gly Gly Ser Gly Gly Gly Ser Ala Ser
1               5                   10

<210> SEQ ID NO 210
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 210

Thr Gly Gly Gly Gly Ser Gly Gly Gly Ser Gly Gly Gly Ser Ala Ser
1               5                   10                  15

<210> SEQ ID NO 211
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 211

Thr Gly Gly Gly Gly Ser Gly Gly Gly Ser Gly Gly Gly Ser Gly Gly
1               5                   10                  15

Gly Ser Ala Ser
            20

<210> SEQ ID NO 212
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 212

Thr Gly Gly Gly Gly Ser Gly Gly Gly Ser Gly Gly Gly Ser Gly Gly
1               5                   10                  15

Gly Ser Gly Gly Gly Ser Ala Ser
            20